US012697313B2

(12) United States Patent
Glimcher et al.

(10) Patent No.: US 12,697,313 B2
(45) Date of Patent: Aug. 4, 2026

(54) METHODS OF TREATING ANEMIA USING FORMOTEROL OR A PHARMACEUTICALLY ACCEPTABLE SALT THEREOF

(71) Applicant: Dana-Farber Cancer Institute, Inc., Boston, MA (US)

(72) Inventors: Laurie H. Glimcher, Boston, MA (US); Shrestha Ghosh, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 19/127,025

(22) PCT Filed: Nov. 3, 2023

(86) PCT No.: PCT/US2023/036800
§ 371 (c)(1),
(2) Date: May 2, 2025

(87) PCT Pub. No.: WO2024/097413
PCT Pub. Date: May 10, 2024

(65) Prior Publication Data
US 2026/0048029 A1 Feb. 19, 2026

Related U.S. Application Data

(60) Provisional application No. 63/537,307, filed on Sep. 8, 2023, provisional application No. 63/455,540, filed
(Continued)

(51) Int. Cl.
*A61K 31/167* (2006.01)
*A61K 31/454* (2006.01)
(Continued)

(52) U.S. Cl.
CPC .......... *A61K 31/167* (2013.01); *A61K 31/454* (2013.01); *A61K 31/706* (2013.01); *A61K 38/1816* (2013.01); *A61P 7/06* (2018.01)

(58) Field of Classification Search
CPC .. A61K 31/167; A61K 31/454; A61K 31/706; A61K 38/1816; A61P 7/06
See application file for complete search history.

(56) References Cited

U.S. PATENT DOCUMENTS 10,722,562 B2 7/2020 Pedersen et al.
2007/0190023 A1 8/2007 Battista et al.
(Continued)

FOREIGN PATENT DOCUMENTS

CN 101926998 B 9/2013
EP 0003664 A1 8/1979
(Continued)

OTHER PUBLICATIONS

Beckman et al., "Changes in beta-2 adrenergic receptor sensitivity with maturation of erythroid progenitor cells." Experientia, 35(12), (1979):1671-1672.
(Continued)

*Primary Examiner* — Deborah D Carr
(74) *Attorney, Agent, or Firm* — Foley Hoag LLP; DeAnn F. Smith; Philip S. Choi

(57) ABSTRACT

The present invention provides methods of treating anemia in a patient in need thereof, comprising administering to the patient in need thereof an effective amount of formoterol or a pharmaceutically acceptable salt thereof (e.g., formoterol fumarate or arformoterol tartrate). The formoterol or a pharmaceutically acceptable salt thereof (e.g., formoterol fumarate or arformoterol tartrate) may be administered conjointly with an erythropoiesis-stimulating agent, option-ally wherein the anemia is refractory to the erythropoiesis-
(Continued)

stimulating agent. The present invention further provides methods of promoting differentiation of an erythroid progenitor cell toward a mature red blood cell in a patient in need thereof, comprising administering an effective amount of formoterol or a pharmaceutically acceptable salt thereof (e.g., formoterol fumarate or arformoterol tartrate). The formoterol or a pharmaceutically acceptable salt thereof (e.g., formoterol fumarate or arformoterol tartrate) may be administered conjointly with other FDA approved drugs such as luspatercept, lenalidomide, erythropoiesis-stimulating agents (ESAs), including but not limited to epoetin alfa or darbepoetin alfa, and/or a hypomethylating agent, such as azacitidine and/or decitabine.

20 Claims, 173 Drawing Sheets

Related U.S. Application Data on Mar. 29, 2023, provisional application No. 63/422,210, filed on Nov. 3, 2022.

(51) Int. Cl.
| | |
|---|---|
| A61K 31/706 | (2006.01) |
| A61K 38/18 | (2006.01) |
| A61P 7/06 | (2006.01) |

(56) References Cited

U.S. PATENT DOCUMENTS

| | | | |
|---|---|---|---|
| 2008/0261932 A1 | 10/2008 | Chiesi et al. |
| 2014/0147393 A1 | 5/2014 | Malhorta et al. |
| 2016/0310410 A1 | 10/2016 | Dhuppad et al. |

FOREIGN PATENT DOCUMENTS

| | | |
|---|---|---|
| WO | WO-2019/020634 A2 | 1/2019 |
| WO | WO-2019/241496 A1 | 12/2019 |
| WO | WO-2023/049851 A1 | 3/2023 |
| WO | WO-2023/239937 A1 | 12/2023 |
| WO | WO-2024/097413 A1 | 5/2024 |
| WO | WO-2025/092300 A1 | 5/2025 |
| WO | WO-2025/231332 A1 | 11/2025 |
| WO | WO-2025/231335 A1 | 11/2025 |

OTHER PUBLICATIONS

Fink et al., "Stimulation of erythropoiesis by beta adrenergic agonists. I. Characterization of activity in polycythemic mice." The Journal of pharmacology and experimental therapeutics 202.1 (1977): 192-198.
Fink et al., "Stimulation of erythropolesis by beta adrenergic agonists. II. Mechanism of action", The Journal of pharmacology and experimental therapeutics 202.1: 199-208 (1977).
Gagic et al., "The effect of clenbuterol and recombinant erythropoietin on tumor growth and the anemia caused by the Walker 256 carcinosarcoma." Life Sciences 61(25) (1997): 2475-2484.
Ganapathy et al., "Health resource utilization for inpatients with COPD treated with nebulized arformoterol or nebulized formoterol", International Journal of Chronic Obstructive Pulmonary Disease: 1793-1801 (2017).
Gehrig et al., "Short Communication: Making Fast-Twitch Dystrophic Muscles Bigger Protects Them from Contraction Injury and Attenuates the Dystrophic Pathology" The American Journal of Pathology, vol. 176, No. 1, (2010).
International Search Report & Written Opinion for International Application No. PCT/US23/36800 dated Feb. 14, 2024.

Jelkmann et al., "beta 2-Adrenergic stimulation of erythropoiesis inbusulfan treated mice" Exp Hematol, vol. 8, No. 6, p. 742-748 (1980). Abstract.
Kellenberger et al., "Formoterol and Isoproterenol Induce c-fos Gene Expression in Osteoblast-Like Cells by Activating Beta 2-Adrenergic Receptors" Bone, vol. 22, No. 5, pp. 471-478 (1998).
Mladenovic et al., "Adrenergic modulation of erythropoiesis: in vitro studies of colony-forming cells in normal and polycythaemic man." British Journal of Haematology 56 (1984): 323-332.
Pathan, "Potential Anaphylaxis to Systemic Phenylephrine: A Case Report." Hospital Pharmacy (2023): 1-5.
Ryall et al., "Intramuscular Beta "2-agonist administration enhances early regeneration and functional repair in rat skeletal muscle after myotoxic injury" J Appl Physiol, vol. 105: p. 165-172 (2008).
Singh et al., "Managing anemia in dialysis patients: hemoglobin cycling and overshoot." Kidney International 74 (2008): 679-683.
Society for Experimental Biology and Medicine, "Effects of in vitro beta-adrenergic activation on rabbit bone marrow erythroid colony forming cells" Proceedings of the Society for Experimental Biology and Medicine 155(3) (1977).
Trofast et al., "Steric aspects of agonism and antagonism at β-adrenoceptors: Synthesis of and pharmacological experiments with the enantiomers of formoterol and their diastereomers", Chirality 3(6): 443-450 (1991).
Abosamak et al., "Beta2 Receptor Agonists and Antagonists." [Updated Jul. 3, 2023]. In: StatPearls [Internet]. Treasure Island (FL): StatPearls Publishing; Jan. 2024.
Alamo et al., "Daily propranolol administration reduces persistent injury-associated anemia after severe trauma and chronic stress," The Journal of Trauma and Acute Care Surgery 82.4 (2017): 714-721.
Brown et al., "Modulation of In Vitro Erythropoiesis," The Journal of Clinical Investigation 60 (1977): 70-77.
Cuesta et al., "The Beta2-adrenergic receptor antagonist ICI-118,551 blocks the constitutively activated HIF signalling in hemangioblastomas from von Hippel-Lindau disease", Scientific Reports 9:10062 (2019).
Fink et al., "Effects of Beta Adrenergic Blocking Agents of Erythropoietin Production in Rabbits Exposed to Hypoxia," The Journal of Pharmacology and Experimental Therapeutics 193.1 (1975): 176-181.
Fink et al., "Stimulation of erythropolesis by beta adrenergic agonists. II. Mechanism of action." The Journal of Pharmacology and Experimental Therapeutics 202(1) (1977): 199-208.
Fox et al., "Polycythemia Vera: Rapid Evidence Review." American Family Physician 103(11) (2021): 680-687.
Haider et al., "Secondary Polycythemia." [Updated May 8, 2023]. In: StatPearls [Internet]. Treasure Island (FL): StatPearls Publishing; Jan. 2024.
Haider et al., Secondary Polycythemia. NCBI Bookshelf. A service of the National Library of Medicine, National Institutes of Health. StatPearls [Internet]. Treasure Island (FL): StatPearls Publishing. May 8, 2023 [online].
Hasan et al., "Discrete β-adrenergic mechanisms regulate early and late erythropoiesis in erythropoietin-resistant anemia." Surgery 162(4) (2017): 901-916.
Hespel et al. "Beta-adrenoceptors and the regulation of blood pressure and plasma renin during exercise." Journal of Applied Physiology 60 (1986): 108-113.
International Search Report and Written Opinion for International Application No. PCT/US25/27445 dated Aug. 21, 2025.
International Search Report and Written Opinion for International Application No. PCT/US25/27449 dated Aug. 22, 2025.
Jefferson et al., "The comparative effects of ICI 118551 and propranolol on essential tremor." British Journal of Clinical Pharmacology 24 (1987): 729-734.
Jelkmann et al., "beta 2-Adrenergic stimulation of erythropoiesis in busulfan treated mice." Experimental Hematology 8(6) (1980): 742-748.
Johnson, "Molecular mechanisms of β2-adrenergic receptor function, response, and regulation." Journal of Allergy and Clinical Immunology 117 (2006): 18-24.

(56)         References Cited

OTHER PUBLICATIONS

Mullally et al., "Physiological Jak2V617F Expression Causes a Lethal Myeloproliferative Neoplasm with Differential Effects on Hematopoietic Stem and Progenitor Cells", Cancer Cell 17 (2010): 584-596.

Nathanson, "ICI 118,551: an effective ocular hypotensive agent with selectivity for the ciliary process 132-adrenoceptor and with minimal cardiac side effects", British Journal of Pharmacology 83 (1984): 821-829.

Östman-Smith, "Reduction by β-adrenoceptor blockade of hypoxia-induced right heart hypertrophy in the rat." British Journal of Pharmacology 116 (1995): 2698-2702.

Pelouch, "The effect of beta adrenergic blockade on pulmonary hypertension, right ventricular hypertrophy and polycythaemia, induced in rats by intermittent high altitude hypoxia Pulmonaler Hochdruck, rechtsventrikul~ ire." Basic Res. Cardiol 73 (1978): 422-432.

Pringle et al., "Characterization of the beta-adrenoreceptors which mediate the isoprenaline-induced changes in finger tremor and cardiovascular function in man." European Journal of Clinical Pharmacology 35 (1988): 507-514.

Shahrokhi, "Propranolol." [Updated May 1, 2023]. In: StatPearls [Internet]. Treasure Island (FL): StatPearls Publishing; Jan. 2024.

Spivak, "Polycythemia vera." Current Treatment Options in Oncology 19 (2018): 1-14.

Tefferi et al., "Polycythemia vera: historical oversights, diagnostic details, and therapeutic views." Leukemia 35 (2021): 3339-3351.

Wu et al., "Blood pressure reduction induced by low dose of epinephrine via different routes in rats." Journal of Cardiovascular Pharmacology 62(3) (2013): 325-328.

Yang et al., "Role of β2-adrenergic receptors in chronic obstructive pulmonary disease." Life Sciences 265 (2021): 118864.

Zivny et al., "Effect of Beta Adrenergic Blocking Agents on Erythropoiesis in Rats," The Journal of Pharmacology and Experimental Therapeutics 226.1 (1983): 222-225.

Zivný et al., "Effect of beta adrenergic blocking agents on erythropoiesis in rats." Journal of Pharmacology and Experimental Therapeutics 226(1) (1983): 222-225.

Selleckchem $ \quad  \quad **$

[Bar graph: MFI CD235a (y-axis) vs. concentration (x-axis)]

y-axis: MFI CD235a
14000
12000
10000
8000
6000
0 x-axis: 0 μM, 0.01 μM, 0.1 μM, 1 μM, 2 μM, 5 μM

Fig. 17

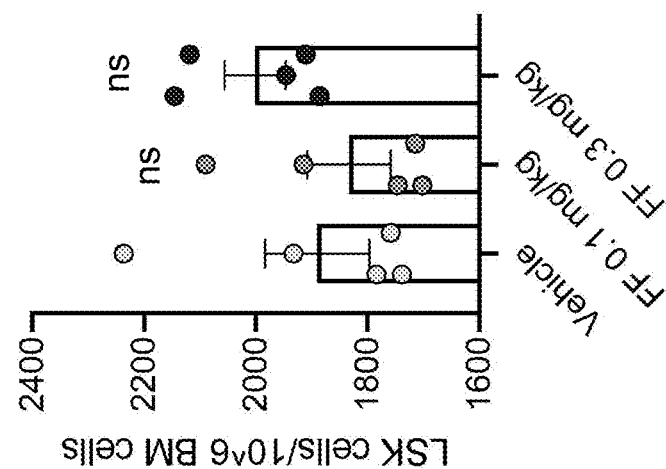
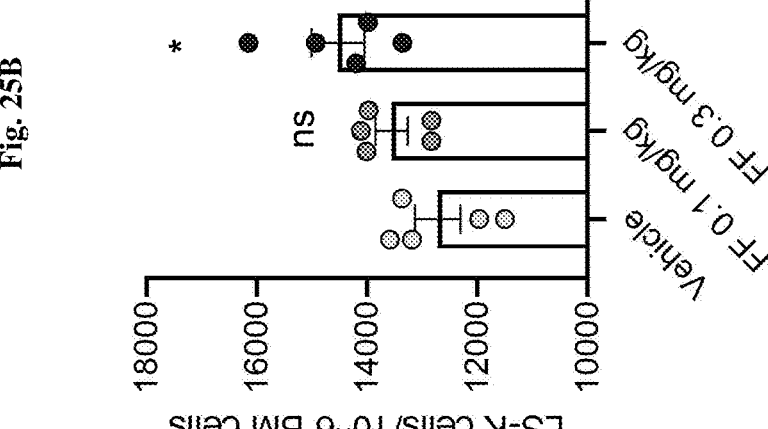
Fig. 25B
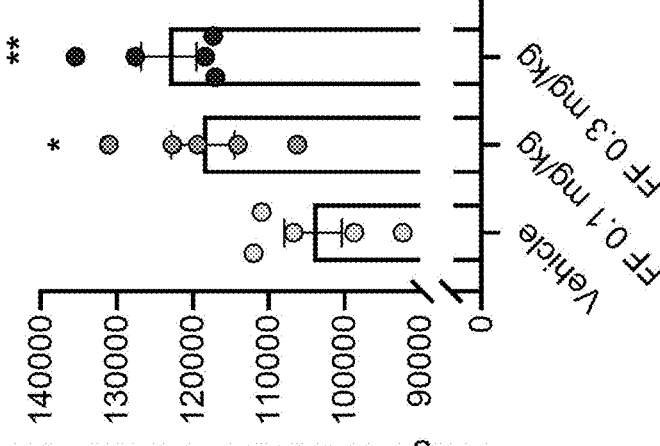

Beta 2 drug treatment *in vivo*: Phenylhydrazine (PHZ) study
Sub-lethal dose (60 mg/kg)+ β2 drugs via ip

5 groups of mice: 5 mice per group
DMSO or FF/Arf (0.3 mg/kg)

FF and Arf treatments mildly increase RBCs parameters after 7 days of administration FF and Arf treatments increase LSKs in the

Fig. 36B                      Fig. 36C

FF and Arf treatments increase erythroid progenitors in the BM

Fig. 39A
Fig. 39B
Long term impact of FF and Arf treatments
on erythroid progenitors in the BM
Sorted LSKs from BM- Plated in semisolid
methylcellulose media for 7 days- FACS
analysis of CFUe progenitors
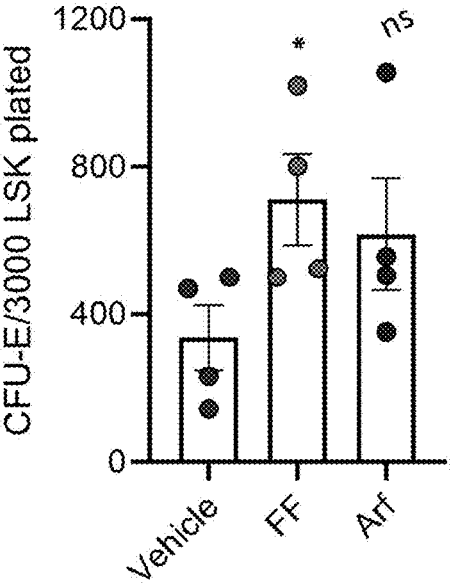
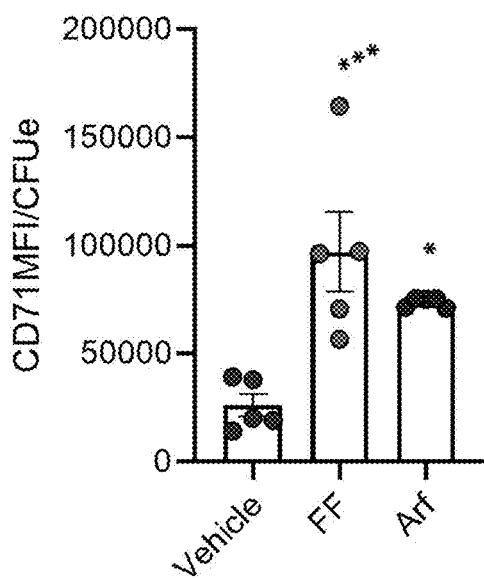

Formoterol treatment *in vivo* via ORAL GAVAGE(o.g.): NO PHZ
Formoterol was dissolved in Sterile Water at 0.4mg/ml conc.

4 groups of mice: 5 mice per group
1: DMSO 2. FF 0.1 mg/kg 3. FF 0.5 mg/kg 4. FF 1.0 mg/kg

D0 D1 D2 D3 D4 D5 D6 D7 D8 D9 D14

Submandibular cheek bleed

CBC profiling sacrifice

BM progenitor profiling

Formoterol treatment *in vivo*: Phenylhydrazine (PHZ) study
Lethal dose of 135 mg/kg on day 0 followed by daily o.g. of
FF of indicated doses Formoterol treatment *in vivo*: Phenylhydrazine (PHZ) study
Sub-lethal dose (60 mg/kg)+ FF via oral gavage Formoterol treatment *in vivo*: (PHZ)
Daily o.g. of FF of indicated doses n=5 per group, All Females;
10-12 weeks old FF enhances mitochondrial biogenesis in BMPs FF does not affect granulocytic myeloid progenitors (GMP) in BM Pre-gated on Viable LS-K BM cells

Fig. 70A
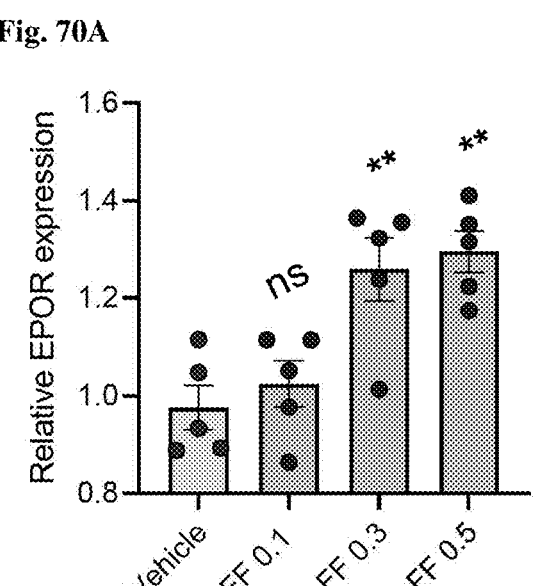
Fig. 70B
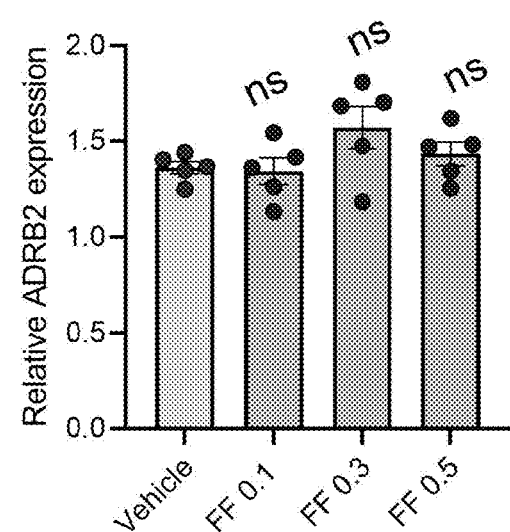
Fig. 70C
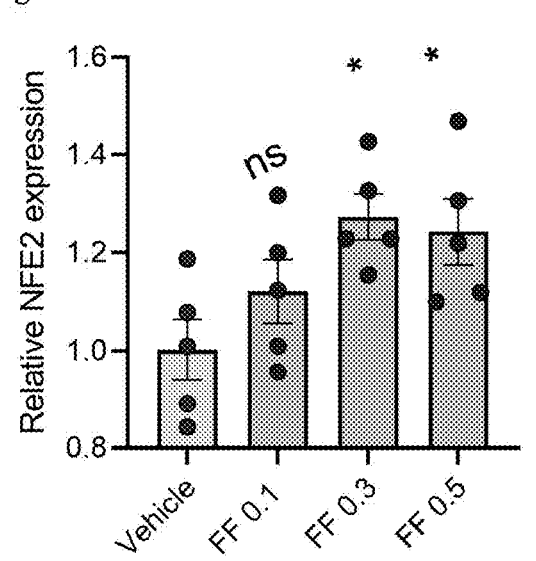
Fig. 70D

Non-EP

Formoterol treatment *in vivo*: NO Phenylhydrazine (PHZ)
Daily i.p. injection of FF of indicated doses n=5 per group All Males;
10-12 weeks old

Bulk RNA sequencing
FF 0.3 mg/kg 3x weekly ip *in vivo*: NO PHZ

2 groups of mice: 5 mice per group
DMSO and 0.3 mg/kg 3x weekly for a month

... 3 x weekly ip injections of FF 0.3 mg/kg

D-1     D0     D3...     D6     D9     D12...     D21... D30

- Euthanized mice at day 30
- Harvested bone marrow
- Sorted erythroid progenitors
- Purified RNA
- Sent for bulk RNA sequencing and analyses

Fig. 87A

| log2FoldChange (FF/Vehicle) | padj | Veh-1 | Veh-2 | Veh-3 | Veh-4 | Veh-5 | FF-1 | FF-2 | FF-3 | FF-4 | FF-5 | Gene name |
|---|---|---|---|---|---|---|---|---|---|---|---|---|
| 1.020955025 | 4.58E-06 | 795.0671 | 676.6501 | 401.4077 | 617.8315 | 699.079 | 1249.491 | 1529.509 | 1347.378 | 1192.506 | 1152.244 | Kif9 |
| 0.481188757 | 0.000153 | 15162.07 | 11876.33 | 12933.65 | 13773.22 | 11615.65 | 19882.6 | 21024.12 | 19520.57 | 18619.56 | 17706.48 | Kif13 |
| 0.655855938 | 0.044142 | 880.731 | 506.0863 | 613.8645 | 1135.035 | 859.8865 | 1246.621 | 1244.63 | 1315.559 | 1290.222 | 1198.506 | Kif11 |
| 0.409502878 | 0.001363 | 3049.75 | 2930.57 | 2670.627 | 2668.253 | 3322.07 | 3953.215 | 4392.059 | 3770.67 | 3591.994 | 3739.684 | Hif1a |
| 0.835195847 | 0.002052 | 52.80521 | 39.10587 | 65.99722 | 76.82318 | 56.81221 | 88.01931 | 116.8989 | 117.3362 | 98.62149 | 101.1307 | Epas1 |
| 1.284423308 | 0.0004 | 5042.399 | 1721.843 | 2491.621 | 3491.668 | 4674.971 | 7380.227 | 9431.482 | 9735.925 | 7597.174 | 8295.944 | Ddit4 |
| 0.989045787 | 1.48E-07 | 1973.719 | 1285.754 | 1815.376 | 2343.648 | 1781.288 | 3227.056 | 3780.059 | 4181.347 | 3613.708 | 3466.416 | Chrp |
| 1.191836722 | 0.00298 | 128.5259 | 58.06629 | 1383.3729 | 1049.556 | 1338.8828 | 2870.0195 | 378.7023 | 235.6669 | 233.4343 | 153.8478 | Rora |

EPAS1- Alias for HIF2α

1

METHODS OF TREATING ANEMIA USING FORMOTEROL OR A PHARMACEUTICALLY ACCEPTABLE SALT THEREOF

CROSS-REFERENCE TO RELATED APPLICATIONS

This application is a U.S. National Stage of PCT/US23/36800, filed Nov. 3, 2023; which claims priority to U.S. Provisional Application No. 63/422,210, filed Nov. 3, 2022, U.S. Provisional Application No. 63/455,540, filed Mar. 29, 2023, and U.S. Provisional Application No. 63/537,307, filed Sep. 8, 2023, the disclosures of each of which are hereby incorporated by reference in their entirety.

BACKGROUND OF THE INVENTION

Anemia affects roughly one-third of the world population (Chaparro and Suchdev (2019). *Ann. N.Y. Acad. Sci.* 1450: 15-31) and is a major co-morbidity in a wide range of hematologic disorders, such as myelodysplastic syndromes (MDS), bone marrow failure (BMF), anemia of inflammatory diseases, such as chronic kidney diseases, ribosomopathies, and leukemias such as acute myeloid leukemia (AML). For example, anemia is a predominant feature in ~80-90% of MDS patients and its treatment remains the primary goal of designing new interventions (Castelli et al. (2018) *Med. Oncol.* 35:76; Feld et al. (2020) *Exp. Rev. Anticancer Ther.* 20:465-482; Steensma (2018) *Blood Cancer J.* 8:47). Conventional erythropoiesis-stimulating agents are only effective in 50-60% of low-risk MDS patients (Schiavon et al. (2018) *Med. Oncol.* 35:76; Park et al. (2019) *Br. J. Haematol.* 184:134-160). As a result, a major fraction of MDS patients eventually becomes transfusion-dependent and non-responsive to a handful of existing FDA-approved drugs, such as hypomethylating agents (Cheng et al. (2021) *Hematol.* 26:261-270; Kordella et al. (2021) *Front. Oncol.* 11:650473; Schiffer et al. (2021) *Exp. Rev. Anticancer Ther.* 21:989-1002), lenalidomide (Hecht et al. (2021) *Ann. Hematol.* 100:1463-1471; ), or luspatercept (Chan et al. (2021) *Fut. Oncol.* 17:1473-1481; Cheng et al. (2021) *Hematol.* 26:261-270; Hecht et al. (2021) *Ann Hematol.* 100:1463-1471; Kordella et al. (2021) *Front. Oncol.* 11:650473; Kubasch et al. (2021) *Blood Adv.* 5:1565-1575; List et al. (2021) *J. Clin. Oncol.* 39:1001-1009), or progress to AML (~25-30% patients), if they are ineligible for the only curative treatment of allogeneic bone marrow transplant. Thus, there is a critical need to identify additional novel therapies to promote erythroid differentiation for alleviating anemia in these disorders.

SUMMARY OF THE INVENTION

The present invention described herein is based, in part, on the discovery of a novel therapeutic approach of targeting anemia (e.g., such as anemia in hematologic malignancies such as MDS, in cancer patients undergoing chemotherapeutic treatments, and other disorders disclosed herein) by administering formoterol or a pharmaceutically acceptable salt thereof (e.g., formoterol fumarate (FF) or arformoterol tartrate (Arf)). It is shown herein that FF/Arf simultaneously augments mitochondrial biogenesis and erythroid differentiation in primary human hematopoietic stem and progenitor cells (HSPCs). FF/Arf treatment significantly enhances erythropoiesis in MDS patient-derived bone marrow cells and therefore offers a potential treatment strategy to improve erythroid differentiation defects in hematological malignancies such as acute myeloid leukemia and other diseases disclosed herein, such as bone marrow failure disorders, including but not limited to Diamond-Blackfan anemia and aplastic anemia. Repurposing formoterol or a pharmaceutically acceptable salt thereof (e.g., formoterol fumarate or arformoterol tartrate) that stimulates erythroid differentiation has significant therapeutic benefits in the treatment of various hematologic disorders associated with anemia, such as aplastic anemia, Diamond-Blackfan anemia, Schwachman-Diamond syndrome, MDS, anemia of inflammatory diseases such as chronic kidney disease, ribosomopathies, hematologic malignances including but not limited to acute myeloid leukemia (AML), chronic lymphocytic leukemia (CLL), and multiple myeloma (MM), anemia secondary to chemotherapy in cancer patients, anemia secondary to an intestinal cancer, and also anemia in general and that associated with aging.

In some aspects, provided herein are methods of treating anemia in a patient in need thereof, the method comprising administering to the patient in need thereof an effective amount of formoterol or a pharmaceutically acceptable salt thereof (e.g., formoterol fumarate or arformoterol tartrate).

In some embodiments, an effective amount of formoterol or a pharmaceutically acceptable salt thereof (e.g., formoterol fumarate or arformoterol tartrate) is a dose that is ≤100µg. In some embodiments, a dose of formoterol or a pharmaceutically acceptable salt thereof (e.g., formoterol fumarate or arformoterol tartrate) is administered daily (e.g., once per day). In some embodiments, an effective amount of formoterol or a pharmaceutically acceptable salt thereof (e.g., formoterol fumarate or arformoterol tartrate) is a dose that is from 0.1 µg/day to 100 µg/day. In some preferred embodiments, an effective amount of formoterol or a pharmaceutically acceptable salt thereof (e.g., formoterol fumarate or arformoterol tartrate) is a dose that is from 1 µg/day to 60µg/day.

In some embodiments, an effective amount of formoterol or a pharmaceutically acceptable salt thereof (e.g., formoterol fumarate or arformoterol tartrate) is a total daily dose that is ≤100µg. In some embodiments, an effective amount of formoterol or a pharmaceutically acceptable salt thereof (e.g., formoterol fumarate or arformoterol tartrate) is a total daily dose that is from 0.1 µg to 100 µg. In some preferred embodiments, an effective amount of formoterol or a pharmaceutically acceptable salt thereof (e.g., formoterol fumarate or arformoterol tartrate) is a total daily dose that is from 1 µg to 60µg.

In some embodiments, the anemia is selected from the group consisting of macrocytic anemia, hemolytic anemia, anemia caused by a ribosomopathy, anemia caused by insufficiency of serine/threonine-protein kinase RIOK2, anemia associated with chronic kidney disease (CKD), anemia caused by one or more mutations and/or deletions in human chromosome 5 or in an ortholog thereof, anemia caused by chromosomal translocations in the NUP98 gene or in an ortholog thereof, such as anemia caused by fusions of NUP98 with Abd-B group HOX genes (e.g., HOXD13), stress-induced anemia, anemia secondary to an intestinal cancer, Diamond Blackfan anemia, aplastic anemia, Schwachman-Diamond syndrome, an anemia associated with an inflammatory disease, such as rheumatoid arthritis or multiple sclerosis, anemia secondary to chemotherapy in cancer patients, and anemia associated with a bone marrow failure syndrome. In some embodiments, the anemia is associated with a cancer, optionally wherein the cancer is a hematologic malignancy, such as a myelodysplastic syndrome (MDS), acute myeloid leukemia (AML), chronic lymphocytic leukemia (CLL) or multiple myeloma (MM). In some embodiments, the anemia is associated with an intestinal cancer, such as a colorectal cancer.

In some aspects, provided herein are methods of promoting differentiation of an erythroid progenitor cell toward a mature red blood cell in a patient by administering an effective amount of formoterol or a pharmaceutically acceptable salt thereof (e.g., formoterol fumarate or arformoterol tartrate). In some embodiments, an effective amount of formoterol or a pharmaceutically acceptable salt thereof (e.g., formoterol fumarate or arformoterol tartrate) is a dose that is ≤100μg. In some embodiments, a dose of formoterol or a pharmaceutically acceptable salt thereof (e.g., formoterol fumarate or arformoterol tartrate) is administered daily (e.g., once per day). In some embodiments, an effective amount of formoterol or a pharmaceutically acceptable salt thereof (e.g., formoterol fumarate or arformoterol tartrate) is a dose that is from 0.1 μg/day to 100 μg/day. In some preferred embodiments, an effective amount of formoterol or a pharmaceutically acceptable salt thereof (e.g., formoterol fumarate or arformoterol tartrate) is a dose that is from 1 μg/day to 60 μg/day.

In some embodiments, an effective amount of formoterol or a pharmaceutically acceptable salt thereof (e.g., formoterol fumarate or arformoterol tartrate) is a total daily dose that is ≤100μg. In some embodiments, an effective amount of formoterol or a pharmaceutically acceptable salt thereof (e.g., formoterol fumarate or arformoterol tartrate) is a total daily dose that is from 0.1 μg to 100μg. In some preferred embodiments, an effective amount of formoterol or a pharmaceutically acceptable salt thereof (e.g., formoterol fumarate or arformoterol tartrate) is a total daily dose that is from 1 μg to 60μg.

In some embodiments, formoterol or a pharmaceutically acceptable salt thereof (e.g., formoterol fumarate or arformoterol tartrate) may be orally administered to the patient. In some embodiments, the patient is a human suffering from anemia. In some embodiments, the methods may further comprise administering (e.g., administering conjointly) to the patient in need thereof an effective amount of an erythropoiesis-stimulating agent (ESA), or other FDA-approved drugs such as luspatercept, lenalidomide and/or a hypomethylating agent, including but not limited to epoetin alfa or darbepoetin alfa, azacitidine or decitabine. In some embodiments, the erythropoiesis-stimulating agent comprises erythropoietin, epoetin alfa, epoetin beta, epoetin omega, epoetin zeta, or darbepoetin alfa.

In some aspects, provided herein are methods of treating anemia in a patient in need thereof, comprising administering to the patient in need thereof an effective amount of formoterol or a pharmaceutically acceptable salt thereof (e.g., formoterol fumarate or arformoterol tartrate) conjointly with an erythropoiesis-stimulating agent, wherein the anemia is refractory to the erythropoiesis-stimulating agent. In some embodiments, the erythropoiesis-stimulating agent comprises erythropoietin, epoetin alfa, epoetin beta, epoetin omega, epoetin zeta, or darbepoetin alfa. In some embodiments, formoterol or a pharmaceutically acceptable salt thereof (e.g., formoterol fumarate or arformoterol tartrate) may be administered conjointly with other FDA-approved drugs such as luspatercept, lenalidomide and/or a hypomethylating agent, such as azacitidine or decitabine. The anemia may be selected from the group consisting of macrocytic anemia, hemolytic anemia, anemia caused by a ribosomopathy, anemia caused by insufficiency of serine/threonine-protein kinase RIOK2, anemia associated with chronic kidney disease (CKD), anemia caused by one or more mutations and/or deletions in human chromosome 5 or in an ortholog thereof, anemia caused by chromosomal translocations in the NUP98 gene or in an ortholog thereof, such as anemia caused by fusions of NUP98 with Abd-B group HOX genes (e.g., HOXD13), stress-induced anemia, anemia secondary to an intestinal cancer, Diamond Blackfan anemia, aplastic anemia, Schwachman-Diamond syndrome, an anemia associated with an inflammatory disease, such as rheumatoid arthritis or multiple sclerosis, anemia secondary to chemotherapy in cancer patients, and anemia associated with a bone marrow failure syndrome.

In some embodiments, a patient is one that would benefit from weight gain. In some embodiments, a patient is one that would benefit from increased bone density. In some embodiments, a patient is one that would benefit from increased muscle mass. In some embodiments, a patient is afflicted by an anemia associated with weight loss, decreased bone density, and/or muscle wasting. In some embodiments, an anemia associated with weight loss, decreased bone density, and/or muscle wasting is an anemia associated with a cancer disclosed herein.

In some embodiments, provided is a method of treating anemia and increasing bodyweight in a subject in need thereof. In some embodiments, a patient is afflicted by an anemia associated with weight loss (e.g., anemia associated with a cancer disclosed herein).

In some embodiments, provided is a method of treating anemia and increasing bone density in a subject in need thereof. In some embodiments, a patient is afflicted by an anemia associated with decreased bone density (e.g., anemia associated with a cancer disclosed herein).

In some embodiments, provided is a method of treating anemia and increasing muscle mass in a subject in need thereof. In some embodiments, a patient is afflicted by an anemia associated with decreased muscle mass (e.g., anemia associated with a cancer disclosed herein).

In some embodiments, the anemia is associated with a cancer. In some embodiments, the cancer is a hematologic malignancy, such as a myelodysplastic syndrome (MDS), acute myeloid leukemia (AML), chronic lymphocytic leukemia (CLL) or multiple myeloma (MM). In some embodiments, the anemia is associated with an intestinal cancer, such as colorectal cancer.

BRIEF DESCRIPTION OF THE DRAWINGS

The drawings included herein, which are composed of the following Figures, are for illustration purposes only and not for limitation.

FIG. 5A shows treatment of primary human HSPCs with formoterol fumarate (FF) enhances expression of mitochondrial DNA encoded genes, MT-ND1, MT-CytB, MT-CO1, and MT-ATP6. FIG. 5B shows that treatment of primary human HSPCs with formoterol fumarate (FF) enhances mitochondrial membrane potential (TMRE staining). FIG. 5C shows that FF treatment increases mitochondrial mass in HSPCs (MitoTracker® staining). * p<0.05, ** p<0.01, one-way analysis of variance (ANOVA)/ Student's t-test. "Ns" (non-significant) applies where statistical significance is not shown. Data represented as mean±SEM. All comparisons were done w.r.t. control (0 µM/ vehicle (DMSO)-treated).

FIG. 6A and FIG. 6B show that intraperitoneal (i.p.) injection of formoterol fumarate (FF) increases erythroid differentiation (CD235a) in RIOK2 KD HSPCs as compared to vehicle (DMSO) treatment. FIG. 6C and FIG. 6D show that i.p. injection of FF increases erythroid differentiation (CD235a) in RPS14 KD HSPCs as compared to vehicle (DMSO) treatment. FIG. 6E and FIG. 6F depict inability of FF to induce erythroid differentiation due to lack of ADRB2 gene that encodes for β2-AR. * p<0.05,  p<0.01, * p<0.001, one-way analysis of variance (ANOVA). Ns: non-significant. Data represented as mean±SEM. All comparisons were done w.r.t. vehicle (DMSO)-treated).

FIG. 8B: Sigma) MDS patient-derived bone marrow cells; n=40 de-identified MDS patients. Vehicle: DMSO; FF: formoterol fumarate. **** p<0.0001, non-parametric Wilcoxon paired signed rank test. All comparisons were done w.r.t. vehicle (DMSO) treated controls.

FIG. 11A shows pictures depicting increased blast forming unit erythroid (BFU-E) in Selleckchem FF and Sigma FF treated MDS bone marrow (BM) cells as compared to vehicle treated BM cells. FIG. 11B and FIG. 11C show the number of erythroid progenitors BFU-E and CFU-E (colony forming unit erythroid) in Vehicle (DMSO) vs. FF-treated MDS bone marrow cells; n=23 MDS patients. Vehicle: DMSO; FF: formoterol fumarate. FIG. 11D shows that FF treatment does not affect viability, myelopoiesis (CFU-GM) or megakaryopoiesis (CFU-Mk) in MDS patient-derived bone marrow cells.  p<0.01, ** p<0.0001, non-parametric Wilcoxon paired signed rank test. Ns: non-significant. All comparisons were done w.r.t. vehicle (DMSO) treated controls.

FIG. 14A shows a graph showing % change in body weights of mice with vehicle or FF treatment at 0.1/0.3/0.5/1.0 mg/kg doses. FIG. 14B shows that FF administration enhances mitochondrial biogenesis as observed by Mito Tracker® staining in the peripheral blood mononuclear cells (PBMCs) after day 14 of daily intraperitoneal (i.p.) injections. FIGS. 14C-14E show that FF treatment mildly increases RBC parameters, such as RBC numbers, hematocrit (HCT)% and Hemoglobin (Hb) in the peripheral blood after 14 days of daily i.p. injections. FIG. 14F and FIG. 14G show that FF treatment does not affect white blood cell (WBC) or monocyte counts in the peripheral blood after 14 days of daily i.p. injections. * p<0.05, ** p<0.01, ANOVA. "Ns" (non-significant) applies where statistical significance is not shown. n=3 mice per group. All comparisons were done w.r.t. vehicle treated (DMSO) controls.

Figure 17:
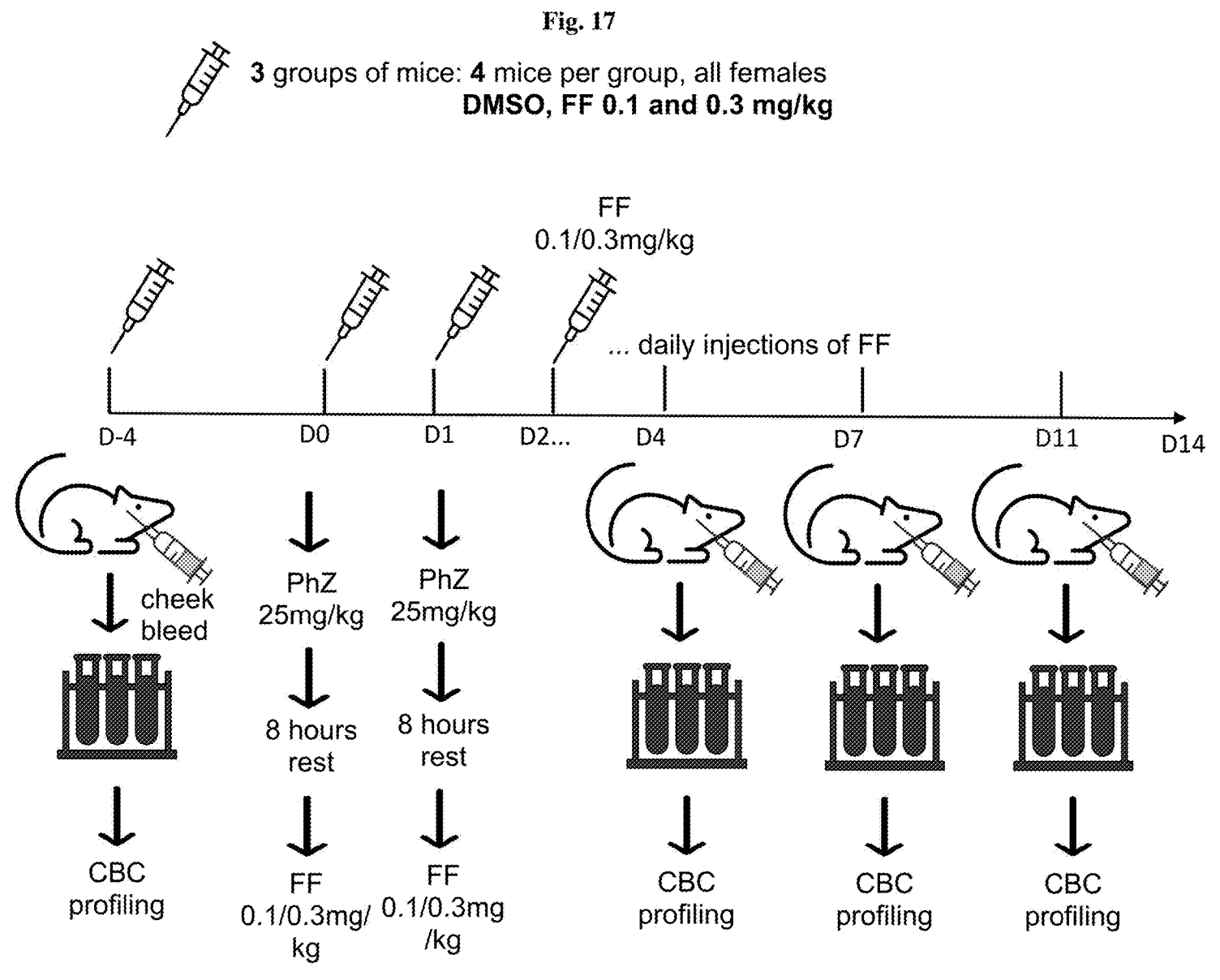

FIG. 17 shows an exemplary work-flow for formoterol fumarate (FF) treatment in vivo with phenylhydrazine (PHZ) study and sub-lethal dose (50 mg/kg).

FIG. 18A show that FF treatment at 0.1/0.3 mg/kg doses increases absolute body weights and % change in body weights of mice after sublethal PHZ-induced hemolytic anemia. PHZ dose: 50 mg/kg. FIG. 18B shows that FF administration enhances and sustains RBC parameters, such as hemoglobin (Hb), hematocrit (HCT)% and RBC numbers in the peripheral blood after PHZ-induced hemolytic anemia. FIG. 18C shows that FF treatment increases WBC and monocyte counts in the peripheral blood after 4 days of daily i.p. injections but does not sustain the impact over 14 days. Platelet counts were not statistically significant. * $p < 0.05$,  $p < 0.01$, ** $P < 0.0001$, one-way and two-way ANOVA. "Ns" (non-significant) applies where statistical significance is not shown. n=4 female mice per group. All comparisons were done w.r.t. vehicle (DMSO) treated controls.

FIG. 19A shows flow plots depicting that FF treatment at 0.1/0.3 mg/kg doses substantially increases RI, RII, RIII and RIV erythroid progenitors in the BM of mice after sublethal PHZ-induced hemolytic anemia. PHZ dose: 50 mg/kg. FIG. 19B shows the quantification of data presented in FIG. 19A showing absolute numbers of RI, RII, RIII and RIV erythroid progenitors per million BM cells in the mice after sublethal PHZ-induced hemolytic anemia. * $p < 0.05$,  $p < 0.01$, * $P < 0.001$, ANOVA. n=4 female mice per group. All comparisons were done w.r.t. vehicle (DMSO) controls.

FIG. 22A shows that FF treatment at 0.1/0.3 mg/kg doses increases absolute body weights and % change in body weights of male mice after sublethal PHZ-induced hemolytic anemia. PHZ dose: 60 mg/kg. FIG. 22B shows that FF administration significantly enhances and sustains RBC parameters, such as hemoglobin (Hb), hematocrit (HCT)% and RBC numbers in the peripheral blood after sublethal PHZ-induced hemolytic anemia. FIG. 22C shows that FF treatment increases WBC and monocyte counts in the peripheral blood after 4 days of daily i.p. injections but does not sustain the impact over 14 days. Platelet counts were not statistically significant. * $p < 0.05$,  $p < 0.01$, * $P < 0.001$, **** $P < 0.0001$, two-way ANOVA. "Ns" (non-significant) applies where statistical significance is not shown. n=5 male mice per group. All comparisons were done w.r.t. vehicle (DMSO) treated controls.

FIG. 23A shows that FF treatment at 0.1/0.3 mg/kg doses substantially increases viability in the BM cells of mice after sublethal PHZ-induced hemolytic anemia; PHZ dose: 60 mg/kg. FIG. 23B shows that FF administration enhances mitochondrial biogenesis as observed by MitoTracker® staining in the BM cells after PHZ-induced hemolytic anemia. FIG. 23C shows that FF administration significantly reduces mitochondrial superoxide production indicating mitochondrial fitness as observed by MitoSox® staining in the BM cells after PHZ-induced hemolytic anemia. * $p < 0.05$, **** $P < 0.0001$, ANOVA. n=5 male mice per group. All comparisons were done w.r.t. vehicle (DMSO) treated controls.

FIG. 25A-FIG. 25B show that formoterol fumarate (FF) enhances LS-K cells in the bone marrow (BM). * $p < 0.05$, ** $p < 0.01$, ANOVA. Ns: non-significant.

FIG. 26A shows flow plots depicting that FF treatment at 0.1/0.3 mg/kg doses substantially increases MEP in the BM of mice after PHZ-induced sublethal hemolytic anemia. The CMP and GMP were not affected. LS-K: Lineage—Scal—Kit+ BM cells. PHZ dose: 60 mg/kg. FIG. 26B-FIG. 26D show the quantification of data presented in FIG. 26A showing absolute numbers of CMP, GMP and MEP progenitors per million BM cells in the mice after PHZ-induced hemolytic anemia. $p < 0.01$, *** $P < 0.001$, ANOVA. Ns: non-significant. n=5 male mice per group. All comparisons were done w.r.t. vehicle (DMSO treated) controls.

FIG. 30A shows flow plots depicting that FF treatment at 0.1/0.3 mg/kg doses substantially increases RI, RII, RIII and RIV erythroid progenitors in the BM of mice after PHZ-induced sublethal hemolytic anemia. PHZ dose: 60 mg/kg. FIG. 30B shows the quantification of data presented in FIG. 30A showing absolute numbers of RI, RII, RIII and RIV erythroid progenitors per million BM cells in the mice after PHZ-induced hemolytic anemia. * $p < 0.05$,  $p < 0.01$, * $P < 0.001$, **** $P < 0.0001$, ANOVA. n=5 male mice per group. All comparisons were done w.r.t. vehicle (DMSO) treated controls.

Figure 34A:
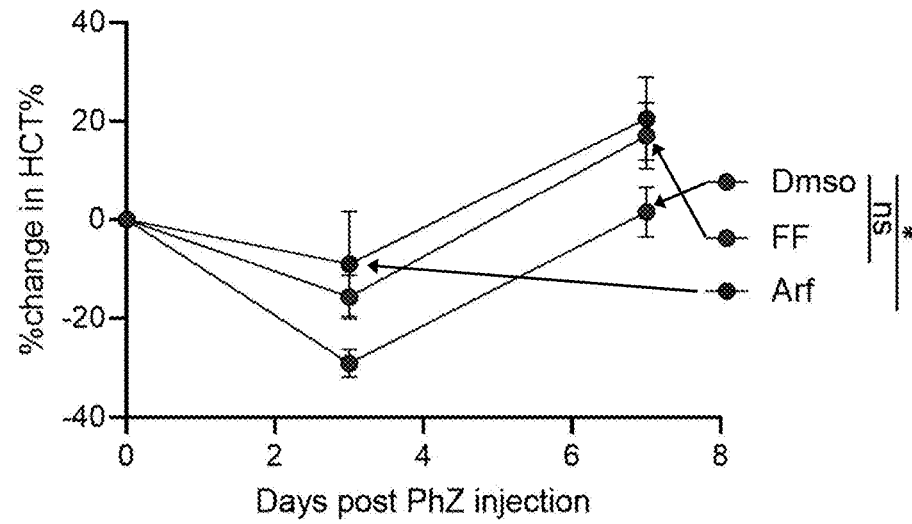
Figure 34B:
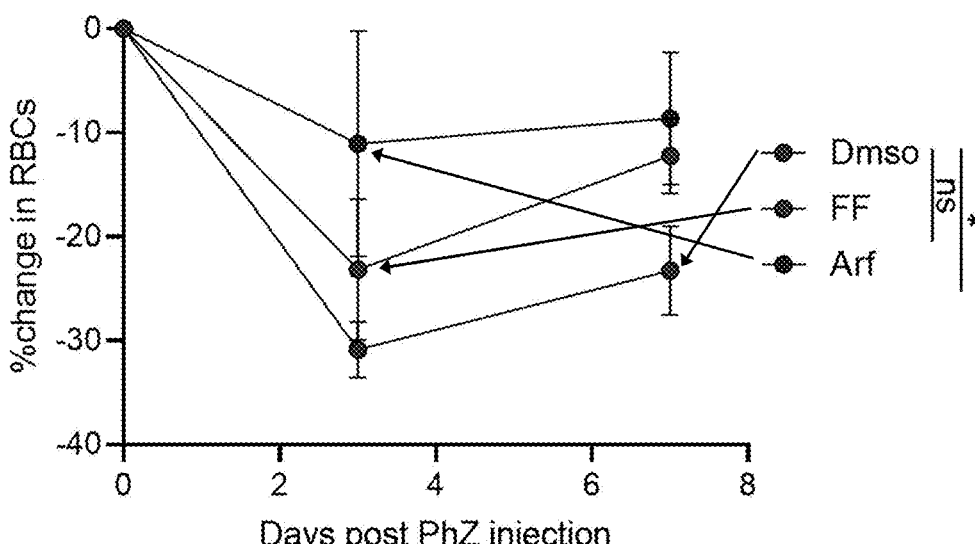

FIG. 34A-FIG. 34B show that FF/Arf treatment via i.p. mildly increase RBC parameters in phenylhydrazine (PHZ)-treated mice at sub-lethal dose (60 mg/kg). FF/Arf treatment increases RBC parameters, such as hematocrit (HCT)% and RBCs in the peripheral blood after 7 days of i.p. administrations. * p<0.05, ANOVA. N=5 male mice per group. All comparisons were done w.r.t. vehicle (DMSO) treated controls. Ns=non-significant.

Figure 35A:
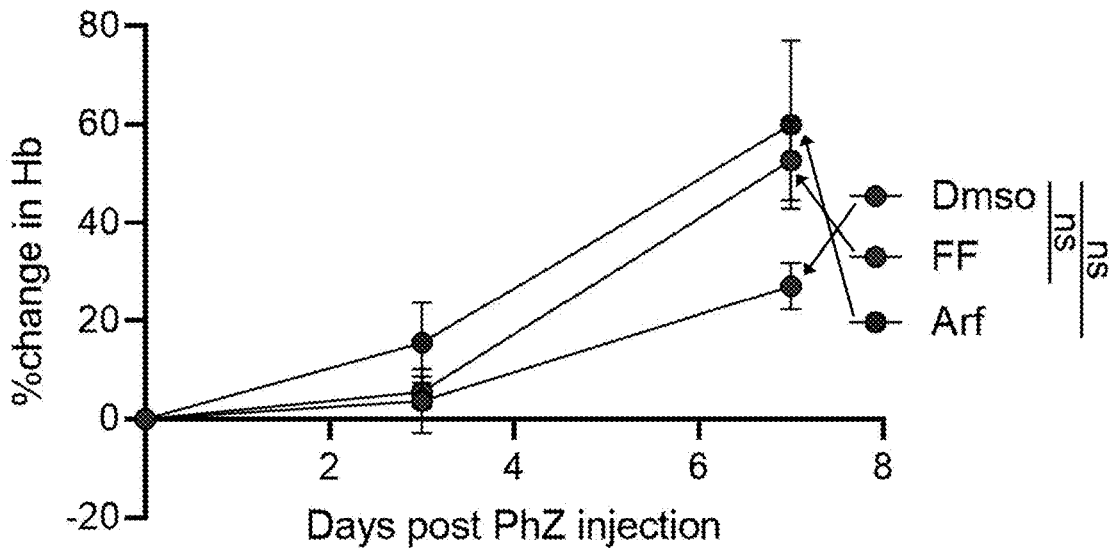
Figure 35B:
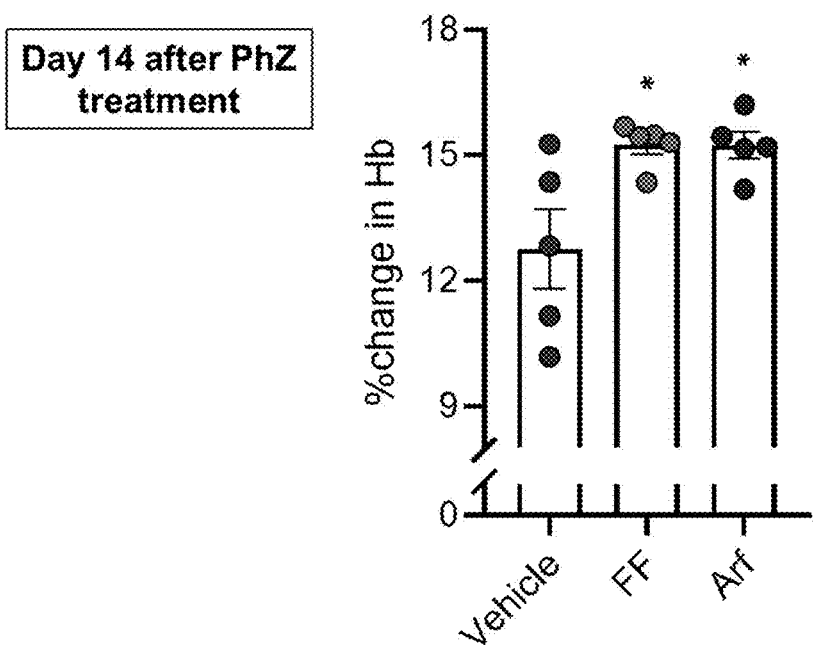

FIG. 35A-FIG. 35B show that FF/Arf treatment via i.p. increase RBC parameters in phenylhydrazine (PHZ)-treated mice at sub-lethal dose (60 mg/kg). FF and Arf treatments increase Hemoglobin (Hb) in the peripheral blood after (FIG. 35A) 7 and (FIG. 35B) 14 days of i.p. administrations. * p<0.05, ANOVA. N=5 male mice per group. All comparisons were done w.r.t. vehicle (DMSO) treated controls. Ns=non-significant.

Figure 36A:
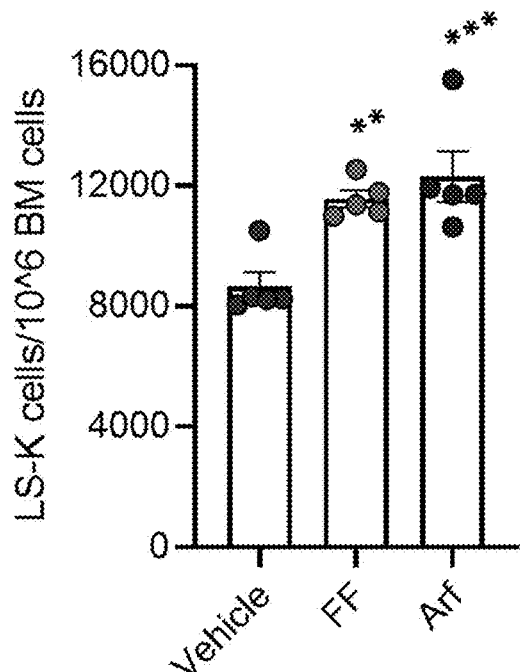
Figure 36A:
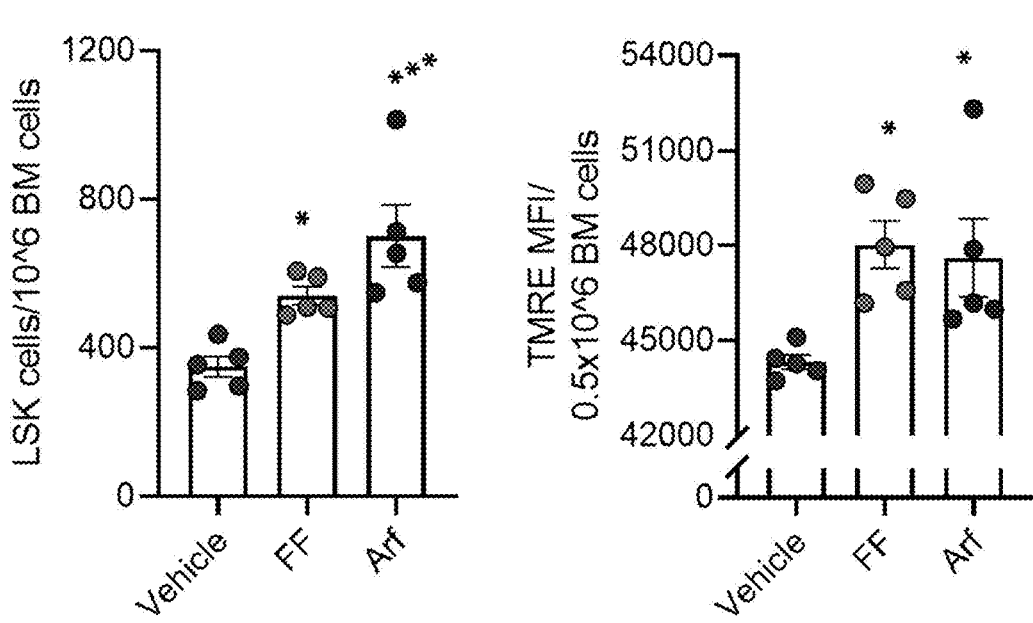

FIG. 36A-FIG. 36C show that FF/Arf treatments via i.p. increase LSK, LS-K, and mitochondrial activity in the BM of phenylhydrazine (PHZ)-treated mice at sub-lethal dose (60 mg/kg). FF and Arf treatments increase (FIG. 36A) LS-K, (FIG. 36B) LSK, and (FIG. 36C) mitochondrial membrane potential (TMRE staining) in the bone marrow progenitors (BMP) after 14 days of i.p. administrations. * p<0.05,  p<0.01, * p<0.001, ANOVA. N=5 male mice per group. All comparisons were done w.r.t. vehicle (DMSO) treated controls. Ns=non-significant.

Figure 37A:
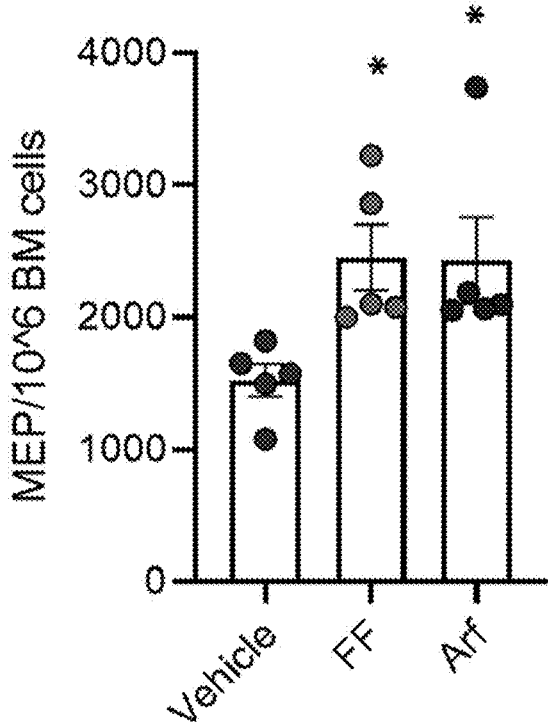
Figure 37B:
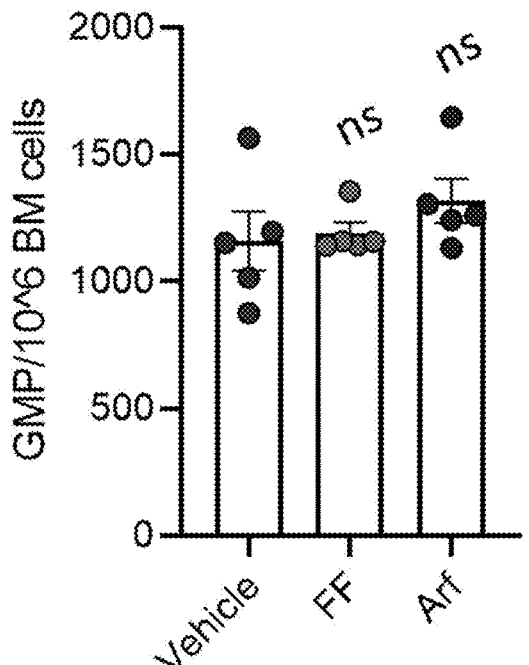

FIG. 37A-FIG. 37B show that FF/Arf i.p. treatment increase megakaryocyte erythrocyte progenitors (MEP), but not granulocyte monocyte progenitors (GMP) in the BM of phenylhydrazine (PHZ)-treated mice at sub-lethal dose (60 mg/kg). FF and Arf treatments increase (FIG. 37A) MEP, but not (FIG. 37B) GMP in the bone marrow progenitors (BMP) after 14 days of i.p. administrations. * p<0.05, ANOVA. N=5 male mice per group. All comparisons were done w.r.t. vehicle (DMSO) treated controls. Ns=non-significant.

Figure 38A:
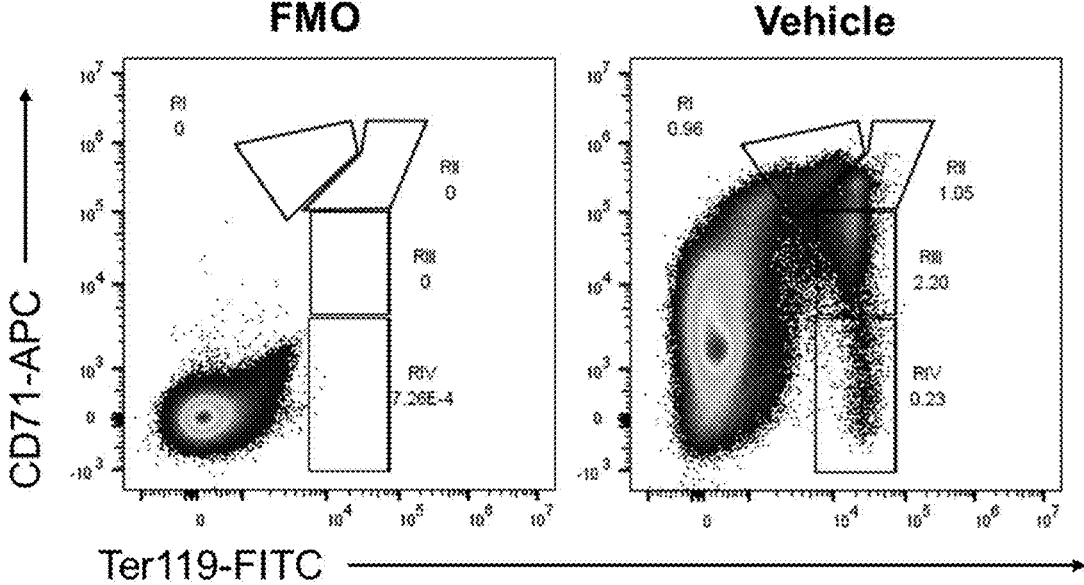
Figure 38A:
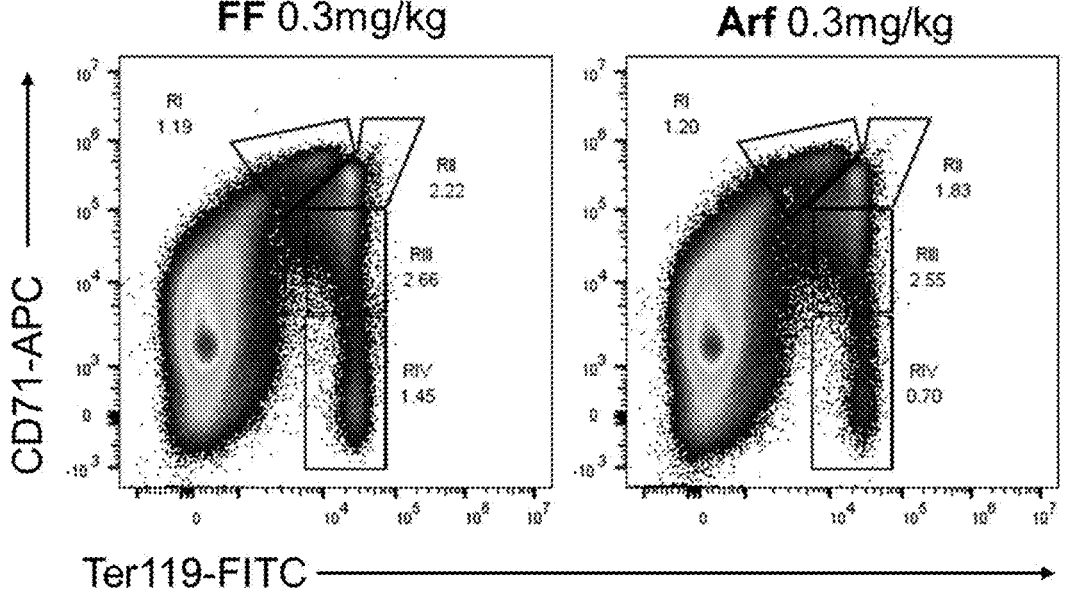
Figure 38B:
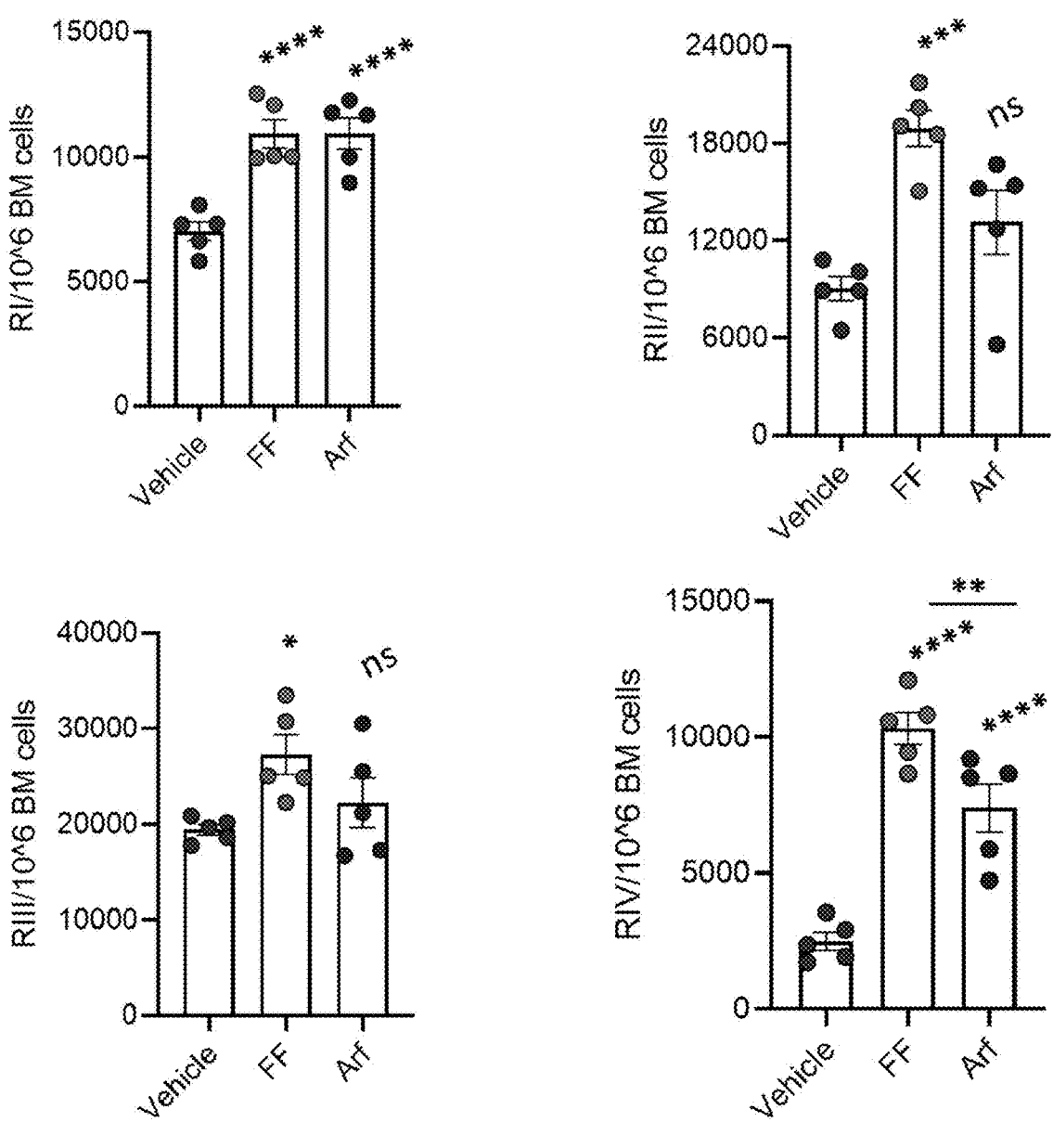

FIG. 38A-FIG. 38B show that FF/Arf treatment via i.p. consistently enhance erythroid progenitors in the bone marrow (BM) of phenylhydrazine (PHZ)-treated mice at sub-lethal dose (60 mg/kg). FIG. 38A shows flow plots depicting that FF/Arf treatments at 0.3 mg/kg doses influence RI, RII, RIII and RIV erythroid progenitors in the BM of mice. FIG. 38B shows quantification of data presented in FIG. 38A showing absolute numbers of RI, RII, RIII and RIV erythroid progenitors per million BM cells in the mice. * p<0.05,  p<0.01, * P<0.001, **** P<0.0001, ANOVA. N=5 male mice per group. All comparisons were done w.r.t. vehicle (DMSO) treated controls. Ns=non-significant.

FIG. 39A-FIG. 39B show that FF treatment via i.p. enhances colony forming unit-erythroid (CFU-e) in the bone marrow (BM) of phenylhydrazine (PHZ)-treated mice at sub-lethal dose (60 mg/kg). FIG. 39A shows a graph depicting that FF treatments at 0.3 mg/kg has long-term impact in the mouse BM to produce CFU-e. FIG. 39B shows a graph depicting that transferrin receptor expression is enhanced in the CFU-e derived from the BMPs of FF/Arf-treated mice. * p<0.05, *** P<0.001, ANOVA. N=5 male mice per group. All comparisons were done w.r.t. vehicle (DMSO) treated controls. Ns=non-significant.

Figure 40:
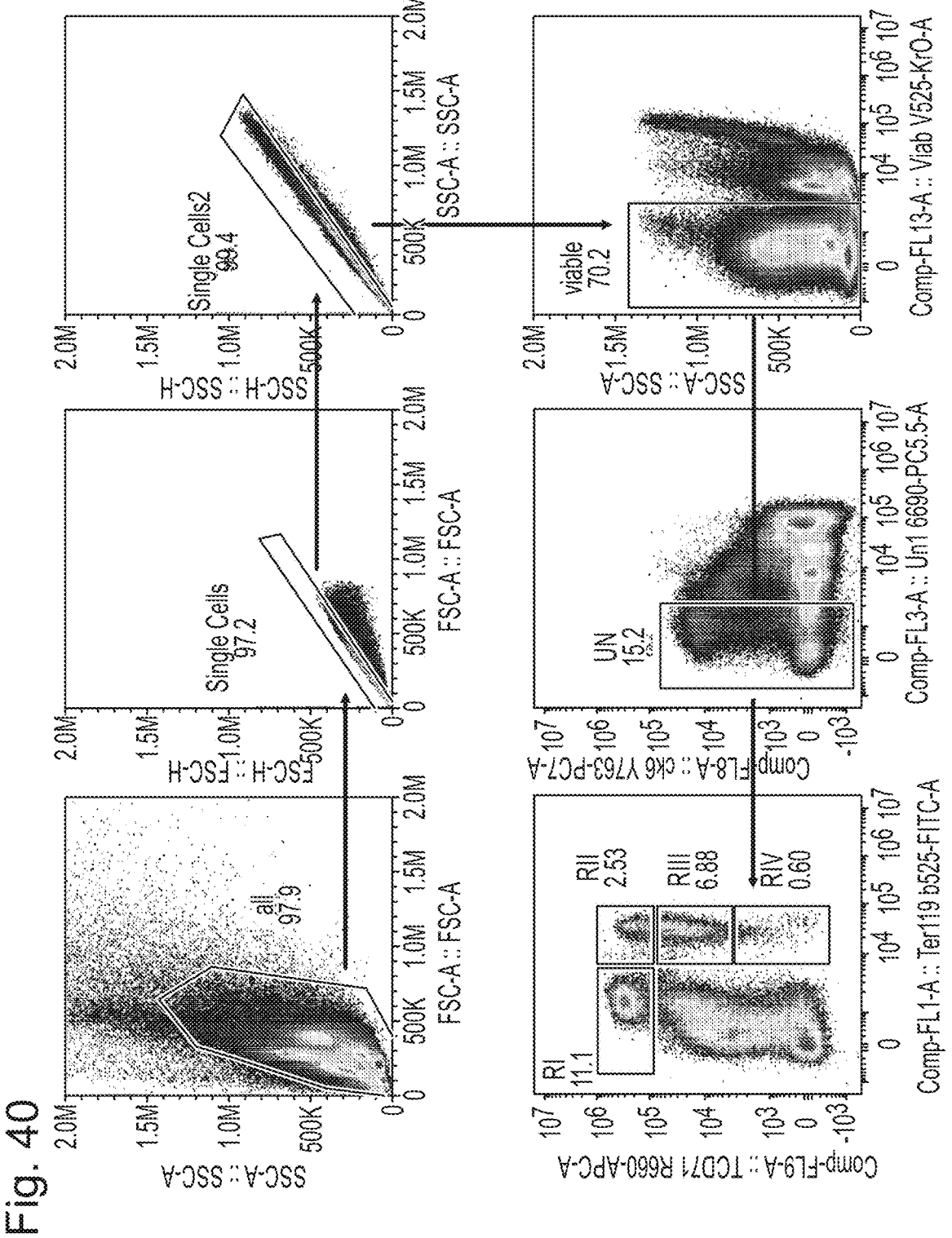

FIG. 40 shows flow cytometry plots to study erythroid progenitors (EryPs) in the BM of mice.

Figure 41:
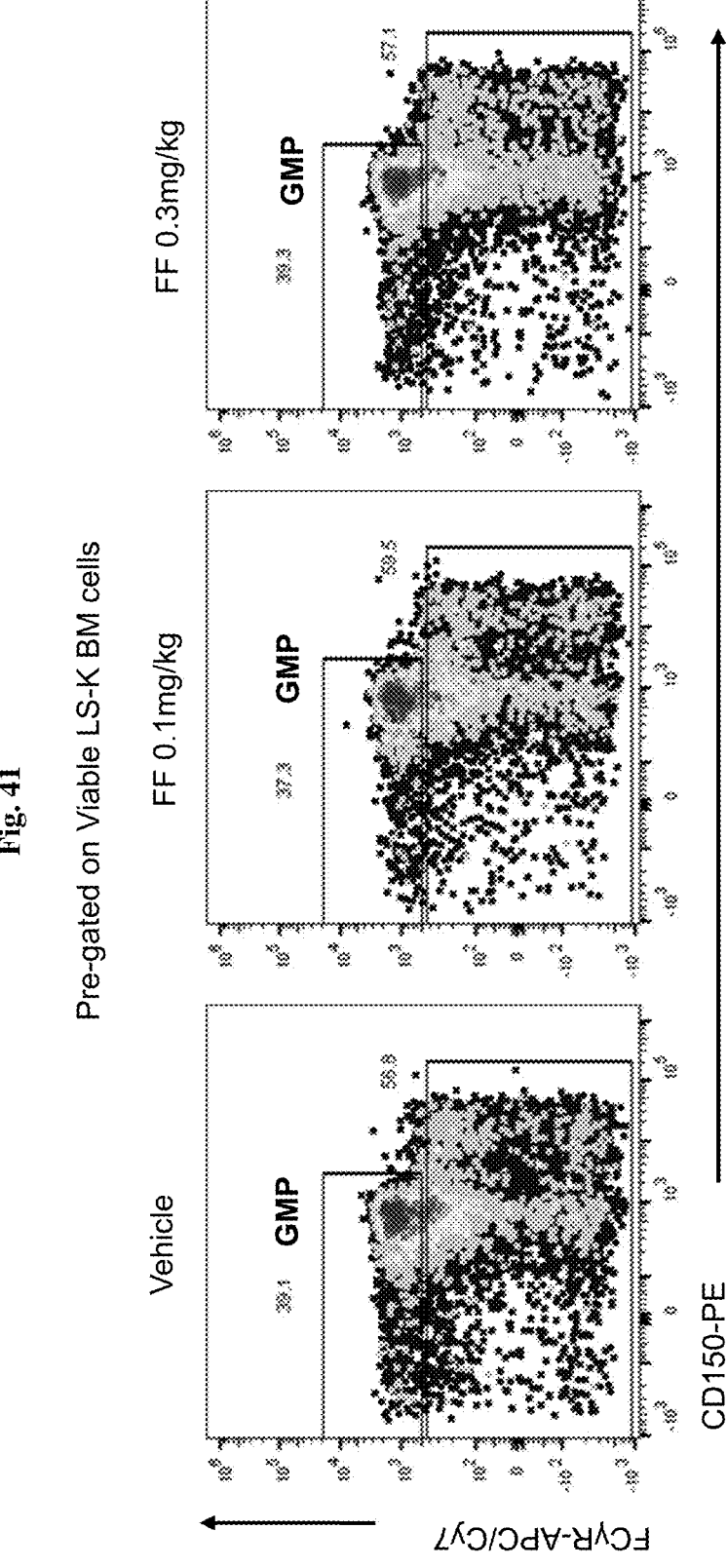

FIG. 41 shows that formoterol fumarate (FF) does not affect granulocytic myeloid progenitors (GMP) in bone marrow (BM).

Figure 42A:
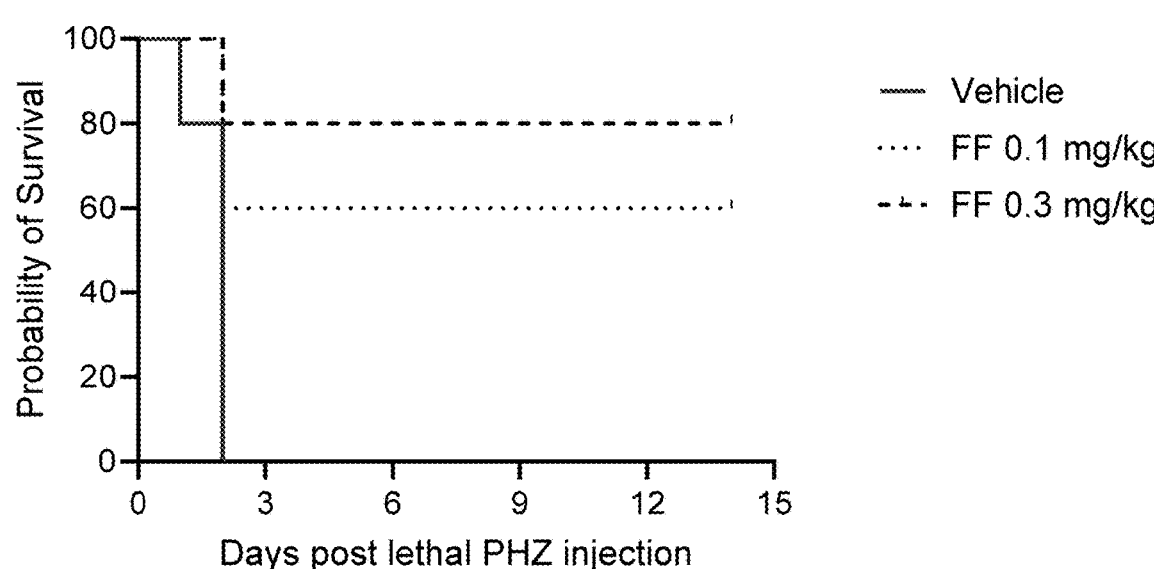
Figure 42B:
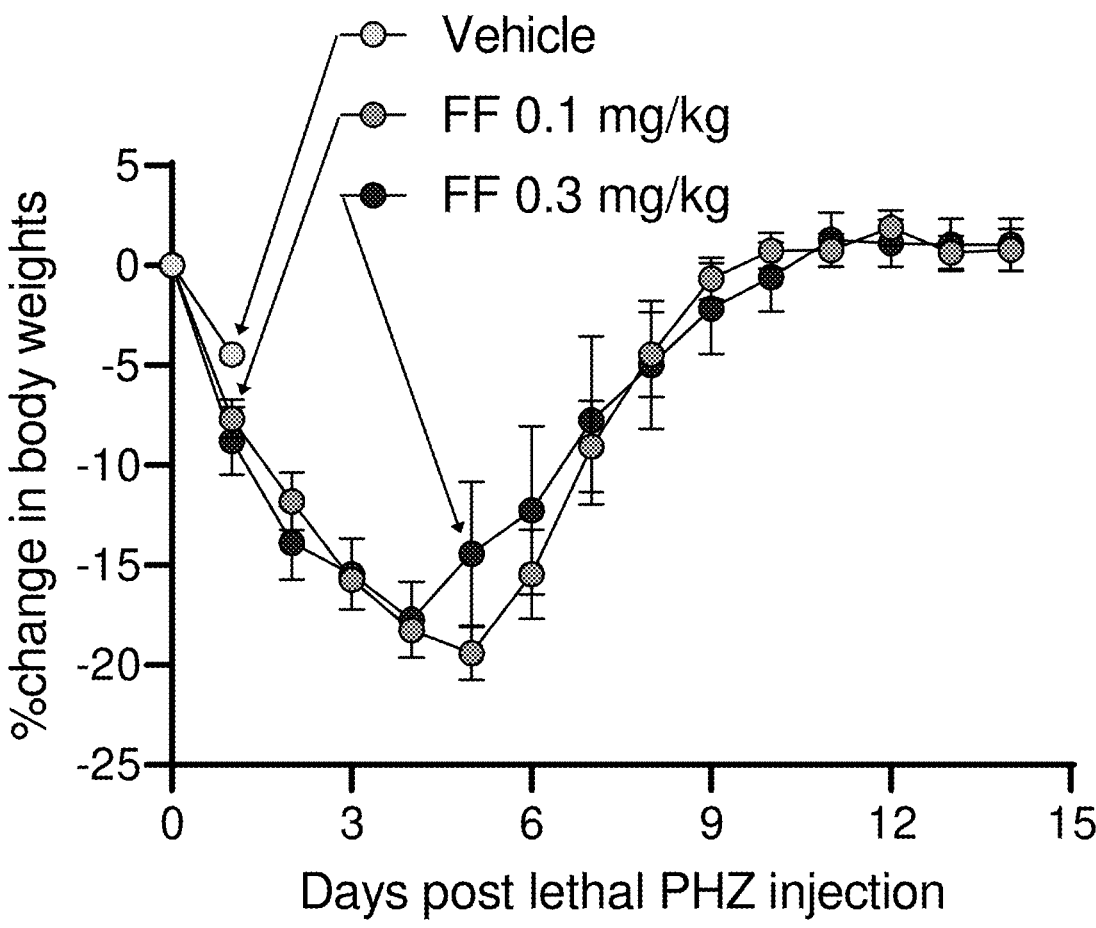
Figure 42C:
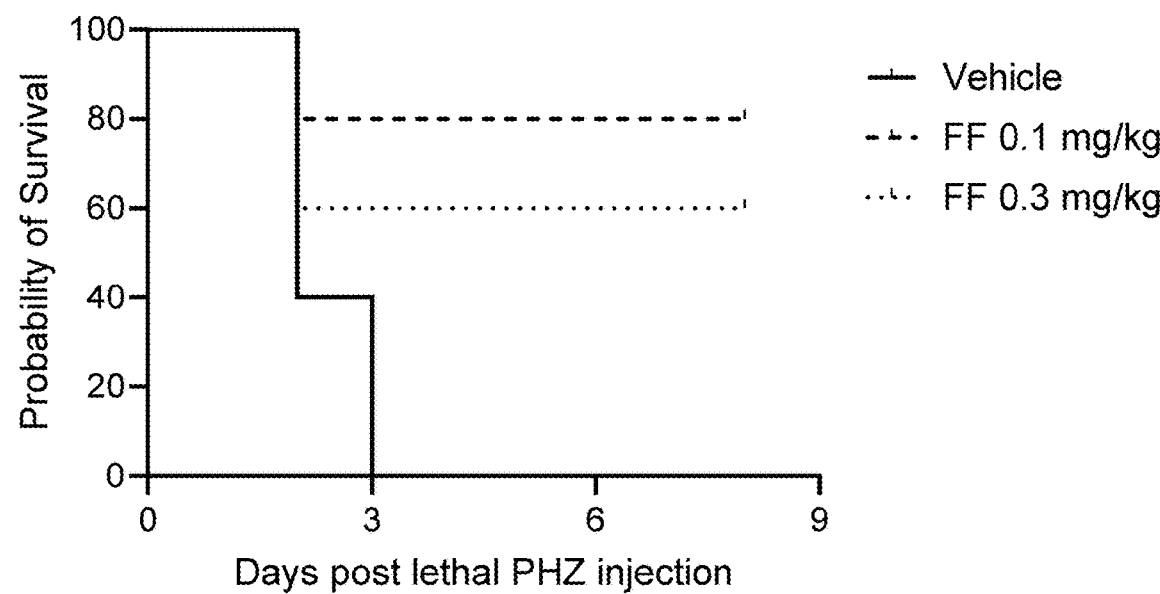
Figure 42D:
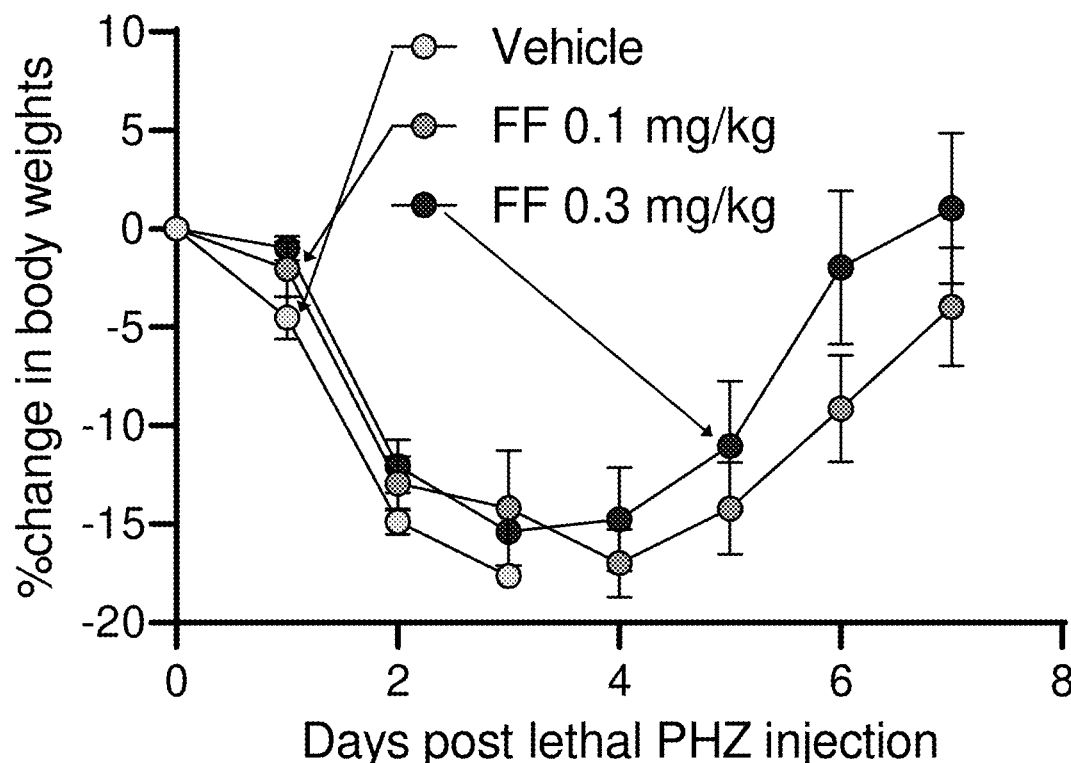

FIG. 42A-FIG. 42D show that formoterol fumarate (FF) treatment confers striking survival benefits to phenylhydrazine (PHZ)-mediated lethal hemolytic anemia in mice (10-12 week old mice). FIG. 42A shows Kaplan-Meier survival plot showing survival benefits of FF treatment at 0.1/0.3 mg/kg doses in male mice after PHZ-induced lethal hemolytic anemia (PHZ-150 mg/kg). n=5 mice/group. In vehicle treated-group (gray circles), 1 mouse died on day 1 and 4 mice died on day 2 after lethal PHZ dose. In FF 0.1 mg/kg group (orange circles), 2 mice died on day 2 and 3 mice are still surviving post lethal PHZ dose. In FF 0.3 mg/kg group (maroon circles), 1 mouse died on day 2 and 4 mice are still surviving post lethal PHZ dose. FIG. 42B is a graph showing that FF treatment at 0.1/0.3 mg/kg doses steadily increases body weights of male mice after PHZ-induced lethal hemolytic anemia. FIG. 42C shows Kaplan-Meier survival plot showing survival benefits of FF treatment at 0.1/0.3 mg/kg doses in female mice after PHZ-induced lethal hemolytic anemia (PHZ-120 mg/kg). n=5 mice/group. In vehicle treated-group (gray circles), 3 mice died on day 2 and 2 mice died on day 3 after lethal PHZ dose. In FF 0.1 mg/kg group (orange circles), 1 mouse died on day 2 and 4 mice are still surviving post lethal PHZ dose. In FF 0.3 mg/kg group (maroon circles), 2 mice died on day 2 and 3 mice are still surviving post lethal PHZ dose. FIG. 42D is a graph showing that FF treatment at 0.1/0.3 mg/kg doses steadily increases body weights of female mice after PHZ-induced lethal hemolytic anemia. * p<0.05, Log-rank (Mantel-Cox) test. n=5 mice per group. All comparisons were done w.r.t. vehicle (DMSO) treated controls.

Figure 43:
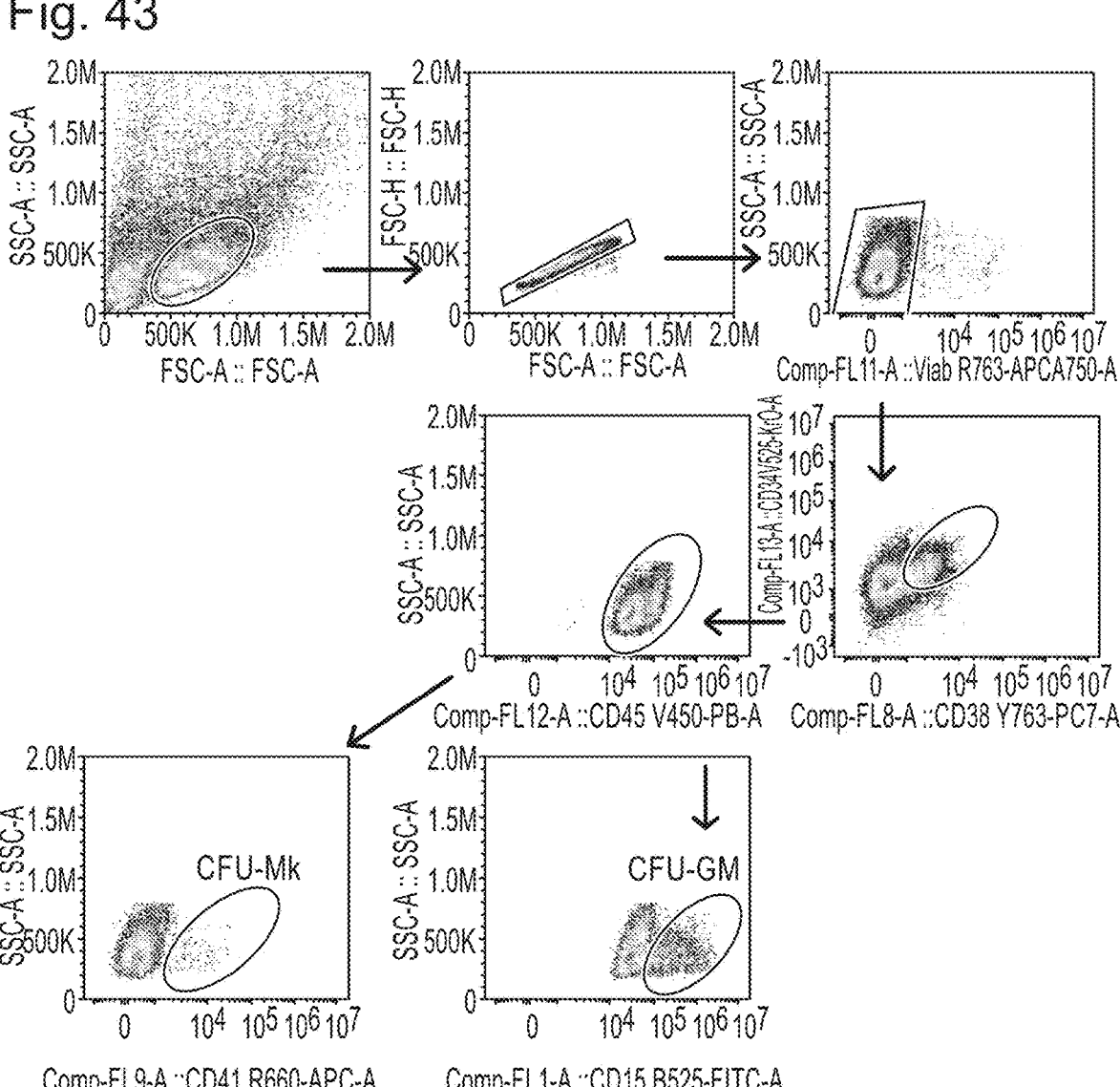
Figure 44:
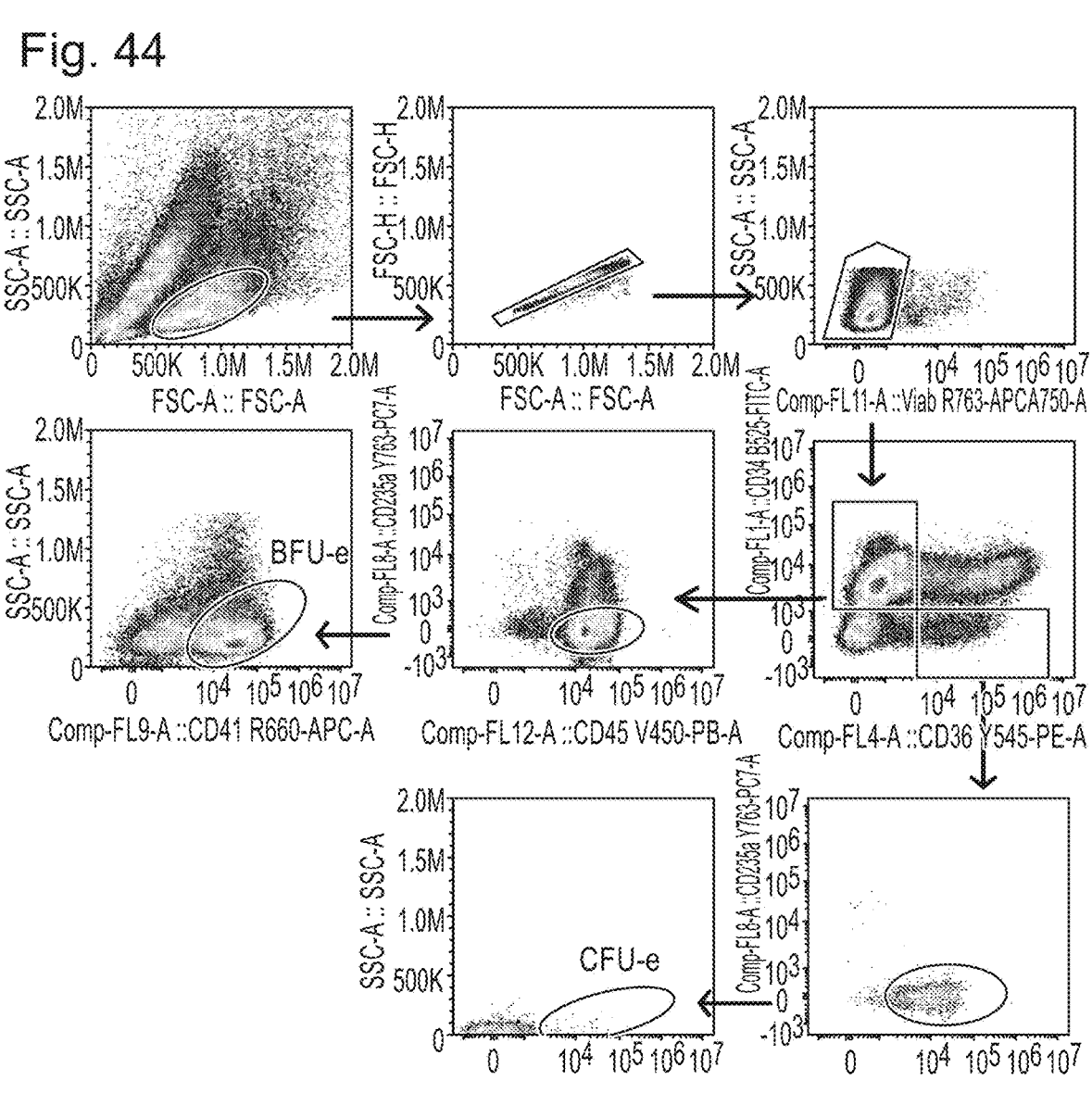

FIG. 43-FIG. 44 show flow cytometry plots of formoterol fumarate (FF) on MDS patient-derived cells using semisolid methylcellulose culture.

Figure 45:
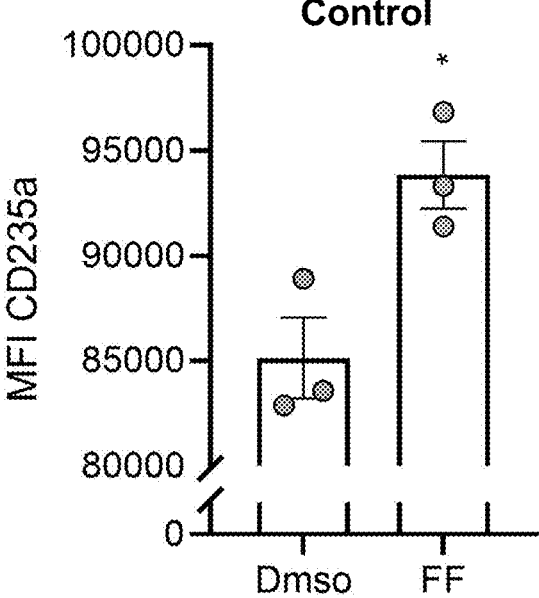
Figure 45:
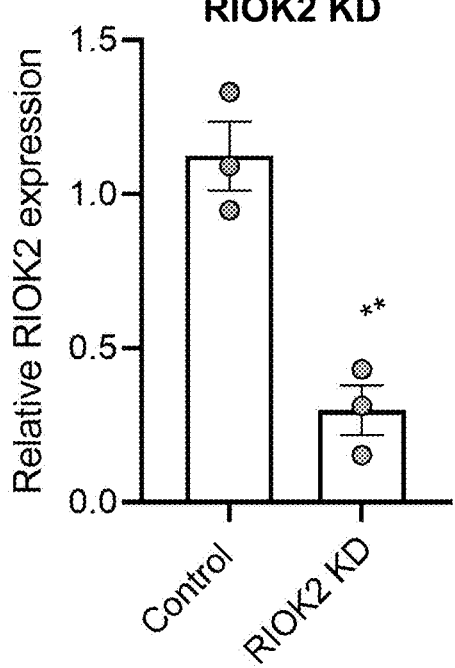
Figure 45:
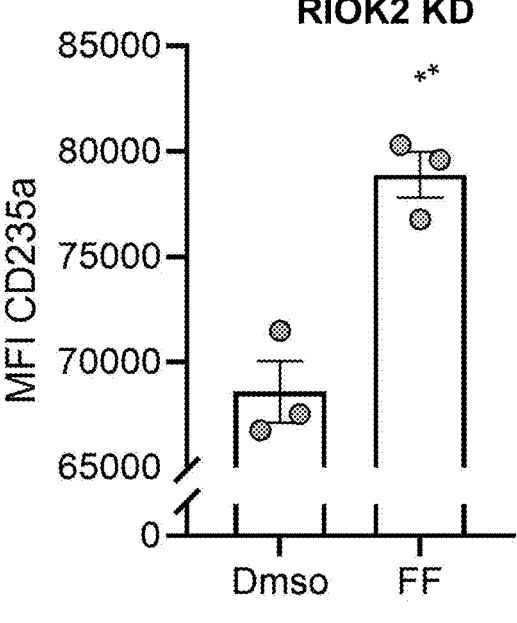

FIG. 45 shows that formoterol fumarate (FF) in vitro markedly rescues erythropoiesis in human hematopoietic stem and progenitor cells having RIOK2 knockdown (RIOK2 KD HSPCs). * p<0.05, ** p<0.01, ANOVA.

Figure 46:
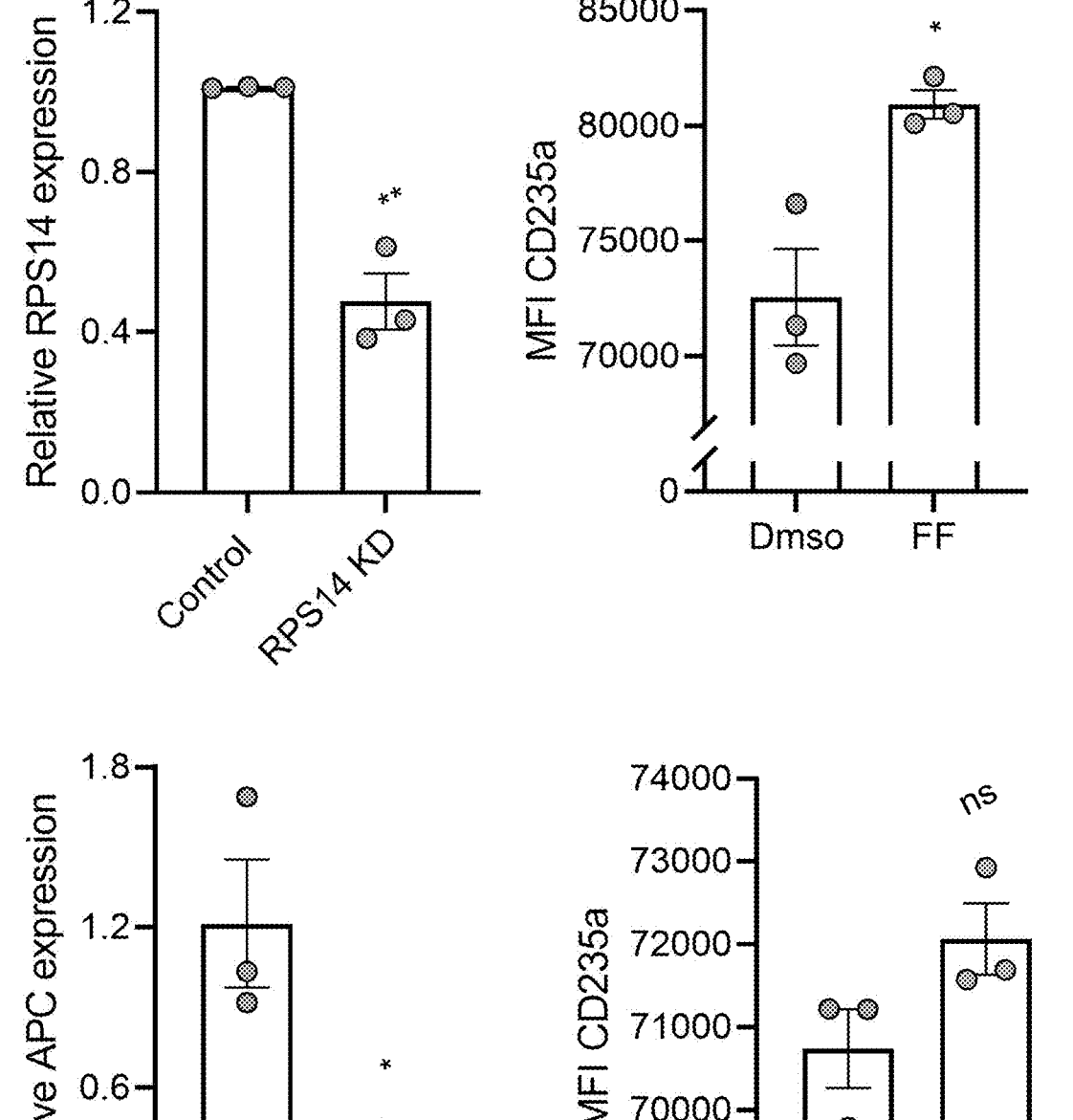

FIG. 46 shows that formoterol fumarate (FF) in vitro moderately rescues erythropoiesis in human hematopoietic stem and progenitor cells having RPS14 and APC knockdown (RPS14 and APC KD HSPCs). * p<0.05, ** p<0.01, ANOVA. Ns: non-significant.

Figure 47:
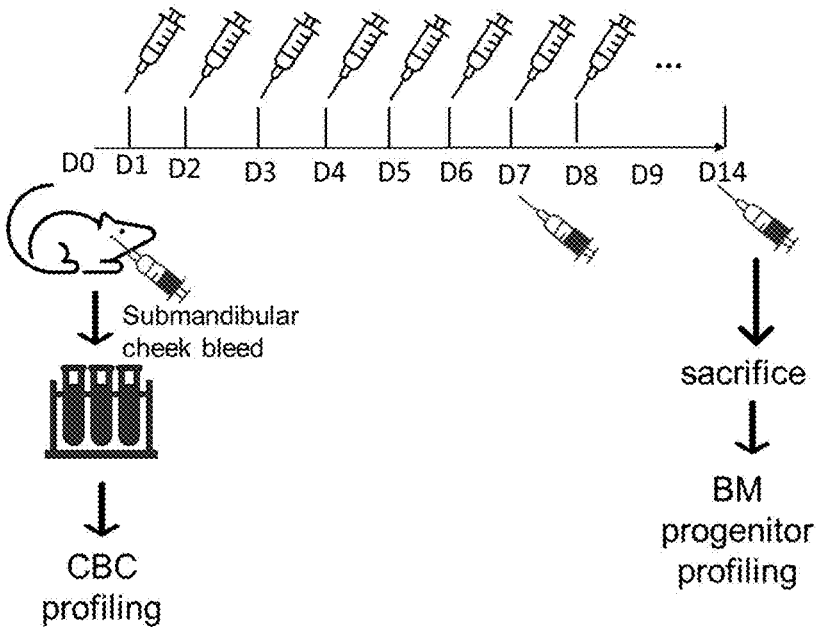

FIG. 47 shows a schematic of FF treatment via o.g. in wild-type mice at steady-state.

Figure 48A:
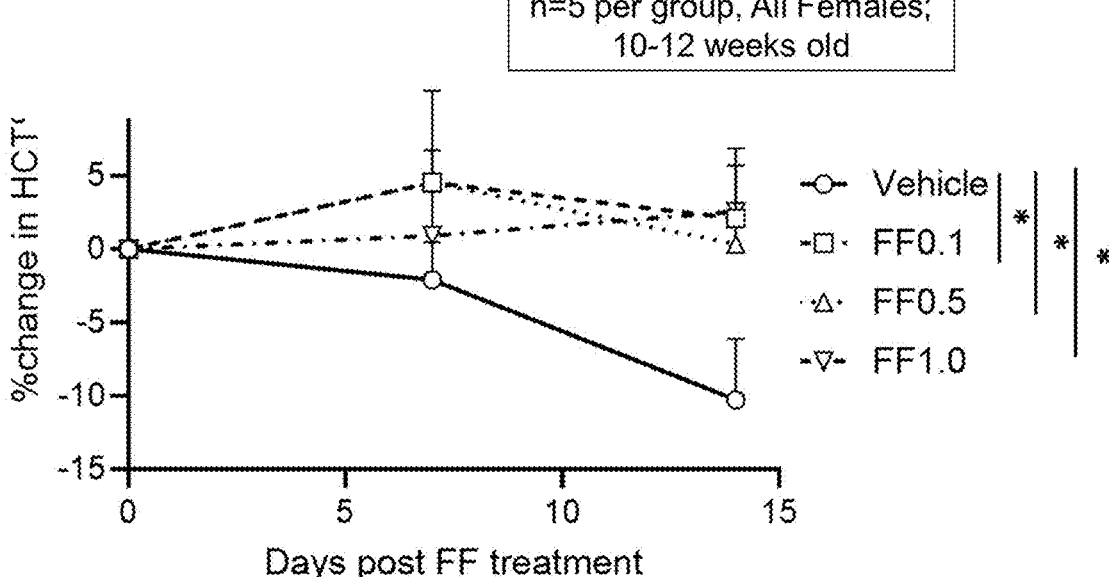
Figure 48B:
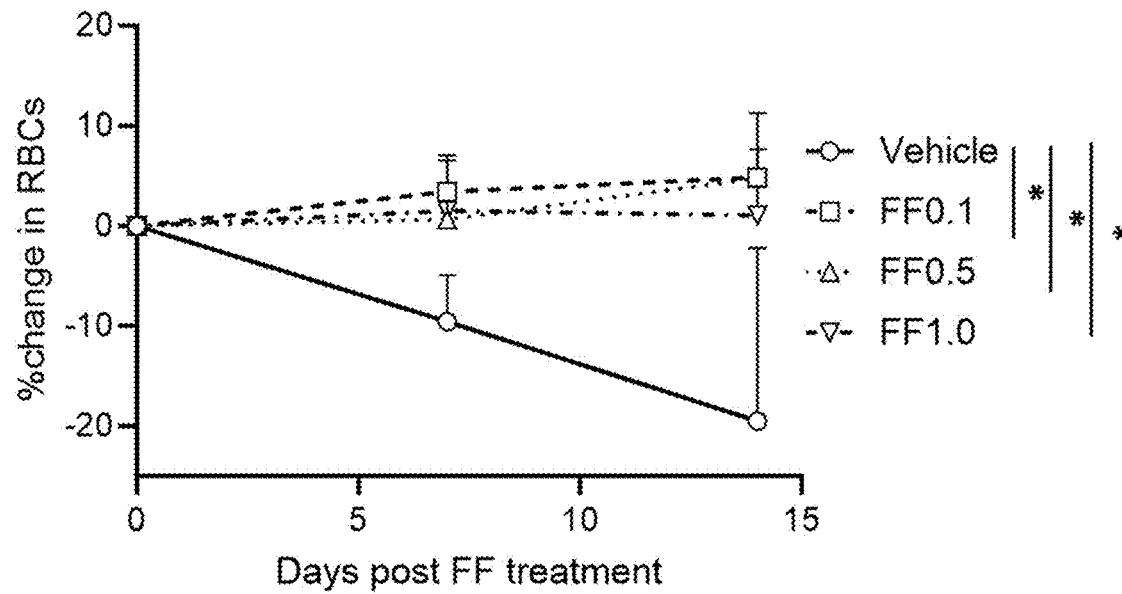
Figure 48C:
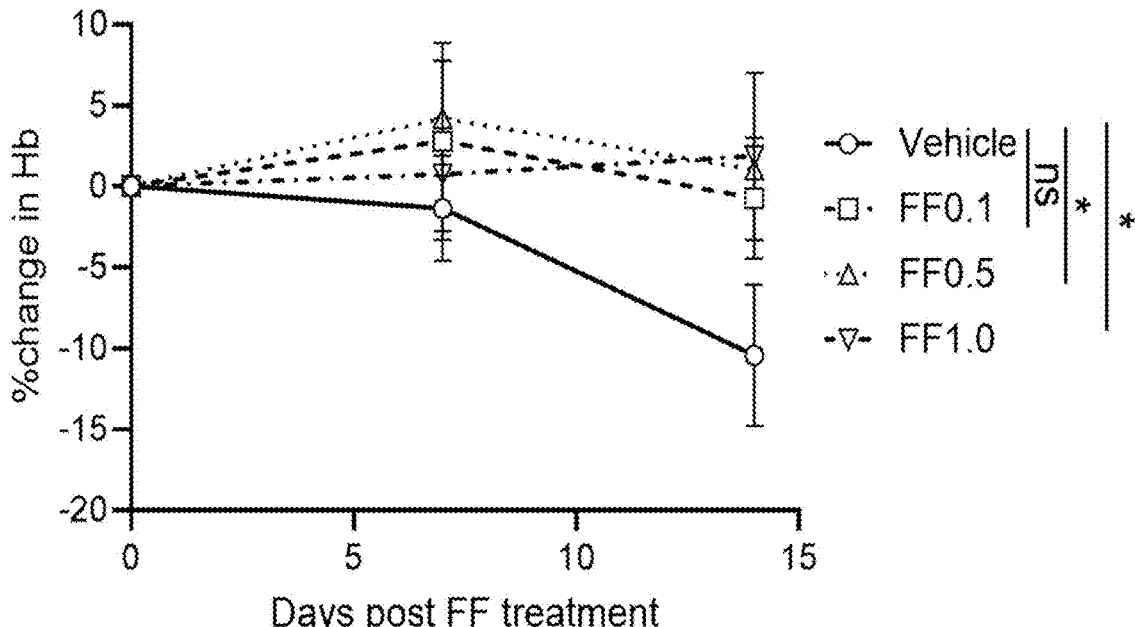

FIG. 48A-FIG. 48C show that FF treatment via o.g. increases RBC parameters in wild-type mice at steady-state. FF treatment increases RBC parameters, such as hematocrit (HCT)%, RBC numbers, and Hemoglobin (Hb) in the peripheral blood after 14 days of daily oral gavage (o.g.) administrations. * p<0.05, ANOVA. N=5 mice per group. All comparisons were done w.r.t. vehicle treated (DMSO) controls. Ns=non-significant.

Figure 49A:
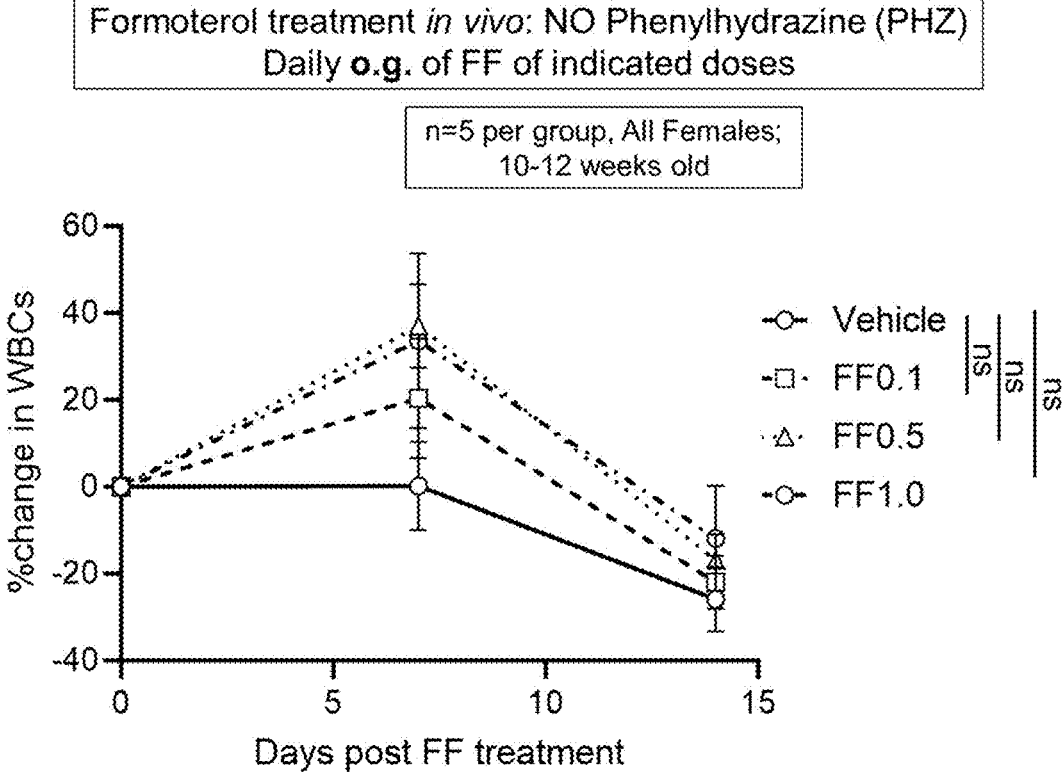
Figure 49B:
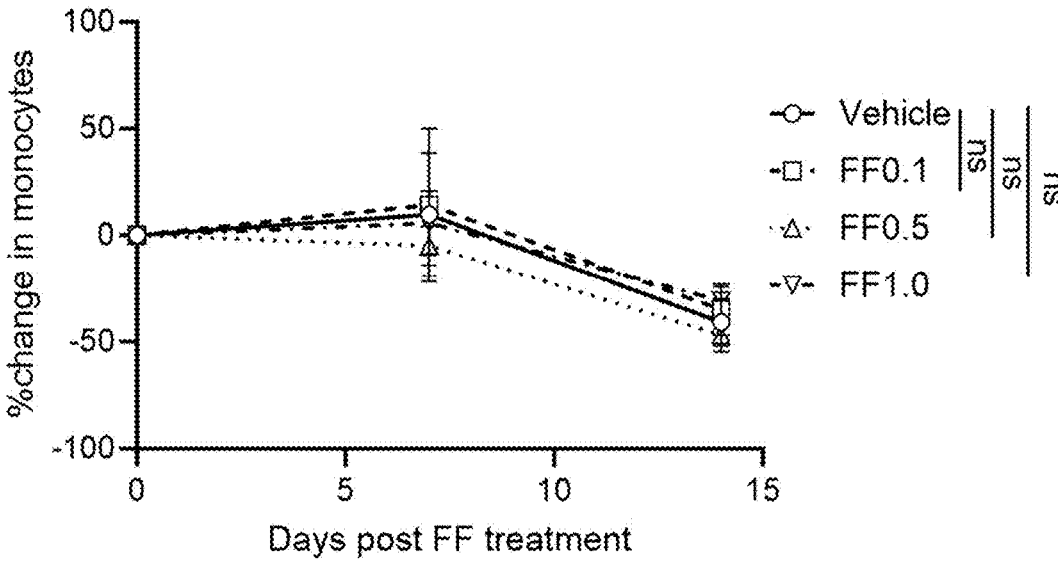
Figure 49C:
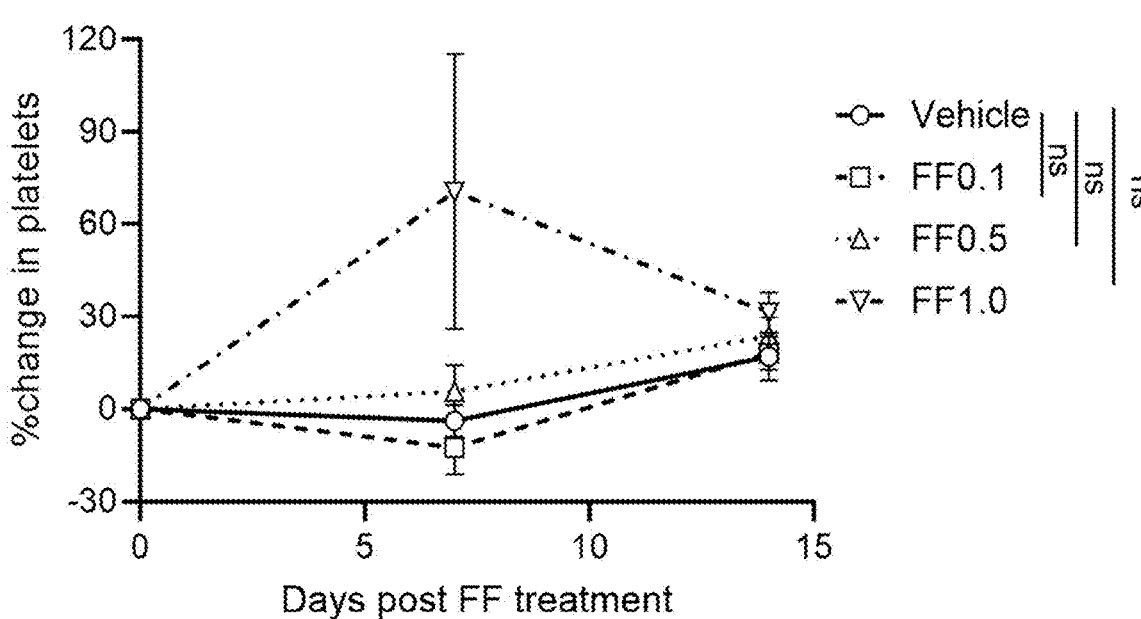

FIG. 49A-FIG. 49C show that FF treatment via o.g. does not alter WBC parameters or platelets in wild-type mice at steady-state. FF treatment does not affect WBC parameters, such as WBCs, monocytes, and platelets in the peripheral blood after 14 days of daily oral gavage (o.g.) administrations. ANOVA. N=5 mice per group. All comparisons were done w.r.t. vehicle treated (DMSO) controls. ns=non-significant.

Figure 50:
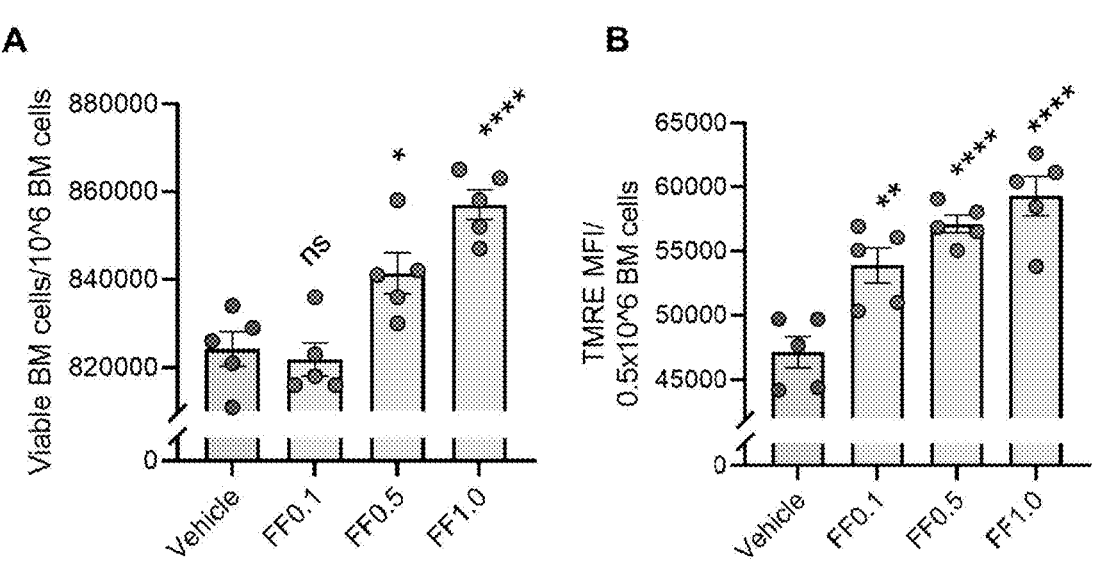

FIG. 50, panels A-B show that FF treatment via o.g. enhances viability and mitochondrial activity of bone marrow progenitors (BMPs) in wild-type mice at steady-state. FF treatment increases viability and mitochondrial membrane potential (measured via TMRE staining) in the BMPs after 14 days of daily oral gavage (o.g.) administrations. * p<0.05,  p<0.01, ** p<0.0001, ANOVA. n=5 mice per group. All comparisons were done w.r.t. vehicle treated (DMSO) controls. ns=non-significant.

Figure 51:
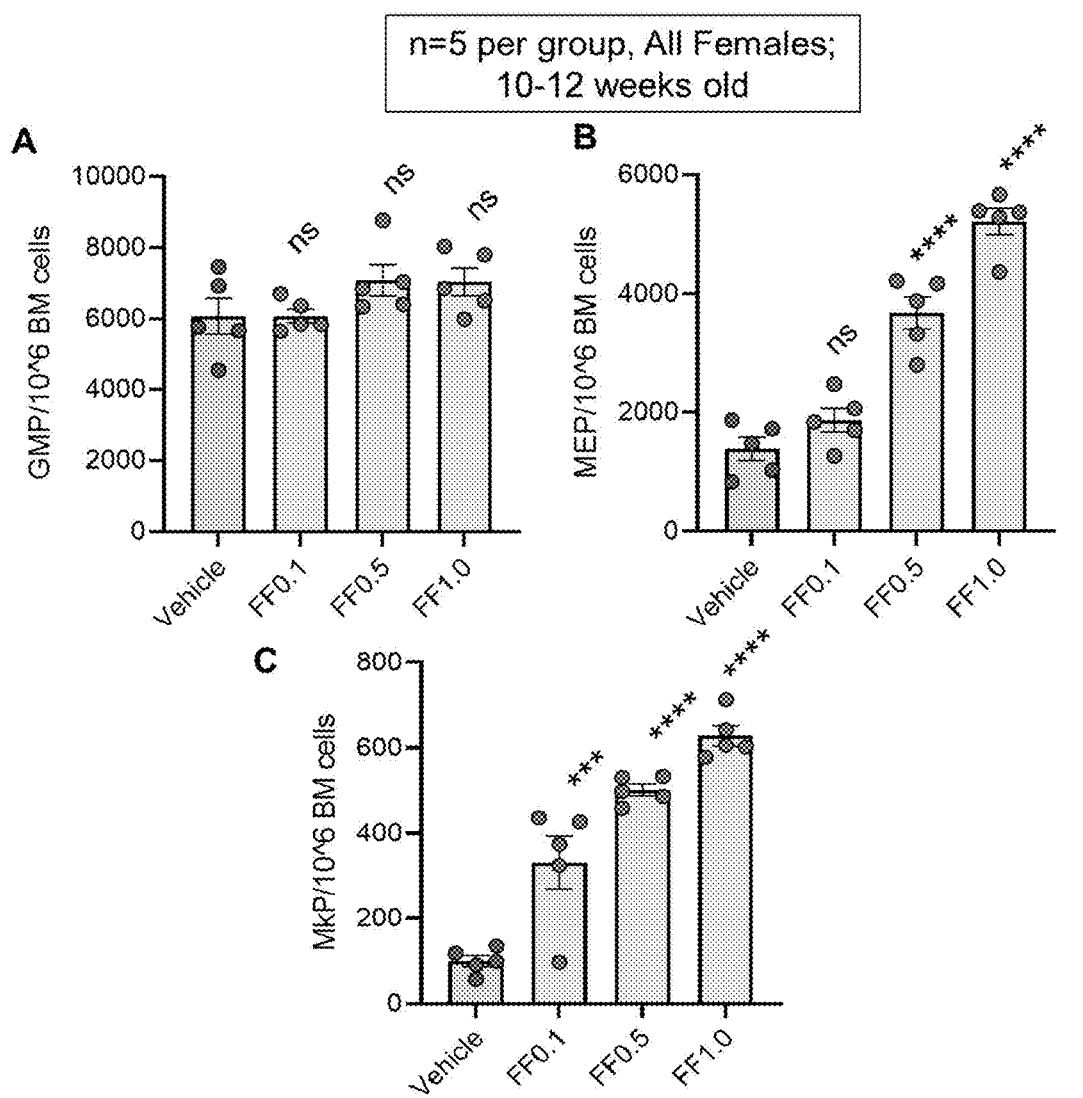

FIG. 51, panels A-C show that FF treatment via o.g. enhances MEP and MkP, but not GMPs in the bone marrow (BM) in wild-type mice at steady-state. FF treatment does not affect granulocyte monocyte progenitors (GMP), but increases megakaryocyte erythroid progenitors (MEP) and megakaryocytic progenitors (MkP) in the BMPs after 14 days of daily oral gavage (o.g.) administrations. * p<0.001, ** p<0.0001, ANOVA. n=5 mice per group. All comparisons were done w.r.t. vehicle treated (DMSO) controls. ns=non-significant.

Figure 52A:
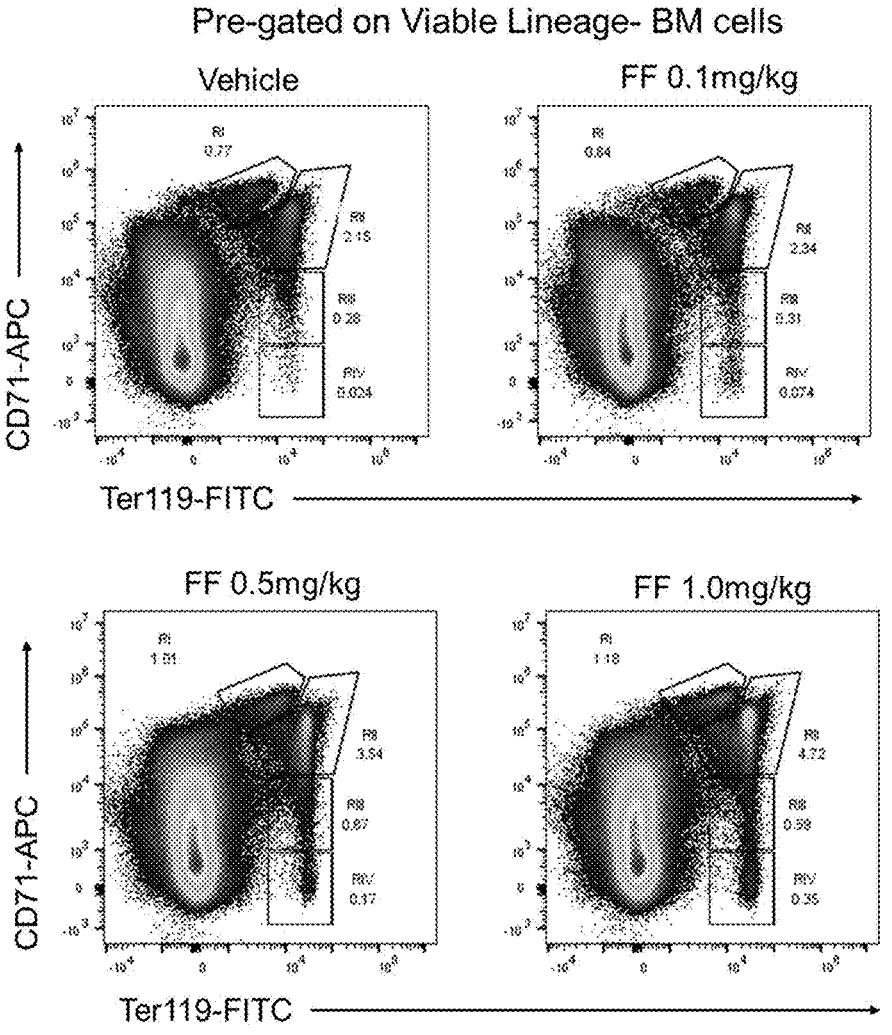
Figure 52B:
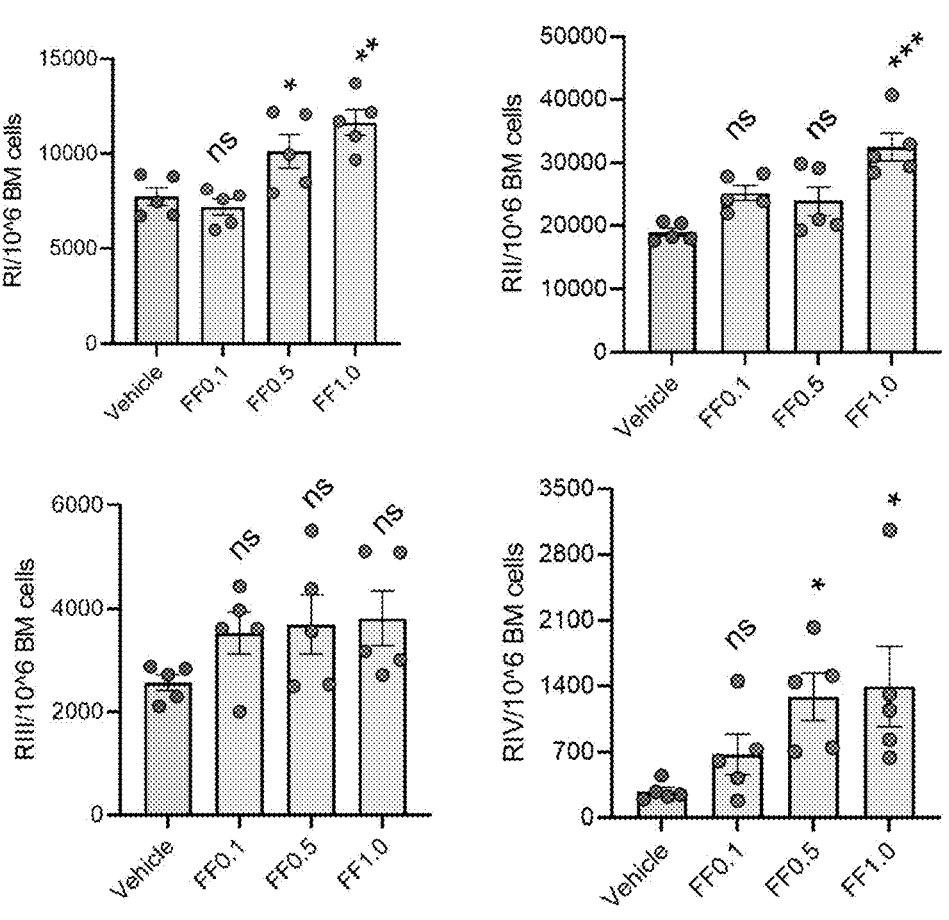

FIG. 52A-FIG. 52B show that FF treatment via o.g. enhances erythroid progenitors in the bone marrow (BM) in wild-type mice at steady-state. FIG. 52A shows flow plots depicting that FF treatment at 0.1/0.5/1.0 mg/kg doses substantially increases RI, RII, RIII and RIV erythroid progenitors in the BM of mice. FIG. 52B shows quantification of data presented in FIG. 52A showing absolute numbers of RI, RII, RIII and RIV erythroid progenitors per million BM cells in the mice. * p<0.05,  p<0.01, * P<0.001, ANOVA. n=5 male mice per group. All comparisons were done w.r.t. vehicle (DMSO) treated controls. ns=non-significant.

Figure 53:
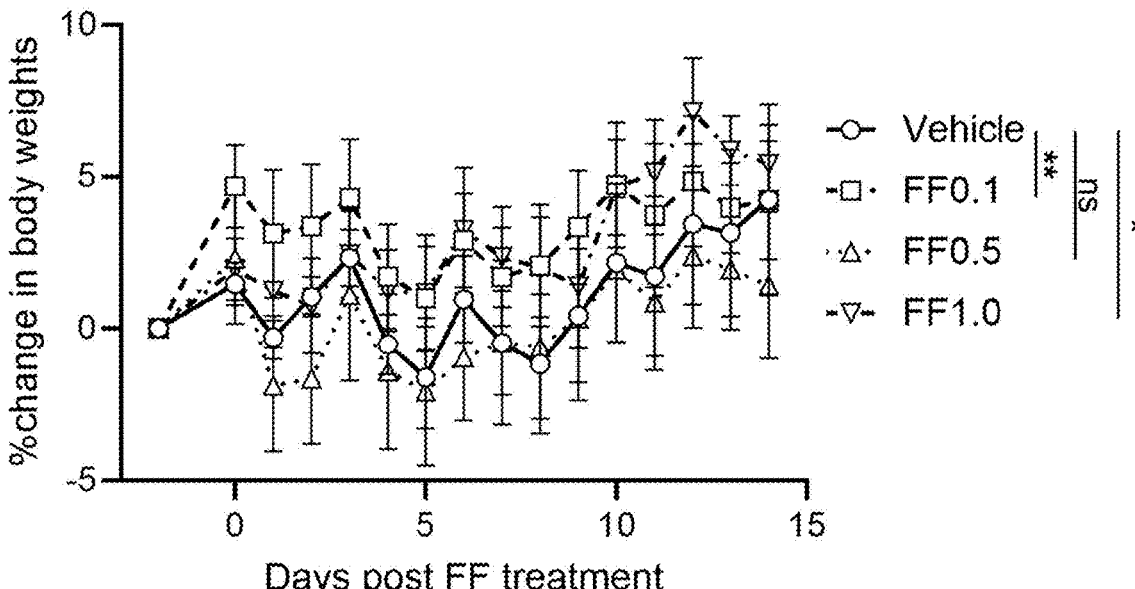

FIG. 53 shows that FF treatment mildly increases body weights in steady state mice after FF treatment via oral gavage (o.g.). Graph showing that FF treatment via oral gavage mildly increases % change in body weights of mice. * p<0.05, ** p<0.01, two-way ANOVA. n=5 male mice per group. All comparisons were done w.r.t. vehicle (DMSO) treated controls. ns=non-significant.

Figure 54:
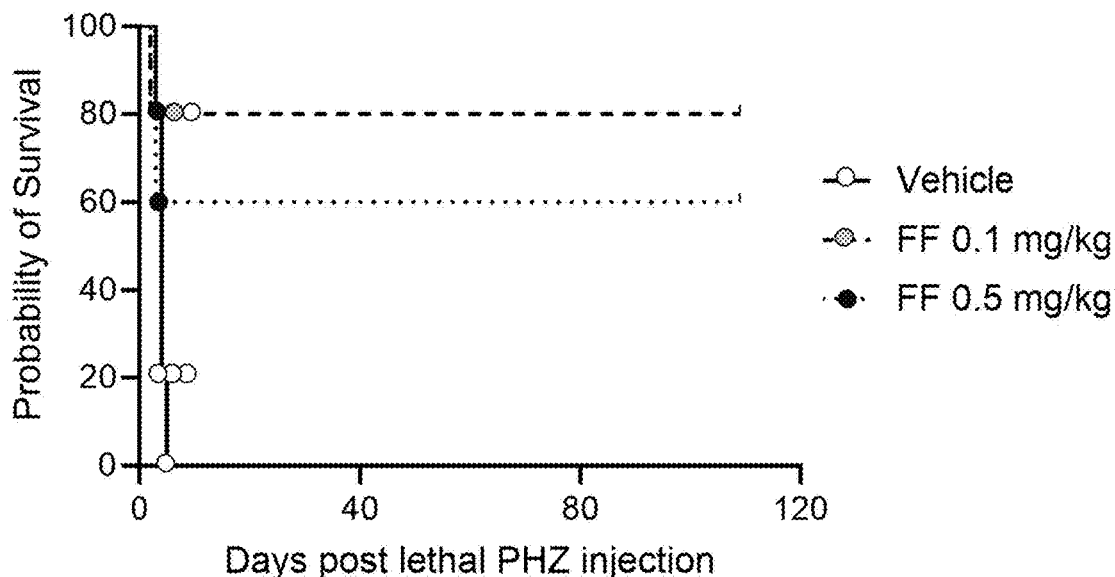

FIG. 54 shows that FF treatment via oral gavage confers striking survival benefits to mice (10-12 weeks old mice) given lethal dose of 135 mg/kg phenylhydrazine (PHZ) treatment. Kaplan-Meier survival plot showing survival benefits of FF treatment via oral gavage at 0.1/0.5 mg/kg doses in mice after PHZ-induced lethal hemolytic anemia (PHZ-135 mg/kg). Log-rank (Mantel-Cox) test. n=5 mice per group. All comparisons were done w.r.t. vehicle (DMSO) treated controls.

Figure 55:
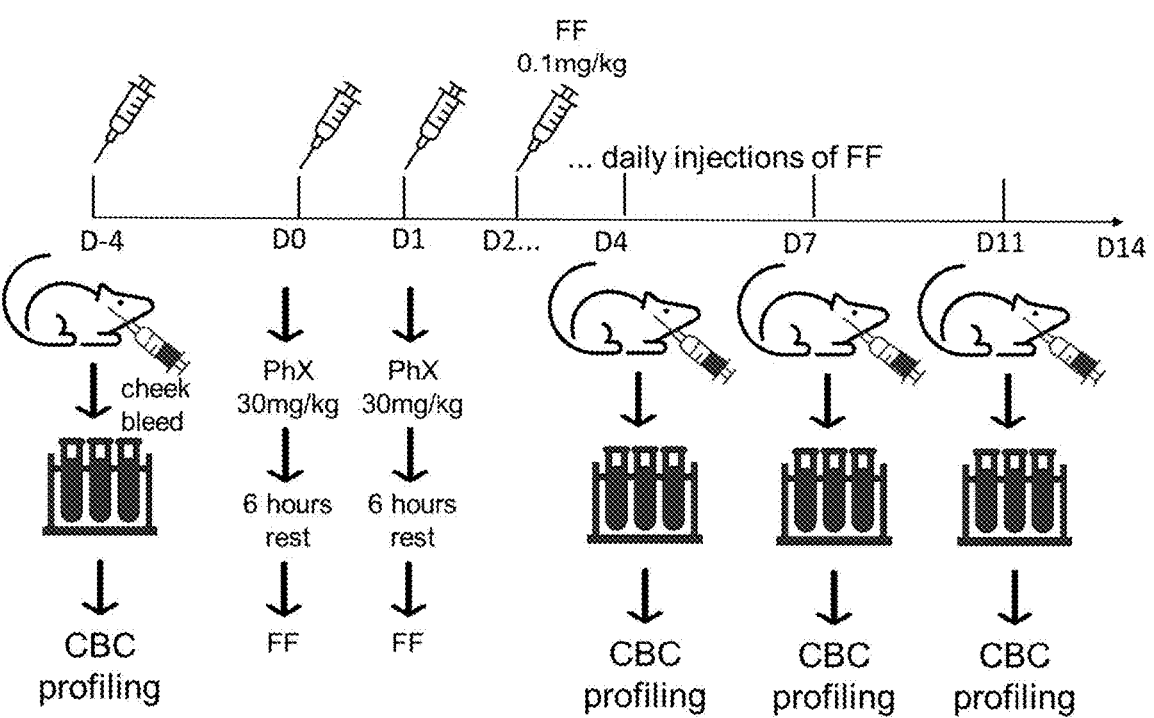

FIG. 55 shows a schematic of FF treatment via o.g. in phenylhydrazine (PHZ)-treated mice at sub-lethal dose of 60 mg/kg.

Figure 56:
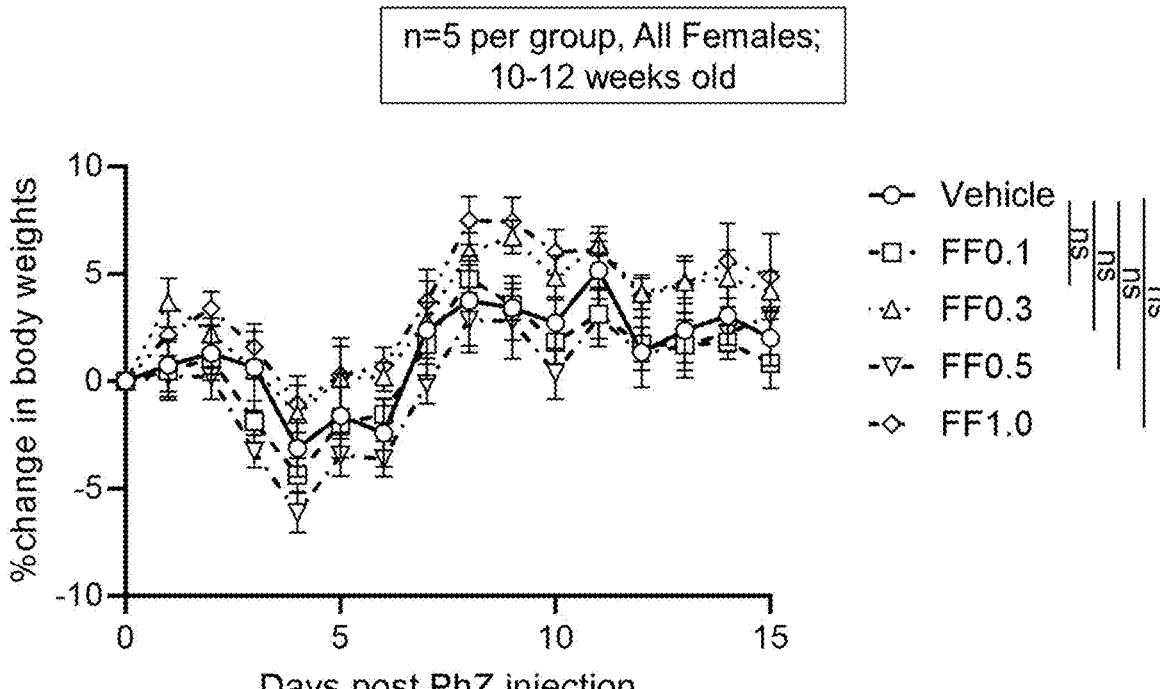

FIG. 56 shows that FF treatment via oral gavage (o.g.) does not affect body weights in phenylhydrazine (PHZ)-treated mice at sub-lethal dose (60 mg/kg). ns=non-significant.

Figure 57A:
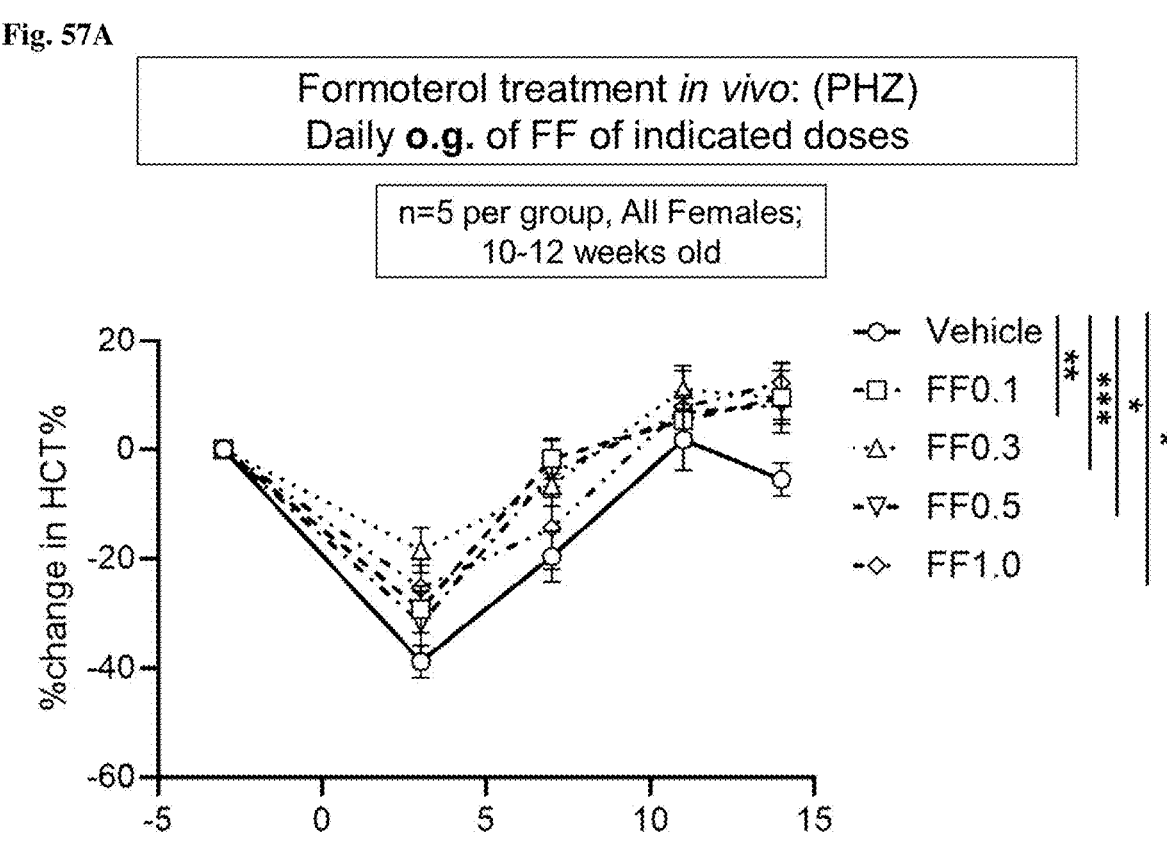
Figure 57B:
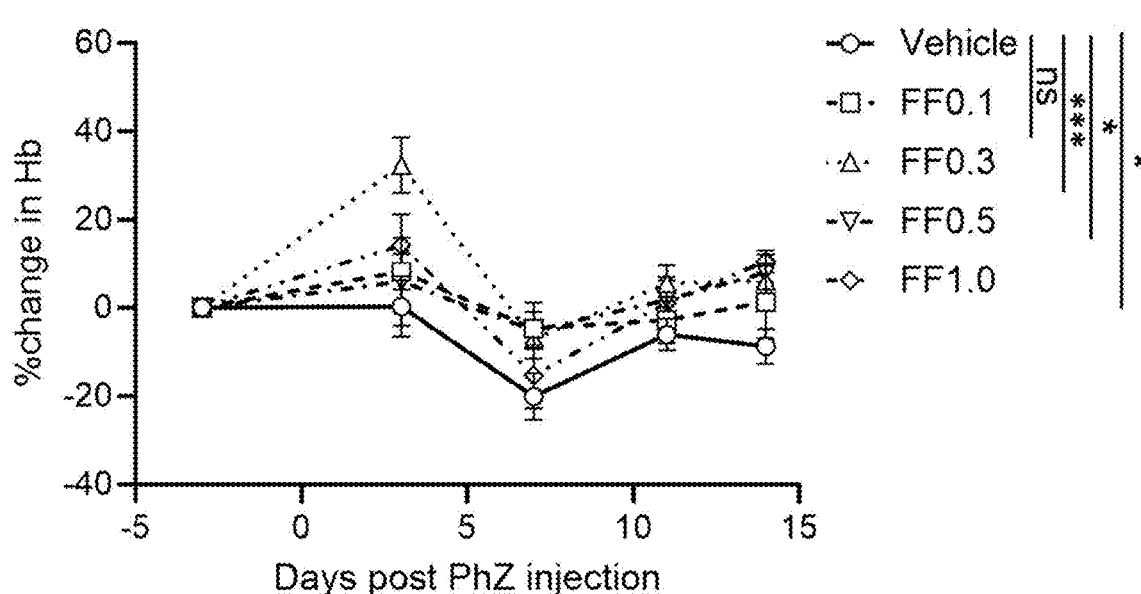

FIG. 57A-FIG. 57B show that FF treatment via o.g. increases RBC parameters in phenylhydrazine (PHZ)-treated mice at sub-lethal dose (60 mg/kg). FF treatment increases RBC parameters, such as hematocrit (HCT)% and Hemoglobin (Hb) in the peripheral blood after oral gavage (o.g.) administrations. * p<0.05,  p<0.01, * P<0.001, ANOVA. n=5 male mice per group. All comparisons were done w.r.t. vehicle (DMSO) treated controls. ns=non-significant.

Figures 58A, 58B:
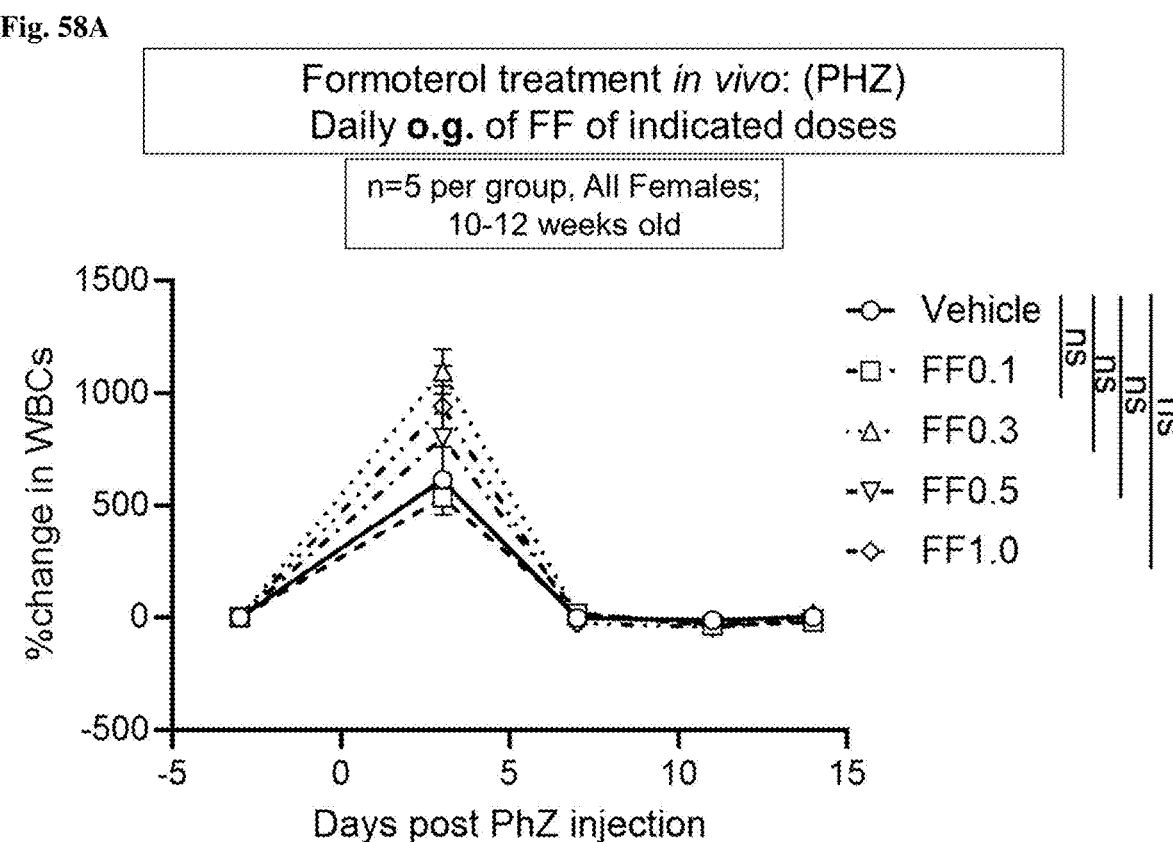

FIG. 58A-FIG. 58B show that FF treatment via o.g. does not affect WBC parameters in phenylhydrazine (PHZ)-treated mice at sub-lethal dose (60 mg/kg). FF treatment does not affect WBC and platelets in the peripheral blood after oral gavage (o.g.) administrations. ANOVA. n=5 male mice per group. All comparisons were done w.r.t. vehicle (DMSO) treated controls. ns=non-significant.

Figure 59A:
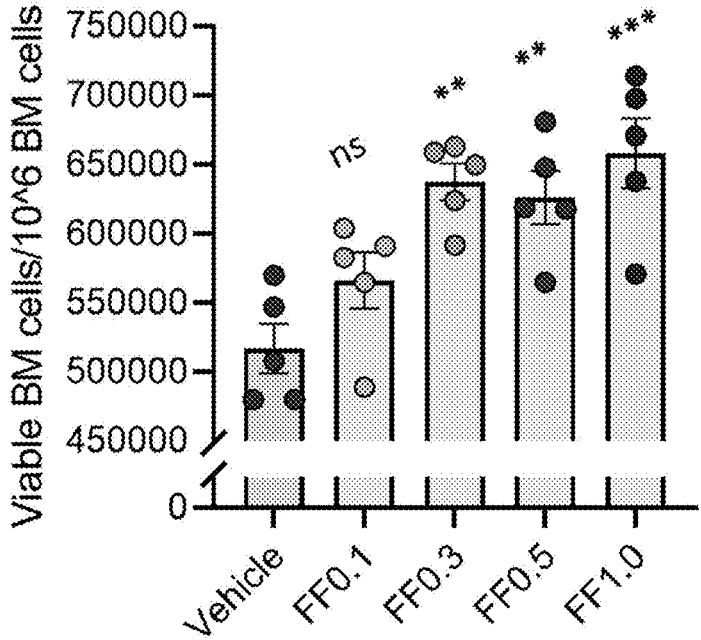
Figure 59B:
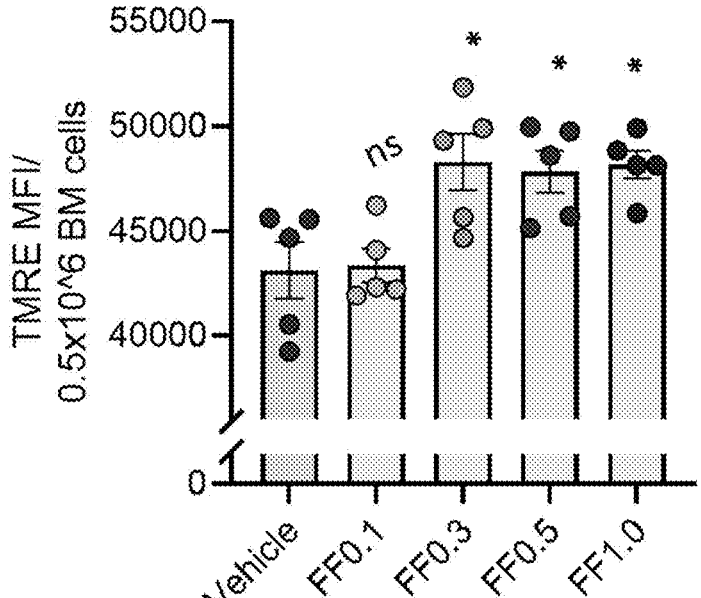

FIG. 59A-FIG. 59B show that FF treatment via o.g. enhances viability and mitochondrial activity of bone marrow progenitors (BMPs) in phenylhydrazine (PHZ)-treated mice at sub-lethal dose (60 mg/kg). FF treatment increases viability and mitochondrial membrane potential (measured via TMRE staining) in the BMPs after 14 days of daily oral gavage (o.g.) administrations. * p<0.05,  p<0.01, * p<0.001, ANOVA. n=5 mice per group. All comparisons were done w.r.t. vehicle treated (DMSO) controls. ns=non-significant.

Figure 60A:
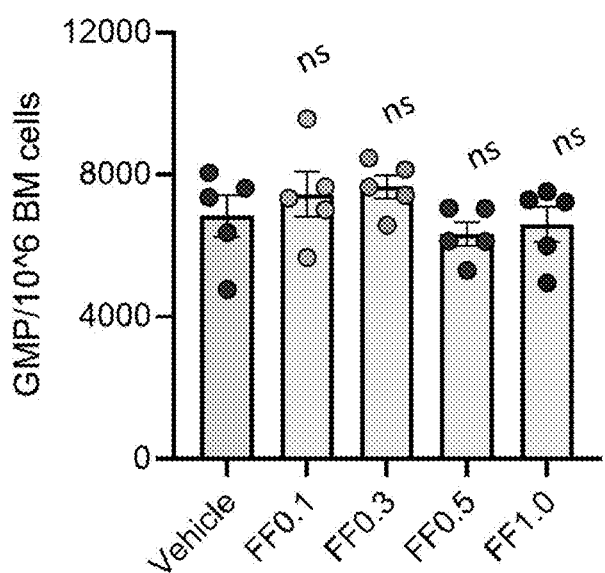
Figure 60B:
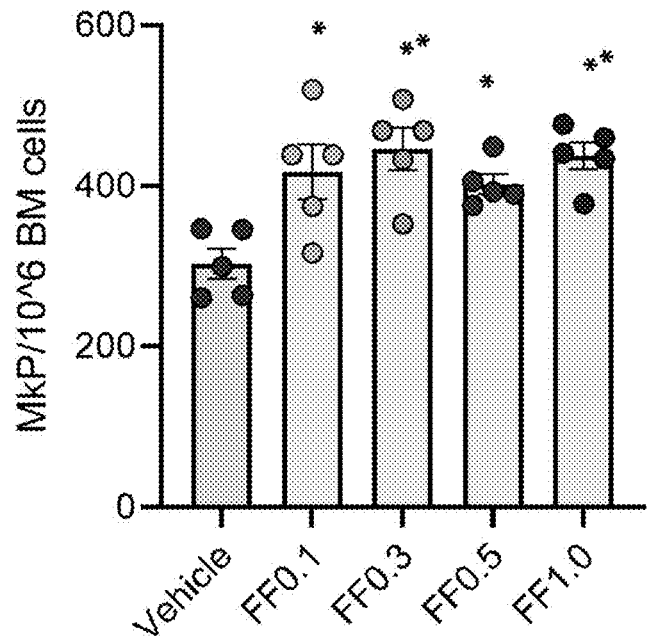

FIG. 60A-FIG. 60B show that FF treatment via o.g. enhances MkP, but not GMPs in the bone marrow (BM) of phenylhydrazine (PHZ)-treated mice at sub-lethal dose (60 mg/kg). FF treatment does not affect granulocyte monocyte progenitors (GMP) but increases megakaryocytic progenitors (MkP) in the BMPs after 14 days of daily oral gavage (o.g.) administrations. * p<0.001, ** p<0.0001, ANOVA. n=5 mice per group. All comparisons were done w.r.t. vehicle treated (DMSO) controls. ns=non-significant.

Figure 61A:
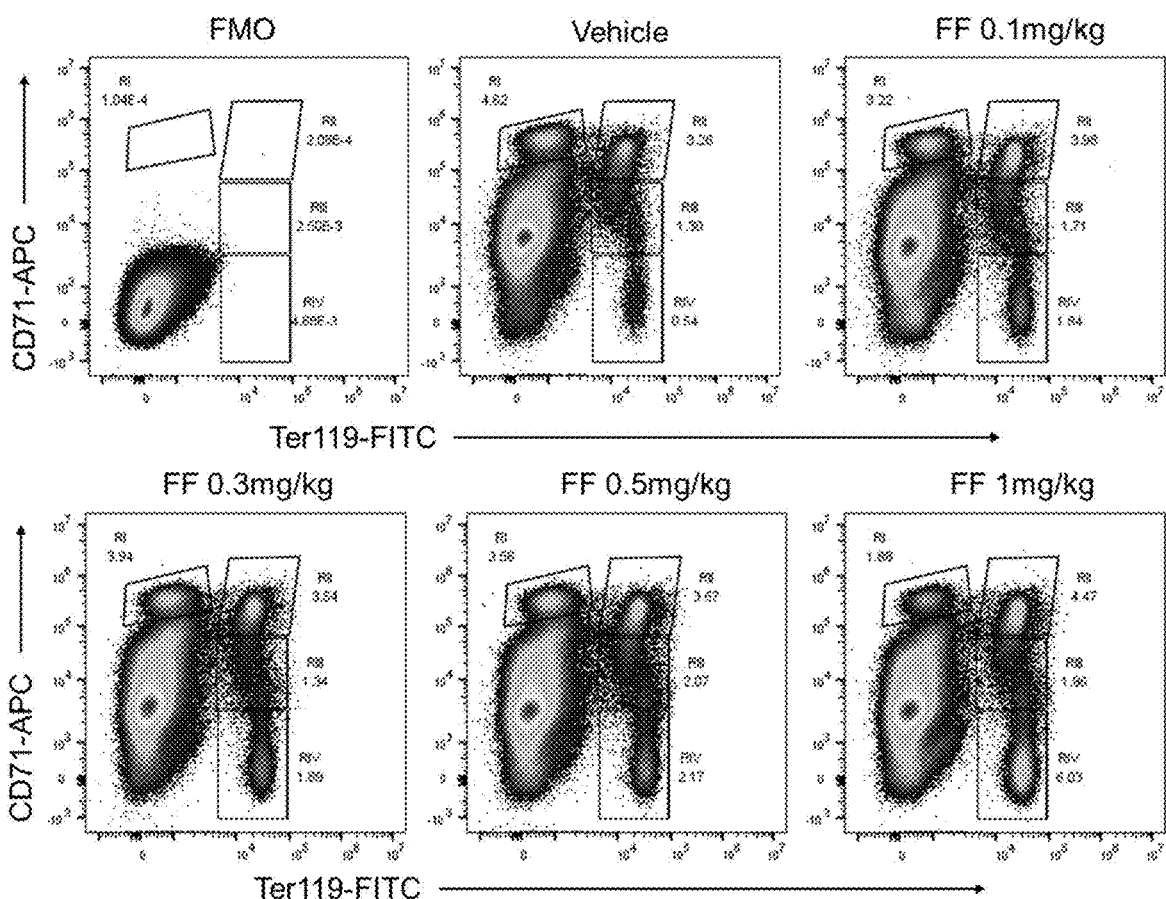
Figure 61B:
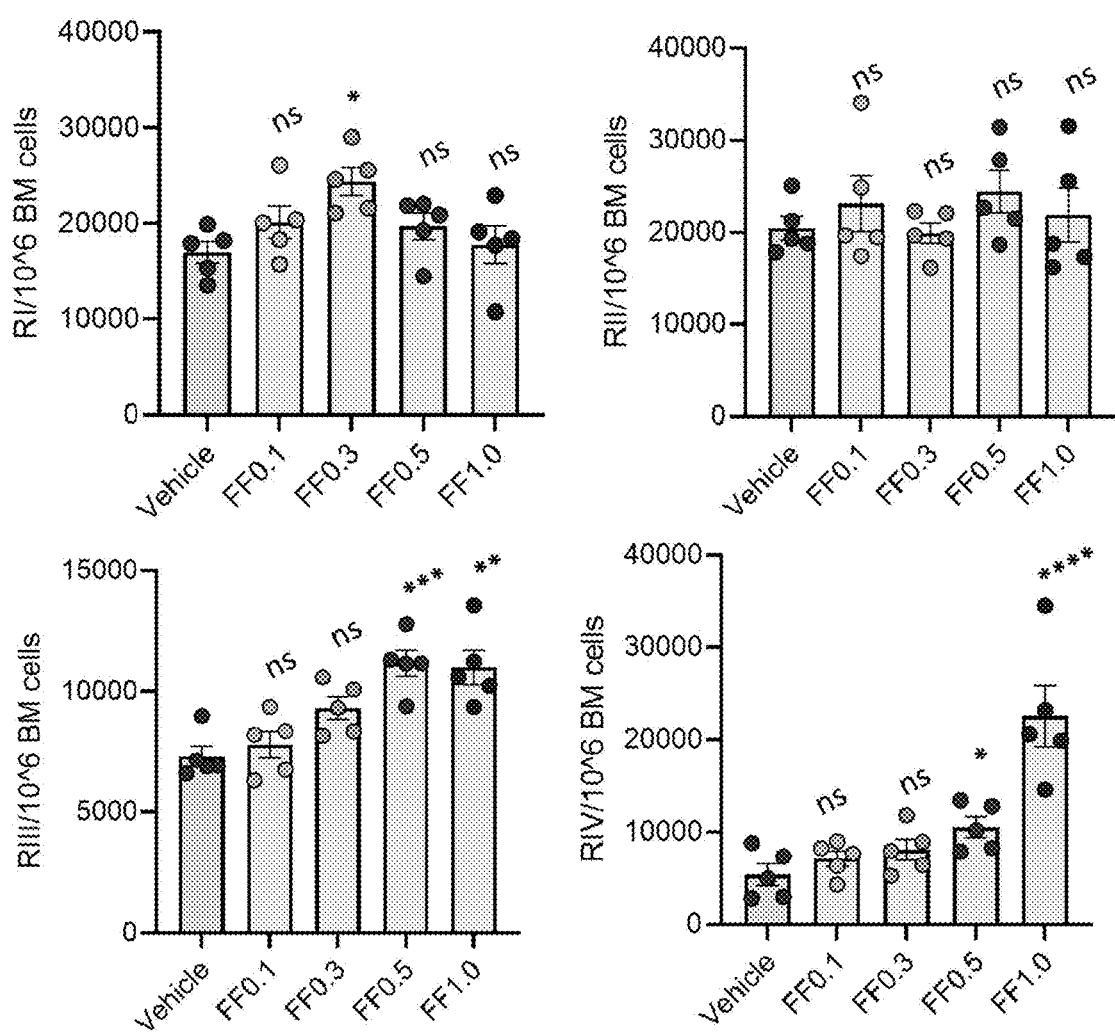

FIG. 61A-FIG. 61B show that FF treatment via o.g. enhances erythroid progenitors in the bone marrow (BM) of phenylhydrazine (PHZ)-treated mice at sub-lethal dose (60 mg/kg). FIG. 61A shows flow plots depicting that FF treatment at 0.1/0.3/0.5/1.0 mg/kg doses substantially increases RI, RII, RIII and RIV erythroid progenitors in the BM of mice. FIG. 61B shows quantification of data presented in FIG. 61A showing absolute numbers of RI, RII, RIII and RIV erythroid progenitors per million BM cells in the mice. * p<0.05,  p<0.01, * P<0.001, **** P<0.0001, ANOVA. n=5 male mice per group. All comparisons were done w.r.t. vehicle (DMSO) treated controls. ns=non-significant.

Figure 62:
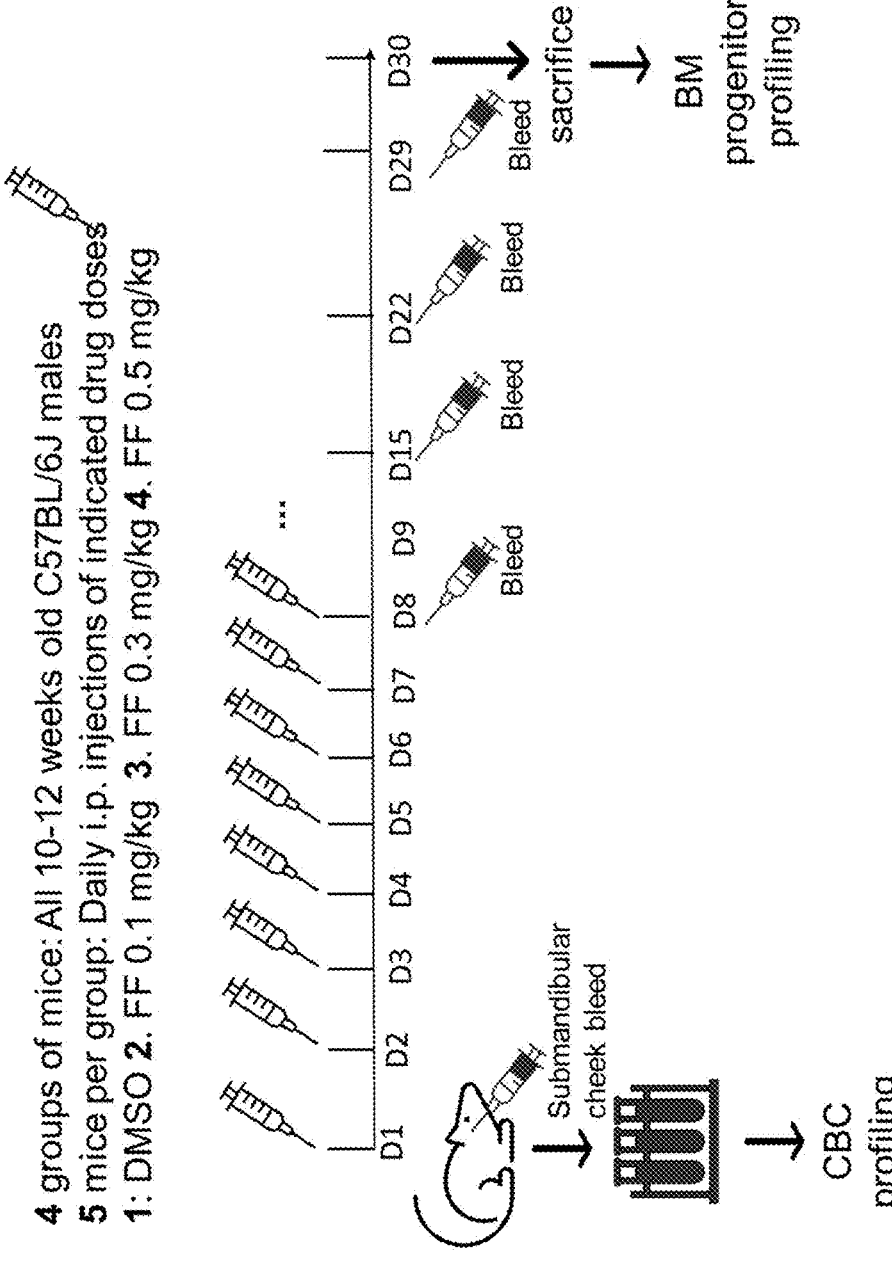

FIG. 62 shows a schematic of experimental setup to analyze effects of formoterol fumarate (FF) in naive mice without any external stress of phenylhydrazine (PHZ).

Figure 63:
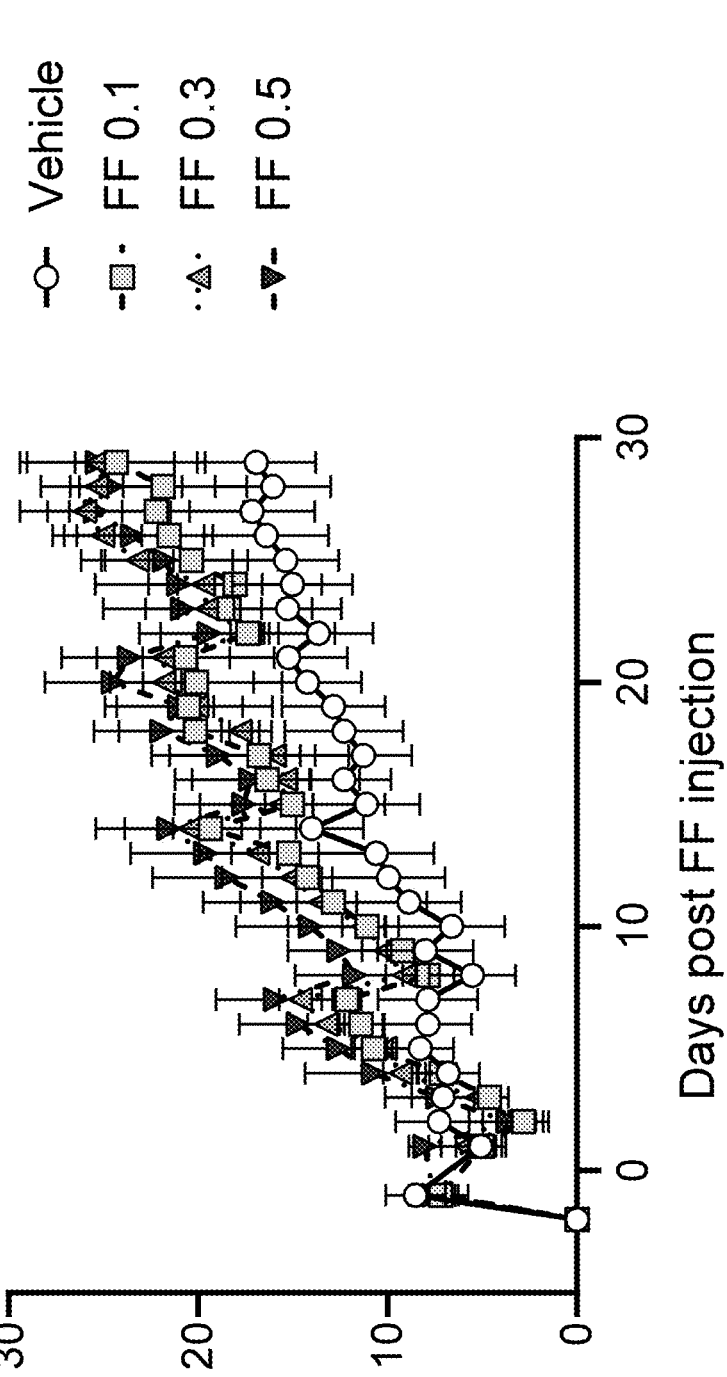

FIG. 63 shows that the FF treatment shown in FIG. 62 increases body weights in wild-type mice at steady-state. Graph showing % change in body weights of mice with vehicle or FF treatment at 0.1/0.3/0.5 mg/kg doses. ** p<0.01, "ns"=non-significant. Although 0.1 and 0.3 mg/kg groups did not show statistical significance in Graphpad PRISM, there is evident increase in body weights ac compared to vehicle-treated controls.

Figure 64A:
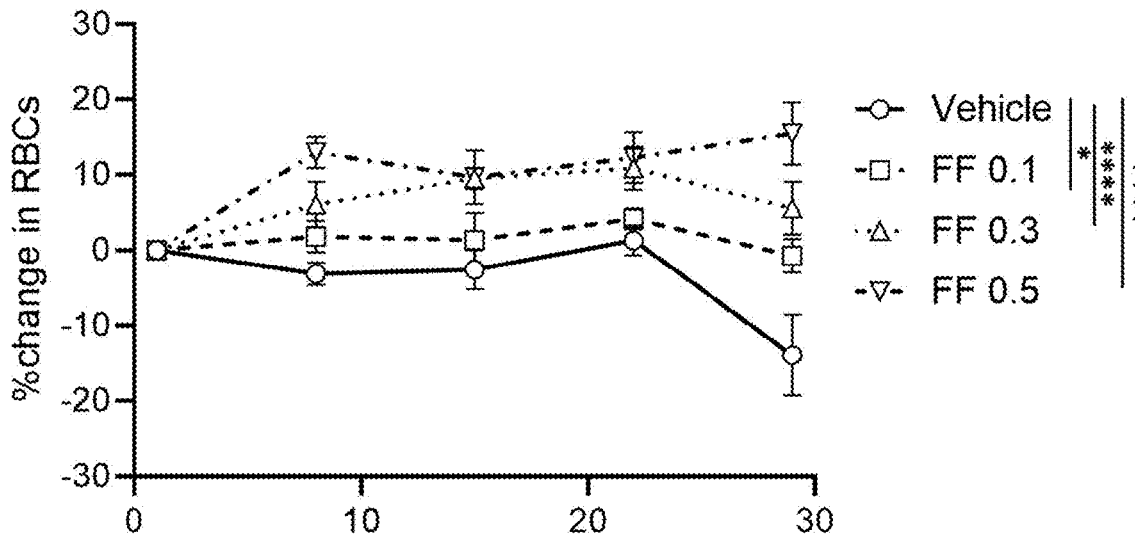
Figure 64B:
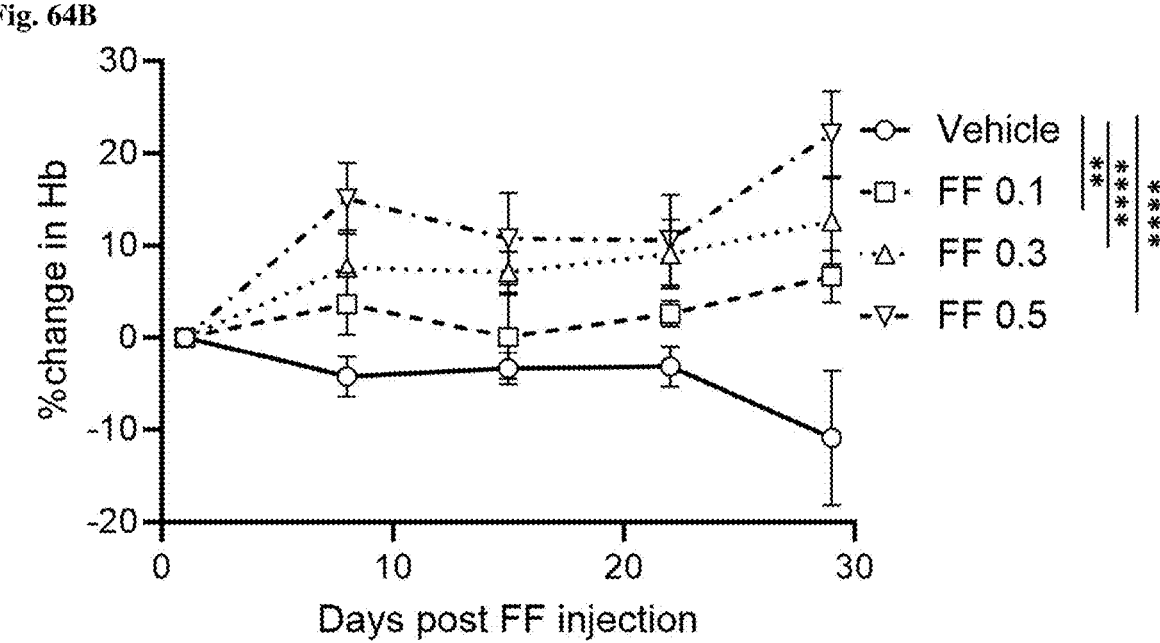
Figure 64C:
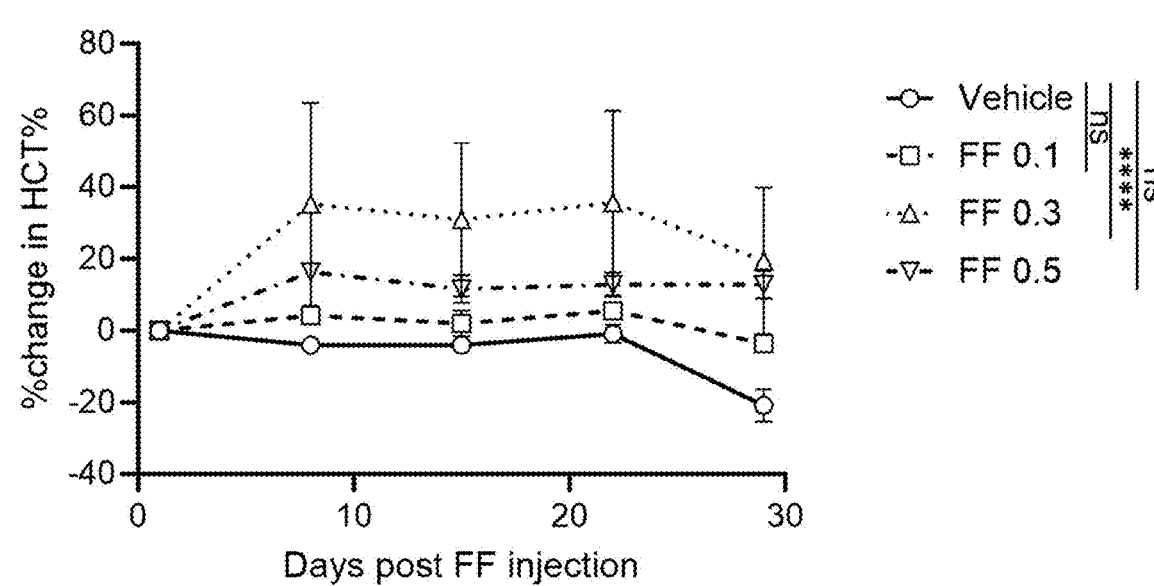

FIG. 64A-FIG. 64C show that the FF treatment shown in FIG. 62 significantly increases red blood cell (RBC) parameters in wild-type mice (10-12 week old male mice). FF administration enhances and sustains RBC parameters, such as (FIG. 64A) RBC numbers, (FIG. 64B) hemoglobin (Hb), and (FIG. 64C) hematocrit (HCT)% in the peripheral blood. 0.1 and 0.5 mg/kg groups did not show statistical significance in HCT% as per Graphpad PRISM. * p<0.05,  p<0.01, * p<0.001, **** P<0.0001, "ns"=non-significant, one-way and two-way ANOVA. n=5 male mice per group. All comparisons were done w.r.t. vehicle (DMSO) treated controls.

Figure 65A:
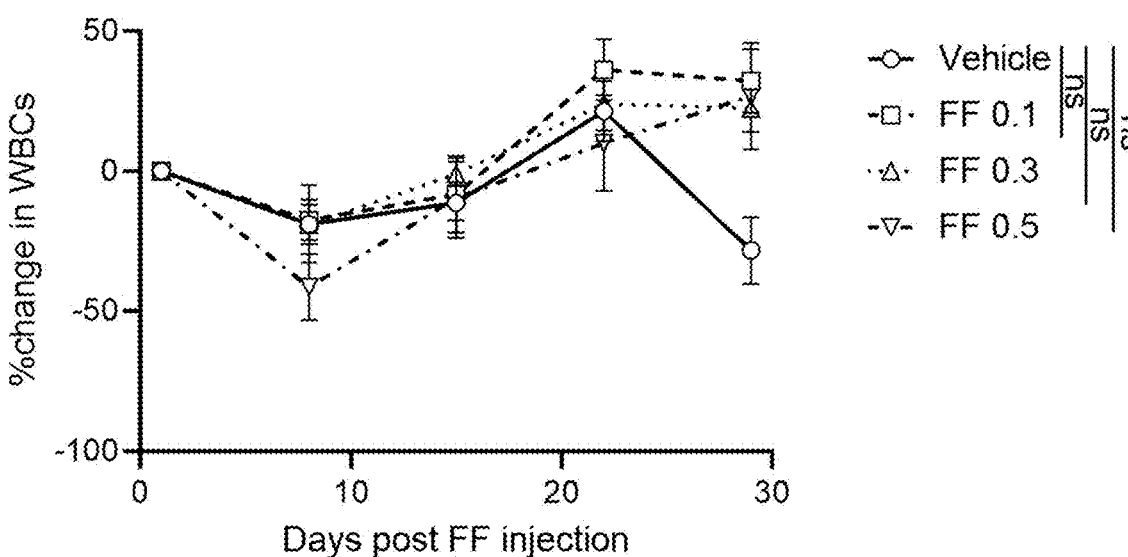
Figure 65B:
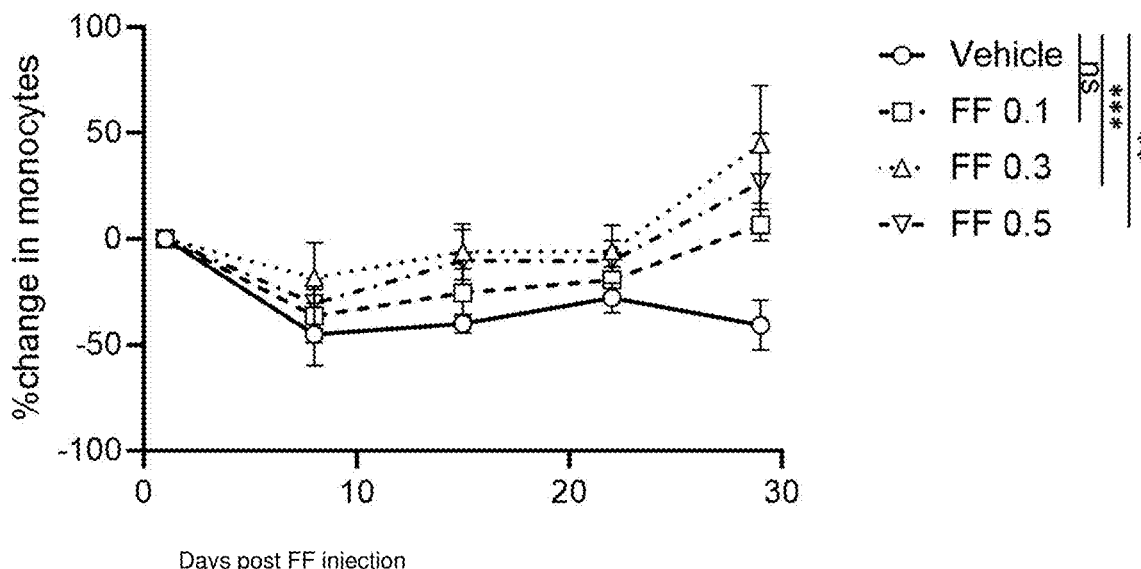
Figure 65C:
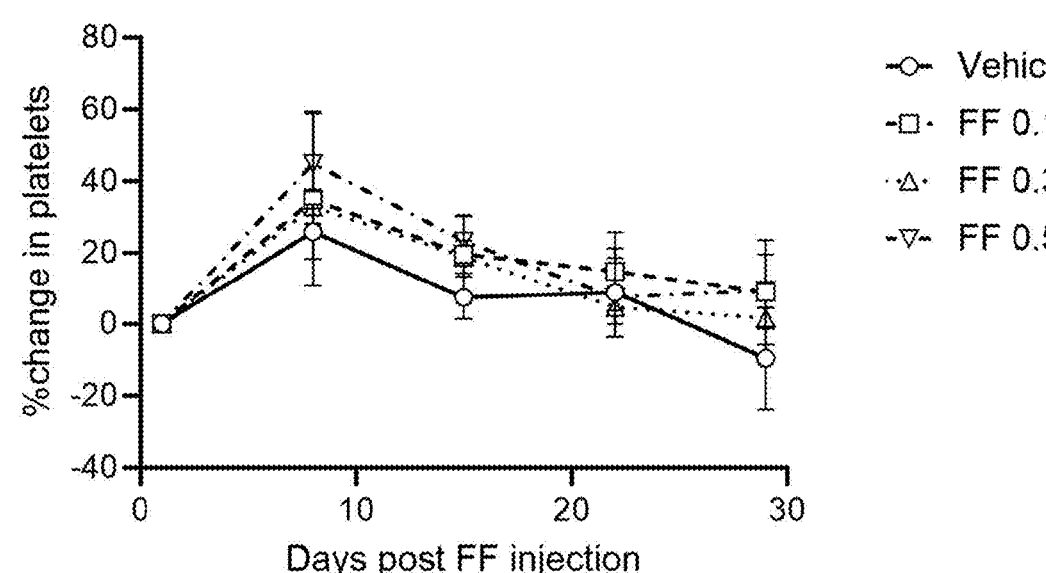

FIG. 65A-FIG. 65C show that the FF treatment shown in FIG. 62 does not affect total white blood cells (non-RBC) parameters in wild-type mice (10-12 week old male mice). FF administration does not influence (FIG. 65A) white blood count (WBC) numbers and (FIG. 65C) platelet counts, but modestly impacts monocyte counts in the peripheral blood of naive mice (FIG. 65B). * p<0.05,  p<0.01, * p<0.001, **** P<0.0001, "ns"=non-significant, one-way and two-way ANOVA. n=5 male mice per group. All comparisons were done w.r.t. vehicle (DMSO) treated controls.

Figure 66A:
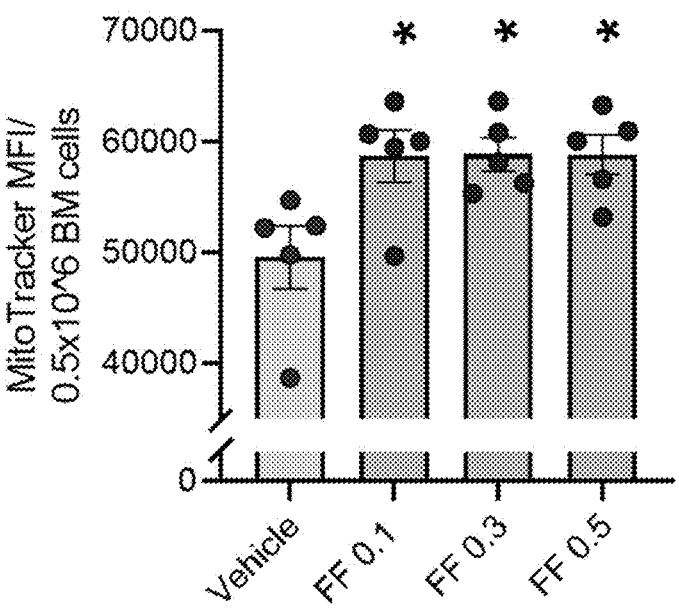
Figure 66B:
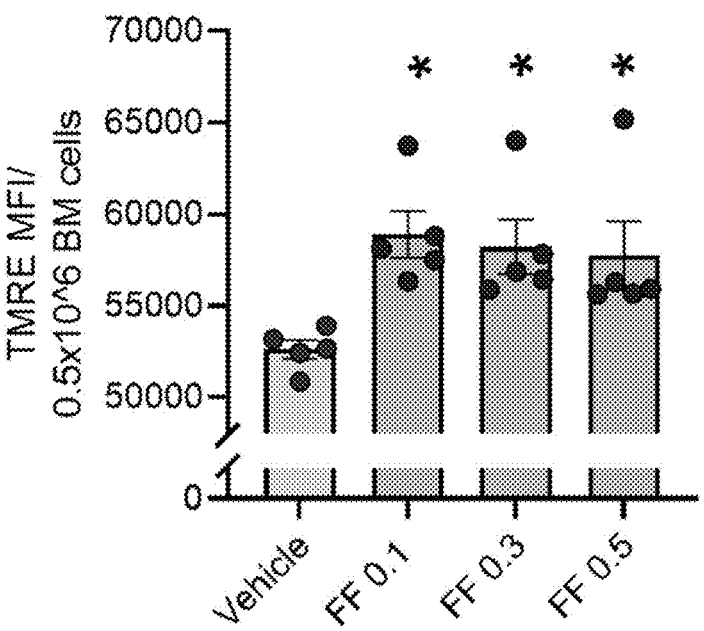
Figure 66C:
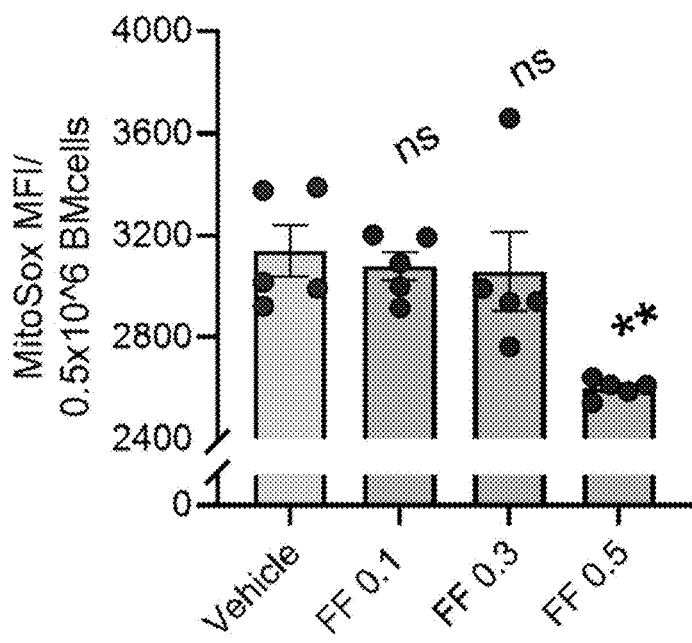

FIG. 66A-FIG. 66C show that FF treatment shown in FIG. 62 significantly enhances mitochondrial biogenesis in bone marrow progenitors (BMPs) of wild-type mice (10-12 week old mice). FIG. 66A shows that FF administration enhances mitochondrial biogenesis as observed by MitoTracker staining in the BMPs of naive mice. FIG. 66B shows that FF administration enhances mitochondrial membrane potential as observed by TMRE staining in the BMPs of naive mice.

FIG. 66C shows that FF administration significantly reduces mitochondrial superoxide production indicating mitochondrial fitness as observed by MitoSox staining in the BMPs of naive mice. * $p<0.05$,  $p<0.01$, * $p<0.001$, **** $P<0.0001$, "ns"=non-significant. n=5 male mice per group. All comparisons were done w.r.t. vehicle (DMSO) treated controls.

Figure 67A:
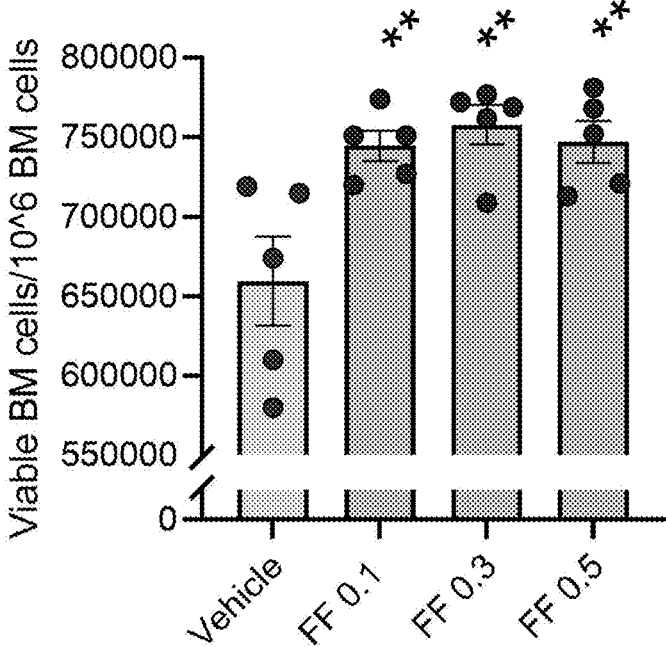
Figure 67B:
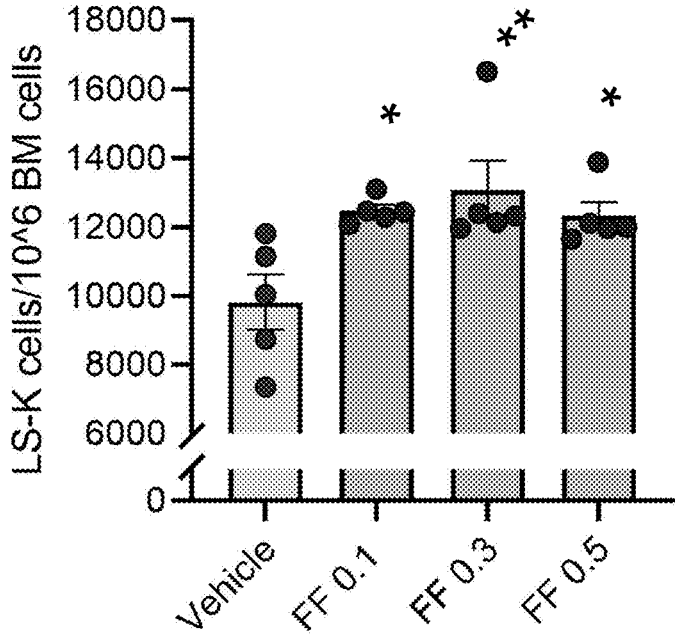

FIG. 67A-FIG. 67B show that FF treatment shown in FIG. 62 significantly enhances viability and LS-K cells (Lineage—Scal—cKit+) in the bone marrow (BM) progenitors of wild-type mice (10-12 week old mice). FF treatment at 0.1/0.3/0.5 mg/kg doses substantially increases (FIG. 67A) viability and (FIG. 67B) LS-K cells in the BM of naive mice. * $p<0.05$, *** $P<0.0001$, ANOVA. n=5 male mice per group. All comparisons were done w.r.t. vehicle (DMSO) treated controls.

Figure 68A:
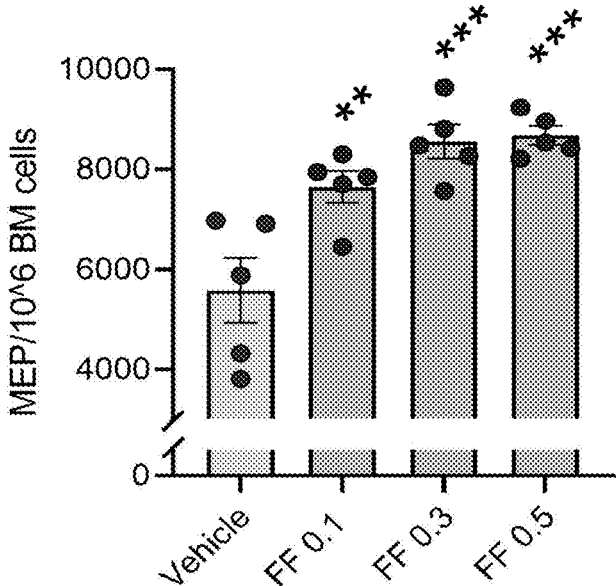
Figure 68B:
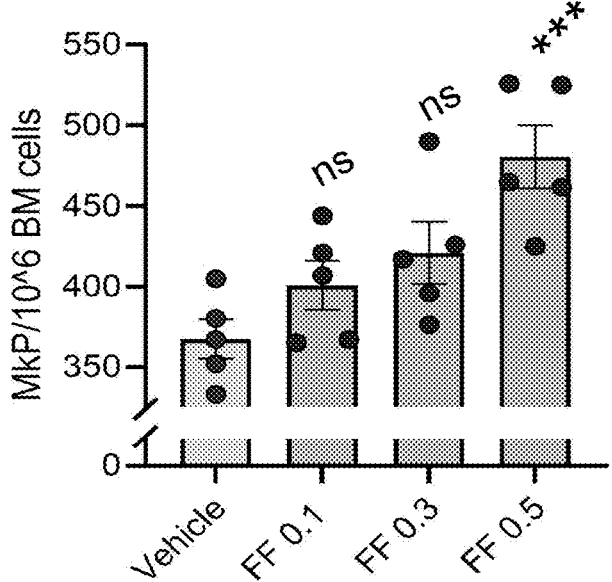
Figure 68C:
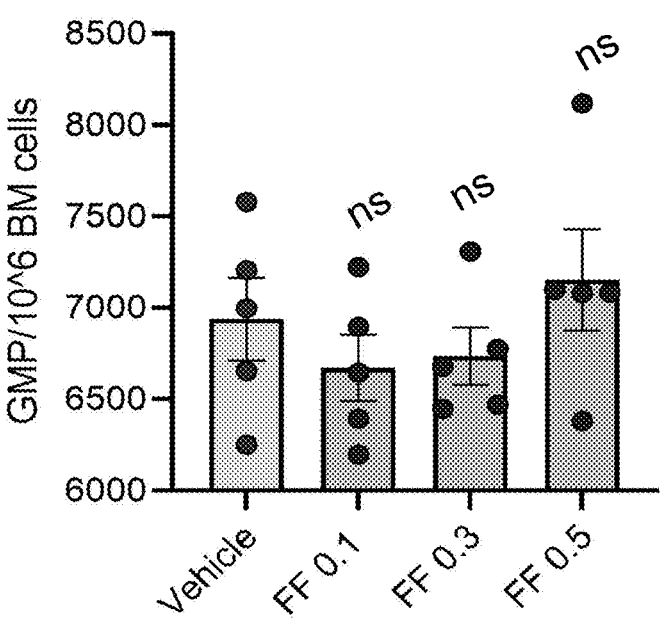
Figure 69A:
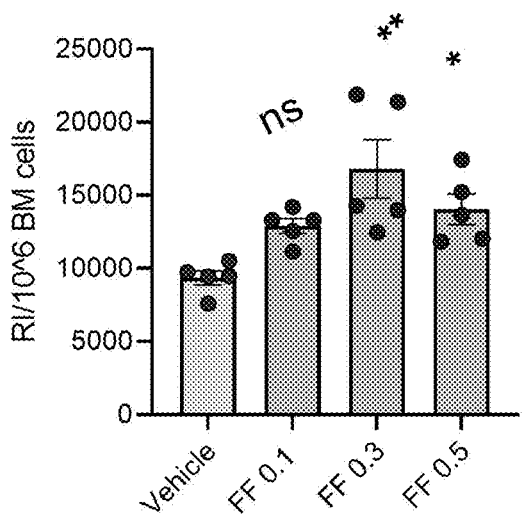
Figure 69B:
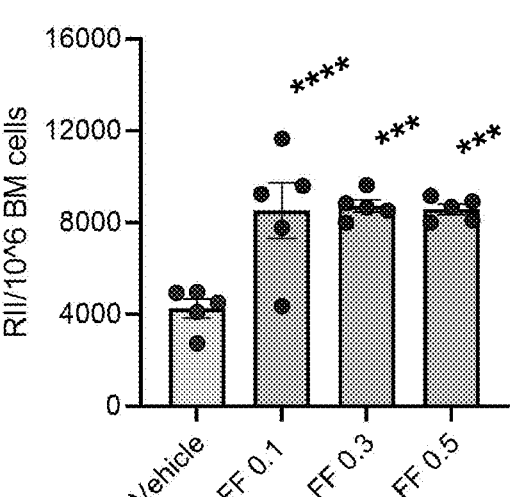
Figure 69C:
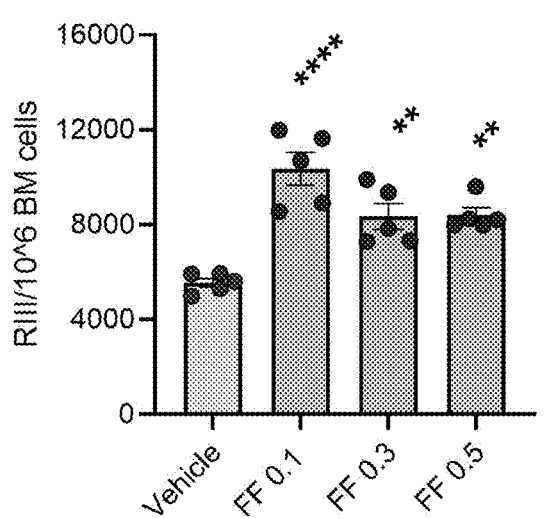
Figure 69D:
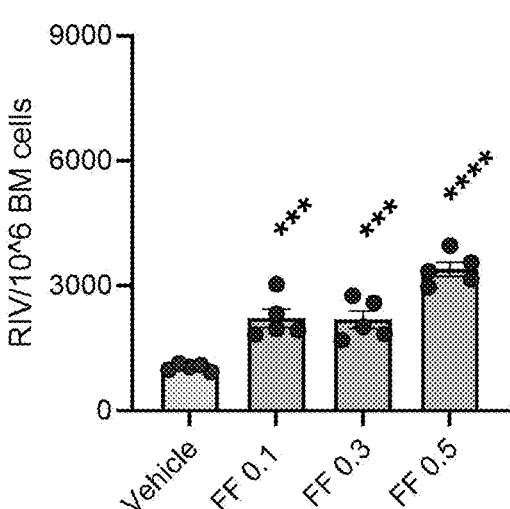

FIG. 68A-FIG. 68C show that FF treatment shown in FIG. 62 significantly elevates megakaryocyte erythroid progenitors (MEP) and megakaryocytic progenitors (MkP), but not granulocyte monocyte progenitors (GMP) in the bone marrow (BM) of naive mice (10-12 week old mice). Flow plots depicting that FF treatment at 0.1/0.3/0.5 mg/kg doses substantially increases (FIG. 68A) megakaryocyte erythroid progenitors (MEP) and (FIG. 68B) megakaryocytic progenitors (MkP) in the BM of wild-type mice, but not (FIG. 68C) granulocyte monocyte progenitors (GMP). LS-K: Lineage—Scal—cKit+ BM cells.  $p<0.01$, * $P<0.001$, "ns"=non-significant, ANOVA. n=5 male mice per group. All comparisons were done w.r.t. vehicle (DMSO treated) controls.

FIG. 69A-FIG. 69D show that FF treatment shown in FIG. 62 significantly elevates erythroid differentiation in the bone marrow (BM) of naive mice (10-12 week old mice). FF treatment at 0.1/0.3/0.5 mg/kg doses substantially increases (FIG. 69A) RI, (FIG. 69B) RII, (FIG. 69C) RIII, and (D) RIV erythroid progenitors in the BM of wild-type mice. Quantification of data showing absolute numbers of RI, RII, RIII and RIV erythroid progenitors per million BM cells in the naive mice. * $p<0.05$,  $p<0.01$, * $P<0.001$, **** $P<0.0001$, "ns"=non-significant, ANOVA. n=5 male mice per group. All comparisons were done w.r.t. vehicle (DMSO) treated controls.

FIG. 70A-FIG. 70D show that FF treatment shown in FIG. 63 significantly elevates erythroid gene expression in sorted erythroid progenitors isolated from the bone marrow (BM) of naive mice (10-12 week old mice). FF treatment at 0.1/0.3/0.5 mg/kg doses substantially increases the expression of erythroid genes, such as (FIG. 70A) EPOR, (FIG. 70B) ASXL1, and (FIG. 70C) NFE2, but does not influence the expression of β2-AR-encoding gene ADRB2 (FIG. 70D) in the sorted erythroid progenitors isolated from the BM of wild-type mice. * $p<0.05$,  $p<0.01$, * $P<0.001$, **** $P<0.0001$, "ns"=non-significant, ANOVA. n=5 male mice per group. All comparisons were done w.r.t. vehicle (DMSO) treated controls. Since FF treatment in naive mice elevates the expression of erythropoietin receptor EPOR in erythroid progenitors, FF can be potentially administered conjointly with erythropoiesis-stimulating agents (ESAs) such as epoetin alfa and other biosimilars of erythropoietin (EPO), in MDS and other anemic patients who do not respond to EPO treatment alone. This elevation of EPOR in erythroid progenitors by FF would also not preclude the conjoint administration of FF with other FDA-approved drugs such as luspatercept, lenalidomide and/or a hypomethylating agent, such as azacitidine and/or decitabine, in MDS and other anemic patients who do not respond to EPO treatment alone.

Figure 71A:
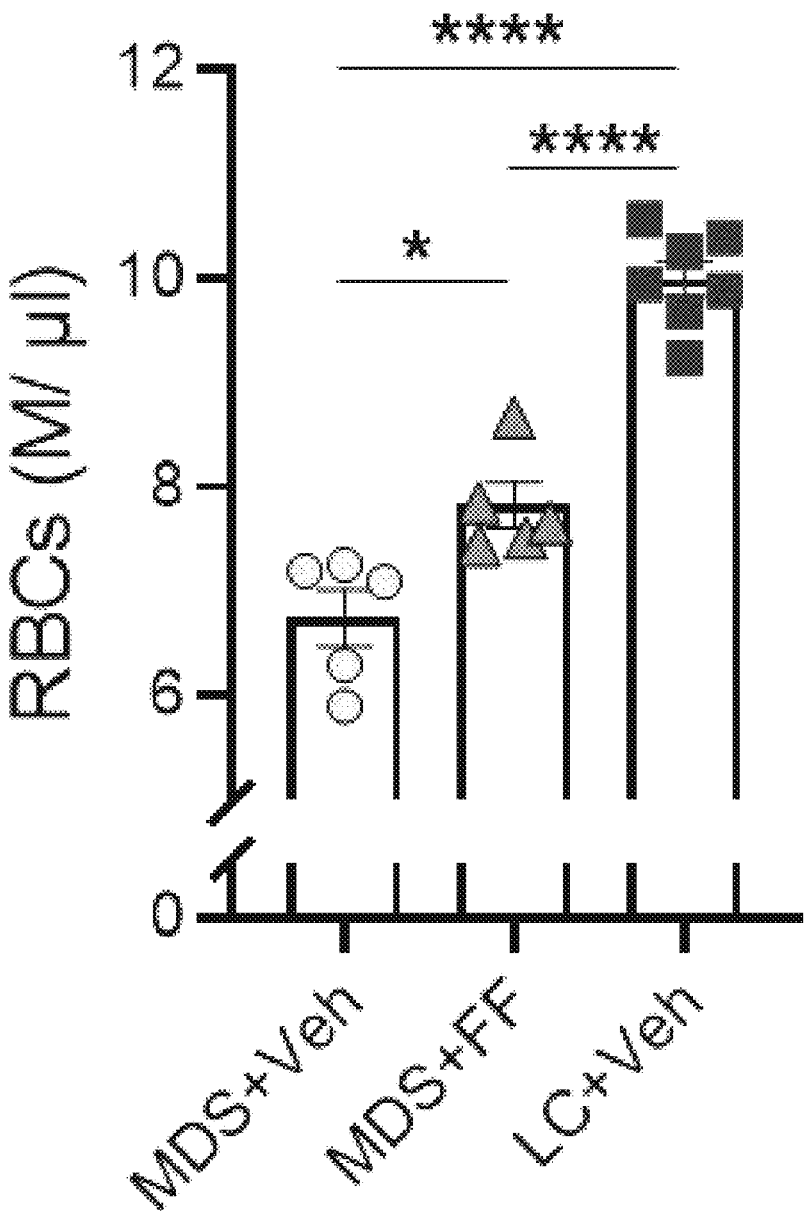
Figure 71B:
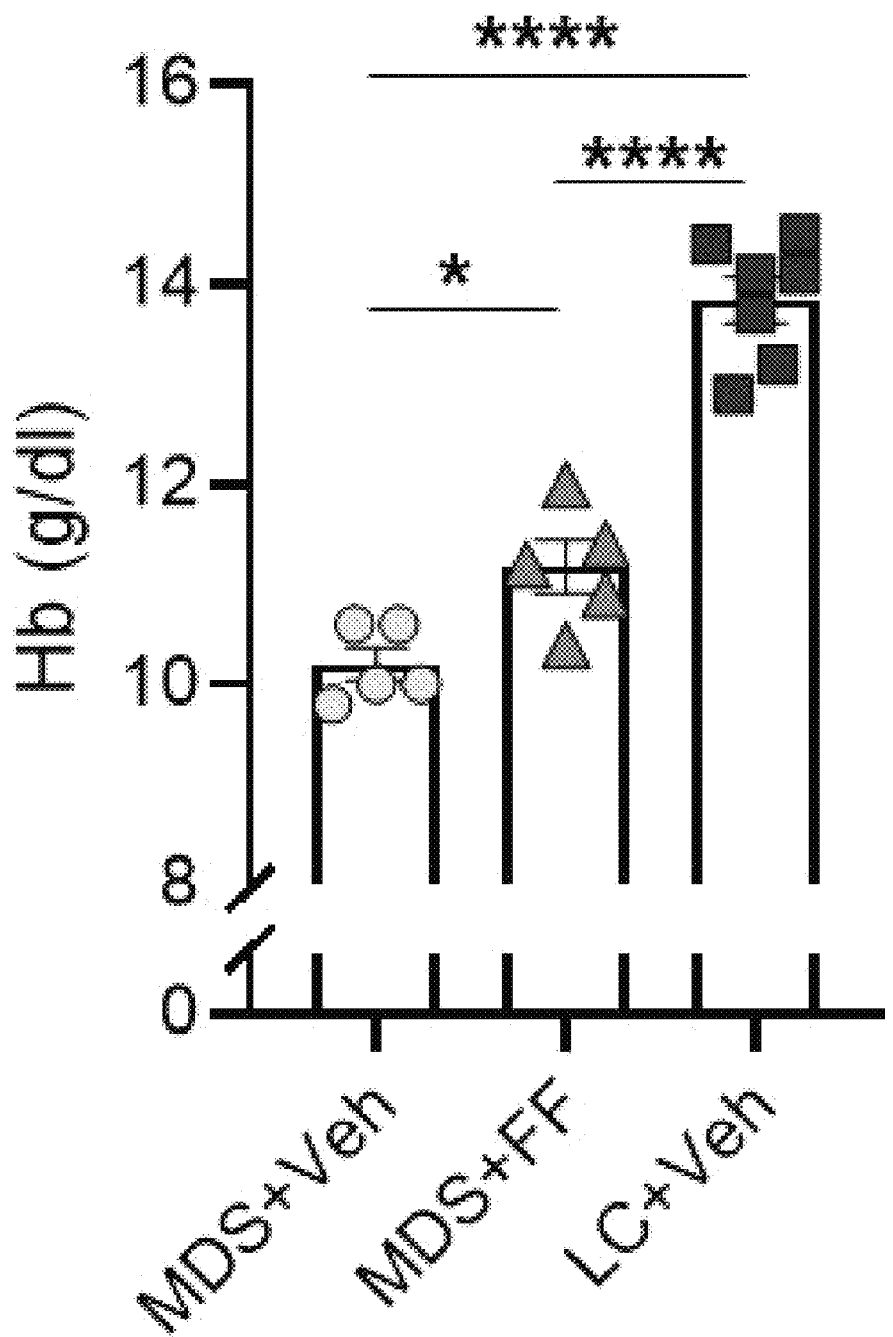
Figure 71C:
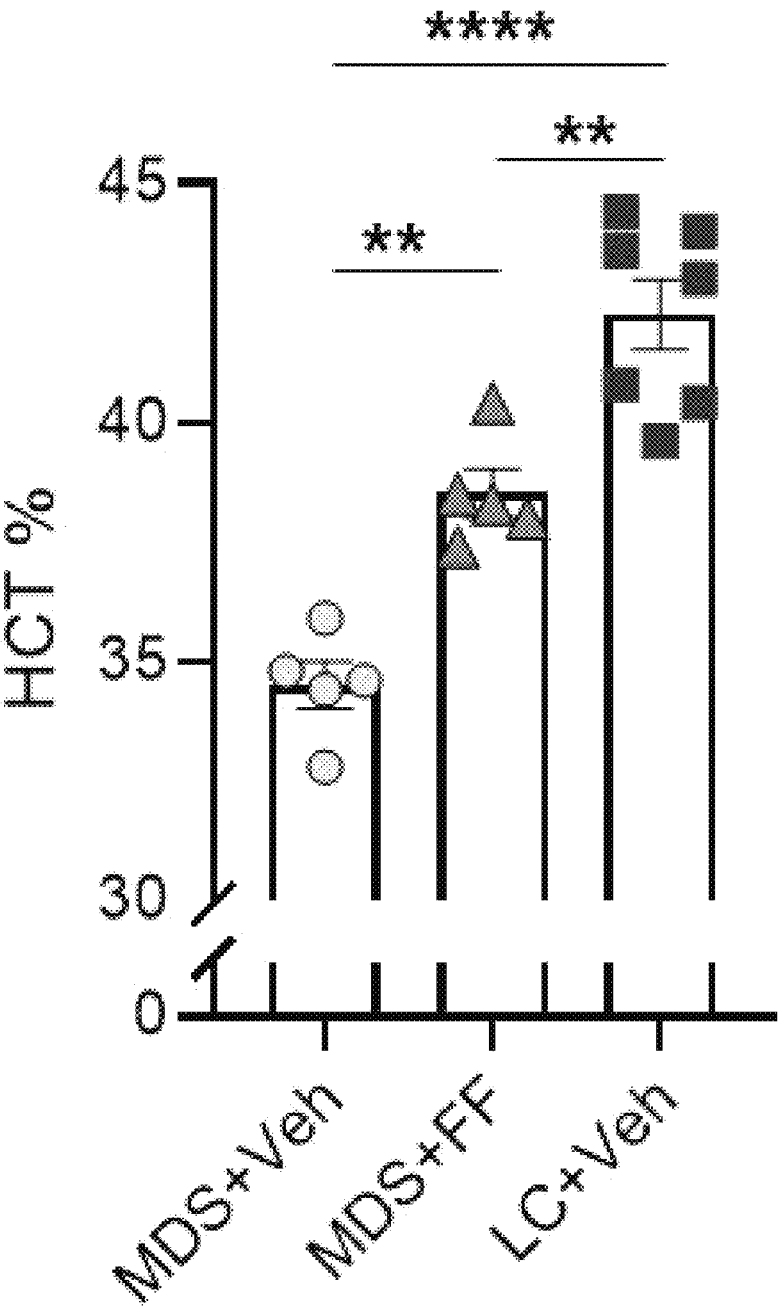

FIG. 71A-FIG. 71C show that FF treatment elevates RBC parameters in MDS/AML mice (NUP98-HOXD13 transgenic mice). FIG. 71A, FIG. 71B and FIG. 71C show FF treatment at a low dose of 0.3 mg/kg thrice weekly (i.p.) alleviates RBC parameters in PB of MDS/AML mice, such as RBCs, hemoglobin (Hb) and hematocrit (HCT%). * $p<0.05$,  p $<0.01$, ** $p<0.0001$, ANOVA. n=5-7 mice per group. Veh: vehicle; LC: littermate control.

Figure 72A:
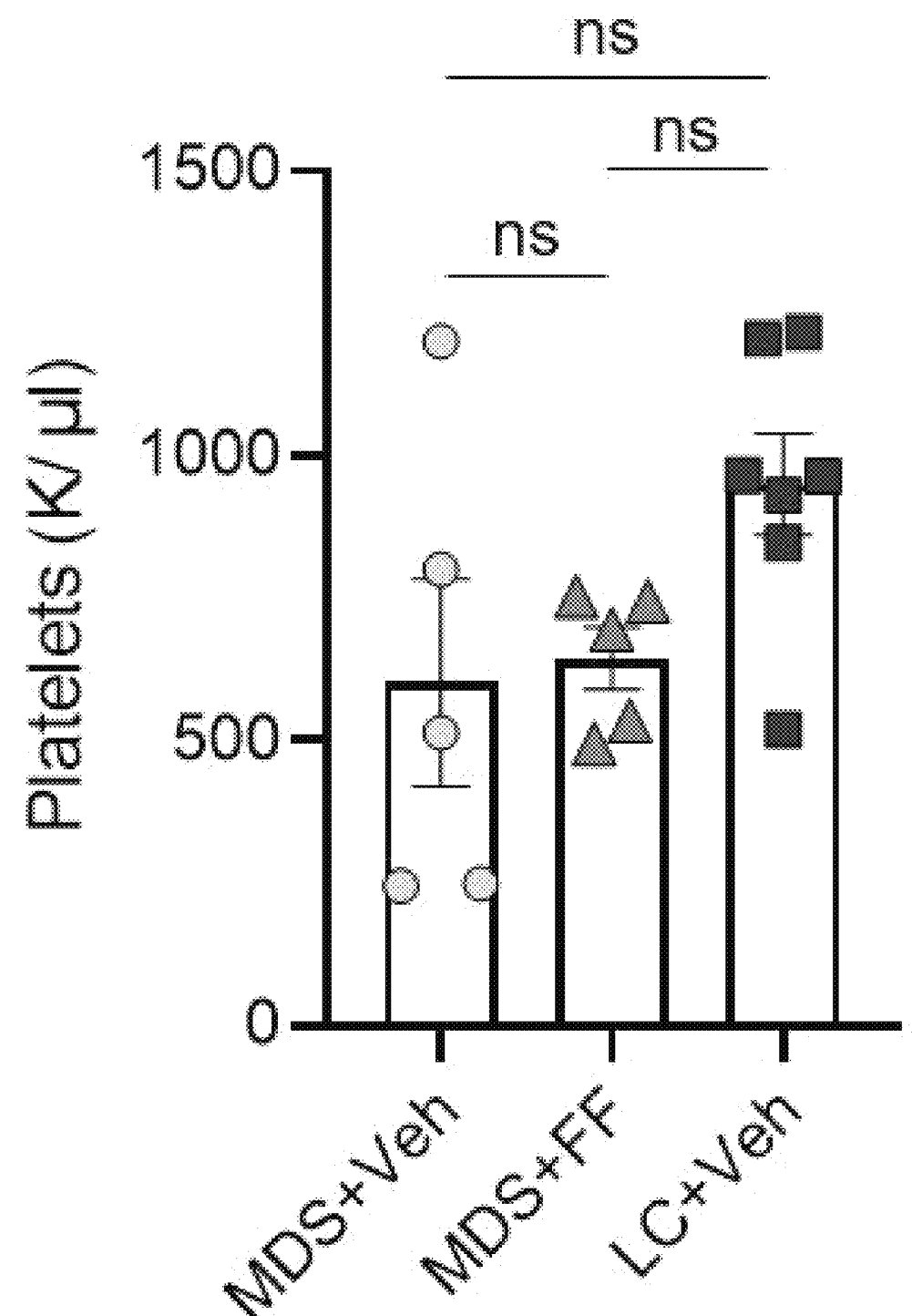
Figure 72B:
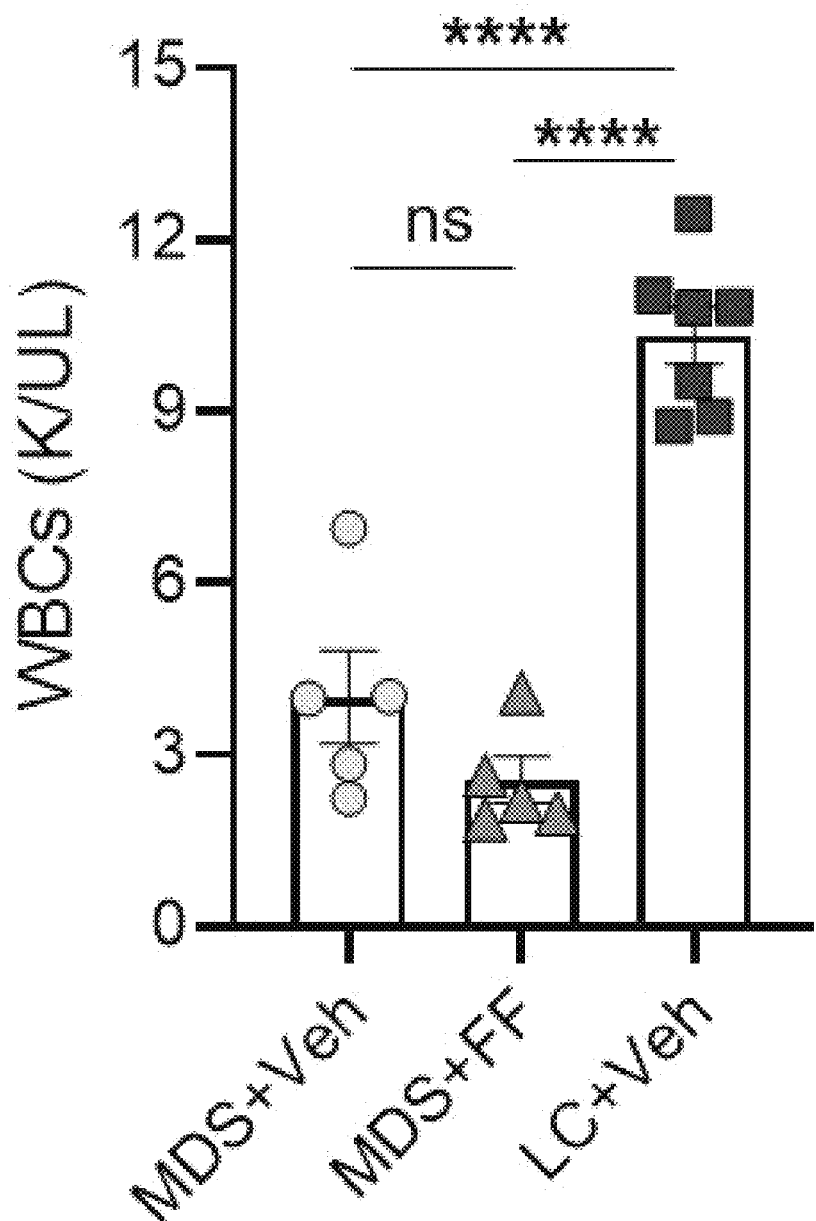
Figure 72C:
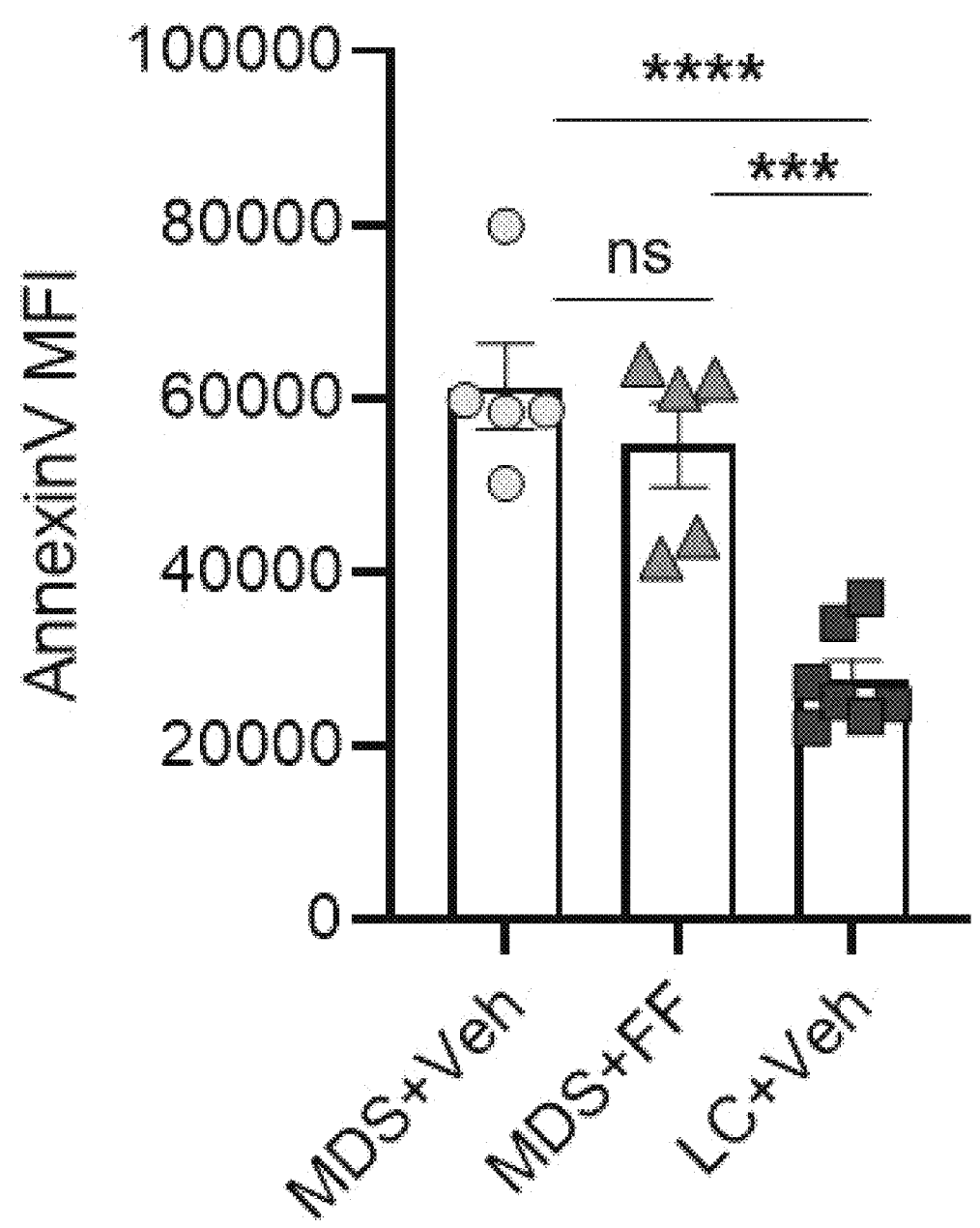

FIG. 72A-FIG. 72C show FF treatment does not affect WBC parameters in MDS/AML mice. FF treatment at a low dose of 0.3 mg/kg thrice weekly (i.p.) has no impact on (FIG. 72A) platelets and (FIG. 72B) WBCs in peripheral blood, and (FIG. 72C) apoptosis (measured by Annexin V staining) in the bone marrow of MDS/AML mice. * $p<0.001$, ** $p<0.0001$, ANOVA. n=5-7 mice per group. Veh: vehicle; LC: littermate control. ns: non-significant.

Figure 73A:
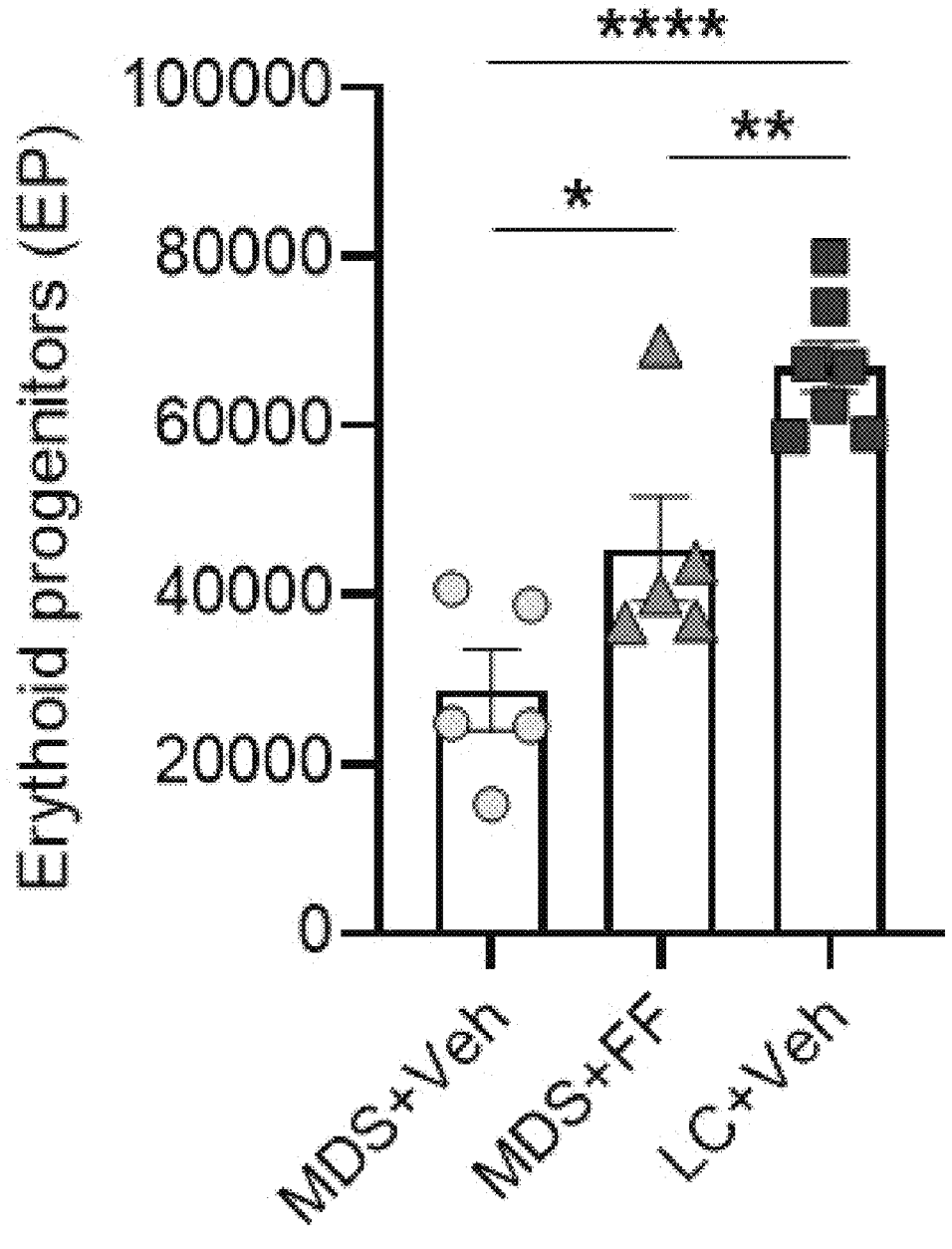
Figure 73B:
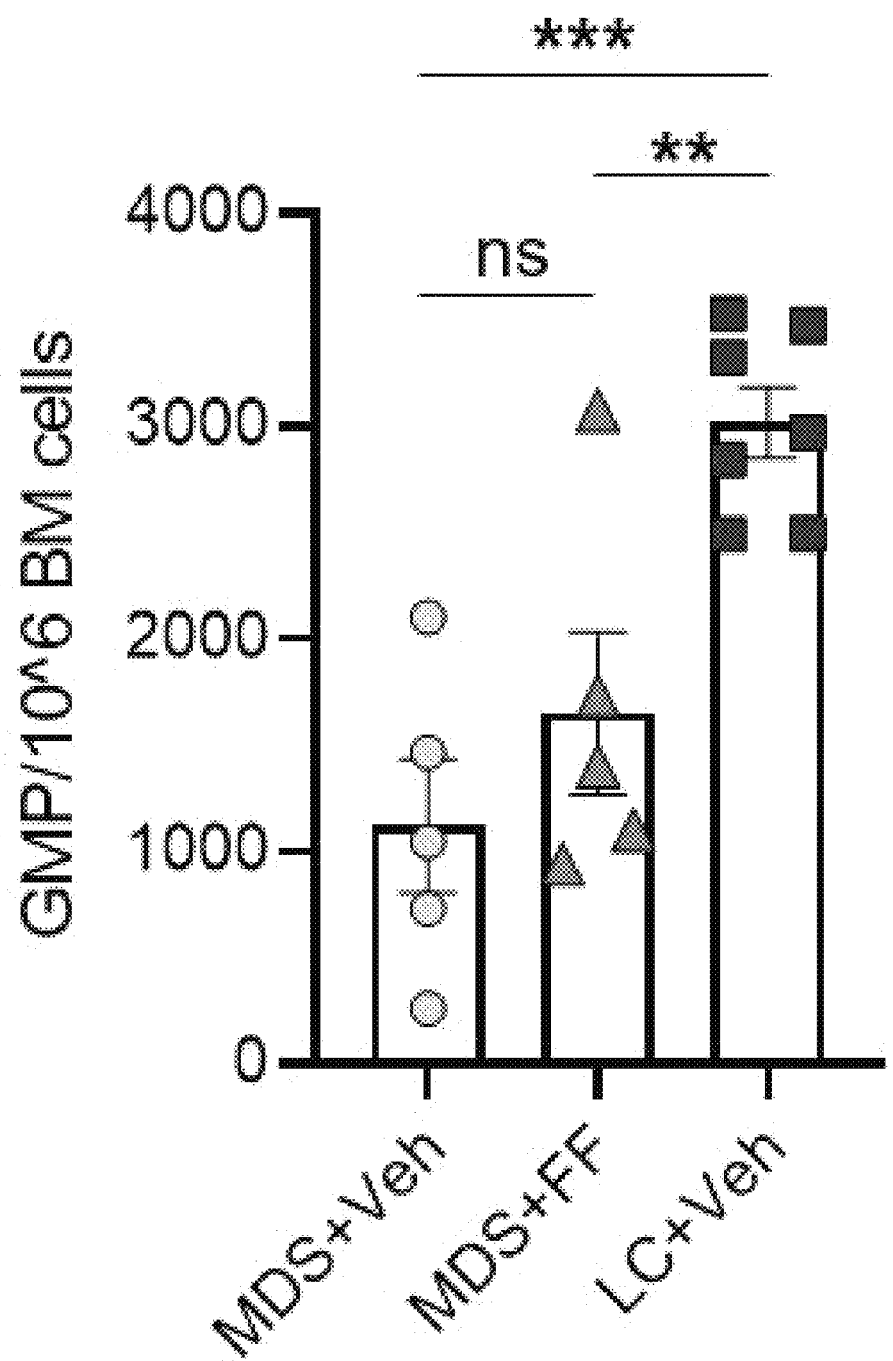
Figure 73C:
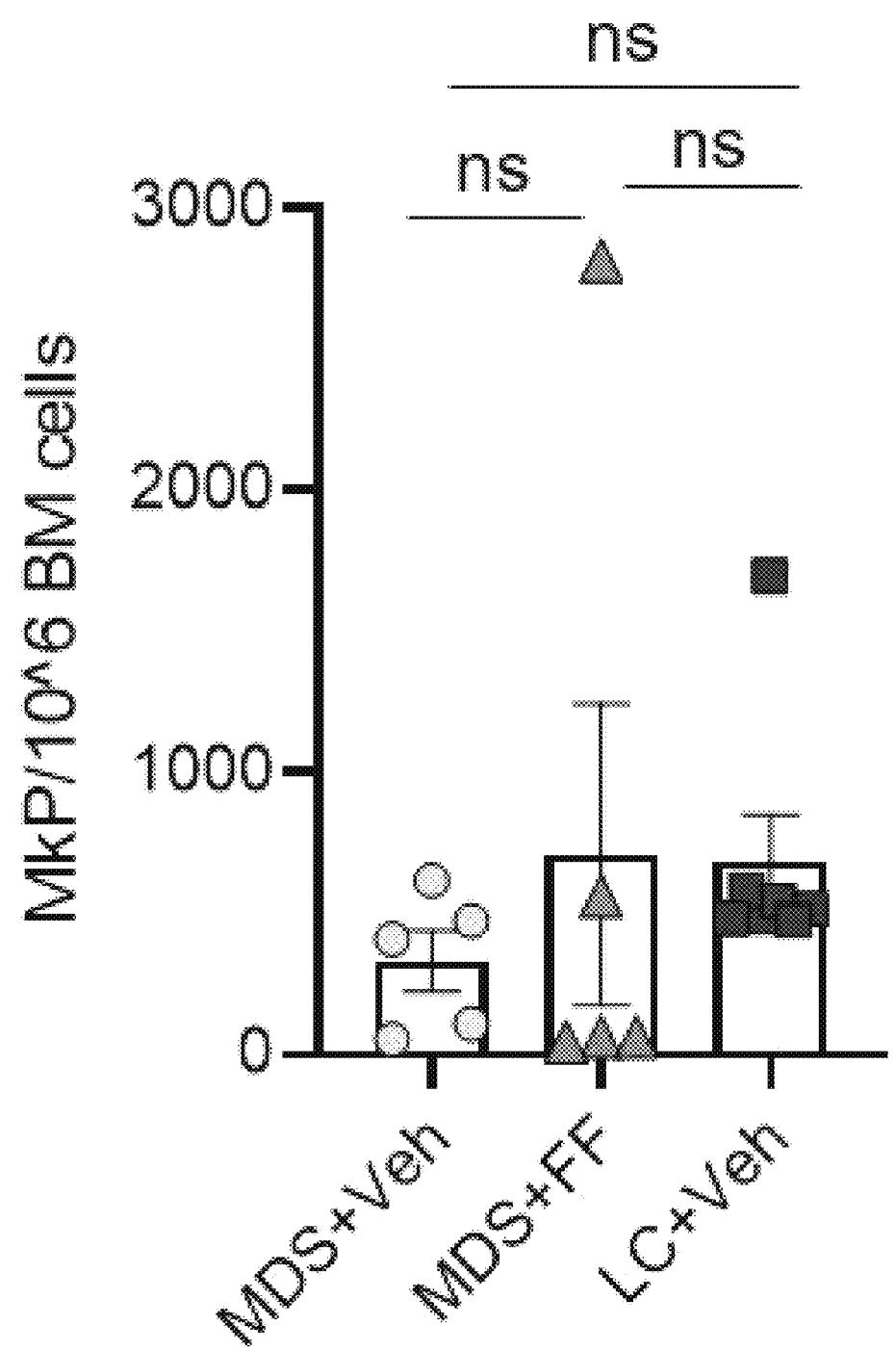

FIG. 73A-FIG. 73C show that FF treatment increases erythroid progenitors in the bone marrow of MDS/AML mice. FF treatment at a low dose of 0.3 mg/kg thrice weekly (i.p.) (FIG. 73A) elevates erythroid progenitors but does not affect (FIG. 73B) granulocytic monocytic progenitors (GMP) or (FIG. 73C) megakaryocytic progenitors (MkP) in the BM of MDS/AML mice. * $p<0.05$,  $p<0.01$, * $p<0.001$, **** $p<0.0001$, ANOVA. n=5-7 mice per group. Veh: vehicle; LC: littermate control. ns=non-significant.

Figure 74A:
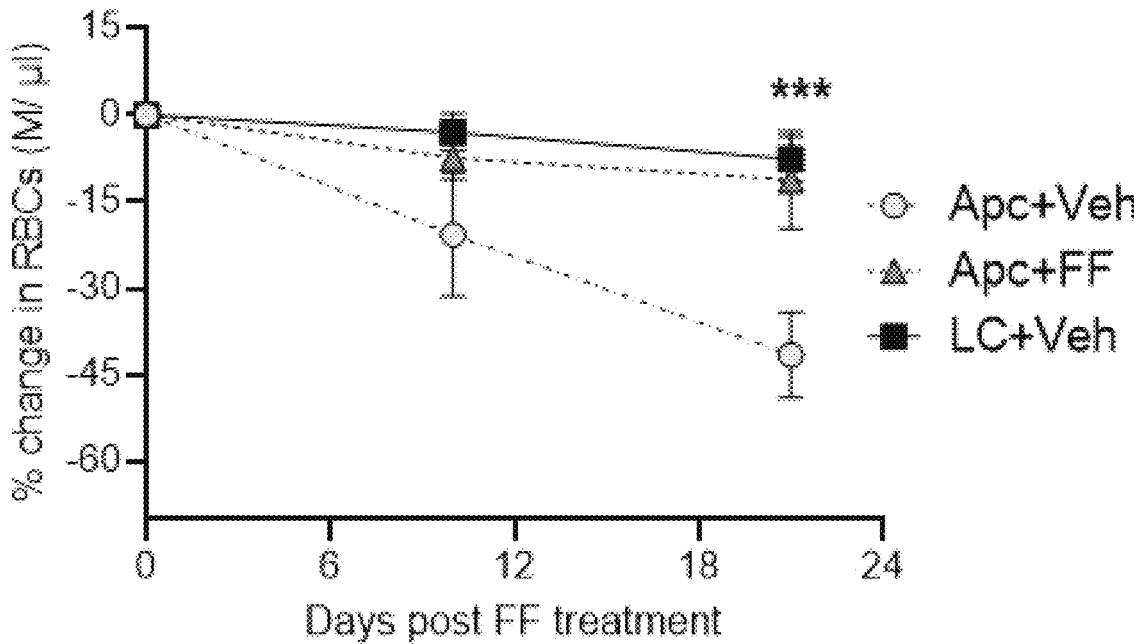
Figure 74B:
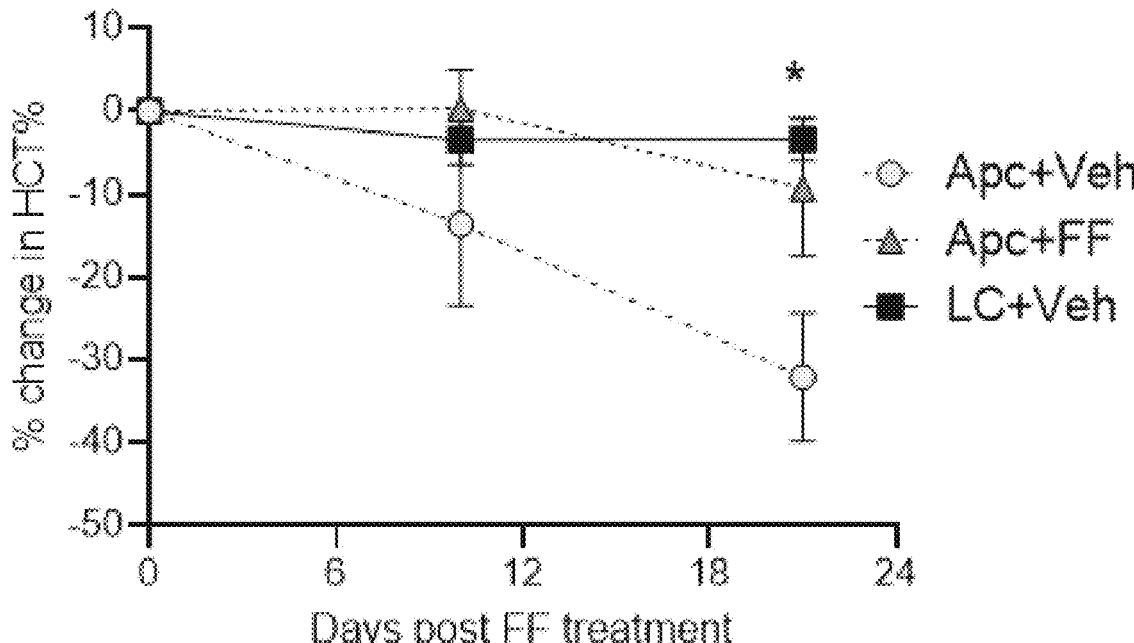
Figure 74C:
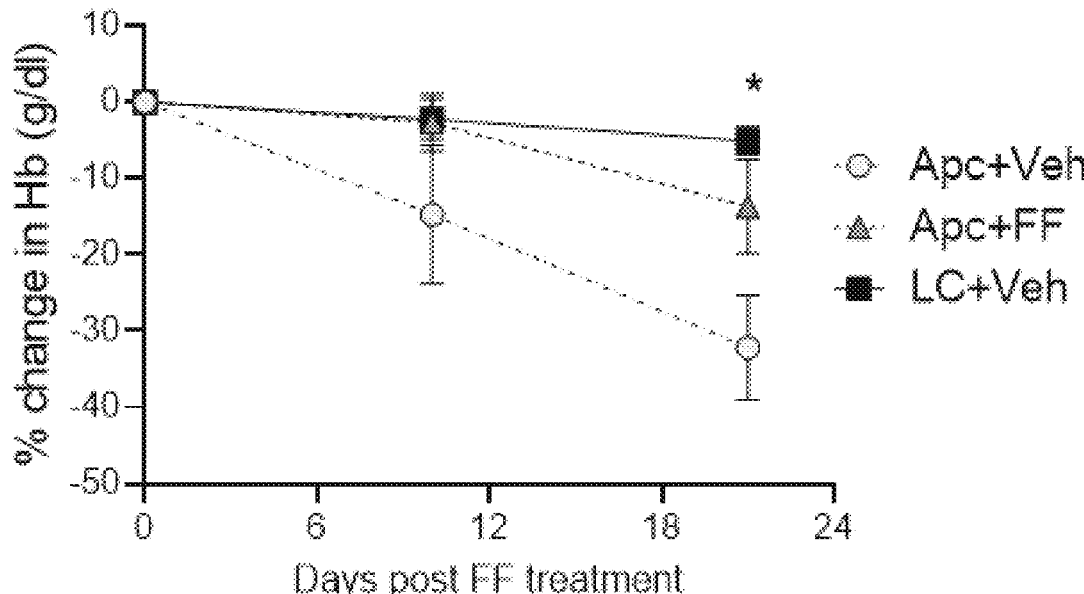

FIG. 74A-FIG. 74C show that FF (i.p.) treatment elevates RBC parameters in Apcmin mice. This is a mouse model of intestinal adenoma that develops anemia. FF treatment at a low dose of 0.3 mg/kg daily (i.p.) alleviates RBC parameters, such as (FIG. 74A) RBCs (FIG. 74B) hematocrit% (HCT%) and (FIG. 74C) hemoglobin (Hb) in Apcmin mice that spontaneously develop anemia at ~3 months age. * $p<0.05$, *** $p<0.001$, 2-way ANOVA. n=5-6 mice per group. Comparisons are shown in between Apcmin+FF versus Apcmin+Veh. Veh: vehicle; LC: littermate control mice.

Figure 75:
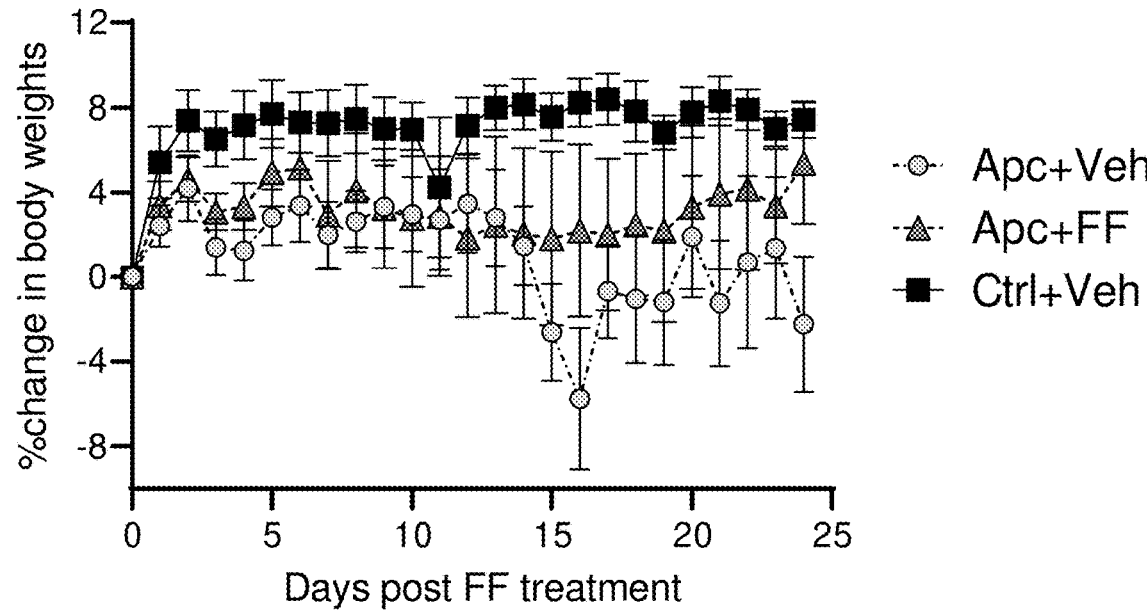

FIG. 75 shows that FF treatment modestly increases body weight in Apcmin mice. n=5-6 mice per group. Veh: vehicle; Ctrl (Control): littermate control mice.

Figure 76:
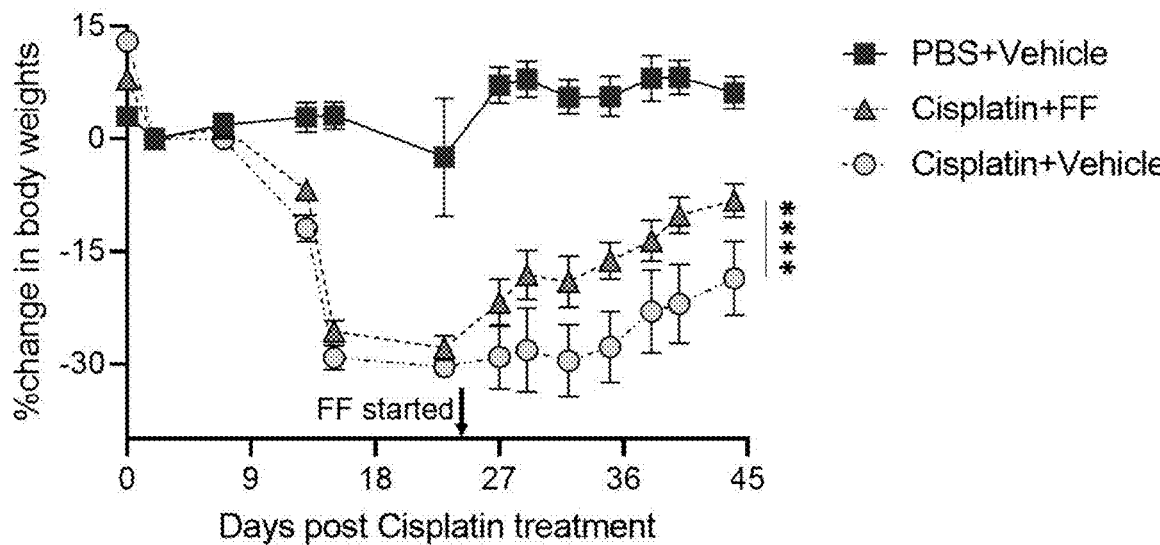

FIG. 76 shows that FF (i.p.) treatment significantly rescues (elevates) body weights in cisplatin-treated/driven chronic kidney disease (CKD) mice as compared to cisplatin+ vehicle treated mice. **** $p<0.0001$, 2-way ANOVA. n=4-5 mice per group. Comparisons are shown in between cisplatin+FF treated mice as compared to cisplatin+ vehicle treated mice.

Figure 77A:
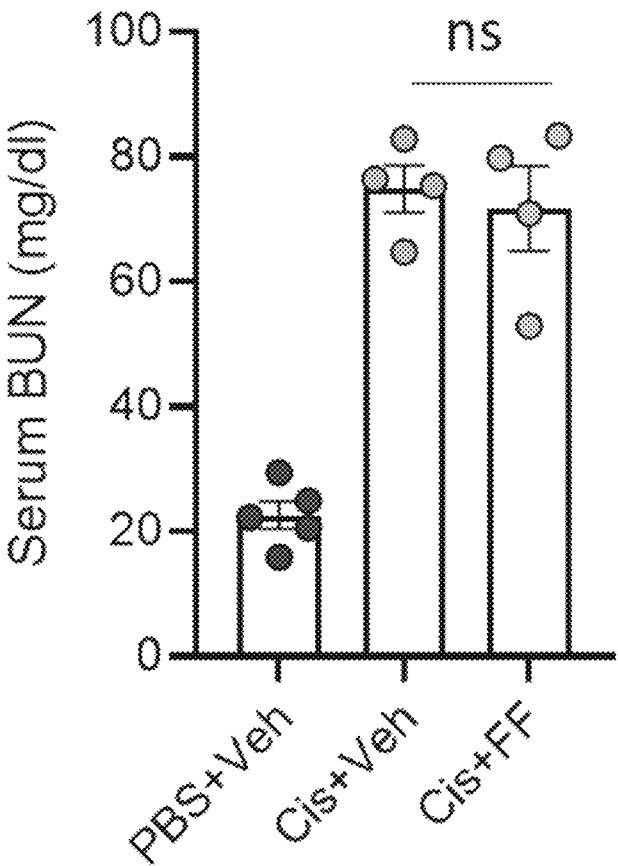
Figure 77B:
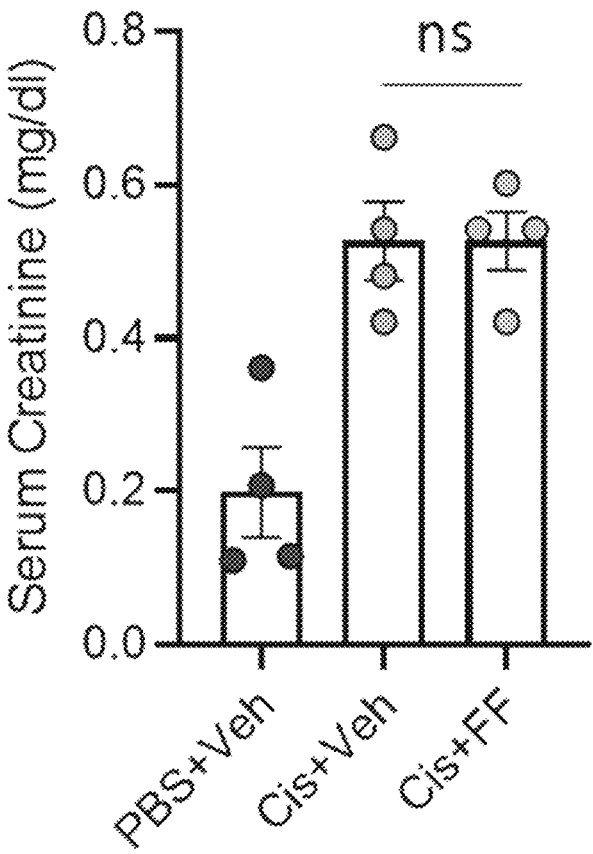

FIG. 77A-FIG. 77B show that cisplatin treatment induces chronic kidney injury (CKD) in wild-type mice. (FIG. 77A) Serum blood urea nitrogen (BUN) and (FIG. 77B) serum creatinine levels showing that cisplatin induces kidney damage characteristic of CKD in mice, and FF treatment does not affect serum BUN and creatinine levels.

Figure 78A:
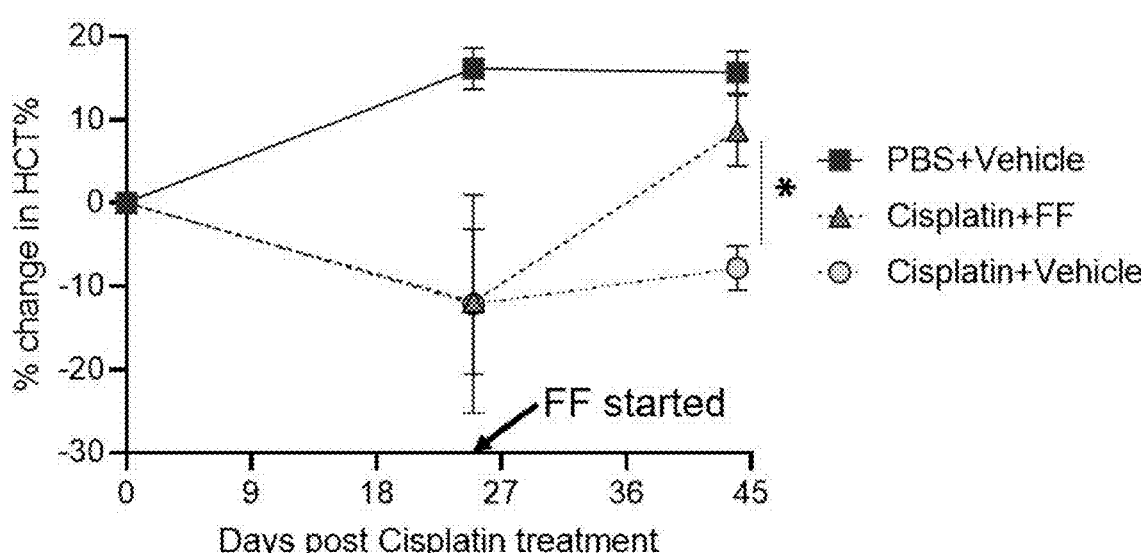
Figure 78B:
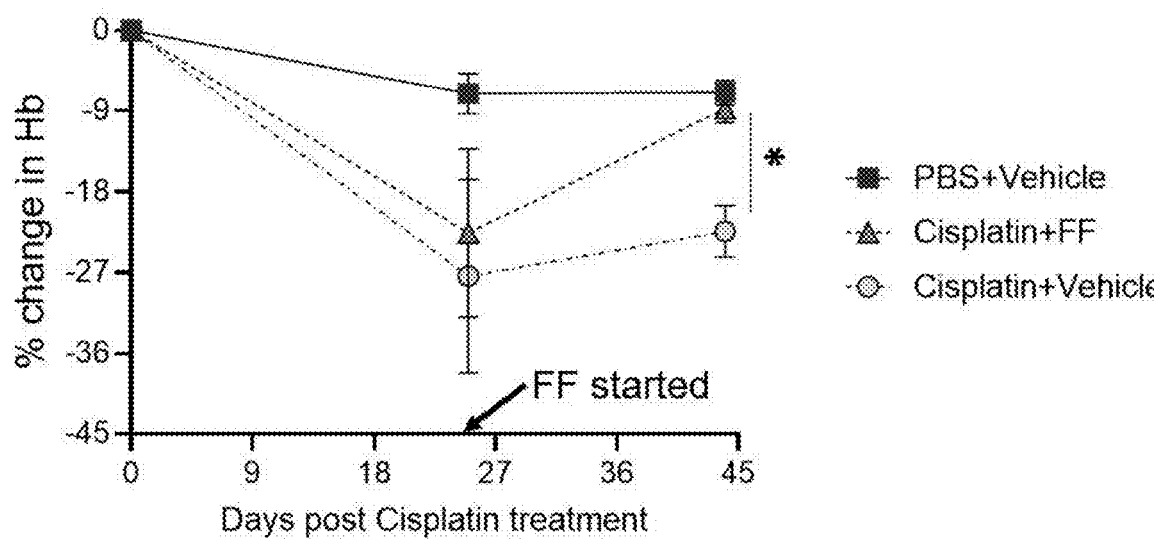
Figure 78C:
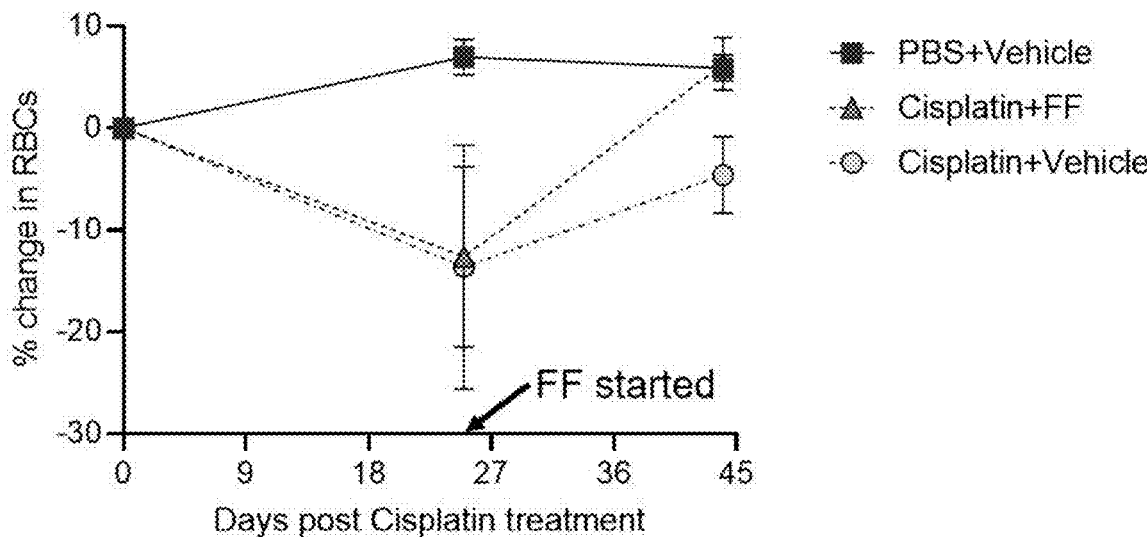

FIG. 78A-FIG. 78C show that FF treatment rescues anemia in cisplatin-treated CKD mice. FF treatment at a low dose of 0.3 mg/kg 3× weekly (i.p.) alleviates RBC parameters, such as % changes in (FIG. 78A) hematocrit% (HCT%) (FIG. 78B) hemoglobin (Hb) and (FIG. 78C) RBCs in mice with cisplatin-driven CKD. * $p<0.05$, 2-way ANOVA. n=4-5 mice per group. Comparisons are shown in between cisplatin+FF treated mice as compared to cisplatin+ vehicle treated mice.

Figure 79A:
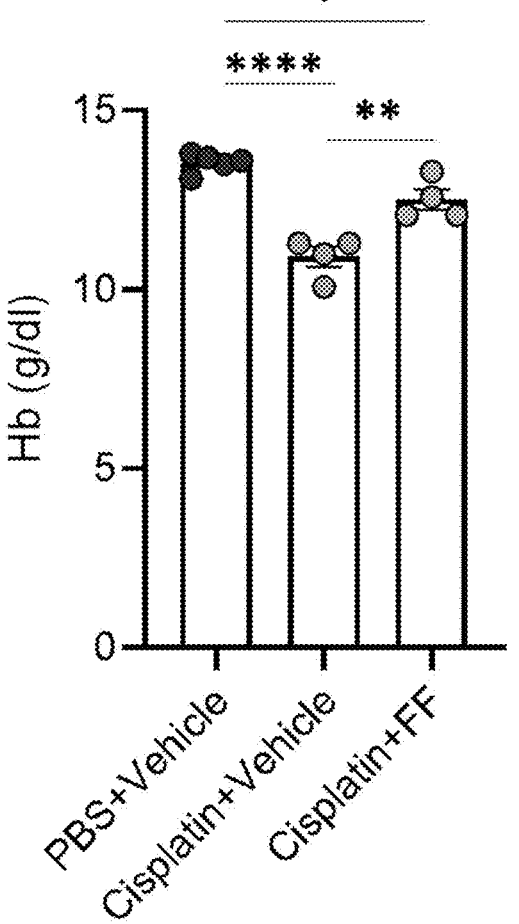
Figure 79B:
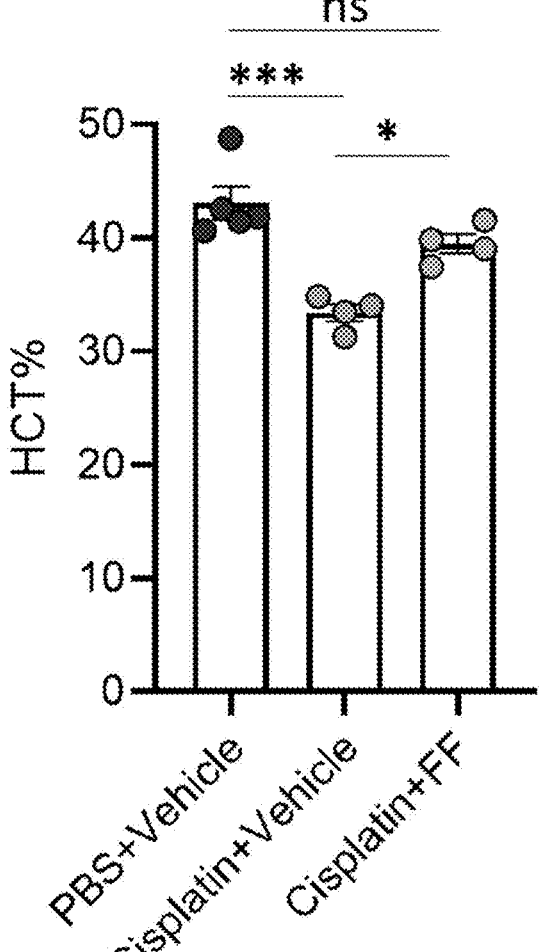
Figure 79C:
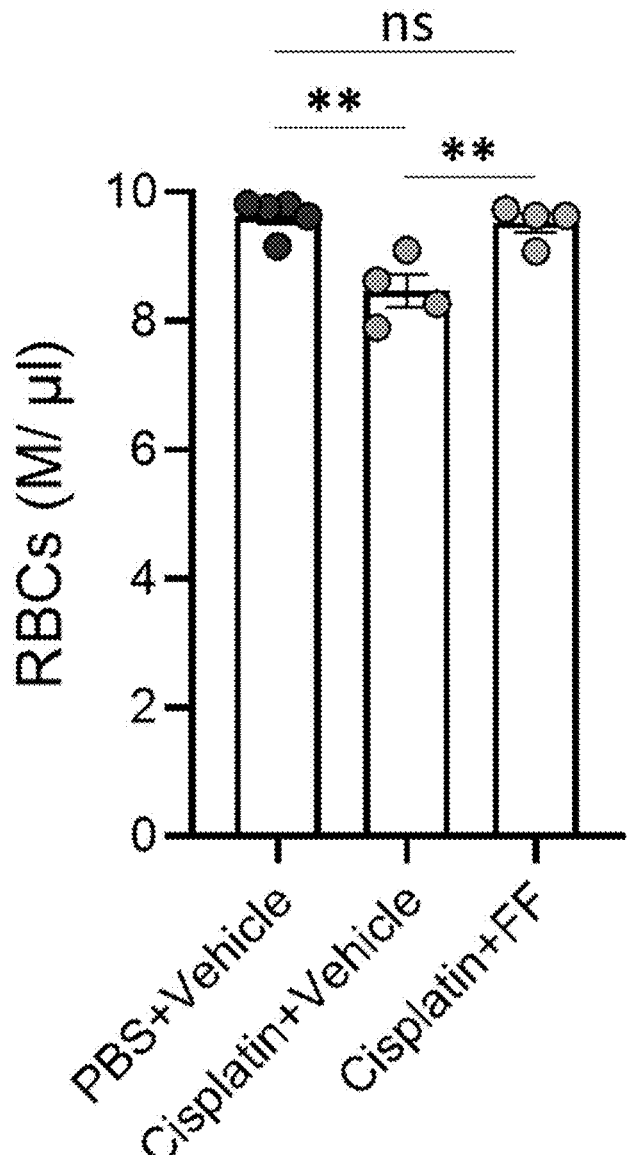

FIGS. 79A-FIG. 79C show that FF treatment elevates RBC parameters in cisplatin-treated CKD mice. FF treatment at a low dose of 0.3 mg/kg 3× weekly (i.p.) alleviates RBC parameters, such as absolute values of (FIG. 79A) hemoglobin (Hb) (FIG. 79B) hematocrit % (HCT %) and (FIG. 79C) RBCs in mice with cisplatin-driven CKD. * p<0.05,  p<0.01, * p<0.001, *** p<0.001, 2-way ANOVA. n=4-5 mice per group. ns: non-significant.

Figure 80A:
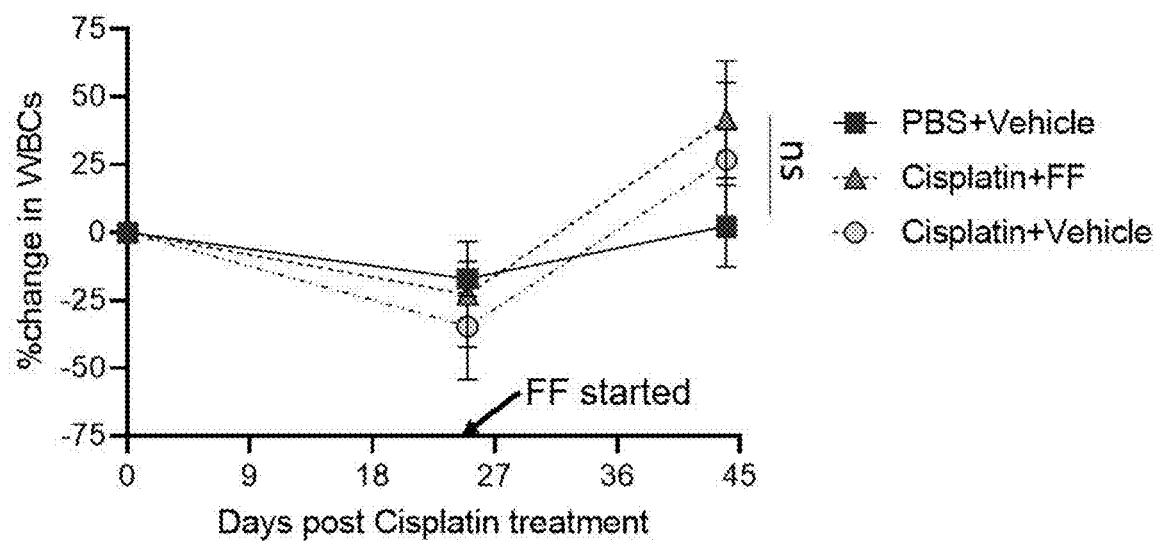
Figure 80B:
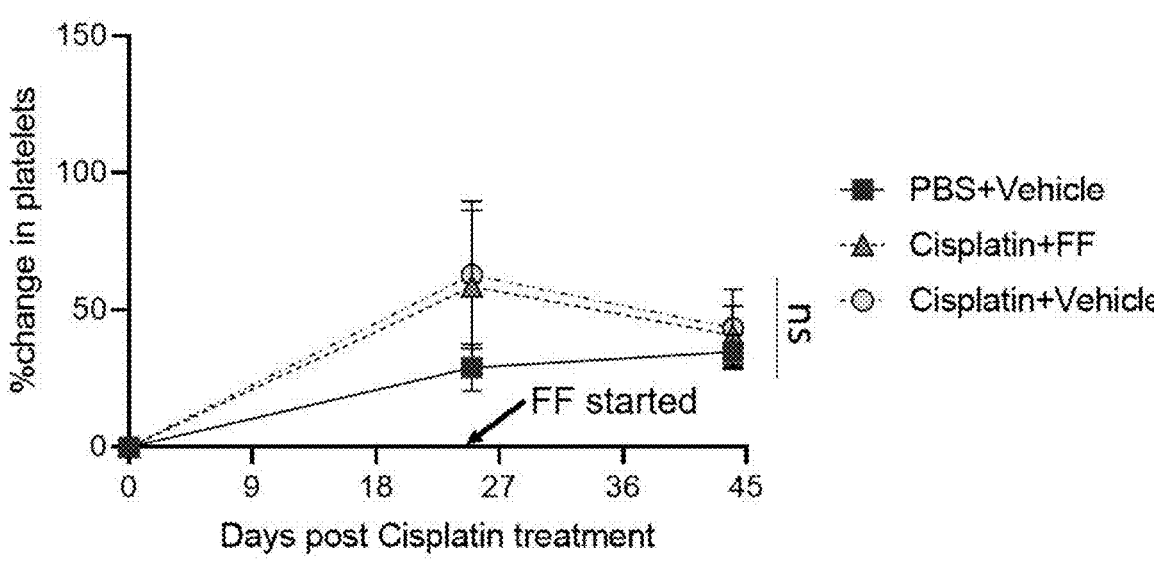

FIG. 80A-FIG. 80B show that FF treatment does not affect WBC parameters in cisplatin-treated CKD mice. FF treatment does not affect (FIG. 80A) WBCs and (FIG. 80B) platelets in mice with cisplatin-driven CKD. 2-way ANOVA. n=4-5 mice per group. Comparisons are shown in between cisplatin+ FF treated mice as compared to cisplatin+ vehicle treated mice. ns: non-significant.

Figure 81A:
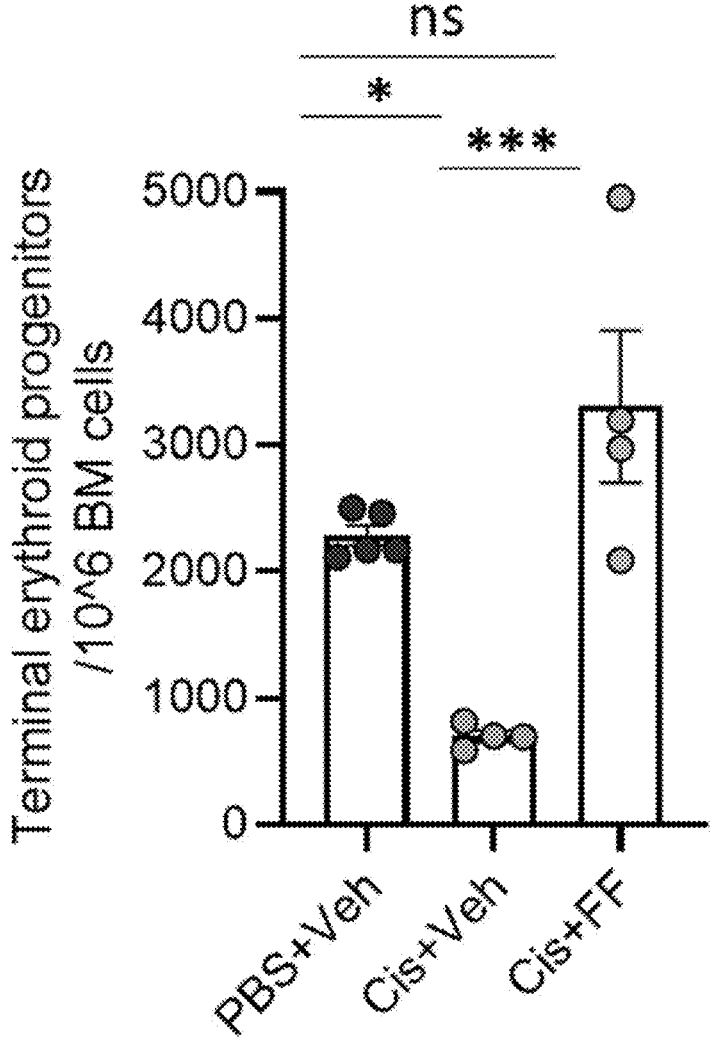
Figure 81B:
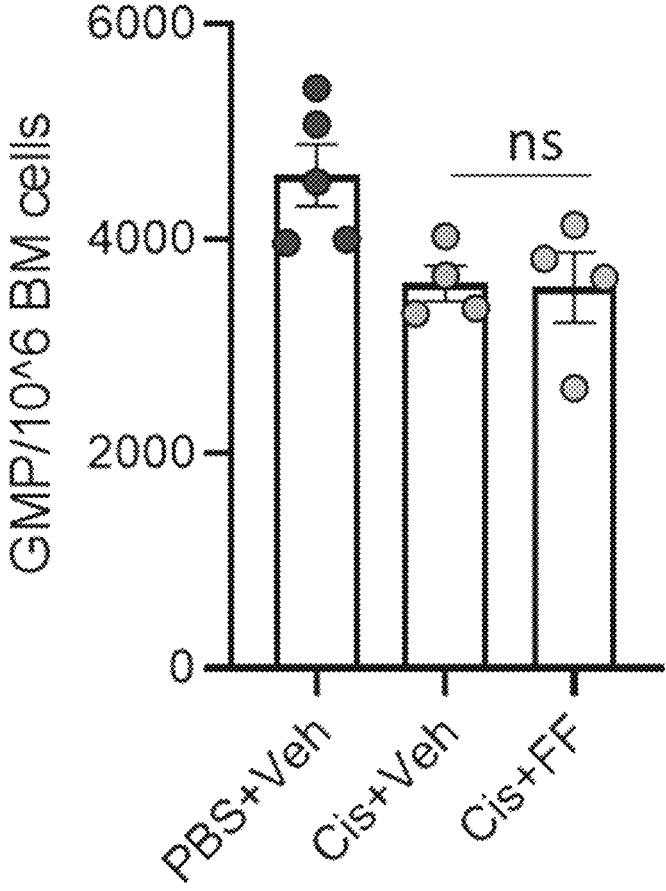
Figure 81C:
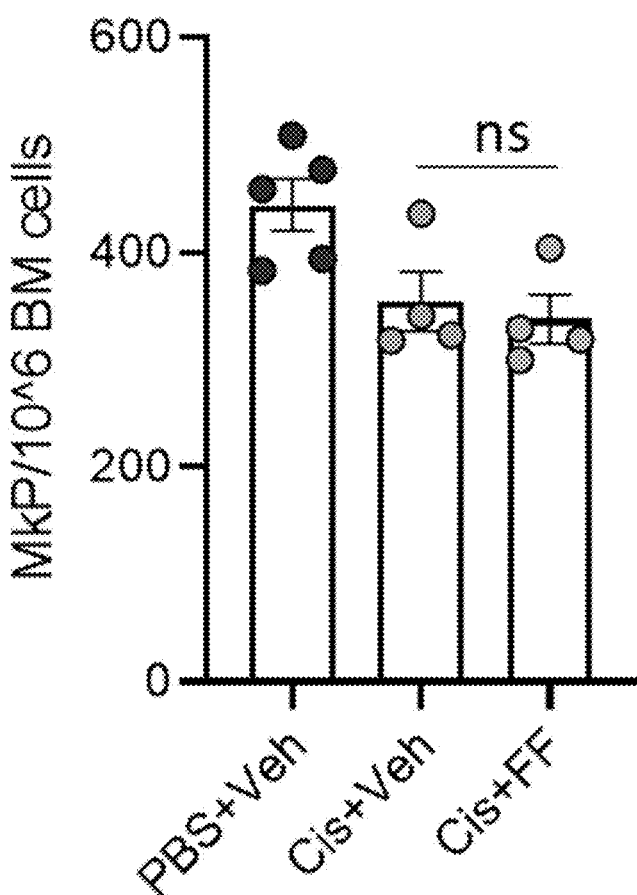

FIG. 81A-FIG. 81C show that FF treatment elevates erythroid progenitors in cisplatin-treated CKD mice. FF treatment at a low dose of 0.3 mg/kg 3× weekly (i.p.) elevates (FIG. 81A) terminal erythroid progenitors, but not (FIG. 81B) granulocytic monocytic progenitors (GMP) or (FIG. 81C) megakaryocytic progenitors (MkP) in the BM of mice with cisplatin-driven CKD. * p<0.05, *** p<0.001, 2-way ANOVA. n=4-5 mice per group. Comparisons are shown in between cisplatin+FF treated mice and cisplatin+ vehicle treated mice. ns: non-significant.

Figure 82A:
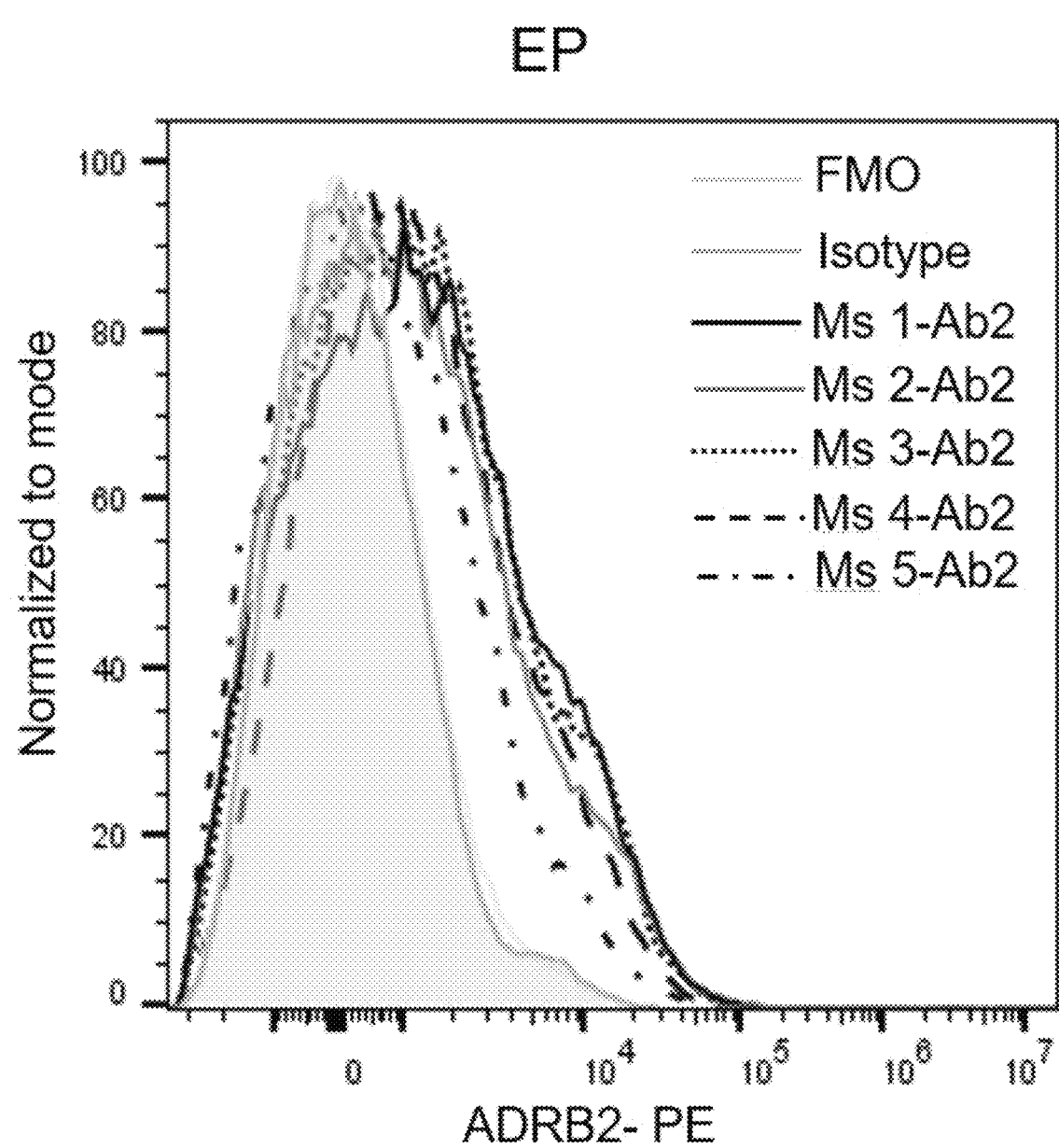
Figure 82B:

FIG. 82A-FIG. 82B show that ADRB2 surface expression is higher on erythroid progenitors (EP) than on non-erythroid progenitors (non-EP) in WT mice. ADRB2 is expressed on the surface of erythroid progenitors in the bone marrow of wild-type mice. FIG. 82A shows a flow plot depicting expression of ADRB2 on the surface of erythroid progenitors (EP). FIG. 82B shows a flow plot depicting minimal expression of ADRB2 on the surface of non-erythroid bone marrow (BM) progenitors (Non-EP). Ms-1-5: Mouse 1-Mouse 5; Ab: antibody against ADRB2.

Figure 83:
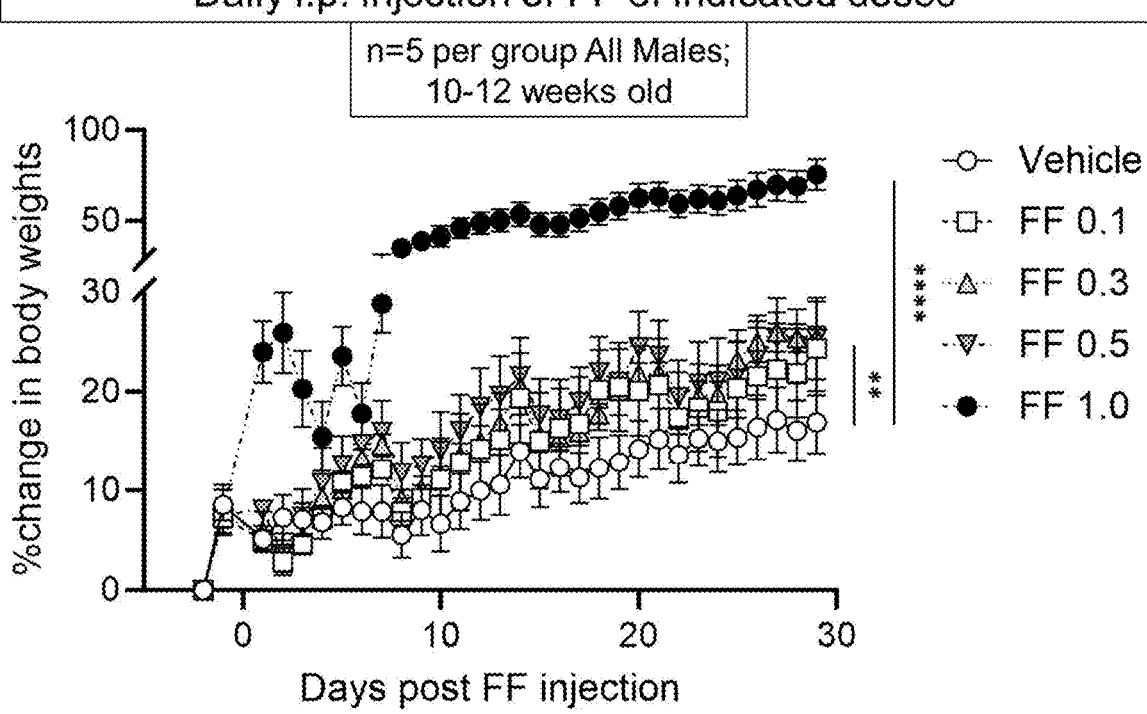

FIG. 83 shows that the FF treatment in naive mice increases body weights in a dose-dependent manner. Graph showing % change in body weights of mice with vehicle or FF treatment at 0.1/0.3/0.5/1.0 mg/kg doses.  p<0.01, ** p<0.0001, "ns"=non-significant.

Figure 84A:
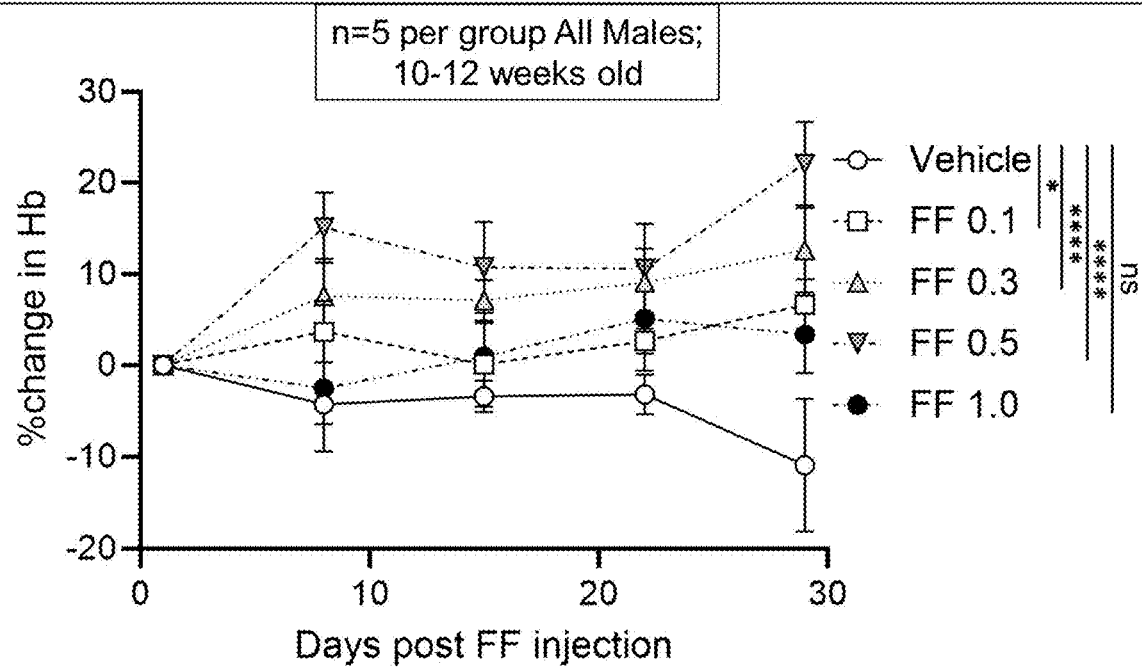
Figure 84B:
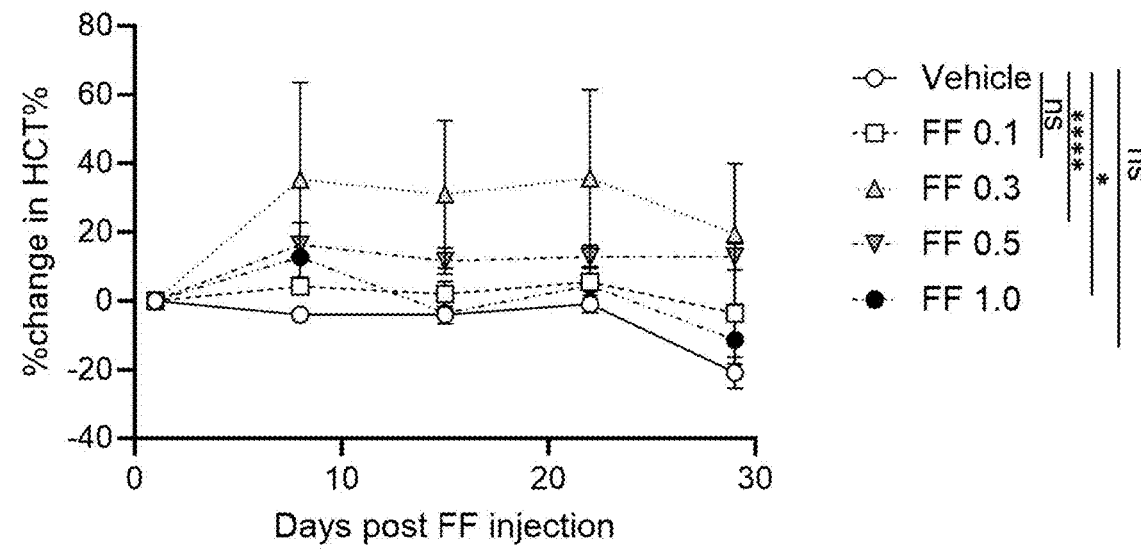
Figure 84C:
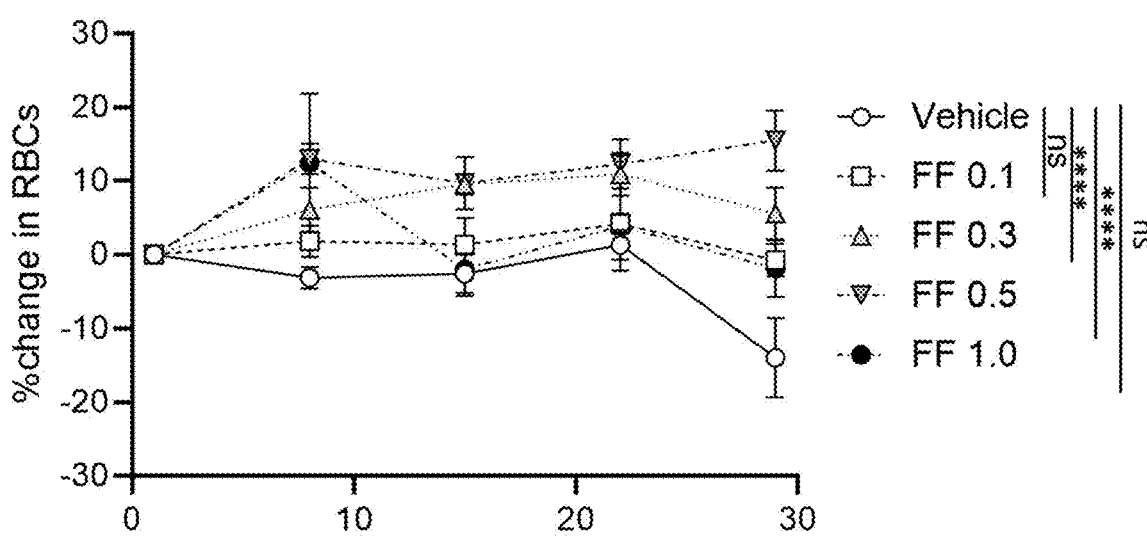

FIG. 84A-FIG. 84C show that the FF treatment in naive mice has a dose-dependent effect on red blood cell (RBC) parameters in wild-type mice (10-12 week old male mice). FF treatment at 0.3 and 0.5 mg/kg doses enhance and sustain RBC parameters, but this effect is not observed at the highest dose of 1.0 mg/kg for each of the following RBC parameters in the peripheral blood: (FIG. 84A) hemoglobin (Hb), (FIG. 84B) hematocrit (HCT)%, and (FIG. 84C) RBC numbers. * p<0.05,  p<0.01, * p<0.001, **** P<0.0001, "ns"=non-significant, one-way and two-way ANOVA. n=5 male mice per group. All comparisons were done w.r.t. vehicle (DMSO) treated controls.

Figure 85A:
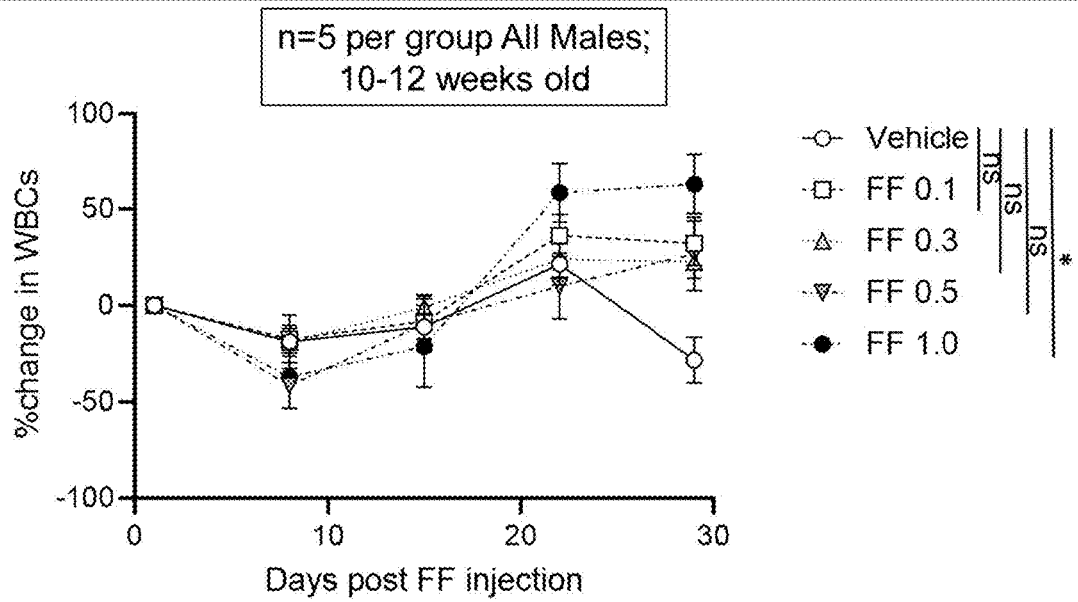
Figure 85B:
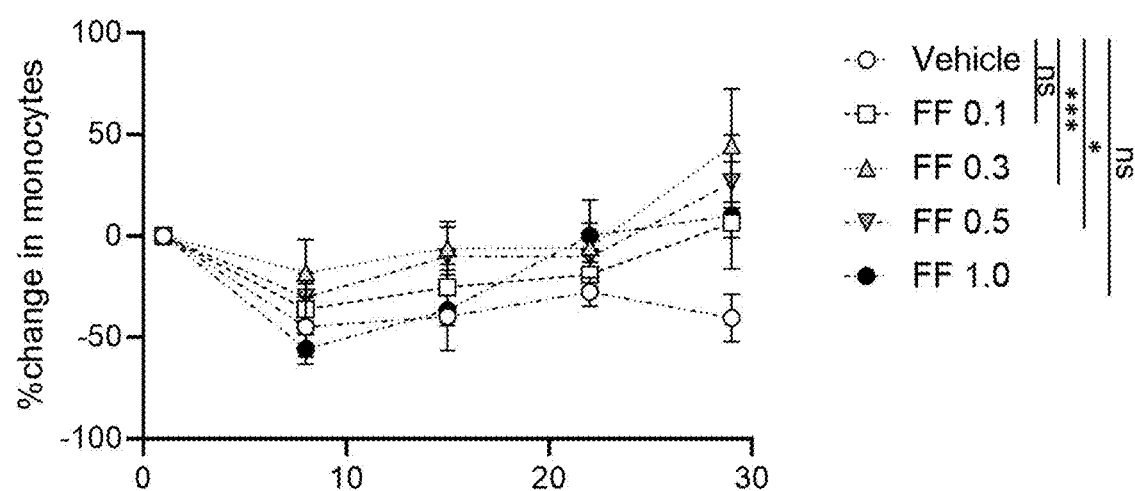
Figure 85C:
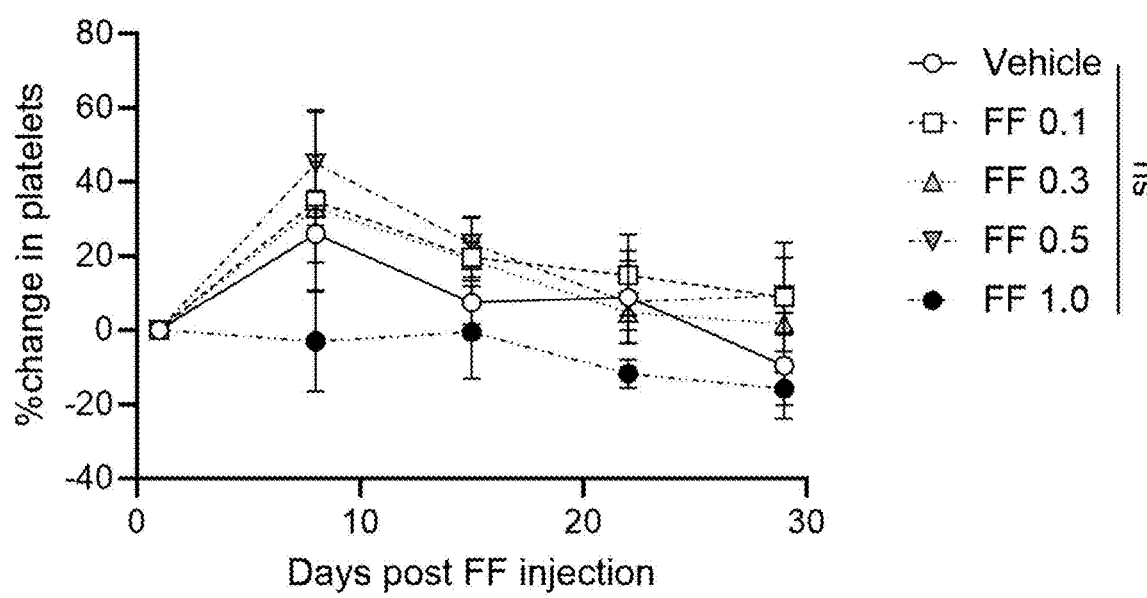

FIG. 85A-FIG. 85C show that the FF treatment in naive mice has modest dose-dependent effects on total white blood cells (non-RBC) parameters in wild-type mice (10-12 week old male mice). FF administration does not influence (FIG. 85A) white blood count (WBC) numbers at the lowest doses and modestly impacts WBC at the highest dose of 1.0 mg/kg. Conversely, FF treatment modestly impacts monocyte counts in the peripheral blood of naive mice (FIG. 85B) at doses of 0.3 and 0.5 mg/kg, but not at the lowest dose (0.1 mg/kg) or highest dose (1.0 mg/kg). No significant effect was observed on platelets at any dose tested. * p<0.05,  p<0.01, * p<0.001, **** p<0.0001, "ns"=non-significant, one-way and two-way ANOVA. n=5 male mice per group. All comparisons were done with respect to vehicle (DMSO) treated controls.

Figure 86:
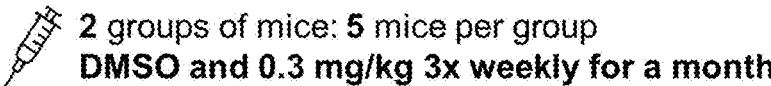
Figure 86:
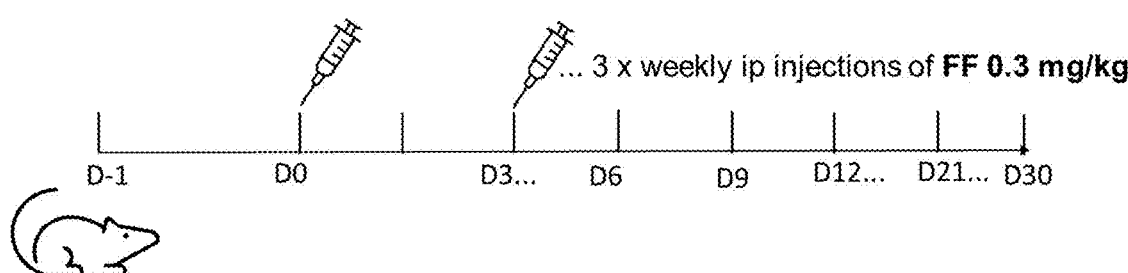

FIG. 86 shows an example work-flow of a bulk RNA sequencing for formoterol fumarate (FF) treated mice.

Figure 87B:
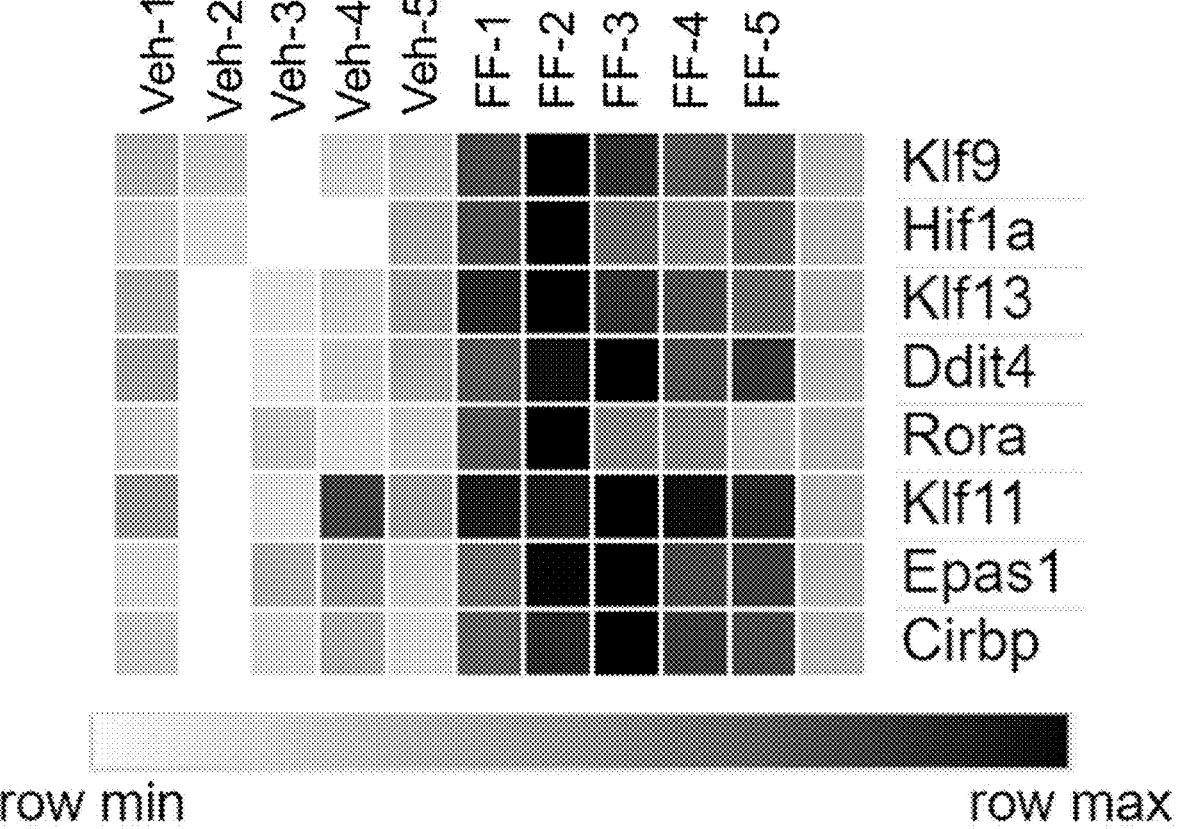

FIG. 87A-B show differential gene expression in erythroid progenitors isolated from bone marrow from FF-treated vs vehicle treated mice with a table showing the change in expression of various genes listed in the last column (FIG. 87A) and a heatmap of changes in gene expression (FIG. 87B).

Figure 88A:
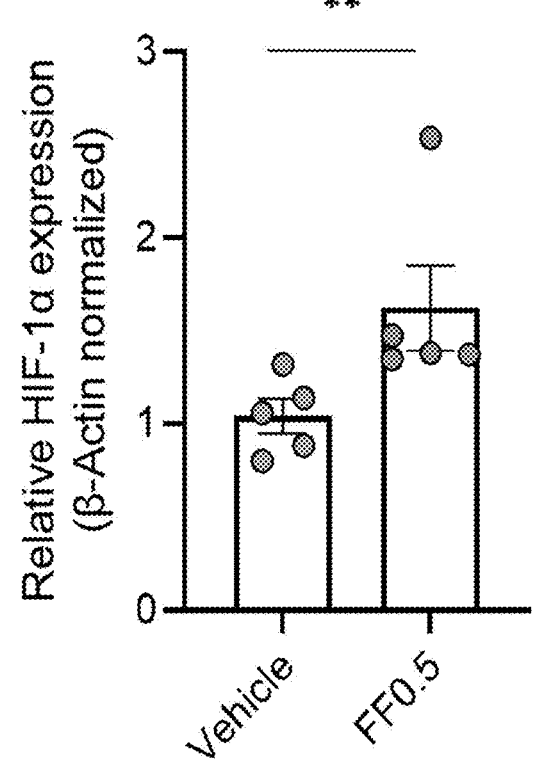
Figure 88B:
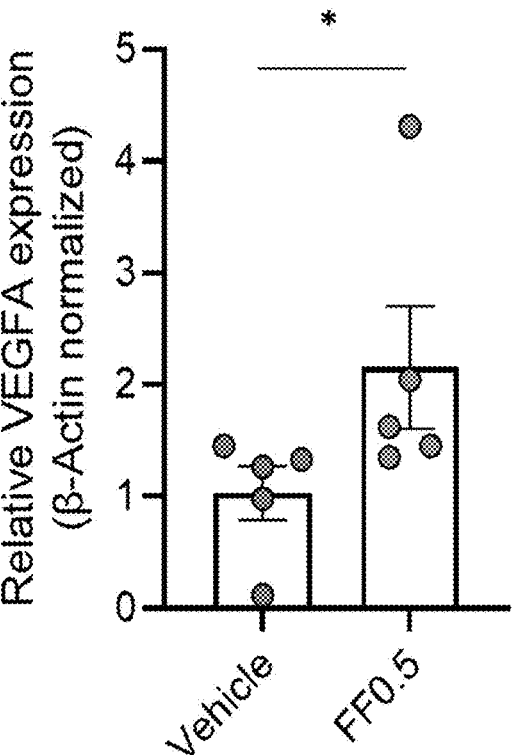

FIG. 88A-B show that FF 0.5mg/kg ip treatment 3× weekly enhances HIF-1α expression (FIG. 88A) and VEGFA expression (FIG. 88B) in bone marrow cells as compared to vehicle-treated mice. * p<0.05, ** p<0.01, nonparametric Mann-Whitney test. Data represented as mean±SEM. All comparisons are done with respect to Vehicle (DMSO-treated).

DETAILED DESCRIPTION OF THE INVENTION

In some aspects, provided herein are methods of treating anemia in a patient in need thereof, the method comprising administering to the patient in need thereof an effective amount of formoterol or a pharmaceutically acceptable salt thereof (e.g., formoterol fumarate or arformoterol tartrate). In some aspects, provided herein are methods of promoting differentiation of an erythroid progenitor cell toward a mature red blood cell in a patient in need thereof, comprising administering an effective amount of formoterol or a pharmaceutically acceptable salt thereof (e.g., formoterol fumarate or arformoterol tartrate). In some embodiments, the methods may further comprise administering to the patient in need thereof an effective amount of an erythropoiesis-stimulating agent. In some aspects, provided herein are methods of treating anemia in a patient in need thereof, comprising administering to the patient in need thereof an effective amount of formoterol or a pharmaceutically acceptable salt thereof (e.g., formoterol fumarate or arformoterol tartrate) conjointly with an erythropoiesis-stimulating agent, wherein the anemia is refractory to the erythropoiesis-stimulating agent (such as erythropoietin, epoetin alfa, epoetin beta, epoetin omega, epoetin zeta, or darbepoetin alfa). In some embodiments, formoterol or a pharmaceutically acceptable salt thereof (e.g., formoterol fumarate or arformoterol tartrate) may be administered conjointly with other FDA-approved drugs such as luspatercept, lenalidomide and/or a hypomethylating agent, such as azacitidine or decitabine.

In some embodiments, formoterol or a pharmaceutically acceptable salt thereof (e.g., formoterol fumarate or arformoterol tartrate) is provided herein for use in treating anemia in a patient. In some embodiments, provided herein are uses of formoterol or a pharmaceutically acceptable salt thereof (e.g., formoterol fumarate or arformoterol tartrate) in the manufacture of a medicament for the treatment of anemia in a patient. In some embodiments, provided herein are pharmaceutical compositions comprising formoterol or a pharmaceutically acceptable salt thereof (e.g., formoterol fumarate or arformoterol tartrate) for use in the treatment of anemia in a patient.

In some embodiments, the anemia is selected from the group consisting of macrocytic anemia, hemolytic anemia, anemia caused by a ribosomopathy, anemia caused by insufficiency of serine/threonine-protein kinase RIOK2, anemia associated with chronic kidney disease (CKD), anemia caused by one or more mutations and/or deletions in human chromosome 5 or in an ortholog thereof, anemia caused by chromosomal translocations in the NUP98 gene or in an ortholog thereof, such as anemia caused by fusions of NUP98 with Abd-B group HOX genes (e.g., HOXD13), stress-induced anemia, anemia secondary to an intestinal cancer, Diamond Blackfan anemia, aplastic anemia, Schwachman-Diamond syndrome, an anemia associated with an inflammatory disease, such as rheumatoid arthritis or multiple sclerosis, anemia associated with a bone marrow failure syndrome and anemia secondary to chemotherapy in cancer patients. In some embodiments, the anemia is associated with a cancer, optionally wherein the cancer is a hematologic malignancy, such as a myelodysplastic syndrome (MDS), acute myeloid leukemia (AML), or any hematologic malignancy disclosed herein.

In some aspects, methods and uses disclosed herein enhance erythropoiesis in MDS patient-derived bone marrow cells and therefore improve erythroid differentiation defects in hematological malignancies such as acute myeloid leukemia and other diseases disclosed herein, such as bone marrow failure disorders, including but not limited to Diamond-Blackfan anemia and aplastic anemia.

In some embodiments, methods and uses disclosed herein further have an effect of increasing bodyweight in a patient. In some embodiments, methods and uses disclosed herein are useful for treating a patient is afflicted by an anemia associated with weight loss (e.g., anemia associated with a cancer disclosed herein). In some embodiments, methods and uses disclosed herein are useful for treating a patient is afflicted by an anemia associated with decreased bone density (e.g., anemia associated with a cancer disclosed herein). In some embodiments, methods and uses disclosed herein are useful for treating a patient is afflicted by an anemia associated with muscle wasting (e.g., anemia associated with a cancer disclosed herein).

In some aspects, the disclosure provides herein new uses of formoterol or a pharmaceutically acceptable salt thereof (e.g., formoterol fumarate or arformoterol tartrate) for oral administration for treatment of anemia as described further herein.

I. Definitions

The articles "a" and "an" are used herein to refer to one or to more than one (i.e. to at least one) of the grammatical object of the article. By way of example, "an element" means one element or more than one element.

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features.

Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., myelomas like multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), myeloma, multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "erythroid progenitor cell" refers to the hematopoietic stem cell-derived progenitor cell that gives rise to erythrocytes (red blood cells) after terminal differentiation.

As used herein, the term "anemia" includes macrocytic anemia, hemolytic anemia, anemia associated with inflammation such as chronic kidney disease (CKD) and other inflammatory diseases such as autoimmune disorders (e.g., rheumatoid arthritis or multiple sclerosis), anemia caused by insufficiency of serine/threonine-protein kinase RIOK2, anemia caused by one or more mutations and/or deletions in human chromosome 5 or in an ortholog thereof, anemia caused by chromosomal translocations in the NUP98 gene or in an ortholog thereof, such as anemia caused by fusions of NUP98 with Abd-B group HOX genes (e.g., HOXD13), stress-induced anemia, aplastic anemia, anemia secondary to an intestinal cancer, Diamond Blackfan anemia, Schwachman-Diamond syndrome or anemia secondary to chemotherapy treatment in cancer patients. The anemia may be an anemia associated with a cancer, optionally wherein the cancer is a hematologic malignancy (e.g., myelodysplastic syndromes (MDS), acute myeloid leukemia (AML), chronic lymphocytic leukemia (CLL) or multiple myeloma (MM)). The anemia may be an anemia associated with an intestinal cancer, such as a colorectal cancer. For example, the anemia may be the result of intestinal adenoma caused by familial adenomatous polyposis (FAP). Adenomatous polyposis coli (APC) is a tumor suppressor gene mutated in colorectal cancers. Alterations in the APC gene generate truncated gene products, leading to activation of the Wnt signaling pathway and deregulation of multiple other cellular processes contributing to tumorigenesis. For more details, please see Su et al. Multiple intestinal neoplasia caused by a mutation in the murine homolog of the APC gene. Science. 1992 May 1;256(5057):668-70 and Moser et al. A dominant mutation that predisposes to multiple intestinal neoplasia in the mouse. Science. 1990 Jan. 19;247(4940):322-4. The anemia may be an anemia associated with a bone marrow failure disorder. The anemia may be an anemia caused or associated with a ribosomopathy. As used herein "ribosomopathies" are diseases caused by defects in ribosomal constituents or in factors with a role in ribosome assembly that trigger defects in ribosome biogenesis. Congenital ribosomopathies display a paradoxical transition from early symptoms due to cellular hypo-proliferation to an elevated cancer risk later in life. More details re: ribosomopathies can be found in Kim R Kampen et al. (2020). *Nucleic Acids Res.* 48(3): 1013-1028. Mutations that disrupt ribosome biogenesis often affect tissues that rely on cell division for their function. Many ribosomopathies have an anemia component, as blood cell production from the bone marrow relies heavily on cell division. Examples of ribosomapthaies include, but are not limited to, Diamond-Blackfan anemia (DBA), 5q-syndrome, Schwachman-Diamond syndrome (SDS), X-linked dyskeratosis congenita (DC), Cartilage-hair hypoplasia (CHH), Treacher-Collins syndrome (TCS), Bowen-Conradi syndrome, and North American Indian childhood cirrhosis.

As used herein, myelodysplastic syndromes (MDS), include, but are not limited to, a heterogeneous group of myeloid neoplasms, which are characterized in common by manifestations of bone marrow failure with abnormal cell morphology and, in some cases, a propensity to acute myeloid leukemia (AML). In some instances, MDS is caused by mutations or deletions on human chromosome 5 or chromosomal translocations in the NUP98 gene (e.g., translocations leading to fusions of NUP98 with Abd-B group HOX genes (e.g., HOXD13)). For more details regarding chromosomal translocations in the NUP98 gene, please see Lin et al. NUP98-HOXD13 transgenic mice develop a highly penetrant, severe myelodysplastic syndrome that progresses to acute leukemia. Blood. 2005 Jul. 1;106(1):287-95.

The term "patient"refers to a human suffering from anemia.

As used herein, the phrase "conjoint administration" refers to any form of administration of two or more different therapeutic agents such that the second agent is administered while the previously administered therapeutic agent is still effective in the body (e.g., the two agents are simultaneously effective in the subject, which may include synergistic effects of the two agents). For example, the different therapeutic agents can be administered either in the same formulation or in separate formulations, either concomitantly or sequentially. In certain embodiments, the different therapeutic agents can be administered within about one hour, about 12 hours, about 24 hours, about 36 hours, about 48 hours, about 72 hours, or about a week of one another. Thus, a subject who receives such treatment can benefit from a combined effect of different therapeutic agents. As used herein, any two agents and/or additional agents may be conjointly administered according to the methods provided herein.

The term "therapeutic effect" refers to a local or systemic effect in humans, caused by a pharmacologically active substance. The term thus means any substance intended for use in the diagnosis, cure, mitigation, or treatment of disease or in the enhancement of desirable physical or mental development and conditions in a patient (e.g., a human suffering from anemia).

The terms "therapeutically-effective amount" and "effective amount" refers to an amount necessary (for example, at dosages and for periods of time and for the means of enteral or oral administration) to achieve the desired therapeutic result of treating anemia. An effective amount of the agonist of $\beta$2-adrenoreceptor may vary according to factors such as the disease state, age, sex, and weight of the individual, and the ability of the monoclonal antibody to elicit a desired response in the individual. An effective amount is also one in which medical provider, e.g., the attending physician, determines that any toxic or detrimental effects of the agonist are outweighed by the therapeutically beneficial effects.

II. Patients

The patient may be any human afflicted by MDS or anemia (e.g., anemia associated with a cancer disclosed herein). The patient may be any aging patient or any patient afflicted by a disorder associated with aging that display anemia.

In some embodiments, a patient is an adult patient. In some embodiments, a patient is 18 years of age or older. In some embodiments, a patient is a geriatric patient. In some embodiments, a patient is 65 years of age or older.

In some embodiments, a patient is a child that is at least 5 years of age (i.e., 5 years of age or older). In some embodiments, a patient is aged 5 to 18 years.

In some embodiments, a patient is one that would benefit from weight gain. In some embodiments, a patient is one that would benefit from increased bone density. In some embodiments, a patient is afflicted by an anemia associated with weight loss and/or decreased bone density (e.g., anemia associated with a cancer disclosed herein).

Methods, uses and compositions encompassed by the present invention can be used in myelodysplastic syndromes (MDS) and anemias, such as, anemia caused by insufficiency of serine/threonine-protein kinase RIOK2, anemia caused by mutations or deletions on human chromosome 5, anemia caused by chromosomal translocations in the NUP98 gene or in an ortholog thereof, such as anemia caused by fusions of NUP98 with Abd-B group HOX genes (e.g., HOXD13), macrocytic anemia, anemia associated with inflammatory disorders, such as rheumatoid arthritis or multiple sclerosis, anemia associated with chronic kidney disease (CKD), stress-induced anemia, chemotherapy-induced anemia in cancer patients, aplastic anemia, anemia secondary to an intestinal cancer, Diamond Blackfan anemia, and Shwachman-Diamond syndrome. Similarly, the methods and compositions encompassed by the present invention can be used across bone marrow failure syndromes since it has been determined that RIOK2 regulates blood cell development and agonists of RIOK2 activity reverse anemia associated with bone marrow failure syndromes, such as aplastic anemia, Diamond Blackfan anemia, dyskeratosis congenita (DC), fanconi anemia (FA), Pearson syndrome, severe congenital neutropenia (SCN), Shwachman-Diamond syndrome (SDS), and others.

III. Administration of Agents

Formoterol or a pharmaceutically acceptable salt thereof (e.g., formoterol fumarate or arformoterol tartrate) can be administered to patients disclosed herein according to methods encompassed by the present invention in a biologically compatible form suitable for pharmaceutical administration in vivo, to enhance their effects. By "biologically compatible form suitable for administration in vivo" is meant a form to be administered in which any toxic effects are outweighed by the therapeutic effects. Administration of formoterol or a pharmaceutically acceptable salt thereof (e.g., formoterol fumarate or arformoterol tartrate) can be in any pharmacological form including a therapeutically active amount of an agent alone or in combination with a pharmaceutically acceptable carrier.

Exemplary formoterol (molecular formula $C_{19}H_{24}N_2O_4$) includes, but is not limited to, formoterol fumarate, arformoterol tartrate, 73573-87-2, n-[2-hydroxy-5-(1-hydroxy-2-{[1-(4-methoxyphenyl)propan-2-yl]amino}ethyl)phenyl] formamide, 128954-45-0, CHEBI: 63082, or formoterolum [INN-Latin]. Commercially available forms of formoterol include, without limitation, AR00CJ9Q from Aaron Chemicals LLC, B1210424 from BenchChem, and AT22502 from AstaTech, Inc.

Formoterol fumarate is the fumarate salt form of formoterol. Exemplary molecular forms of formoterol fumarate disclosed herein include formoterol fumarate ($C_{42}H_{52}N_4O_{12}$), formoterol fumarate hydrate (molecular formula $C_{42}H_{54}N_4O_{13}$), and formoterol fumarate dihydrate (molecular formula $C_{42}H_{56}N_4O_{14}$). Additional identifiers of formoterol fumerate include, without limitation, (±)-2-hydroxy-5-[(1RS)-1-hydroxy-2-[(1RS)-2-(4-methoxyphenyl)-1-methylethyl]-amino]ethyl]formanilide fumarate, (E)-but-2-enedioic acid;N-[2-hydroxy-5-[(1R)-1-hydroxy-2-[[(2R)-1-(4-methoxyphenyl)propan-2-yl]amino]ethyl]phenyl] formamide (IUPAC name), 43229-80-7 (CAS), CHEBI: 31633, D01373 (ATC code), and 7848436/53477580 (PubChem). Commercially available forms of formoterol fumarate include, without limitation, Foradil® from Astellas Pharma Inc., Perforomist® from Mylan Specialty L.P. (Viatris); generic formoterol fumarate solutions from Mylan Pharmaceuticals Inc., Alembic Pharmaceuticals Inc. (i.e., formoterol fumarate), Bryant Ranch Prepack, Lupin Pharmaceuticals, Inc., and Teva Pharmaceuticals USA, Inc. ; A826230 from Amadis Chemical, 33055 from AstaTech, Inc., and 141492 from ChemShuttle.

Formoterol is well known in the art, such as U.S. Pat. Nos. 3,994,974 A 6,268,533 B1. Other methods of formulations, described in Remington's Pharmaceutical Sciences, 21st Edition, University of the Sciences in Philadelphia, Philadelphia, Pa., USA (2006) can be employed in implementing the present invention. As used herein, formoterol includes all stereoisomers (e.g., (R)- and (S)-isomers), including all enantiomers (R;R and S;S) and all diastereomers (R;S and S;R).

Arformoterol (molecular formula $C_{19}H_{24}N_2O_4$) is a stereoisomer of formoterol. Additional identifiers of arformoterol include, without limitation, N-[2-hydroxy-5-[(1R)-1-hydroxy-2-[(2R)-1-(4-methoxyphenyl)propan-2-yl]amino]ethyl]phenyl]formamide (IUPAC), (R,R)-Formoterol, 67346-49-0 (CAS), CHEBI: 408174, DB01274 (DrugBank), and 3083544 (PubChem).

As used herein, "arformoterol" includes salt forms of arformoterol. Arformoterol tartrate is the tartrate salt form of arformoterol. Exemplary molecular forms of arformoterol tartrate disclosed herein include arformoterol tartrate ($C_{23}H_{30}N_2O_{10}$ or $C_{19}H_{24}N_2O_4·C_4H_6O_6$). Additional identifiers of arformoterol tartrate include, without limitation, N-[2-hydroxy-5-[(1R)-1-hydroxy-2-[[(1R)-2-(4-methoxyphenyl)-1-methylethyl]amino]ethyl]phenyl]-formamide, (2R,3R)-2,3-dihydroxybutanedioate (1:1 salt) (IUPAC), (R,R)-Arformoterol tartrate, 200815-49-2 (CAS), and 9827062 (PubChem). Commercially available forms of arformoterol tartrate include, without limitation, Brovana® (arformoterol tartrate) from Sunovion Pharmaceuticals, Inc., SML1667 from Sigma-Aldrich, S5217 from Selleckchem, 6219 from Tocris Bioscience, and A12795 from AdooQ Bioscience.

Further details related to arformoterol can be found in U.S. Pat. Nos. 9,499,475 B2 and 9,029,421 B2, hereby incorporated by reference.

Administration of a therapeutically active amount of the therapeutic composition encompassed by the present invention is defined as an amount effective, at dosages and for periods of time necessary, to achieve the desired result. For example, a therapeutically active amount of an agent can vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

Agents encompassed by the present invention can be administered either alone or conjointly with an additional therapy. In the conjoint therapy, an agent encompassed by the present invention and another agent, such as an erythropoiesis-stimulating agent (e.g., erythropoietin, epoetin alfa, epoetin beta, epoetin omega, epoetin zeta, darbepoetin alfa), or other FDA-approved drugs such as luspatercept, lenalidomide and/or a hypomethylating agent, such as azacitidine or decitabine, can be delivered to the same or different cells and can be delivered at the same or different times. The agents encompassed by the present invention can be incorporated into pharmaceutical compositions suitable for administration. Such compositions can comprise one or more agents or one or more molecules that result in the production of such one or more agents and a pharmaceutically acceptable carrier.

The therapeutic agent described herein (e.g., formoterol or a pharmaceutically acceptable salt thereof, such as formoterol fumarate or arformoterol tartrate) can be administered in a convenient manner such as by oral administration, injection (subcutaneous, intravenous, intraperitoneal (i.p.) etc.), inhalation, transdermal application, or rectal administration. Depending on the route of administration, the active compound can be coated in a material to protect the compound from the action of enzymes, acids and other natural conditions which can inactivate the compound. For example, for administration of agents, by other than parenteral administration, it can be desirable to coat the agent with, or co-administer the agent with, a material to prevent its inactivation.

As described in detail below, the pharmaceutical compositions encompassed by the present invention (e.g., a composition comprising formoterol or a pharmaceutically acceptable salt thereof, such as formoterol fumarate or arformoterol tartrate) can be specially formulated for administration in solid or liquid form, including those adapted for the following: (1) oral administration, for example, drenches (aqueous or non-aqueous solutions or suspensions), tablets, boluses, powders, granules, pastes; or (2) parenteral administration, for example, by subcutaneous, intramuscular, intraperitoneal (i.p.) or intravenous injection as, for example, a sterile solution or suspension.

The phrase "pharmaceutically acceptable" is employed herein to refer to those agents, materials, compositions, and/or dosage forms which are, within the scope of sound medical judgment, suitable for use in contact with the tissues of human beings without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the chemical from one organ, or portion of the body, to another organ, or portion of the body. Each carrier must be "acceptable" in the sense of being compatible with the other ingredients of the formulation and not injurious to the patient. Those skilled in the art will recognize, or be able to employ suitable pharmaceutically-acceptable carriers for the therapeutic agent disclosed herein (e.g., formoterol or a pharmaceutically acceptable salt thereof, such as formoterol fumarate or arformoterol tartrate) from the pharmaceutically-acceptable carriers known in pharmaceutical science (See, for example, Adejare, Adeboye, ed. *Remington: the science and practice of pharmacy*. Academic Press, 2020).

The term "pharmaceutically-acceptable salts" refers to the relatively non-toxic, inorganic and organic acid addition salts of the therapeutic agent disclosed herein (i.e., formoterol, the pharmaceutically-acceptable salts of which include, for example, formoterol fumarate and arformoterol tartrate). These salts can be prepared in situ during the final isolation and purification of the therapeutic agents, or by separately reacting a purified therapeutic agent in its free base form with a suitable organic or inorganic acid, and isolating the salt thus formed. Those skilled in the art will recognize, or be able to employ suitable pharmaceutically-acceptable salts for the therapeutic agents disclosed herein (e.g., formoterol, the pharmaceutically-acceptable salts of which include, for example, formoterol fumarate and arformoterol tartrate) from the pharmaceutically-acceptable salts known in pharmaceutical science (See, for example, Berge et al. (1977) *J. Pharm. Sci.* 66:1-19).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods encompassed by the present invention include those suitable for oral administration, intravenous administration and/or administration by injection (e.g., intraperitoneal (i.p.) injection). The formulations can conveniently be presented in unit dosage form and can be prepared by any methods well-known in the art of pharmacy. The amount of active ingredient which can be combined with a carrier material to produce a single dosage form will vary depending upon the host being treated, the particular mode of administration. In some embodiments, formoterol or a pharmaceutically acceptable salt thereof (e.g., formoterol fumarate or arformoterol tartrate) is in a form formulated for oral administration. Exemplary oral forms of formoterol can be found in the art, such as Yokoi et al. (1983) *Life Sciences* 33:1665-1672. In some embodiments, the agent provided herein is an oral formulation of formoterol or a pharmaceutically acceptable salt thereof (e.g., formoterol fumarate or arformoterol tartrate).

In general, the formulations are prepared by uniformly and intimately bringing into association a therapeutic agent with liquid carriers, or finely divided solid carriers, or both, and then, if necessary, shaping the product.

Formulations suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound can also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered peptide or peptidomimetic moistened with an inert liquid diluent.

Tablets, and other solid dosage forms, such as dragees, capsules, pills and granules, can optionally be scored or prepared with coatings and shells, such as enteric coatings and other coatings well-known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions, which can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions encompassed by the present invention suitable for parenteral administration comprise one or more therapeutic agents in combination with one or more pharmaceutically-acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents that delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution, which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of formoterol or a pharmaceutically acceptable salt thereof (e.g., formoterol fumarate or arformoterol tartrate), in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents encompassed by the present invention are administered as pharmaceuticals, to humans, they can be given per se or as a pharmaceutical composition containing, for example, 0.1 to 99.5% (more preferably, 0.5 to 90%) of active ingredient in combination with a pharmaceutically acceptable carrier.

It will be understood that the total daily dosage of the compounds of the present invention will be decided by the attending physician within the scope of sound medical judgment. The specific therapeutically effective dose level for any particular subject will depend upon a variety of factors including the anemia being treated and the severity of the anemia; the specific composition employed, the age, body weight, general health, sex and diet of the subject; the time of administration, route of administration, and plasma half-life of the specific compound employed; the duration of the treatment; drugs used conjointly or coincidental with the specific agonist employed; and like factors well known in the medical arts. The daily dosage of the active ingredient may include, but is not limited to, about 0.1 to 100 µg per adult per day. Typically, the pharmaceutical compositions contain 0.1, 1.0, 5.0, 10.0, 12.0, 15.0, 20.0, 50, 75, 100 µg of formoterol or a pharmaceutically acceptable salt thereof (e.g., formoterol fumarate or arformoterol tartrate), preferably 1 to 60 µg. In some embodiments, an effective amount of formoterol or a pharmaceutically acceptable salt thereof (e.g., formoterol fumarate or arformoterol tartrate) is a dose that is ≤100 µg/day. In some embodiments, an effective amount of formoterol or a pharmaceutically acceptable salt thereof (e.g., formoterol fumarate or arformoterol tartrate) is a dose that is from 0.1 µg/day to 100 µg/day. In some preferred embodiments, an effective amount of formoterol or a pharmaceutically acceptable salt thereof (e.g., formoterol fumarate or arformoterol tartrate) is a dose that is from 1 µg/day to 60 µg/day. In some embodiments, provided are methods of treating anemia by administering to a patient a tablet or capsule comprising formoterol or a pharmaceutically acceptable salt thereof (e.g., formoterol fumarate or arformoterol tartrate) at a dose of 0.1 µg to 100 µg. In some embodiments, the tablet or capsule is administered once per day. In some embodiments, a patient is administered a tablet or capsule comprising formoterol or a pharmaceutically acceptable salt thereof (e.g., formoterol fumarate or arformoterol tartrate) at a dose of 1 µg to 60 µg once per day.

In some embodiments, provided are methods of treating anemia by administering to a patient one or more tablets or capsules comprising formoterol or a pharmaceutically acceptable salt thereof (e.g., formoterol fumarate or arformoterol tartrate), such that a subject receives a total daily dose of 0.1 µg to 100 µg, preferably a total daily dose of 1 µg to 60 µg.

An effective amount of the drug is ordinarily supplied in a dose and route of administration to achieve an effective amount of formoterol or a pharmaceutically acceptable salt thereof (e.g., formoterol fumarate or arformoterol tartrate) to treat anemia and plasma levels of 0.03-150 pg/mL, preferably 0.3-30 pg/mL.

Actual dosage levels of the active ingredients in pharmaceutical compositions encompassed by the present invention can be determined by the methods encompassed by the present invention to obtain an amount of the active ingredient, which is effective to achieve the desired therapeutic response for a particular patient, composition, and mode of administration, without being toxic to the patient.

EXAMPLES

Example 1: Formoterol Fumarate (FF) Enhances Erythroid Differentiation and Mitochondrial Functions Described herein is a novel therapeutic approach of targeting anemia in MDS and other human disorders by utilizing formoterol fumarate (FF), an FDA-approved 2-adrenoreceptor agonist for COPD and asthma treatment (Hanania et al. (2019) *Int J Chron Obstruct Pulmon Dis.* 14: 117-127; Sharafkhaneh et al. (2010) *Int J Chron Obstruct Pulmon Dis.* 5: 357-366). It is shown herein that formoterol fumarate (FF) simultaneously augments mitochondrial biogenesis and erythroid differentiation in primary human hematopoietic stem and progenitor cells (HSPCs). Corroborating this, depletion of ADRB2 that encodes $\beta$2-adrenoreceptor ($\beta$2-AR) markedly impairs erythroid differentiation as well as mitochondrial biogenesis. FF treatment significantly enhanced erythropoiesis in MDS patient-derived bone marrow cells. Administration of FF significantly enhanced erythroid differentiation and RBC parameters in wild-type mice under both steady state and stress-induced hemolytic anemia settings. FF treatment conferred striking survival benefits to mice in response to lethal hemolytic anemia. Thus, a novel use of an existing FDA-approved drug is uncovered to reverse anemia and offer therapeutic benefits in a spectrum of human diseases, including but not limited to, such as hematologic malignancies, aplastic anemia, anemia of chronic kidney diseases, ribosomopathies, anemia secondary to chemotherapeutic agents in cancer patients, and bone marrow failure (BMF) disorders.

Hematological Disorders and Mitochondrial Dysfunction.

Mitochondrial dysfunction is often associated with the pathogenesis of hematological disorders, such as MDS and AML (Fontenay et al. (2006) *Oncogene* 25:4757-4767). For example, altered mitochondrial transcription (Schildgen et al. (2011) *Exp. Hematol.* 39:666-675), deregulated HIF1$\alpha$ expression (Liu et al. (2019) *Oncol. Lett.* 17:5395-5402; Stergiou et al. (2021) *Int. J. Mol. Sci.* 22), presence of isocitrate dehydrogenase (IDH) mutations expressing oncogenic metabolite 2-hydroxy-glutarate (2-HG) (Gonzalez-Menendez et al. (2021) *Cell Rep.* 34:108723; Intlekofer et al. (2018) *Nature* 559:125-129; Testa et al. (2020) *Cancers* 12:2427), elevation of mitochondrial oxidative stress markers (Saigo et al. (2011) *J. Int. Med. Res.* 39:1941-1945), and presence of aberrant oxidation and mutations in mitochondrial DNA (mtDNA) (Coelho-Silva et al. (2021) *Sci. Rep.* 11:1675; Schildgen et al. (2011) *Exp. Hematol.* 39:666-675; Ward et al. (2021) *Blood Adv.* 5:2216-2228; Wulfert et al. (2008) *Exp. Hematol.* 36:577-586) strongly implicate defective mitochondrial functions as a critical player in MDS pathogenesis. MtDNA encodes 13 polypeptides in conjunction with nuclear encoded transcriptional and translational machineries that form indispensable components of the electron transport chain (ETC) responsible for oxidative phosphorylation (OXPHOS) (Itoh et al. (2021) *Science* 371:846-849; Kummer and Ban (2021) *Nat. Rev. Mol. Cell Biol.* 22:307-325). Hence, mitochondrial and nuclear genomes remain interwoven in a tightly-balanced relationship to dictate cellular metabolism and prevent deregulation which inevitably alters metabolite profiles (Alston et al. (2021) *J. Pathol.*; Ito and Ito (2018) *Exp Hematol* 64:1-11;

Schildgen et al. (2011) *Exp. Hematol.* 39:666-675; Zheng et al. (2017) *Chin. J. Physiol.* 60:338-344). Consistently, elevation of tryptophan catabolismetabolites in MDS patient sera (Berthon et al. (2013) *Leuk. Res.* 37:573-579) and increased reactive oxygen metabolites in patients with karyotypic abnormalities (Cano et al. (2011) *J. Proteome Res.* 10:2873-2881; Fracchiolla et al. (2003) *Haematologica* 88:594-597; Poulaki et al. (2020) *Cancers* (Basel) 12; Zhong et al. (2015) *Genet. Mol. Res.* 14:13709-13718), further underscore the involvement of deregulated metabolites and metabolic pathways in MDS etiology. Dysregulated metabolite levels are also reported in bone marrow failure disorders (Zhong et al. (2015) *Genet. Mol. Res.* 14:13709-13718). The present disclosure encompasses a recognition that mitochondrial defects contribute to the pathogenesis of hematological disorders.

$\beta$2 Adrenergic Receptor (b2-AR) Agonists and Mitochondrial Biogenesis $\beta$2-AR are cell-membrane spanning receptors for adrenaline (epinephrine) that mediate smooth muscle relaxation and bronchodilation via adenylate cyclase stimulation (Abosamak and Shahin (2021). In StatPearls (Treasure Island (FL)); Johnson (2006) *J Allergy Clin Immunol* 117, 18-24; quiz 25; Yang et al. (2021) *Life Sci* 265: 118864). $\beta$2-AR is encoded by the ADRB2 gene. The long-acting selective $\beta$2-AR agonist formoterol fumarate (FF) is FDA-approved for the treatment of COPD and asthma (Hanania et al. (2019) *Int J Chron Obstruct Pulmon Dis* 14: 117-127; Ni et al. (2018) *Cochrane Database Syst Rev* 12, CD011594; Sharafkhaneh et al. (2010) *Int J Chron Obstruct Pulmon Dis* 5: 357-366). FF is highly specific for $\beta$2-AR as examined in ADRB2-depleted mice (Cameron et al. (2017) *Sci Rep* 7: 10578). Interestingly, FF is reported to augment mitochondrial biogenesis in several in vitro and in vivo models (Peterson et al. (2013) *Bioorg Med Chem Lett* 23: 5376-5381; Wills et al. (2012) *J Pharmacol Exp Ther* 342: 106-118), such as ischemia-reperfusion mediated kidney injury (Jesinkey et al. (2014) *J Am Soc Nephrol* 25: 1157-1162), spinal cord injury (Scholpa et al. (2019) *Exp Neurol* 322: 113064), and traumatic brain injury (Vekaria et al. (2020) *Neurobiol Dis* 140: 104866.0). FF not only upregulates the expression of mtDNA encoded genes, but also promotes mitochondrial oxygen consumption rates (OCR) in vitro and ex vivo (Arif et al. (2019) *Kidney Int* 96: 656-673). However, the underlying mechanisms of FF-mediated enhancement of mitochondrial biogenesis remain poorly defined.

Results

Formoterol Fumarate (FF) Enhances Erythroid Differentiation and Mitochondrial Functions in Primary Human Hematopoietic Stem and Progenitor Cells (HSPCs).

Figure 1A:
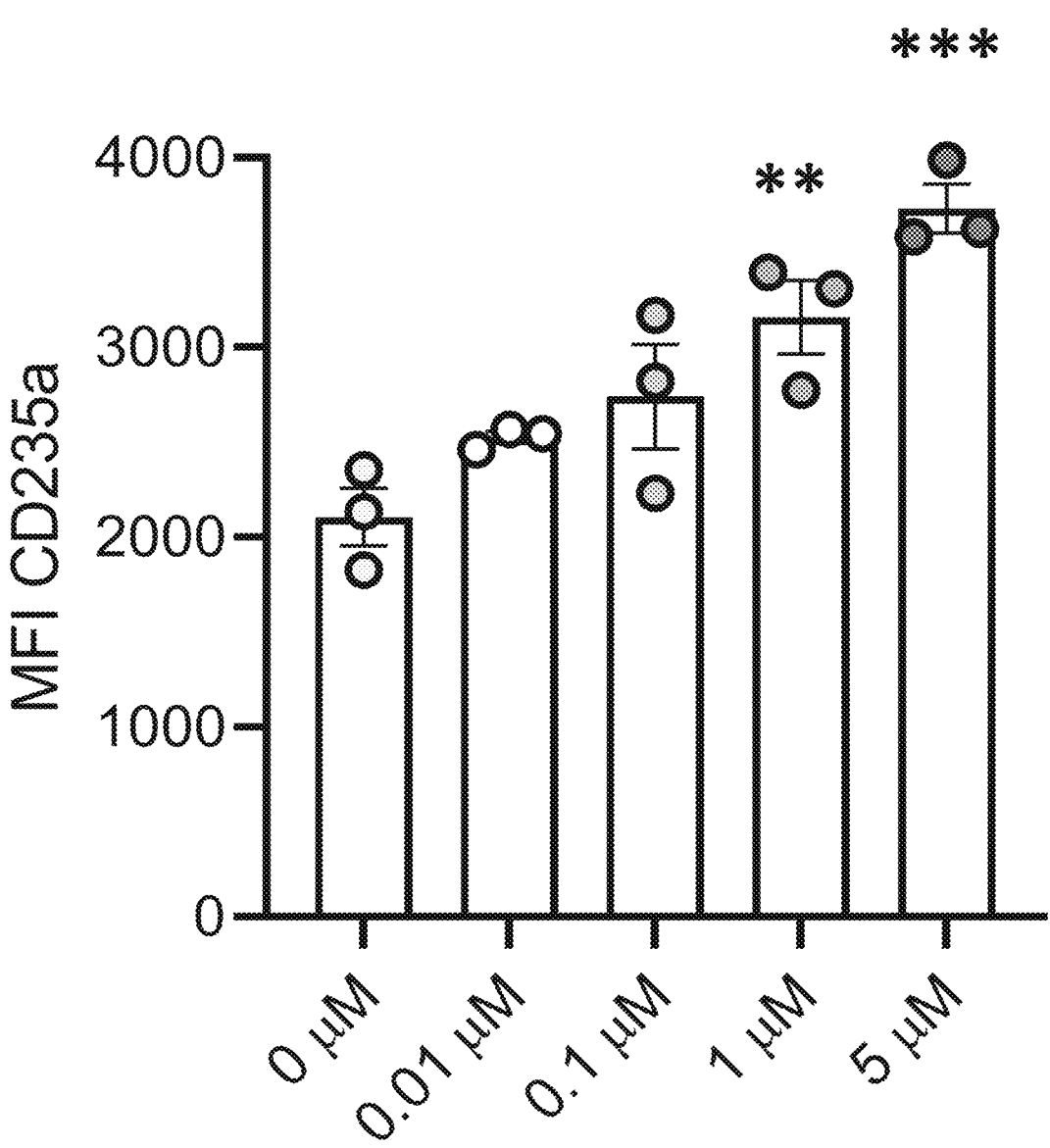
FIG. 1A-FIG. 1D show that formoterol fumarate induces erythropoiesis. Administration of formoterol fumarate (FF) to primary human HSPCs (FIG. 1A) enhances erythroid differentiation (CD235a) dose-dependently, but does not affect viability (FIG. 1B), megakaryocytic (CD41-61) (FIG. 1C), or myeloid (CD11b) differentiation (FIG. 1D). n=3 healthy donor-derived HSPCs.  p<0.01, * p<0.001, one-way analysis of variance (ANOVA). "Ns" (non-significant) applies where statistical significance is not shown. Data represented as mean±SEM. All comparisons were done w.r.t. control (0 μM: vehicle (DMSO)-treated).
Figure 1B:
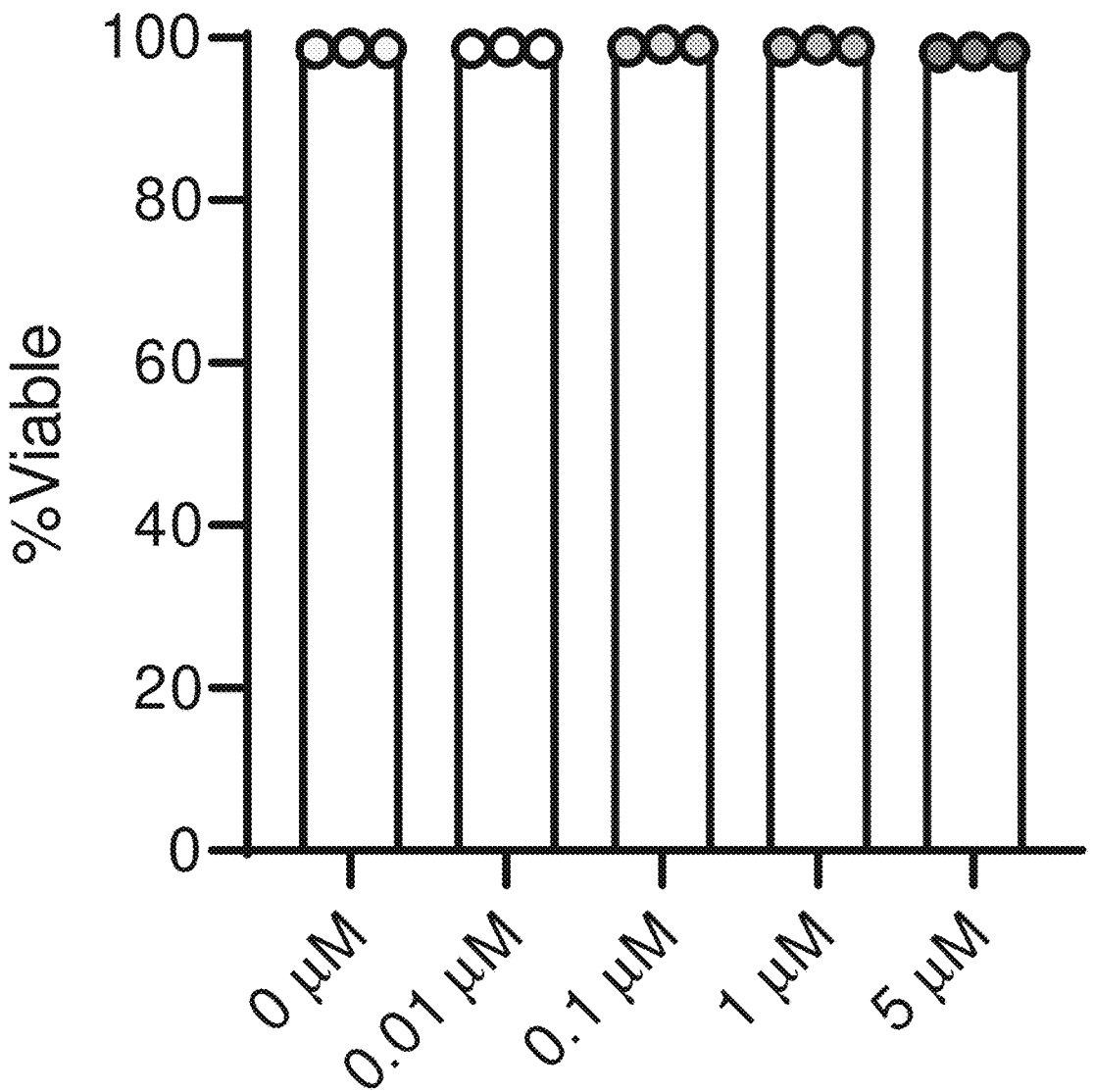
Figure 1C:
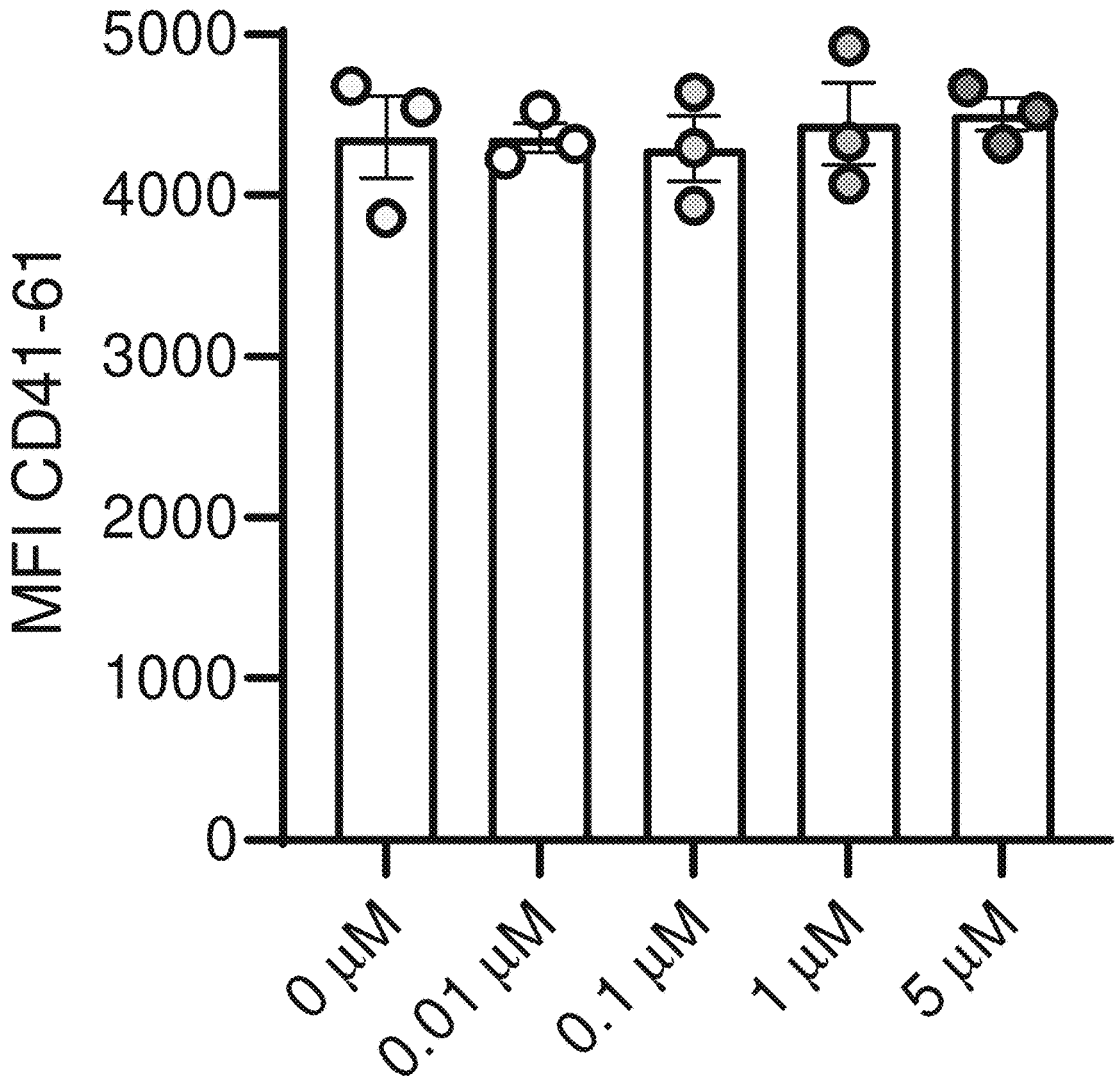
Figure 1D:
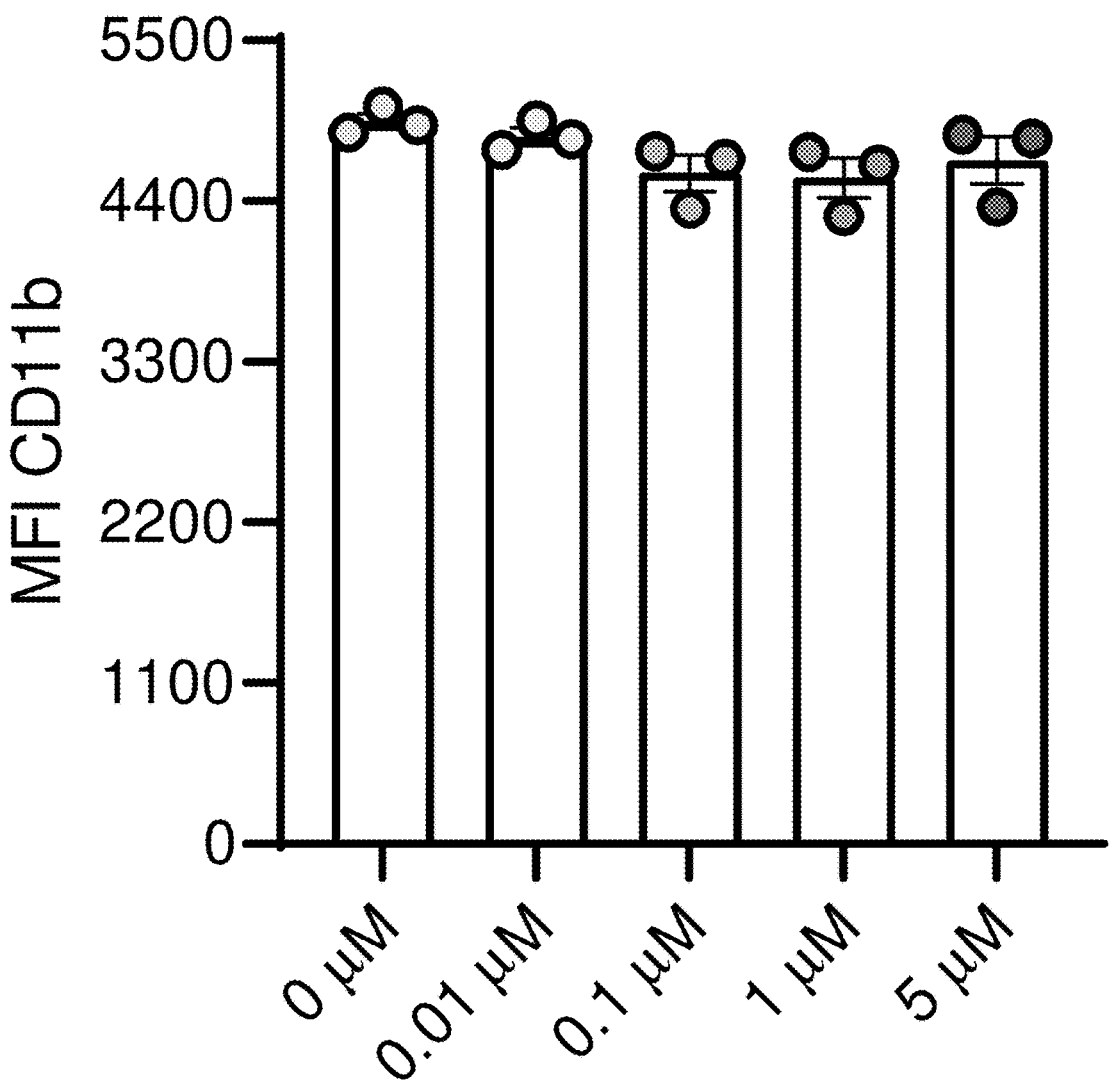
Figure 2:
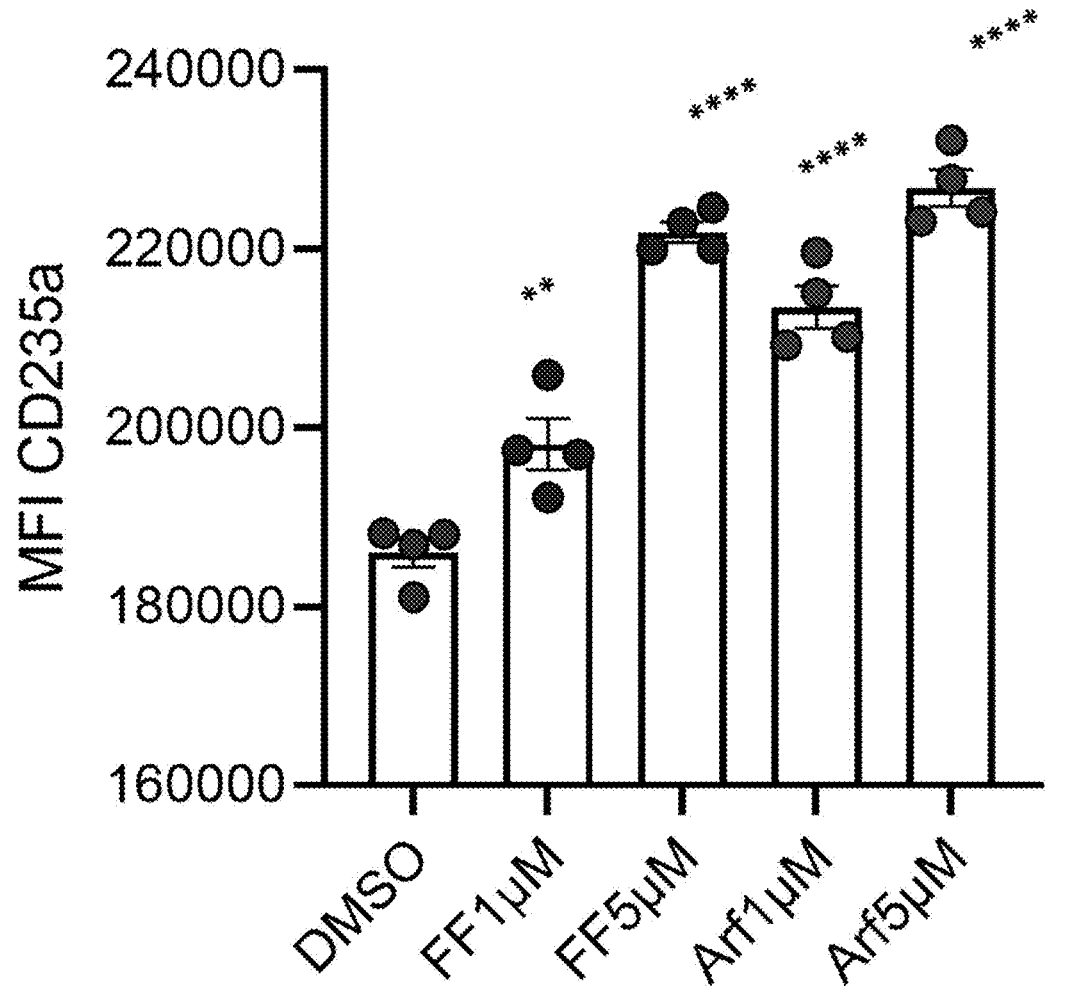
FIG. 2 shows that formoterol fumarate (FF) and arformoterol tartrate (Arf) induce erythropoiesis. Administration of formoterol fumarate (FF) or arformoterol tartrate (Arf) at 1/5 μM to primary human HSPCs induces erythroid differentiation (CD235a) dose-dependently. Representative of n=5 healthy donor-derived HSPCs; n=4 technical replicates within each donor.  p<0.01, * p<0.001, **** p<0.0001, one-way analysis of variance (ANOVA). Data represented as mean±SEM. All comparisons were done w.r.t. control (DMSO) treated). ns=non-significant.
Figure 3A:
FIG. 3A-FIG. 3B show that formoterol fumarate boosts erythropoiesis. Administration of formoterol fumarate (FF) from Selleckchem (FIG. 3A) and Sigma (FIG. 3B) enhances erythroid differentiation in primary human HSPCs isolated from n=4 healthy donors.  p<0.01, * p<0.001, one-way analysis of variance (ANOVA). "Ns" (non-significant) applies where statistical significance is not shown. Data represented as mean±SEM. All comparisons were done w.r.t. control (0 µM: vehicle (DMSO)-treated).
Figure 3B:
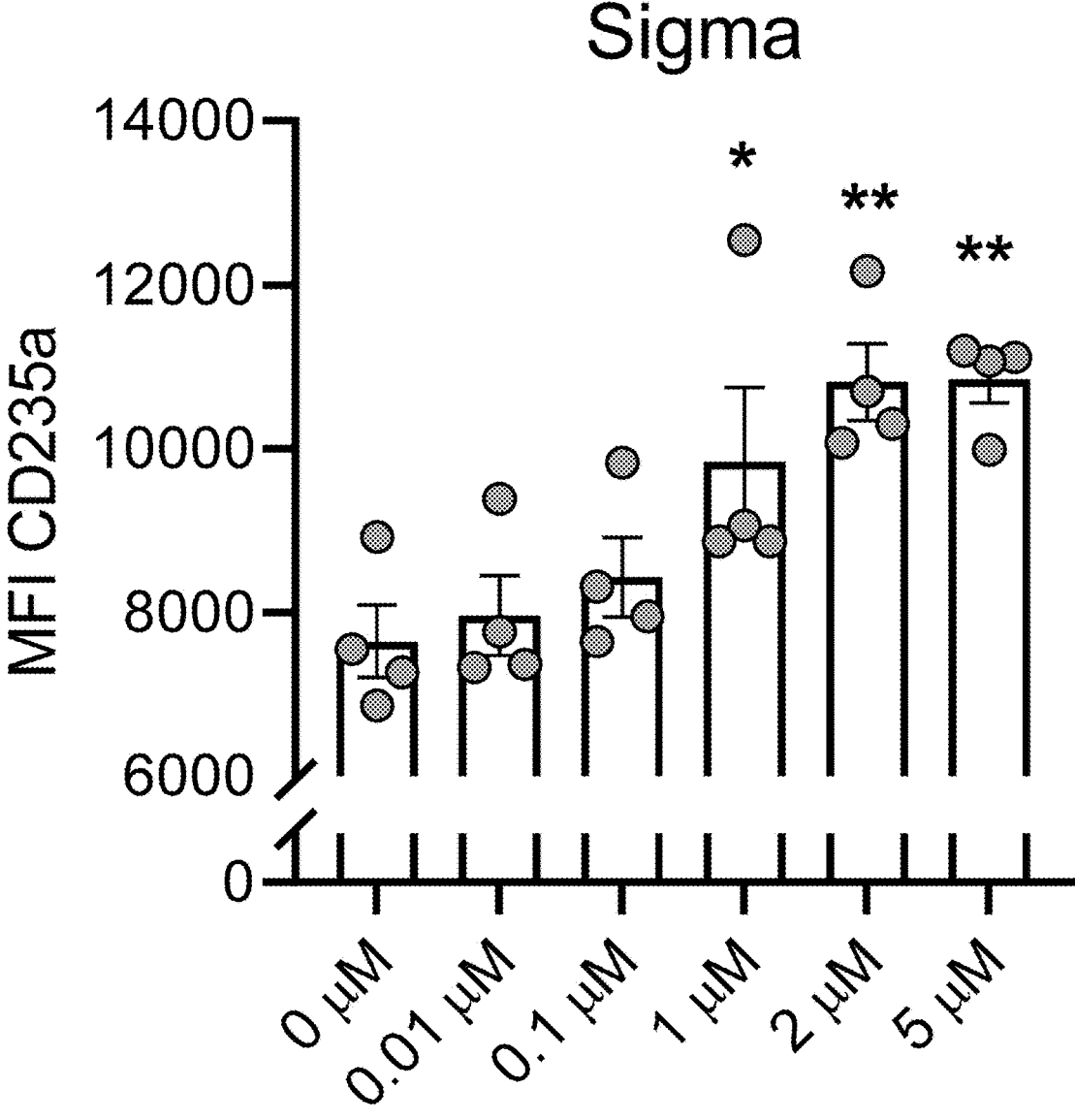
Figure 4:
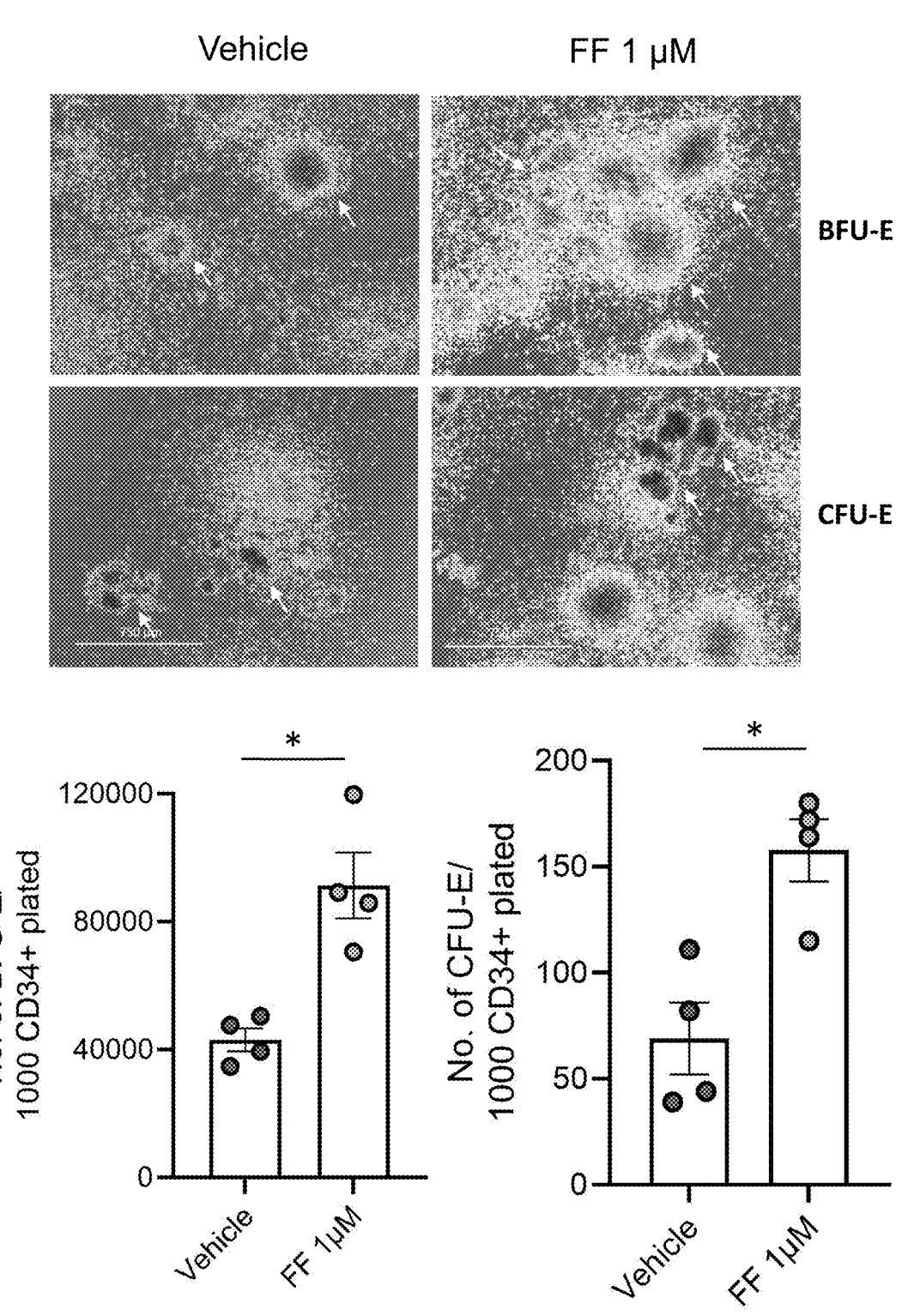
FIG. 4 shows that administration of formoterol fumarate (FF) in primary human HSPCs enhances blast forming unit-erythroid (BFU-E) and colony forming unit-erythroid (CFU-E) formation, which are the precursors for red blood cells (RBCs). n=4 healthy donor-derived HSPCs. * p<0.05, Student's t-test. Data represented as mean±SEM. All comparisons were done w.r.t. control i.e. vehicle (DMSO treated).
Figure 5A:
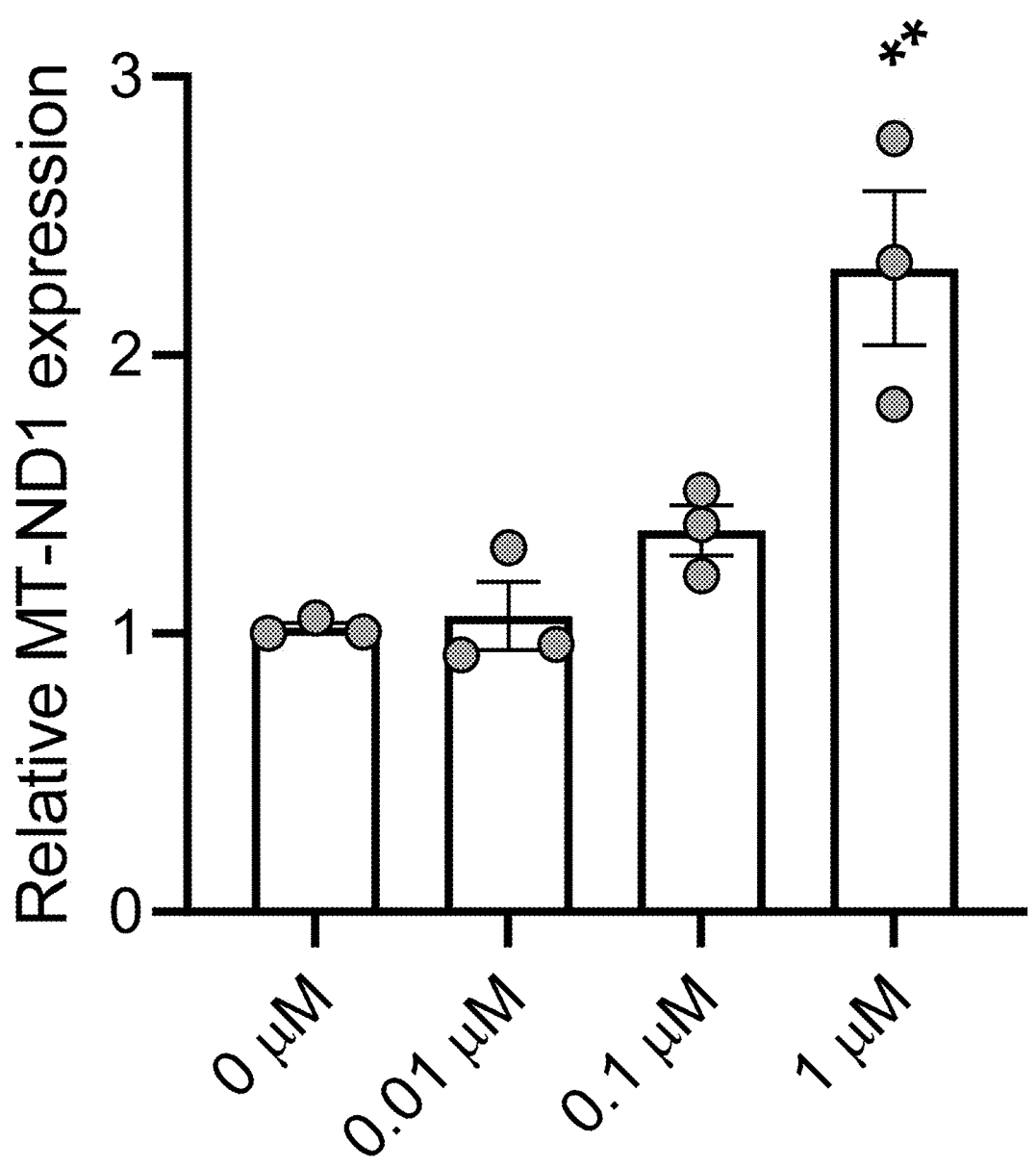
FIG. 5A-FIG. 5C show that formoterol fumarate (FF) enhances mitochondrial functions.
Figure 5A:
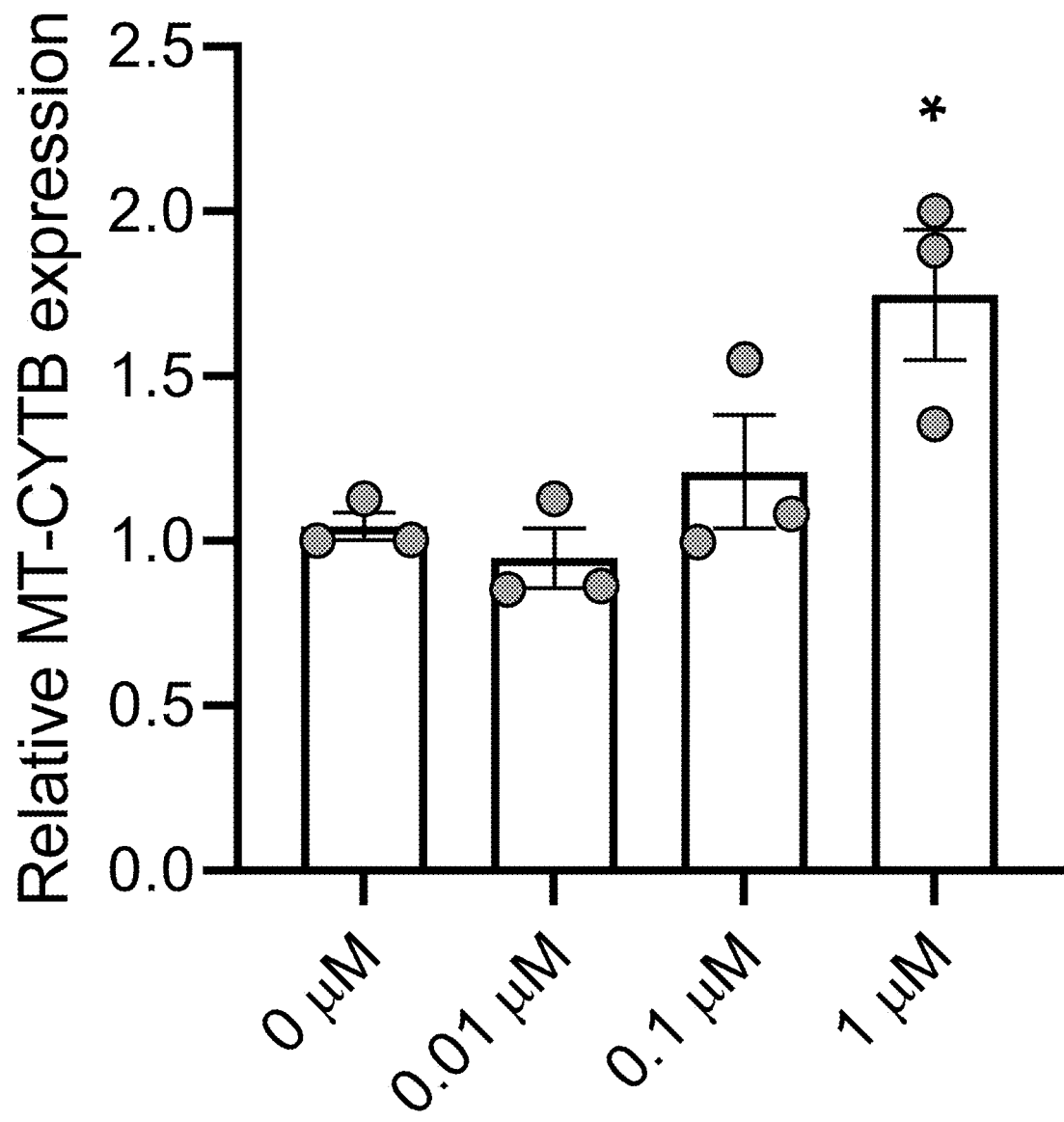
Figure 5A:
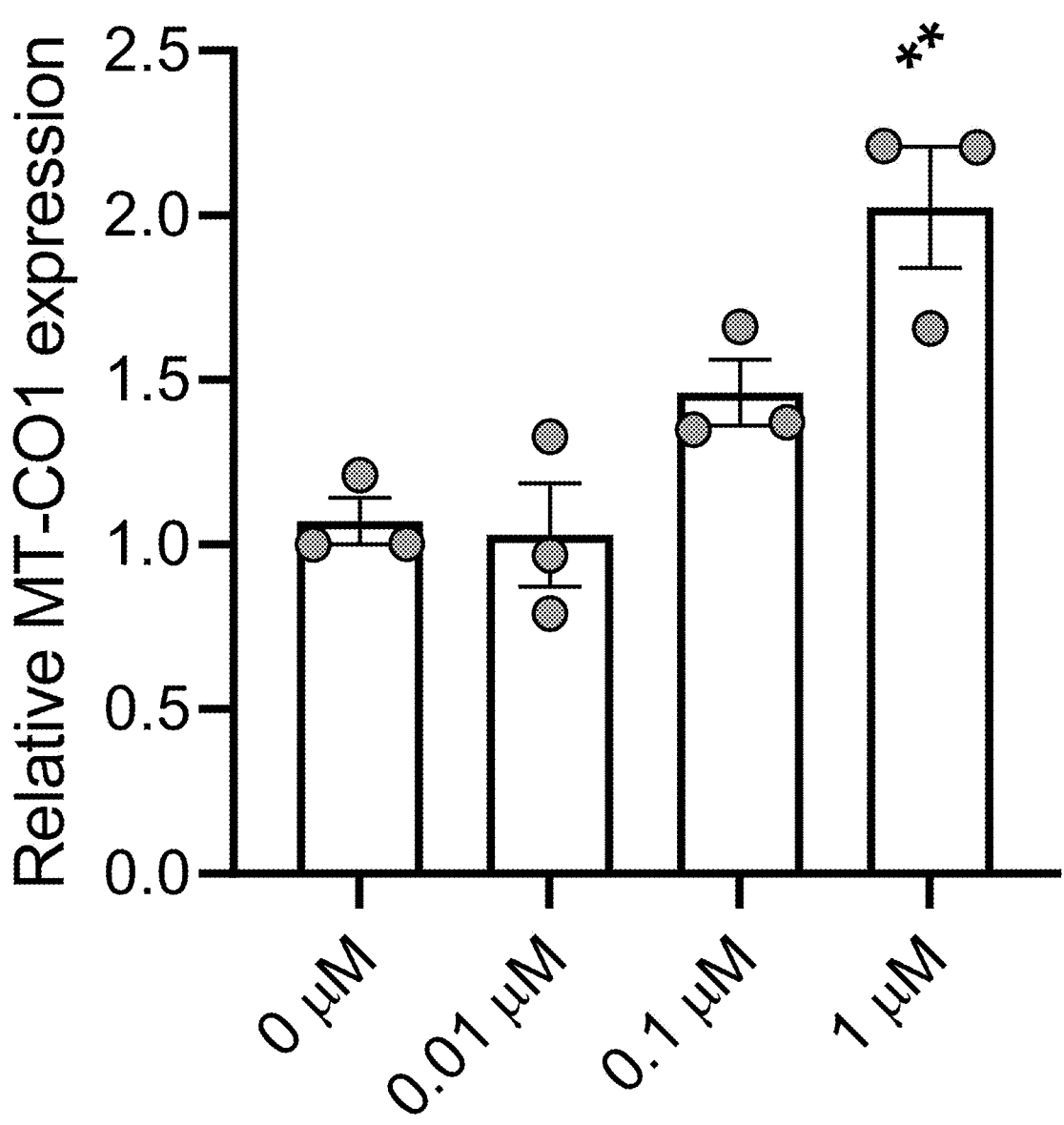
Figure 5A:
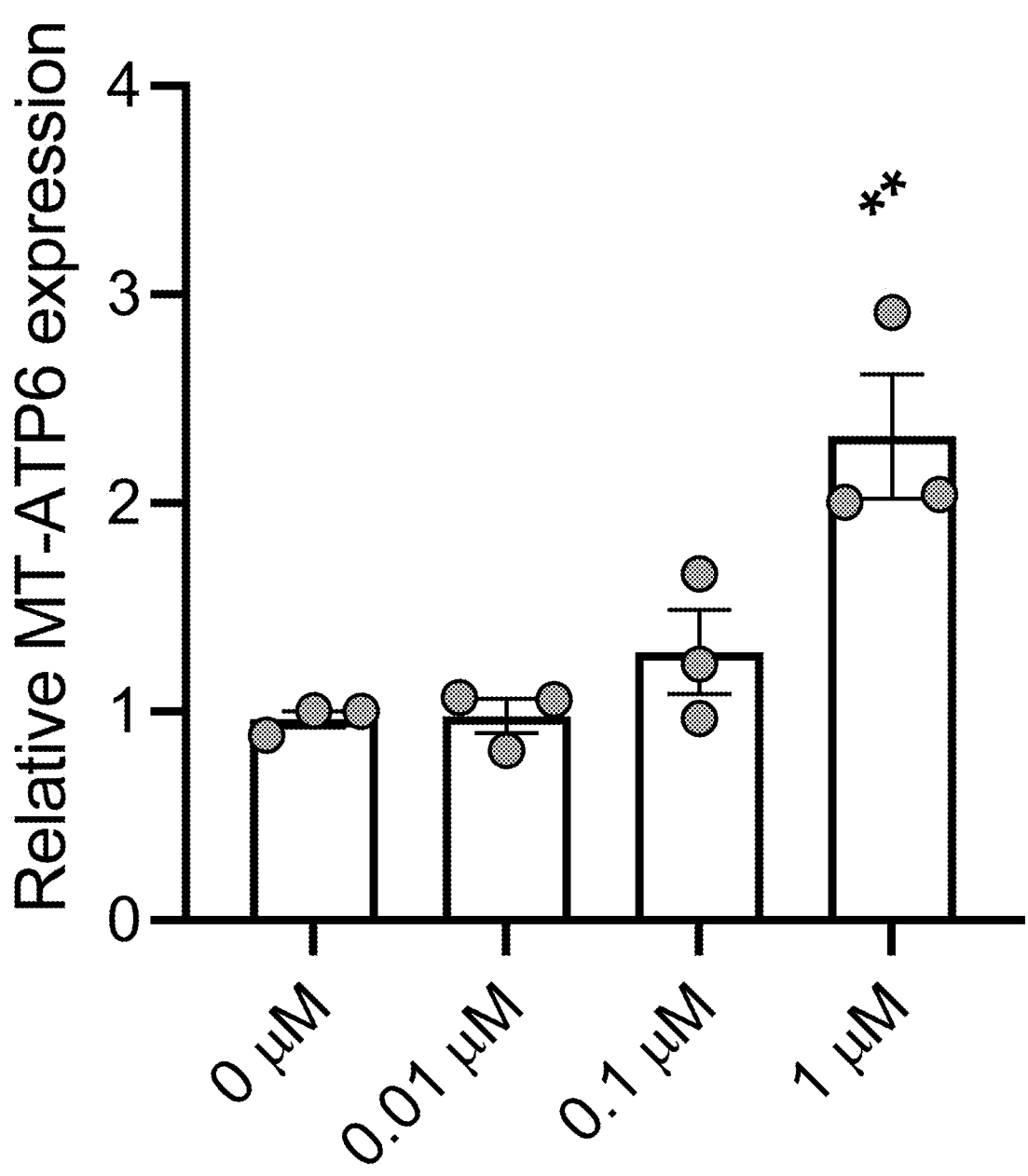
Figure 5B:
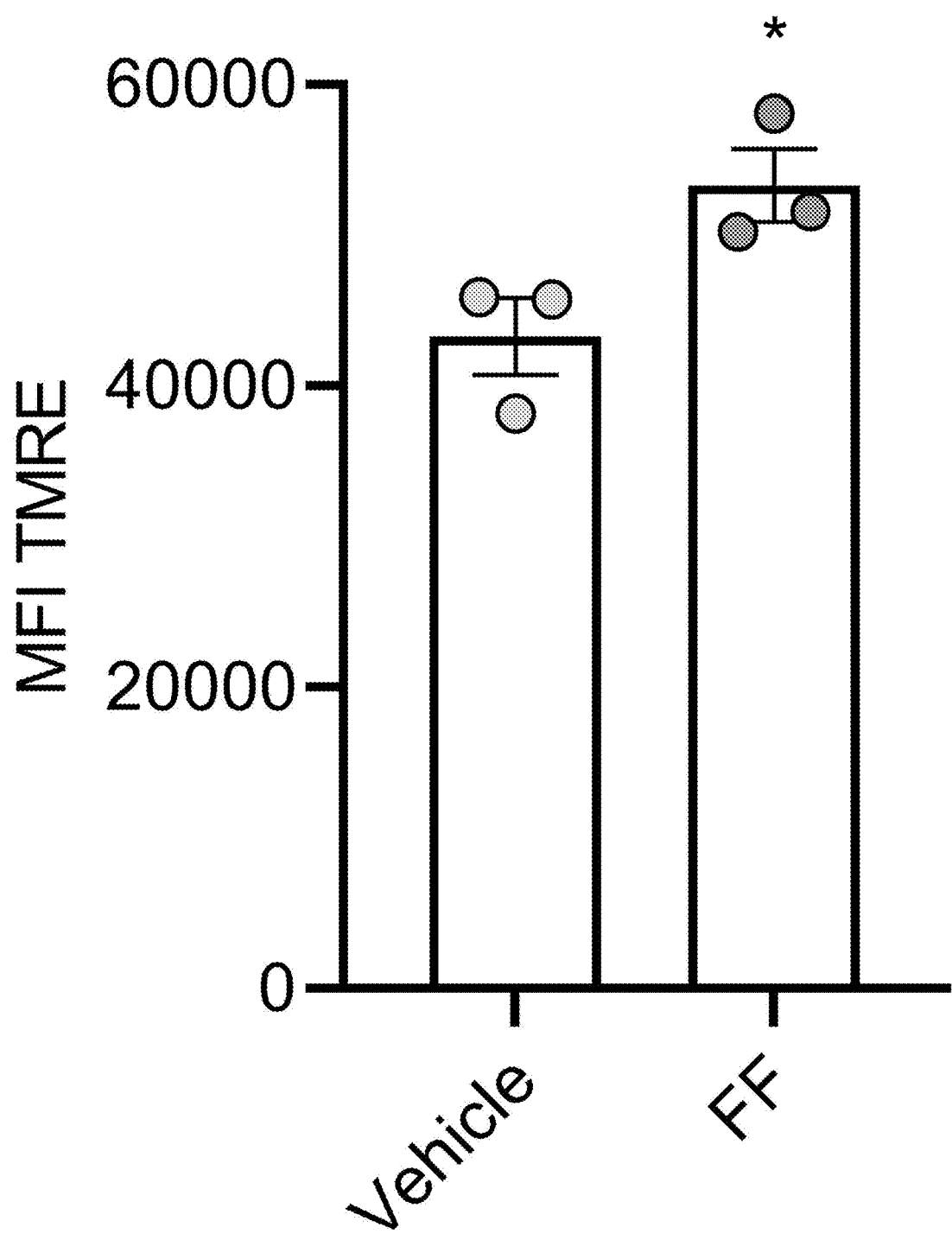
Figure 5C:
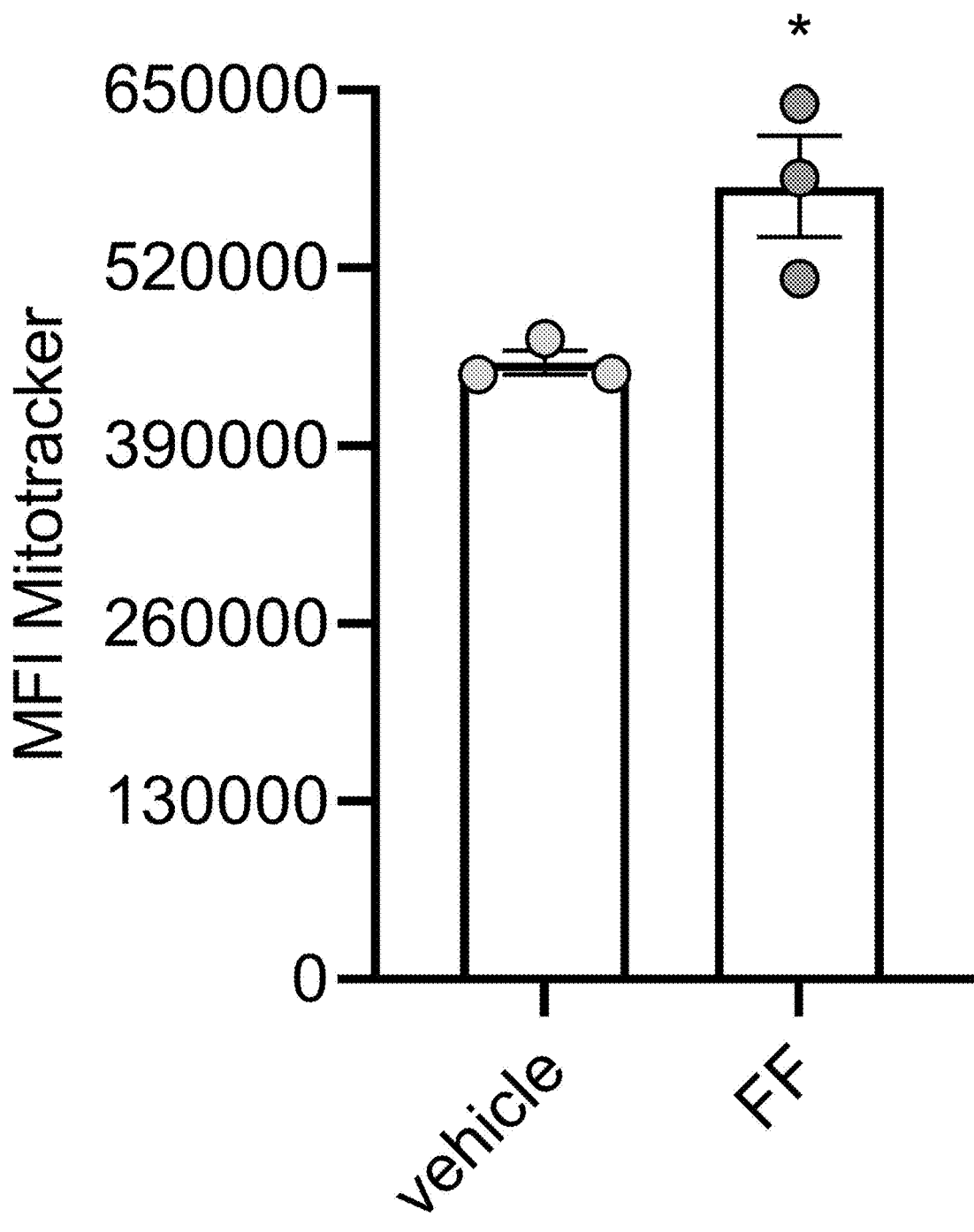

Given the involvement of $\beta$2-AR in erythropoiesis, it was hypothesized that administration of long-acting selective $\beta$2-AR agonist FF might promote erythroid differentiation. To address this, primary human HSPCs were treated with varying doses of FF (Selleckchem). Remarkably, FF administration elevated erythroid differentiation in primary human HSPCs in a dose-dependent manner (FIG. 1A), without affecting viability, megakaryopoiesis or myelopoiesis (FIG. 1B and FIG. 1D). As confirmation, formoterol fumarate (FF) from 2 different vendors (Selleckchem and Sigma) similarly enhanced erythroid differentiation in primary human HSPCs (FIG. 3A and FIG. 3B). To ascertain if FF administration plays a role further upstream in the erythroid differentiation pathway, methylcellulose colony-formation assays were performed. Indeed, FF treatment significantly increased blast-forming unit-erythroid (BFU-E) and colony-forming unit-erythroid (CFU-E) formation (FIG. 4). Corroborating with existing literature, treatment with FF enhanced expression of mtDNA encoded genes required for OXPHOS (FIG. 4A), and elevated mitochondrial mass and membrane potential in primary human HSPCs (FIG. 5B and FIG. 5C). These data indicate therapeutic potential of FF in the alleviation of anemia.

FF Treatment in in Vitro and Ex Vivo Models of MDS

Figure 6A:
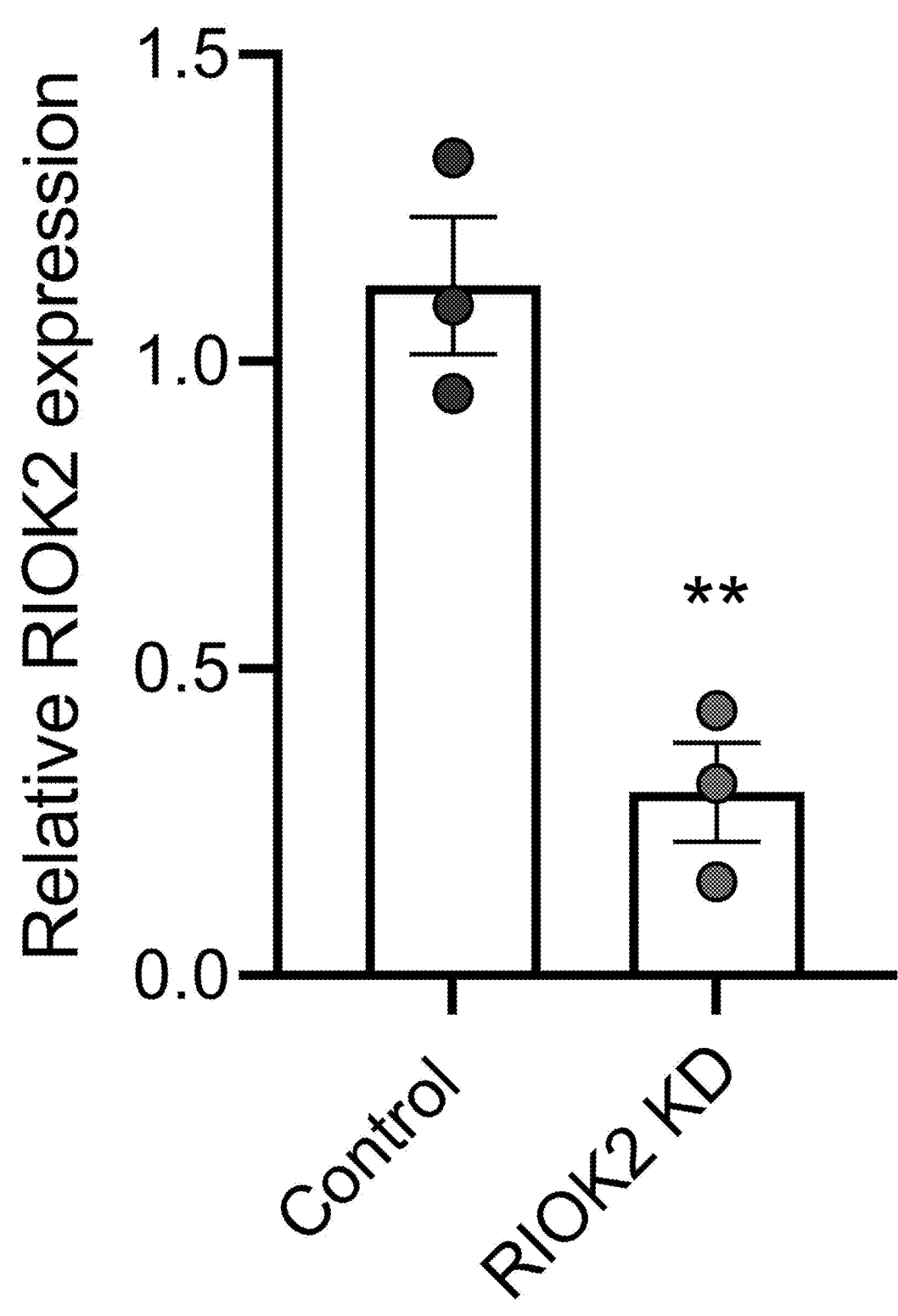
FIG. 6A-FIG. 6F show that formoterol fumarate (FF) stimulates erythroid differentiation in RIOK2 knockdown (KD) and RPS14 KD HSPCs, but not in ADRB2-deficient HSPCs.
Figure 6B:
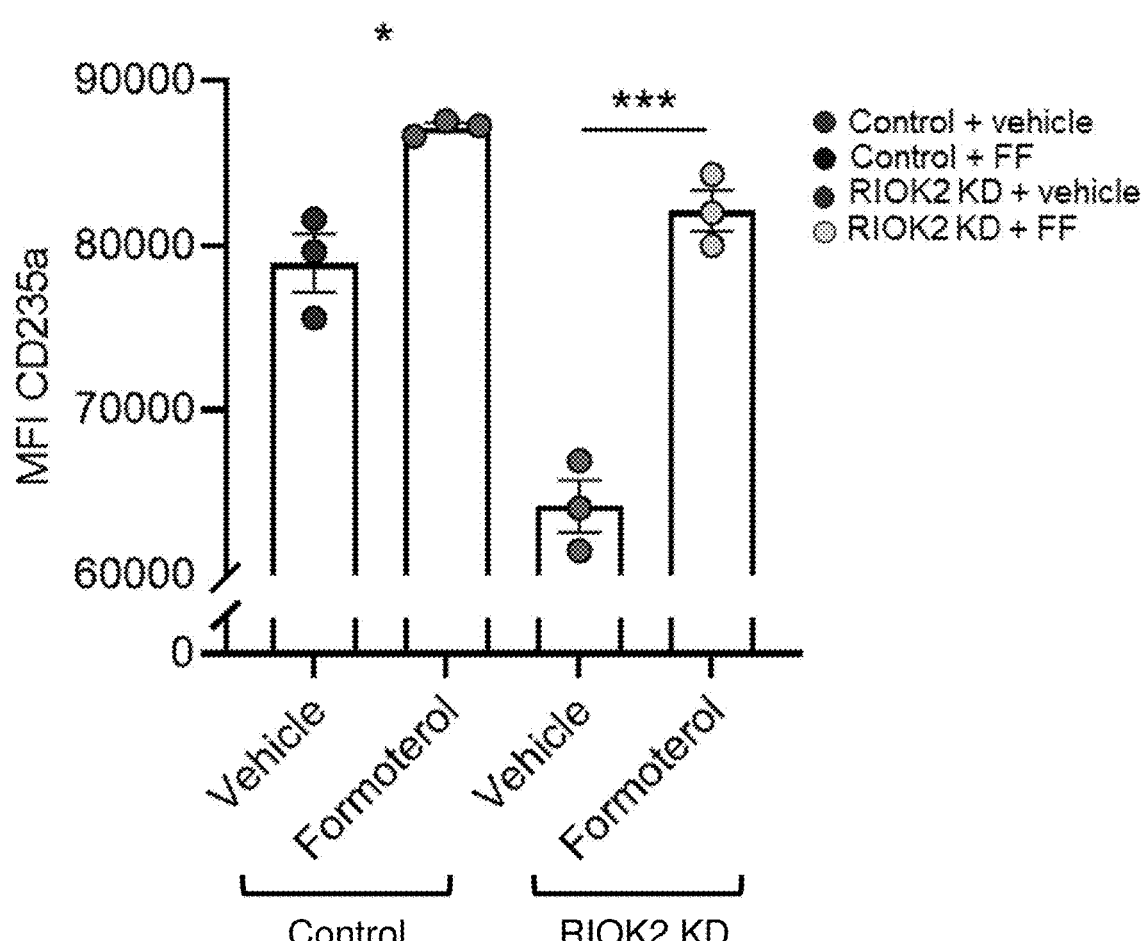
Figure 6C:
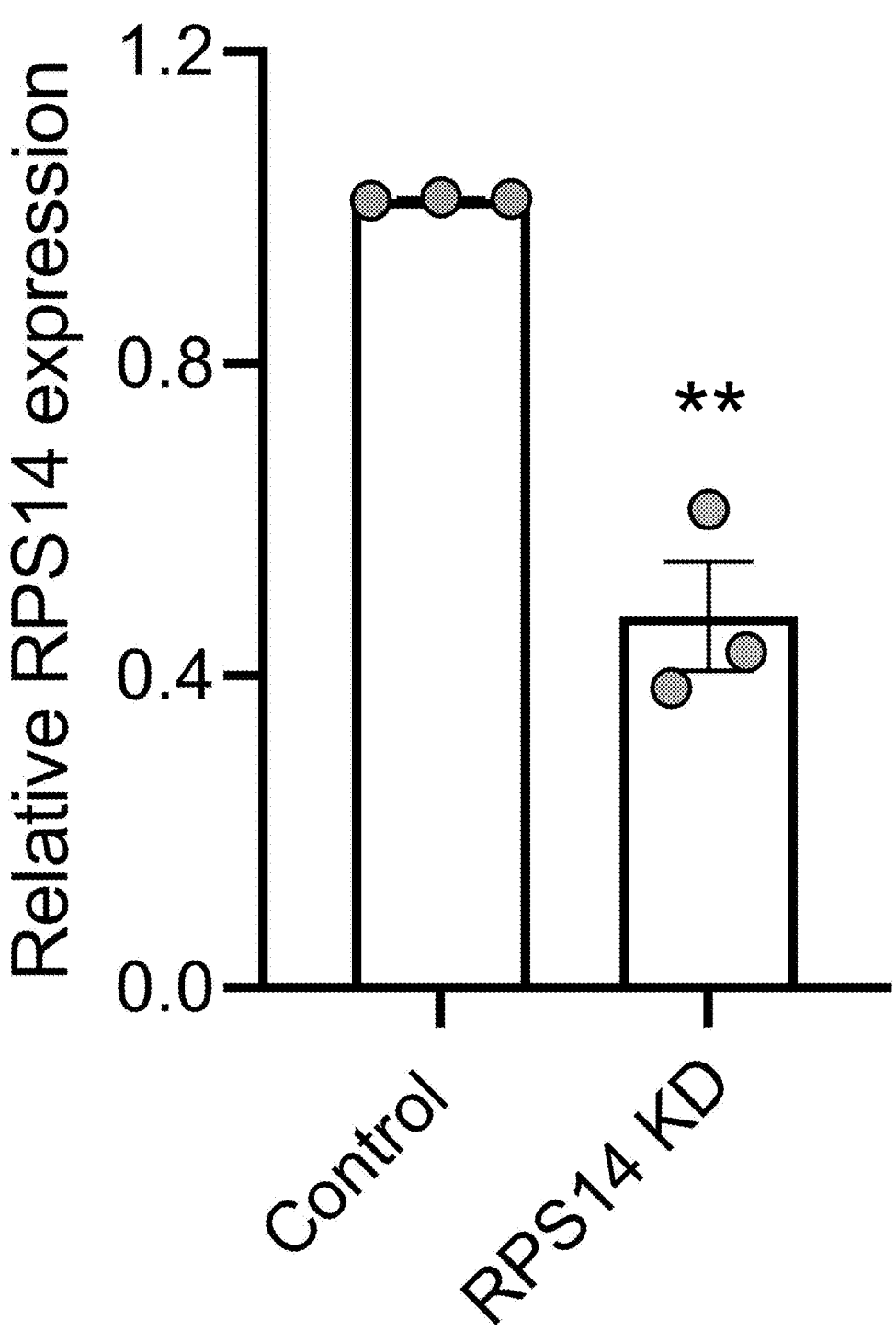

Since RIOK2-deficient primary human HSPCs effectively model impaired erythropoiesis leading to anemia (Ghosh et la. (2022) *Nat Immunol* 23: 109-121), it was next investigated whether treatment with formoterol fumarate (FF) alleviates anemia in this in vitro model. To address this, RIOK2-proficient and deficient primary human HSPCs via CRISPR-Cas9 based genome-editing were generated (FIG. 6A), as previously described (Ghosh et al. (2022) *Nat Immunol* 23: 109-121). Formoterol fumarate consistently enhanced erythroid differentiation in the control HSPCs (FIG. 6B). Remarkably, administration of FF stimulated erythropoiesis in RIOK2-knockdown (KD) HSPCs (FIG. 6B). Of note, FF treatment elevated erythroid differentiation of RIOK2-deficient HSPCs to levels comparable with basal erythropoiesis in control cells (FIG. 6B). Since RPS14 deletion is reported to be MDS-genic (Ebert et al. (2008) *Nature* 451: 335-339; Schneider et al. (2016) *Nat Med* 22: 288-297), RPS14 was similarly knocked down in primary human HSPCs (FIG. 6C).

Figure 6D:
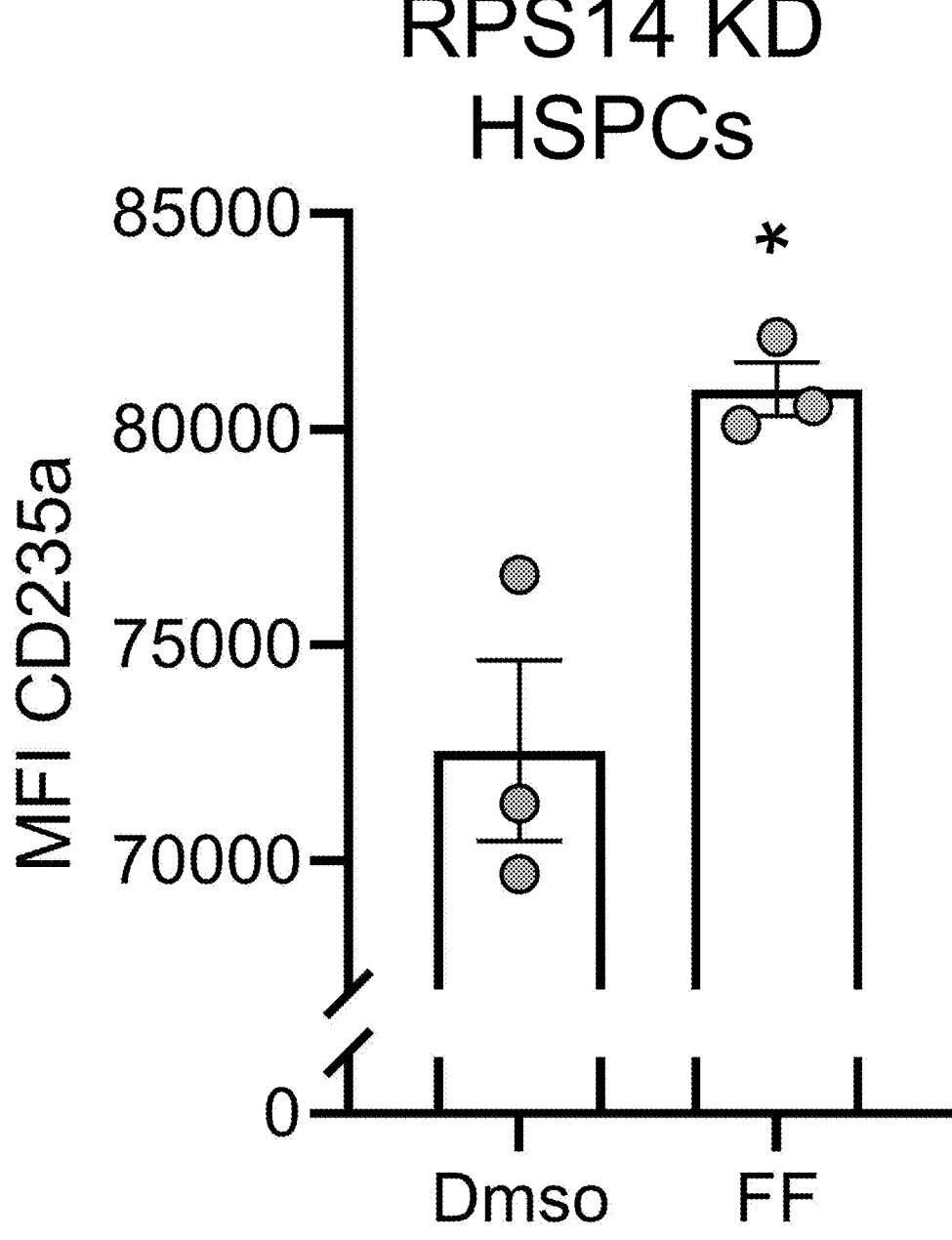
Figure 6E:
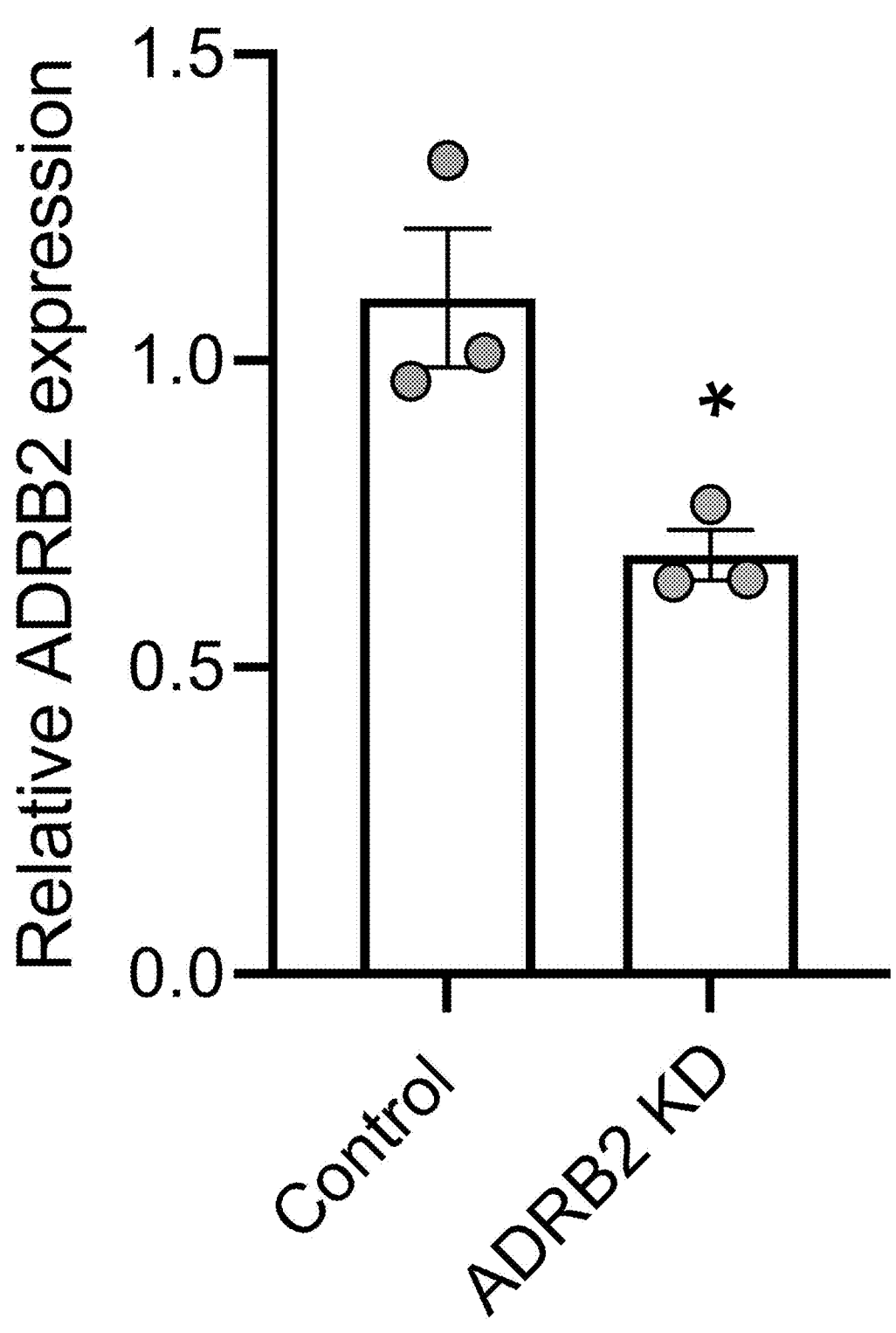
Figure 6F:
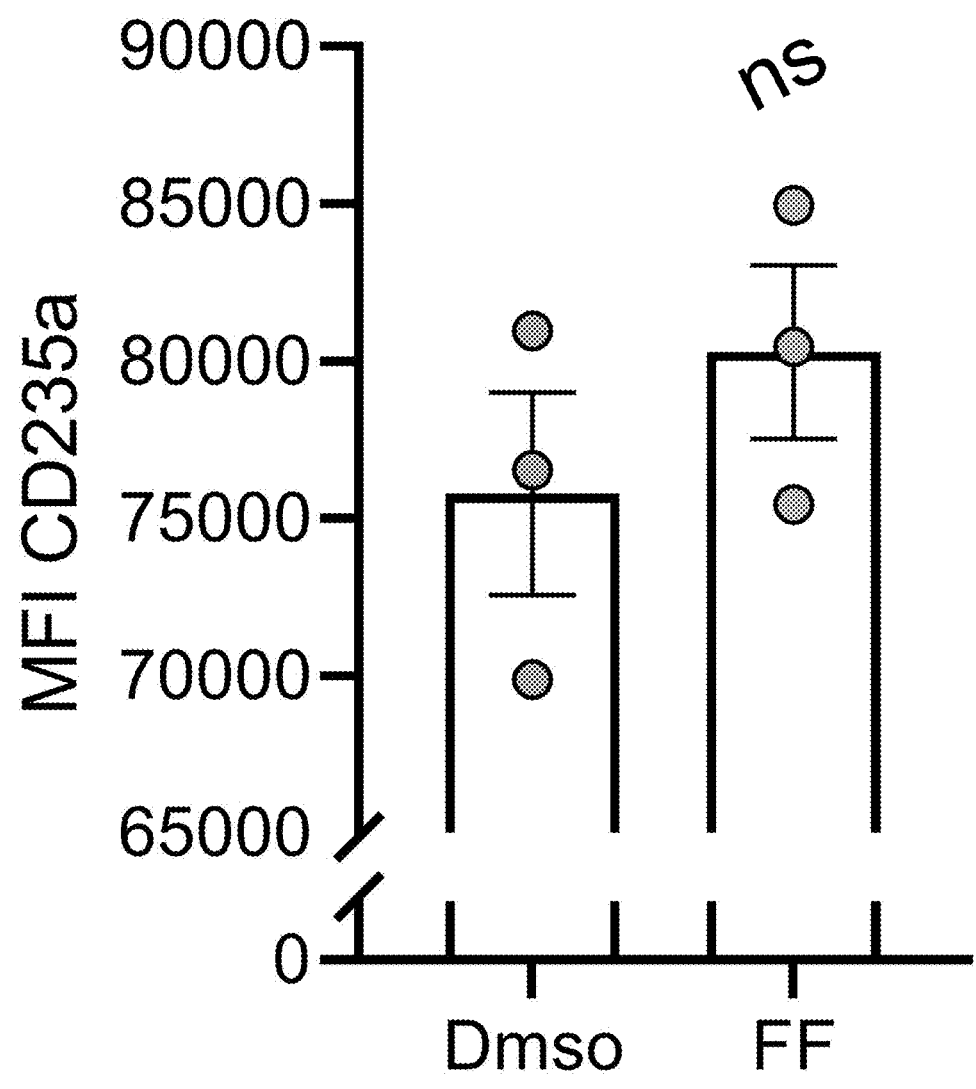
Figure 7:
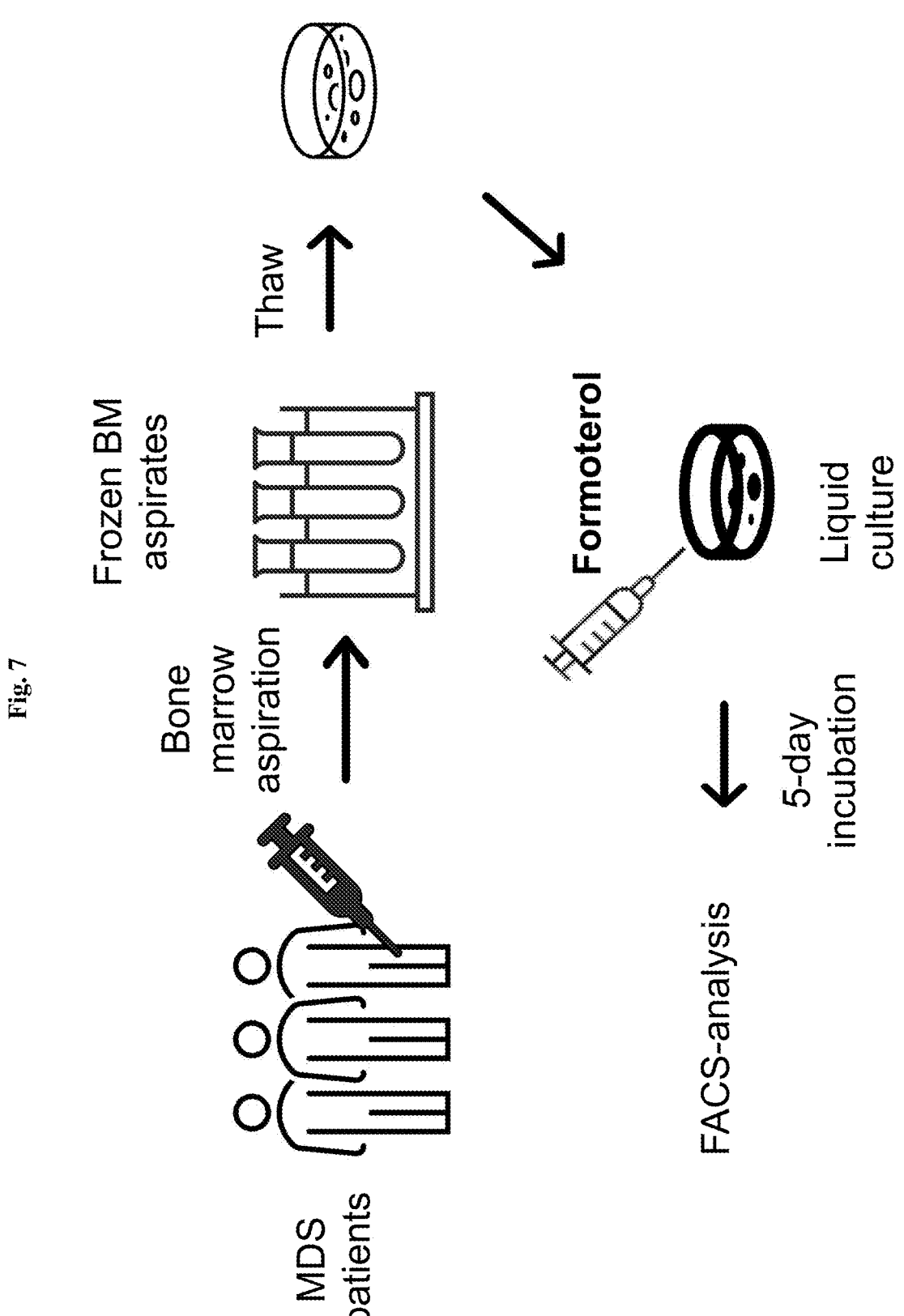
FIG. 7 shows an exemplary work-flow to study the impact on formoterol fumarate (FF) on MDS patient-derived cells using liquid culture.
Figure 8A:
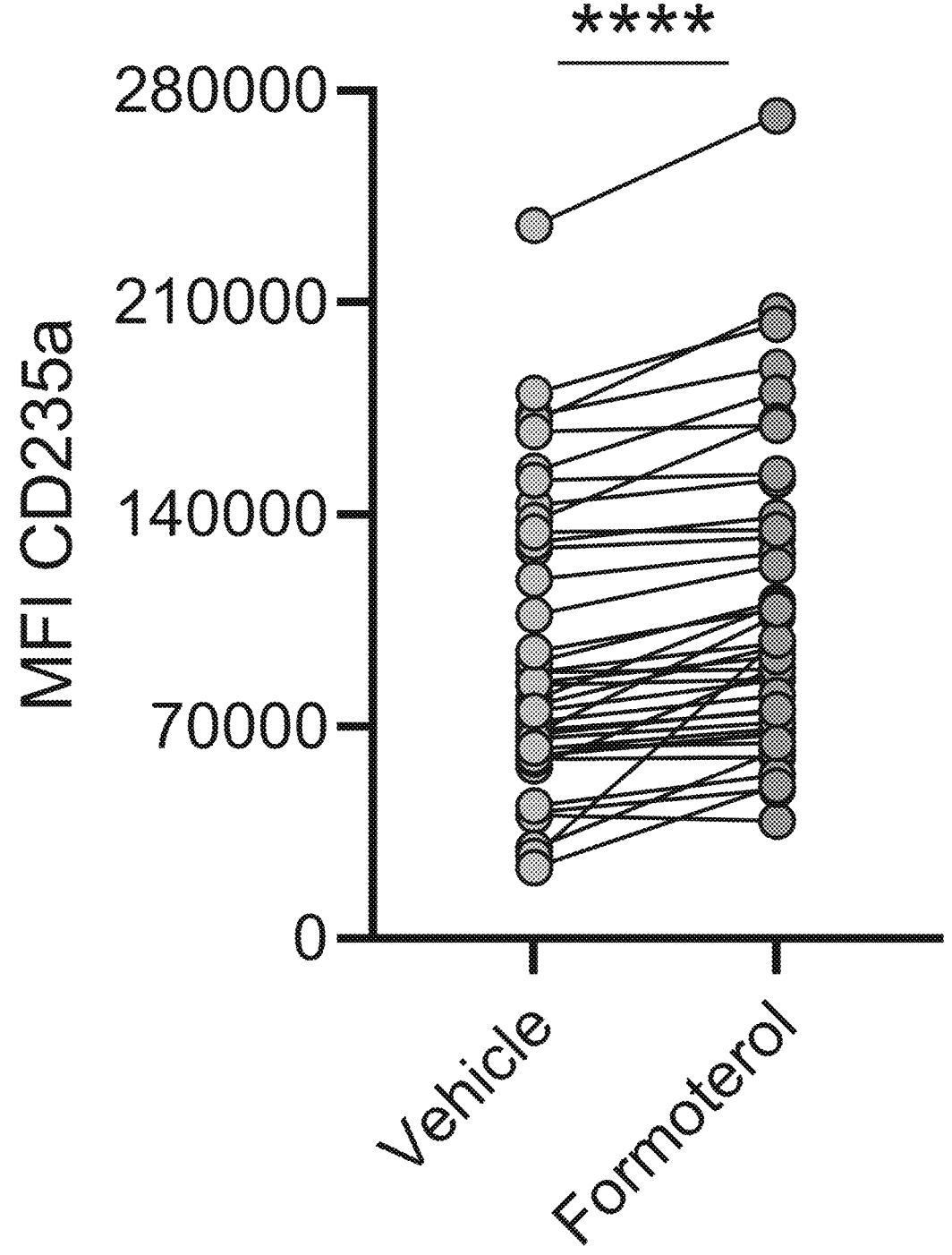
FIG. 8A-FIG. 8B show that formoterol fumarate (FF) enhances erythroid differentiation in MDS patient-derived bone marrow cells. Erythroid differentiation (CD235a) in vehicle (DMSO) vs. FF-treated (FIG. 8A: Selleck.
Figure 8B:
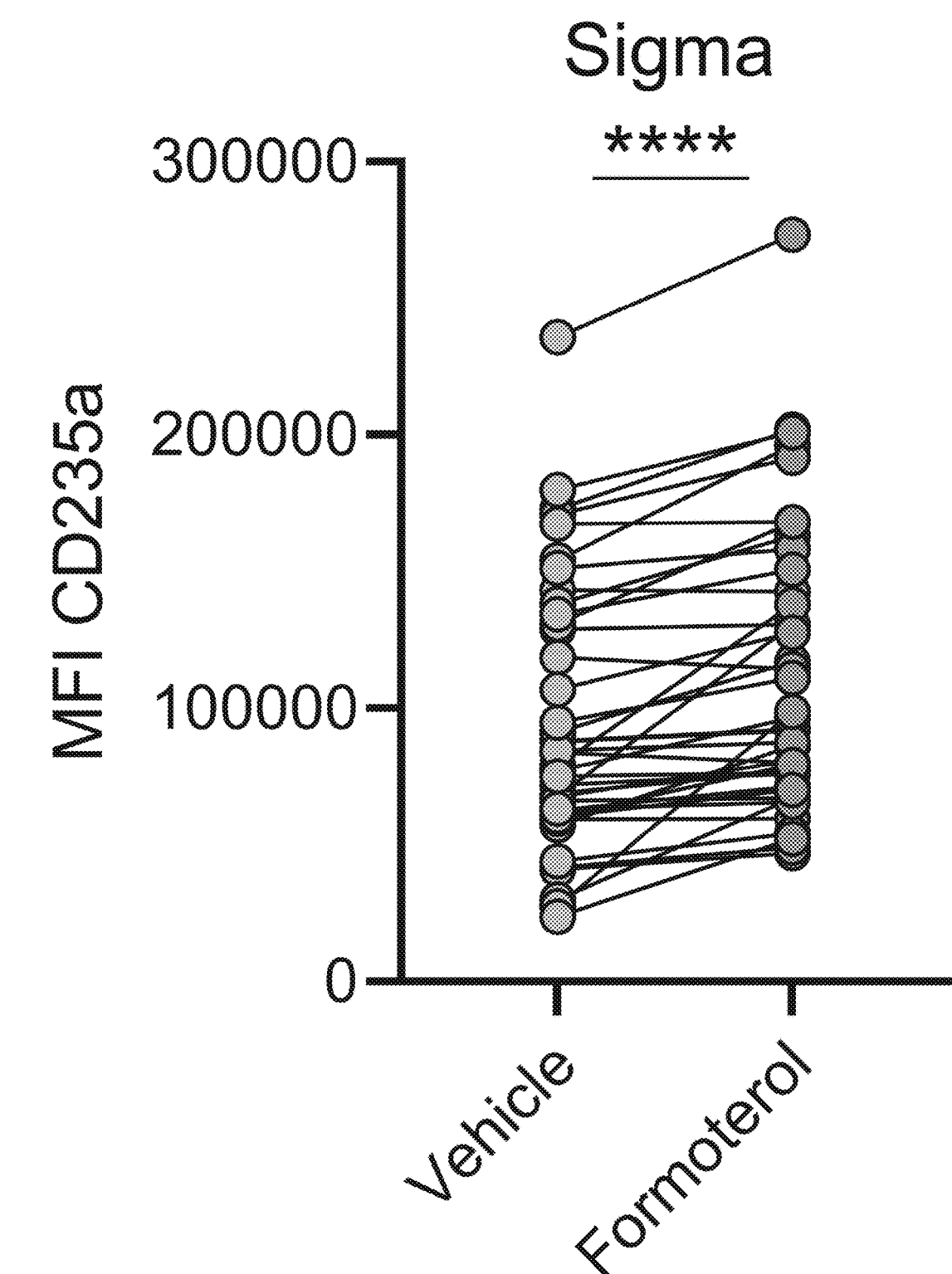
Figure 9:
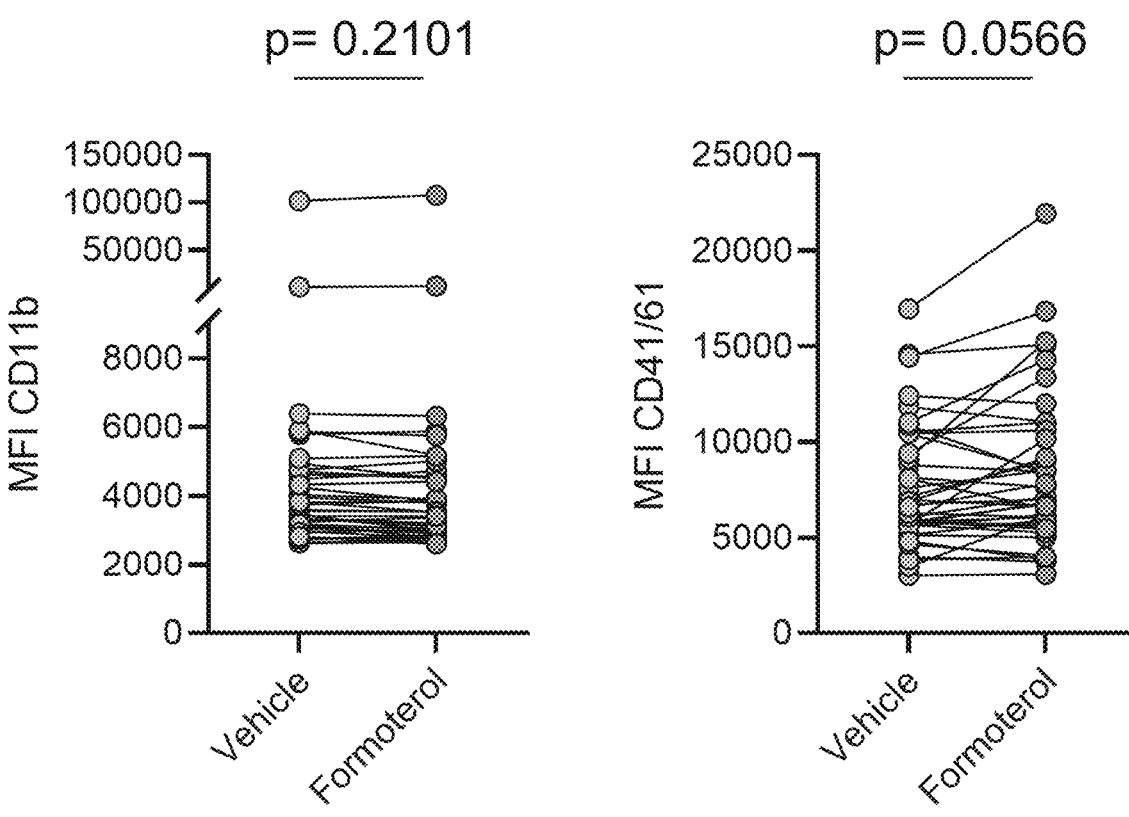
FIG. 9 shows results of the liquid culture (ex vivo) experiment showing that formoterol fumarate (FF) does not affect myelopoiesis/megakaryopoiesis in 40 MDS patient-derived cells.
Figure 10:
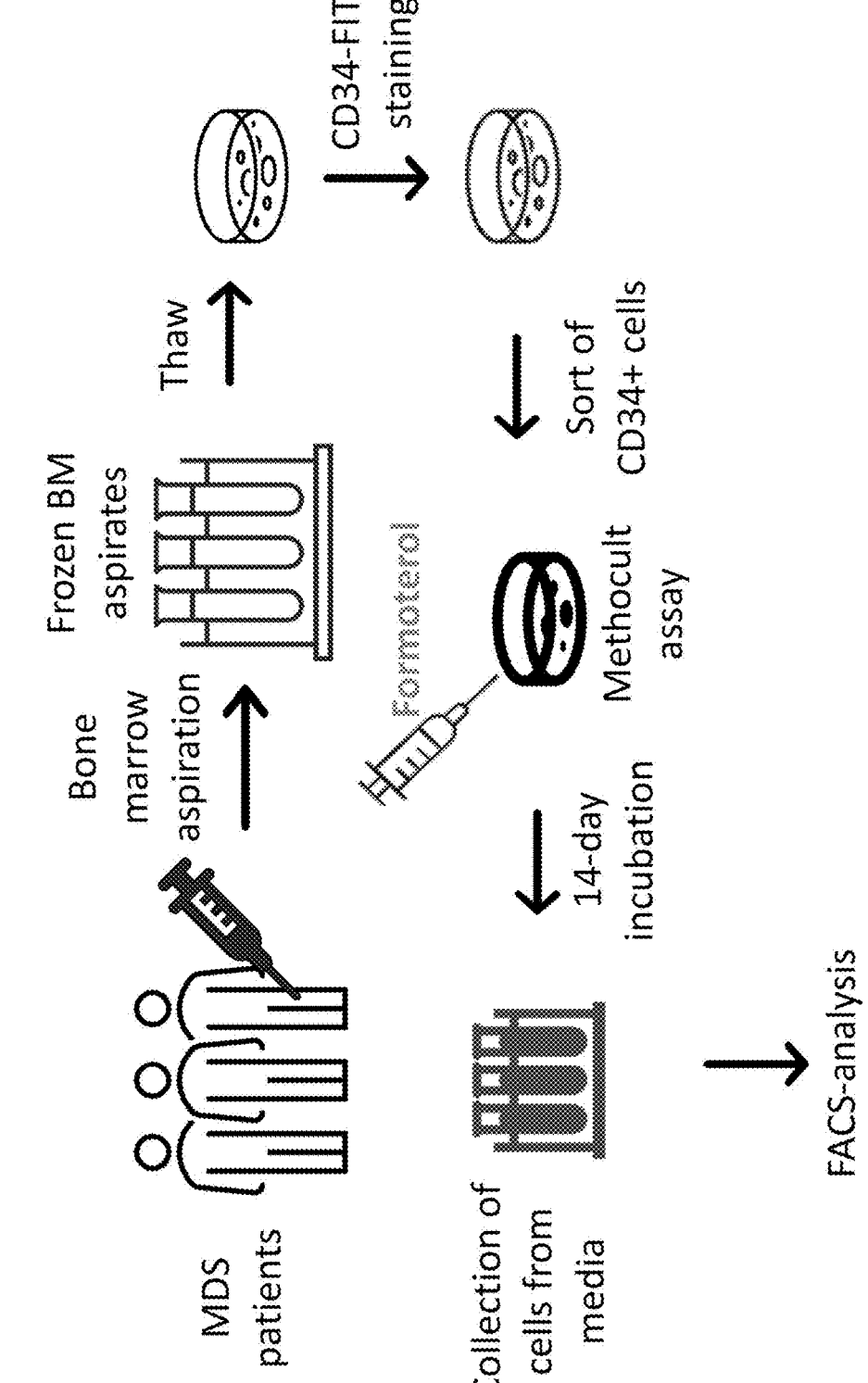
FIG. 10 shows an exemplary work-flow to study the impact on formoterol fumarate (FF) on hematopoietic progenitors isolated from MDS patients.
Figure 11A:
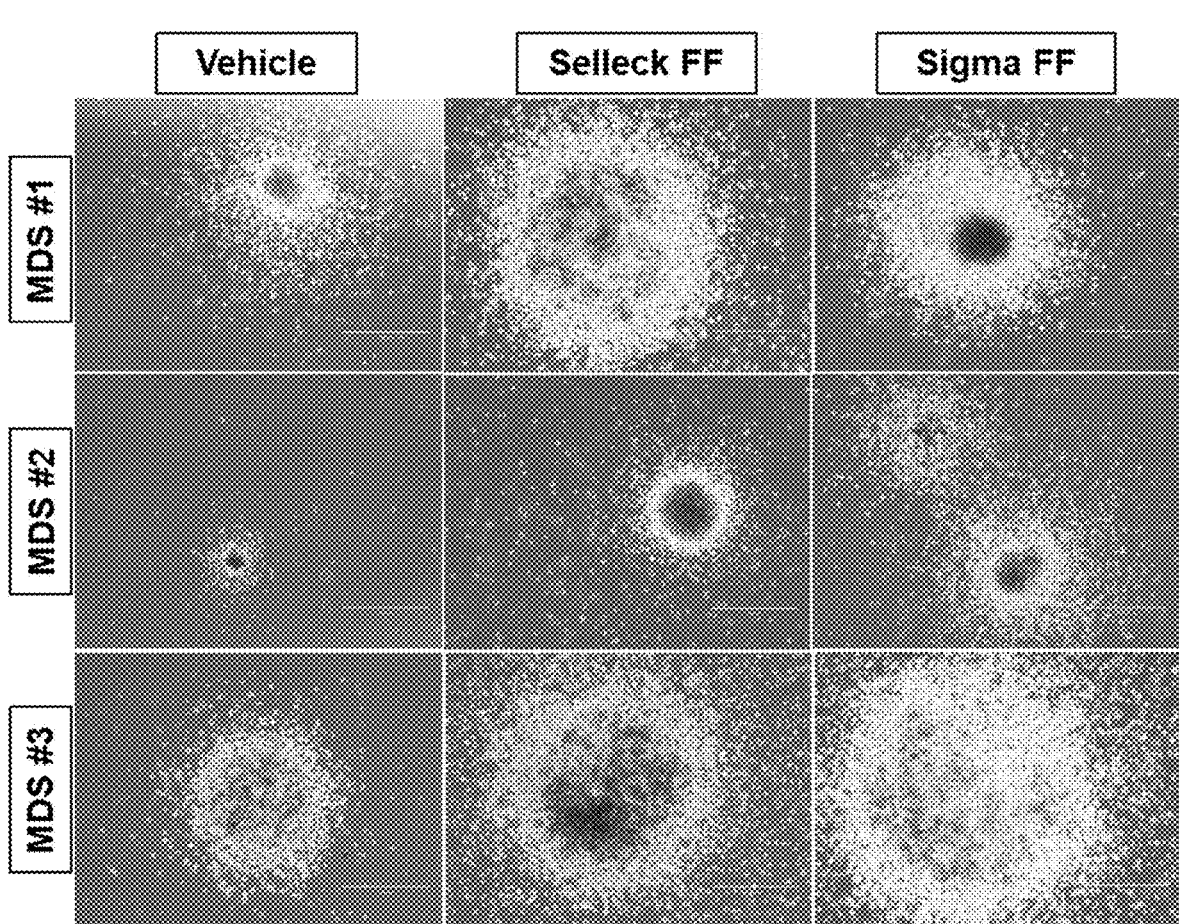
FIG. 11A-FIG. 11D show that formoterol fumarate (FF) enhances differentiation of erythroid progenitors in MDS patient-derived bone marrow cells.
Figure 11B:
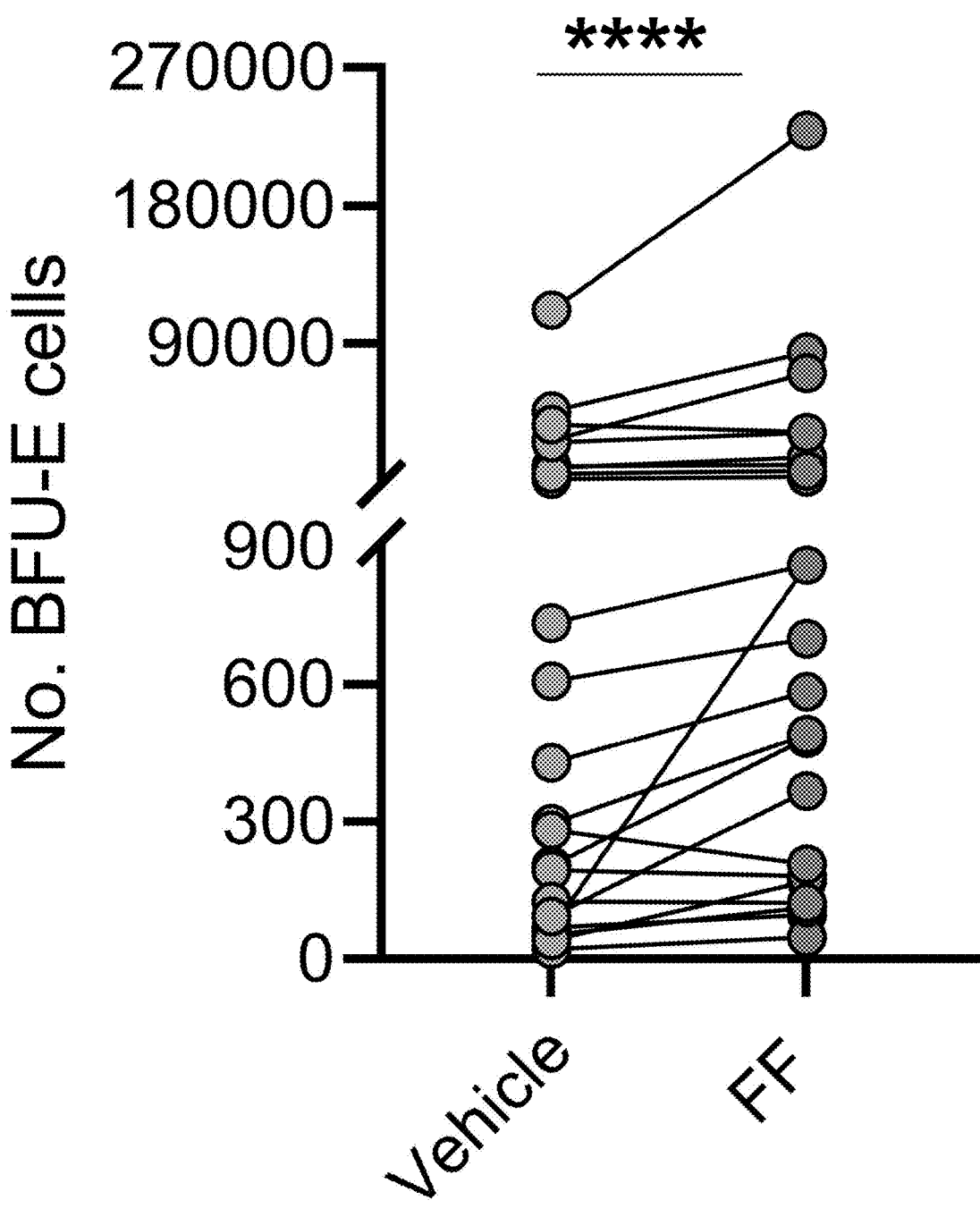
Figure 11C:
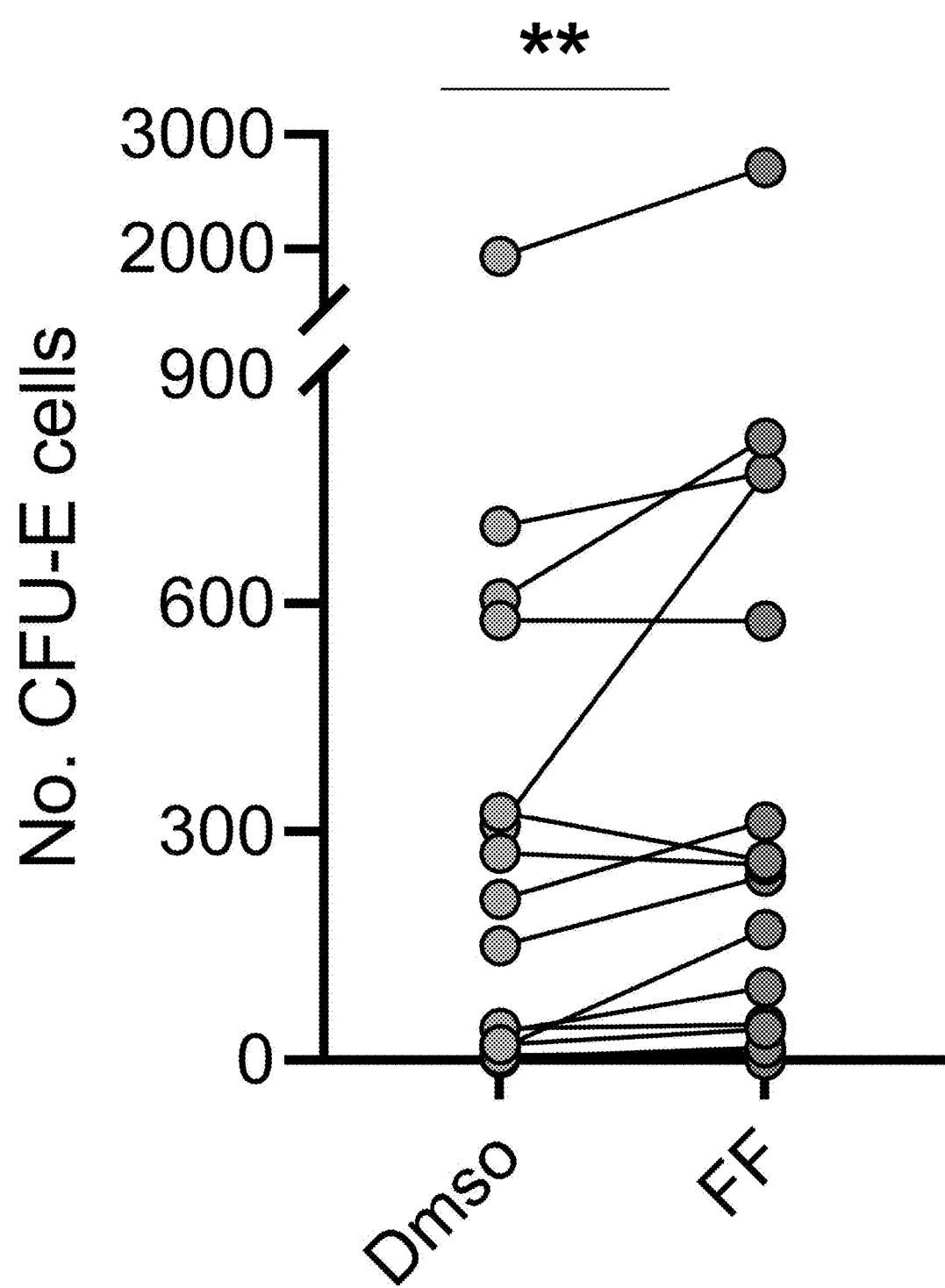
Figure 11D:
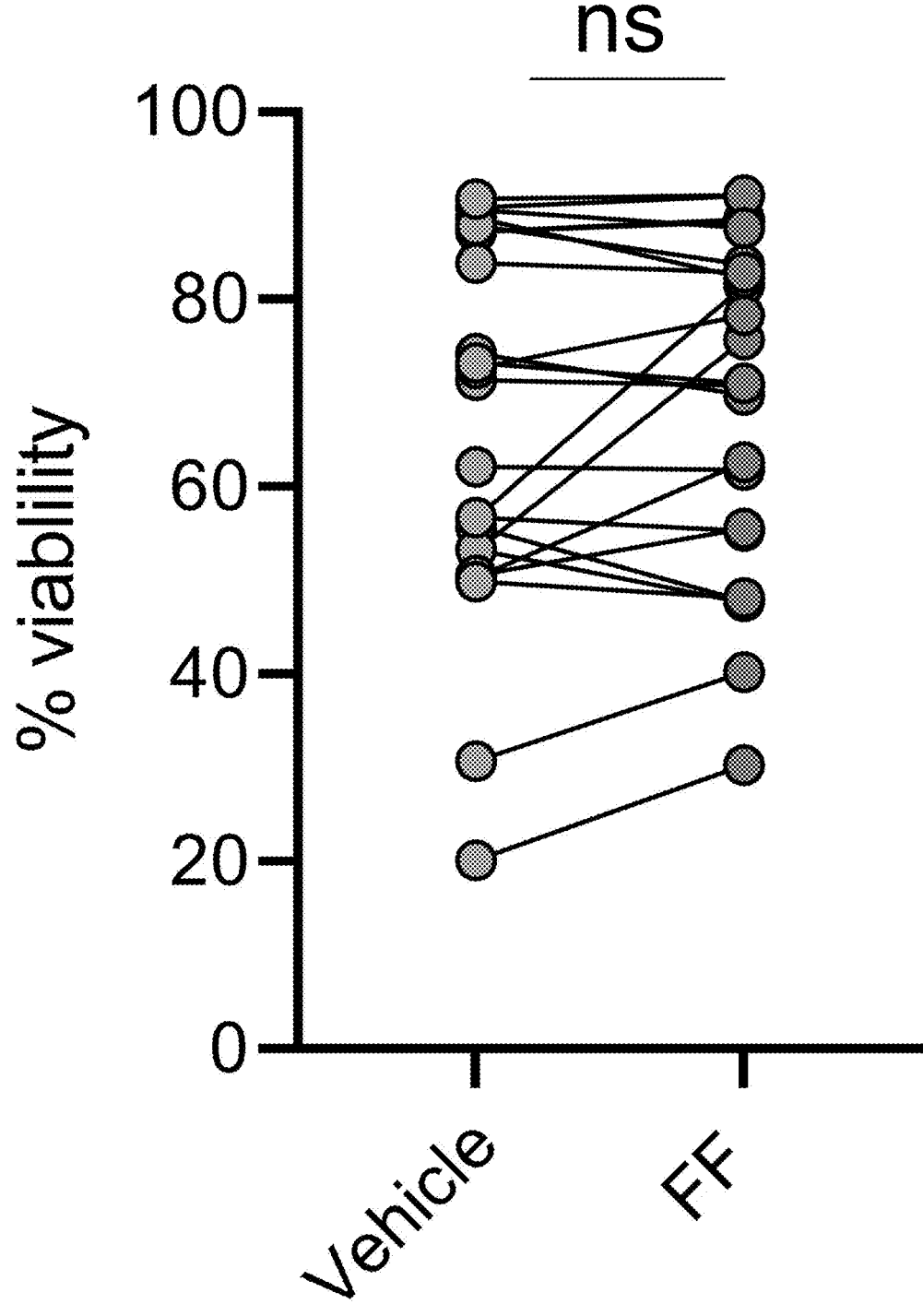
Figure 11D:
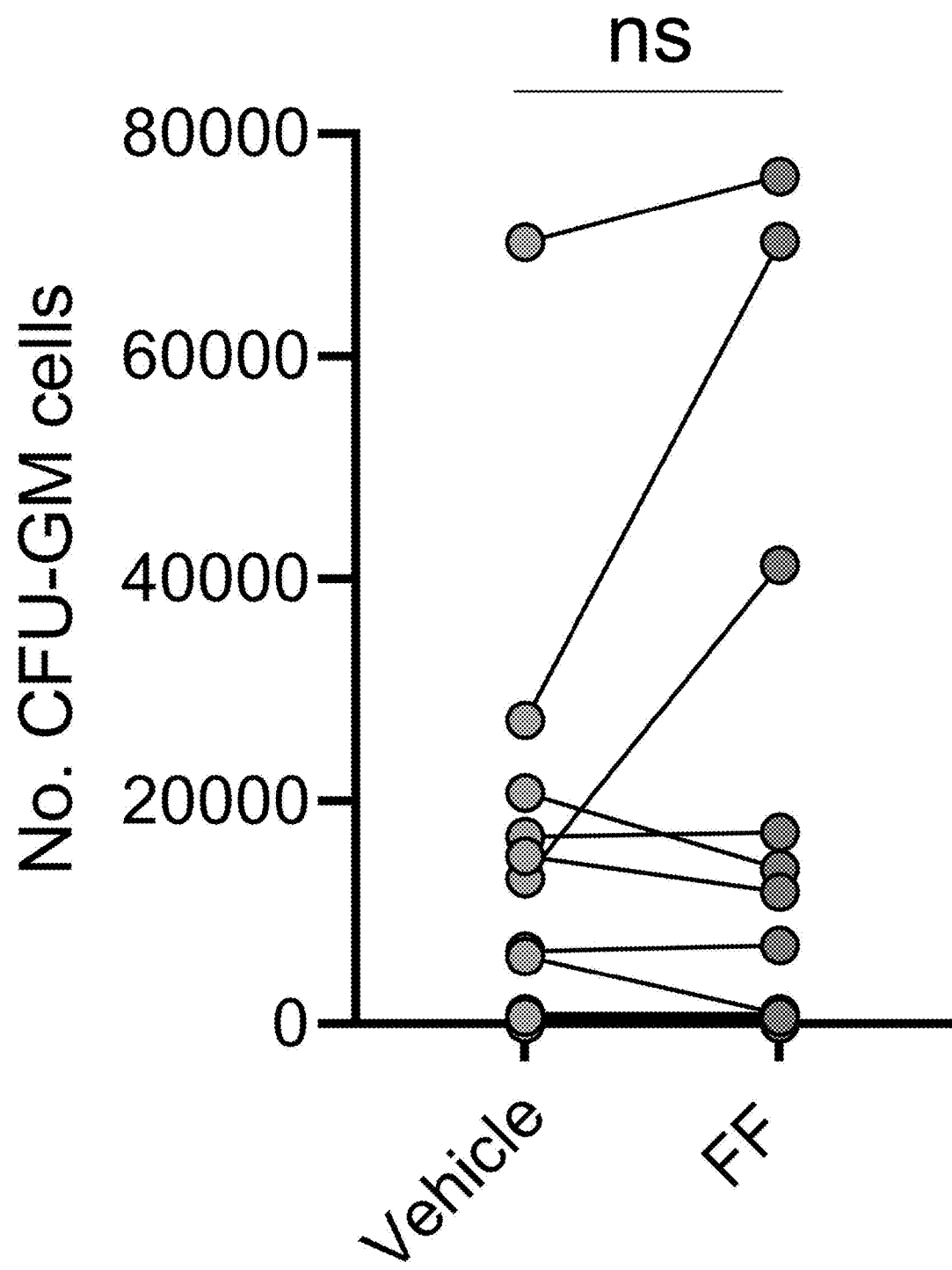
Figure 11D:
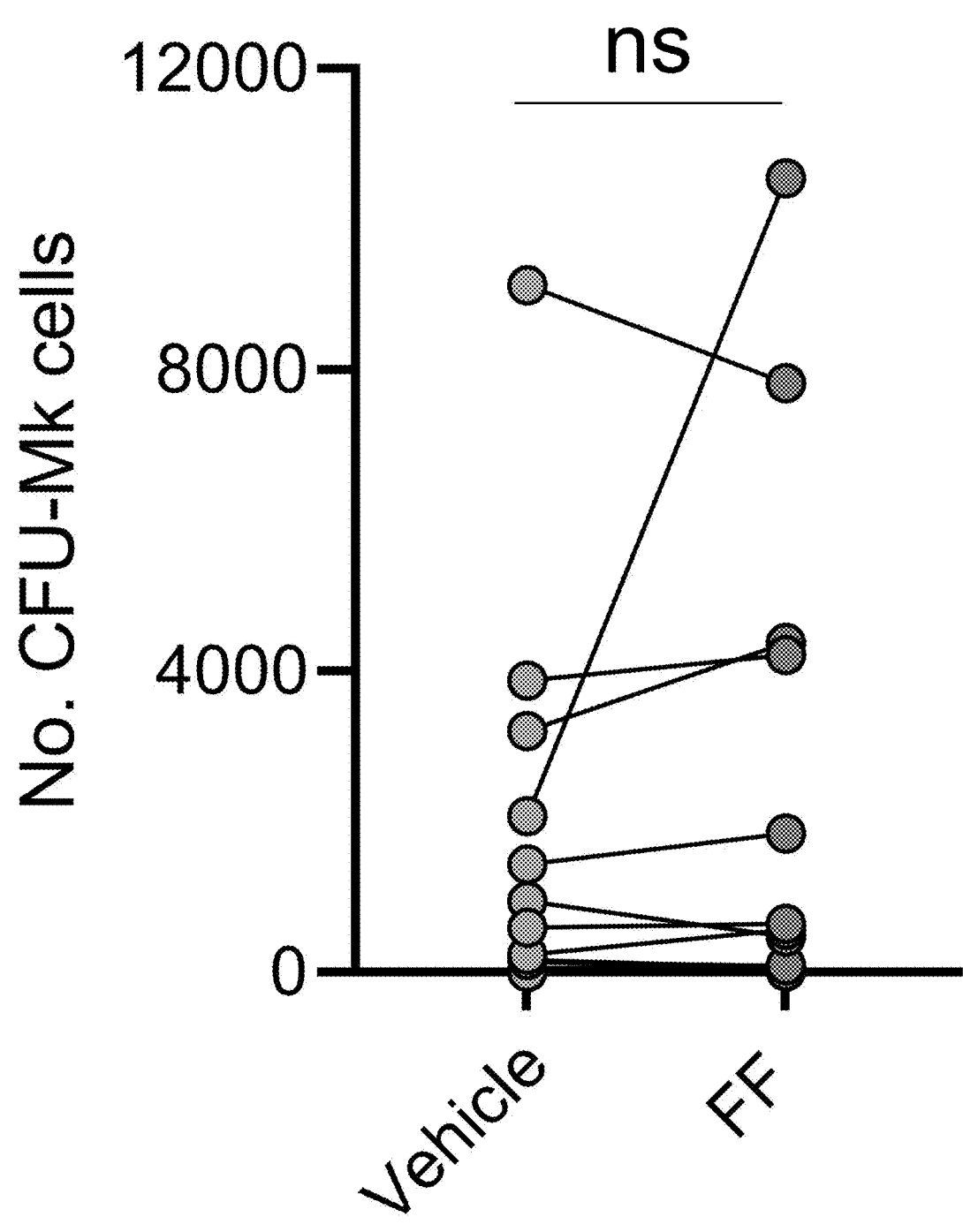
Figure 12:
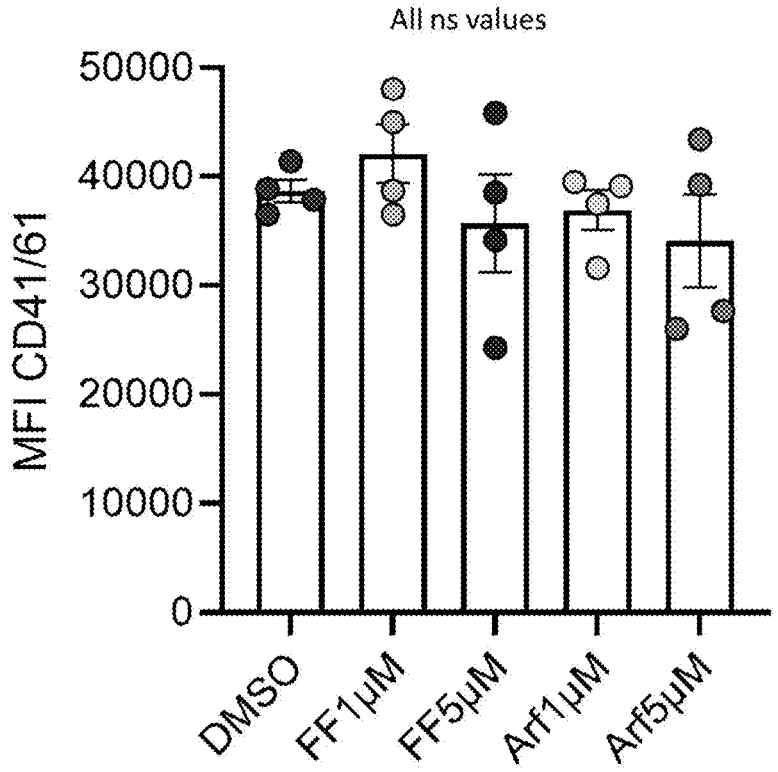
FIG. 12 shows that agonists and antagonists of β2 adrenergic receptors do not affect megakaryopoiesis. Administration of formoterol fumarate (FF) or arformoterol tartrate (Arf) at 1/5 µM to primary human HSPCs does not influence megakaryocytic differentiation (CD41/61). Representative of n=5 healthy donor-derived HSPCs; n=4 technical replicates within each donor. One-way analysis of variance (ANOVA). Data represented as mean±SEM. All comparisons were done w.r.t. control (DMSO) treated). ns=non-significant.
Figure 13:
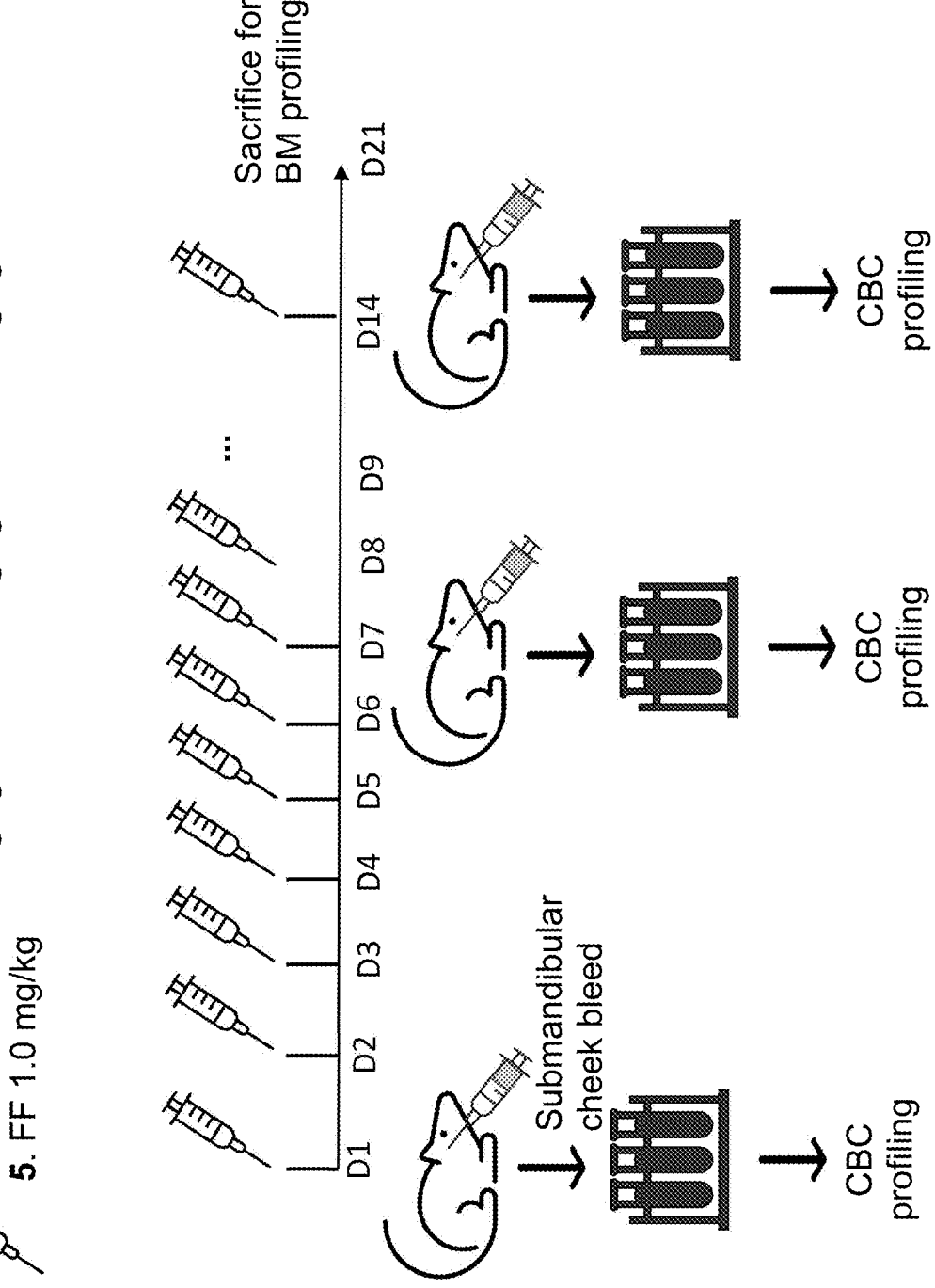
FIG. 13 shows an exemplary work-flow of a pilot study for formoterol fumarate (FF) treatment in vivo.

Administration of FF significantly increased erythroid differentiation in RPS14 KD HSPCs (FIG. 6D). Next, to validate the specificity of FF for β2-adrenoreceptors, ADRB2 was knocked down in primary human HSPCs and treated with FF. FF treatment failed to induce erythropoiesis in ADRB2-deficient HSPCs due to lack of ADRB2 gene that encodes for β2-AR These findings prompted further testing to determine whether administration of FF in MDS patient-derived bone marrow (BM) samples improves erythroid differentiation in an ex vivo setting. To explore this, cells isolated from BM aspirates of de-identified MDS patients were procured. Next, the MDS patient-derived BM cells were placed in liquid erythroid differentiation culture, as previously described (Khajuria et al. (2018) *Cell* 173: 90-103), with or without FF treatment. Indeed, treatment with FF (from Selleckchem) significantly enhanced erythroid differentiation in BM cells in the majority of MDS patients, although a few MDS patients' bone marrow (BM) cells were unresponsive (FIG. 8A). To further validate this observation, the impact of FF from another vendor (Sigma) was tested on MDS patient-derived cells. Similarly, FF (from Sigma) boosted erythropoiesis in the majority of MDS patients (FIG. 8B). Next, CD34+ progenitors were FACS-sorted from the MDS patient-derived BM aspirates and seeded in semi-solid methylcellulose culture media with vehicle (DMSO) or FF treatment. FF significantly boosted both BFU-E and CFU-E formation in MDS patient-derived BM progenitors (FIGS. 11A-11C). However, FF administration produced insignificant effects on the viability, myeloid and megakaryocytic differentiation of MDS patient-derived BM cells (FIG. 11D). Hence, it was concluded that formoterol fumarate (FF) potently augments erythroid differentiation in not only primary hematopoietic stem cells from healthy individuals but also BM cells derived from MDS patients. Therefore, the FDA-approved drug formoterol fumarate could be repurposed to reverse anemia in a range of hematological disorders.

FF Treatment Alleviates Anemia in Vivo

Figure 14A:
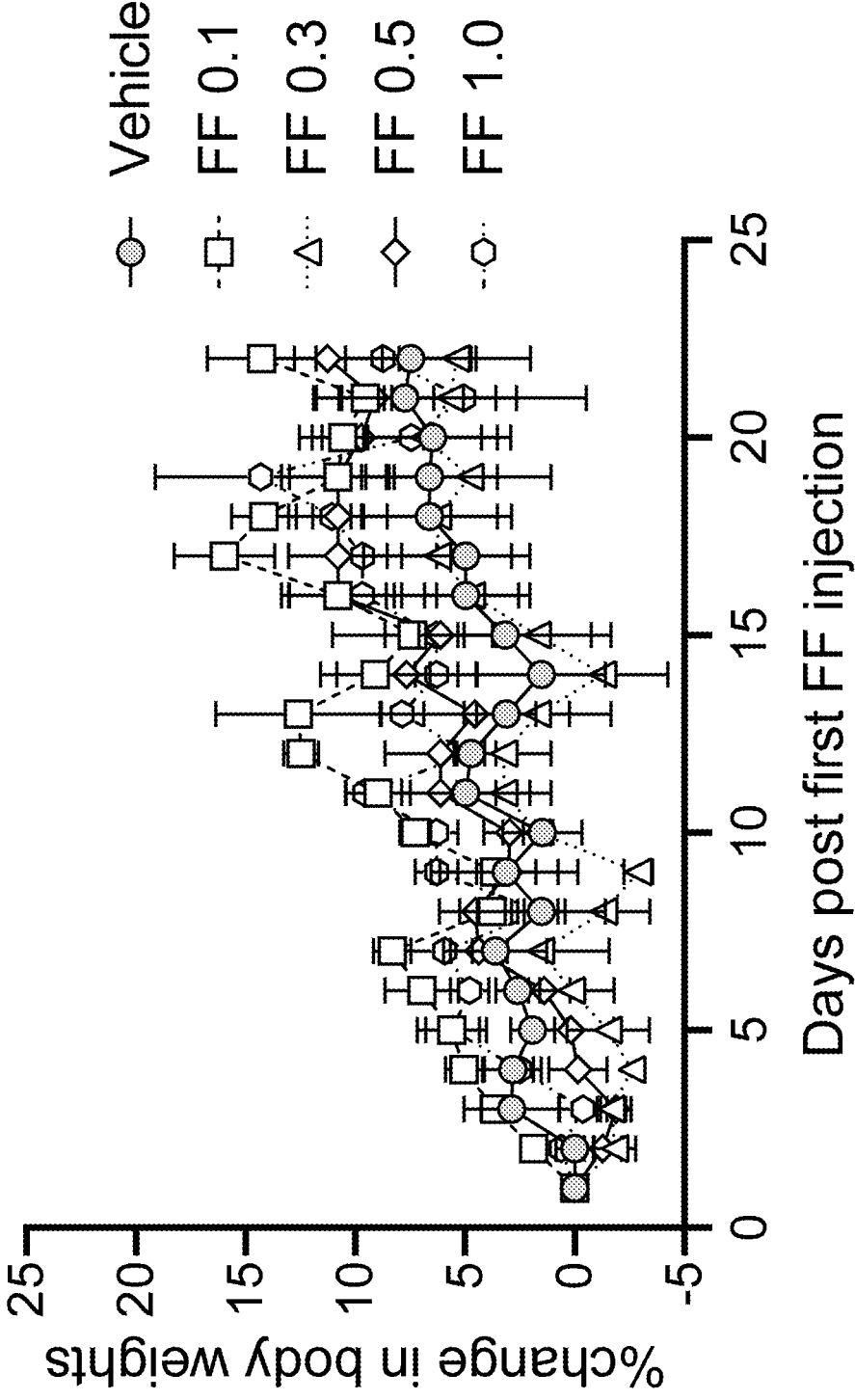
FIG. 14A-FIG. 14G show that formoterol fumarate (FF) treatment mildly increases RBC parameters in wild-type mice at steady-state.
Figure 14B:
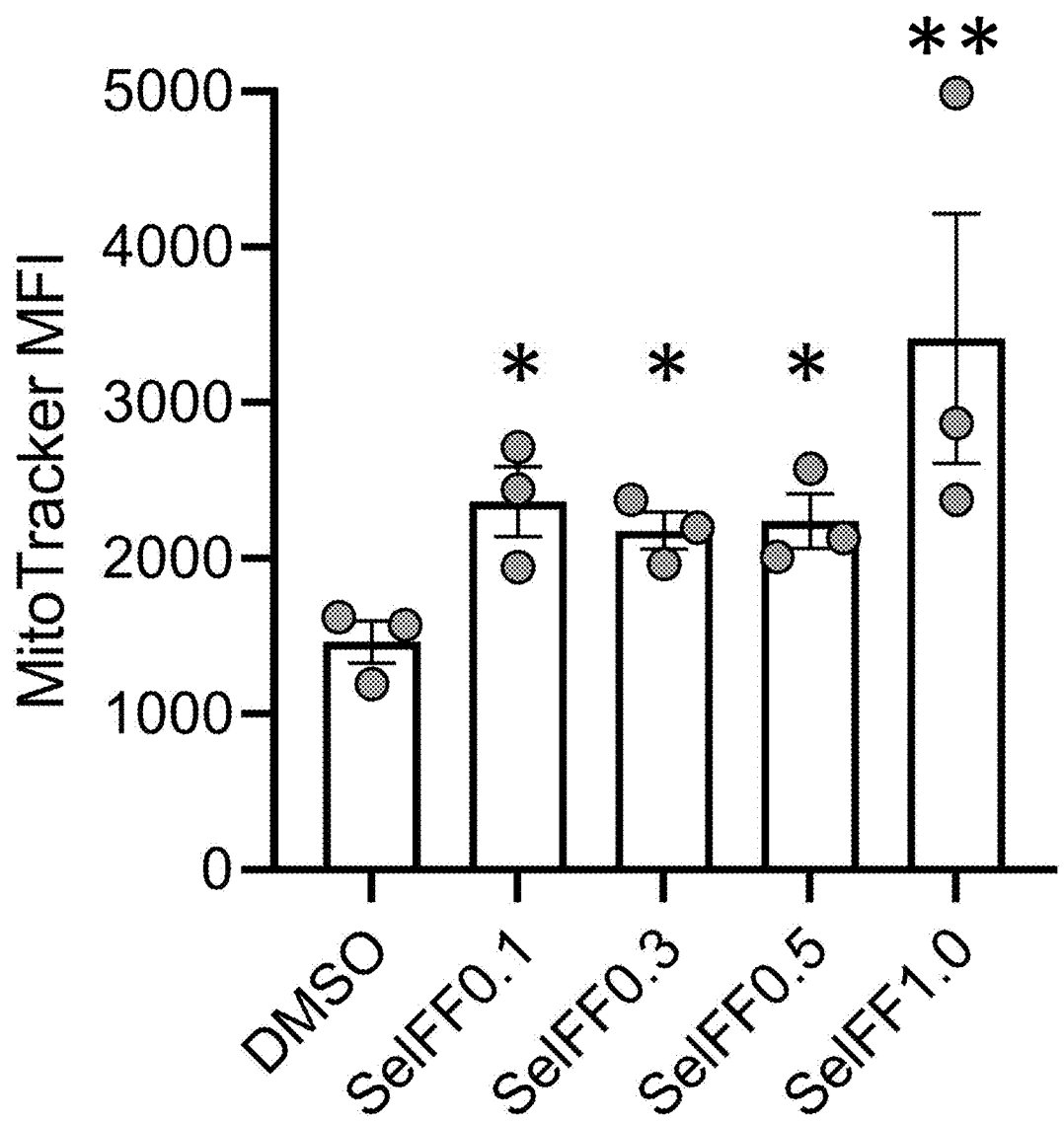
Figure 14C:
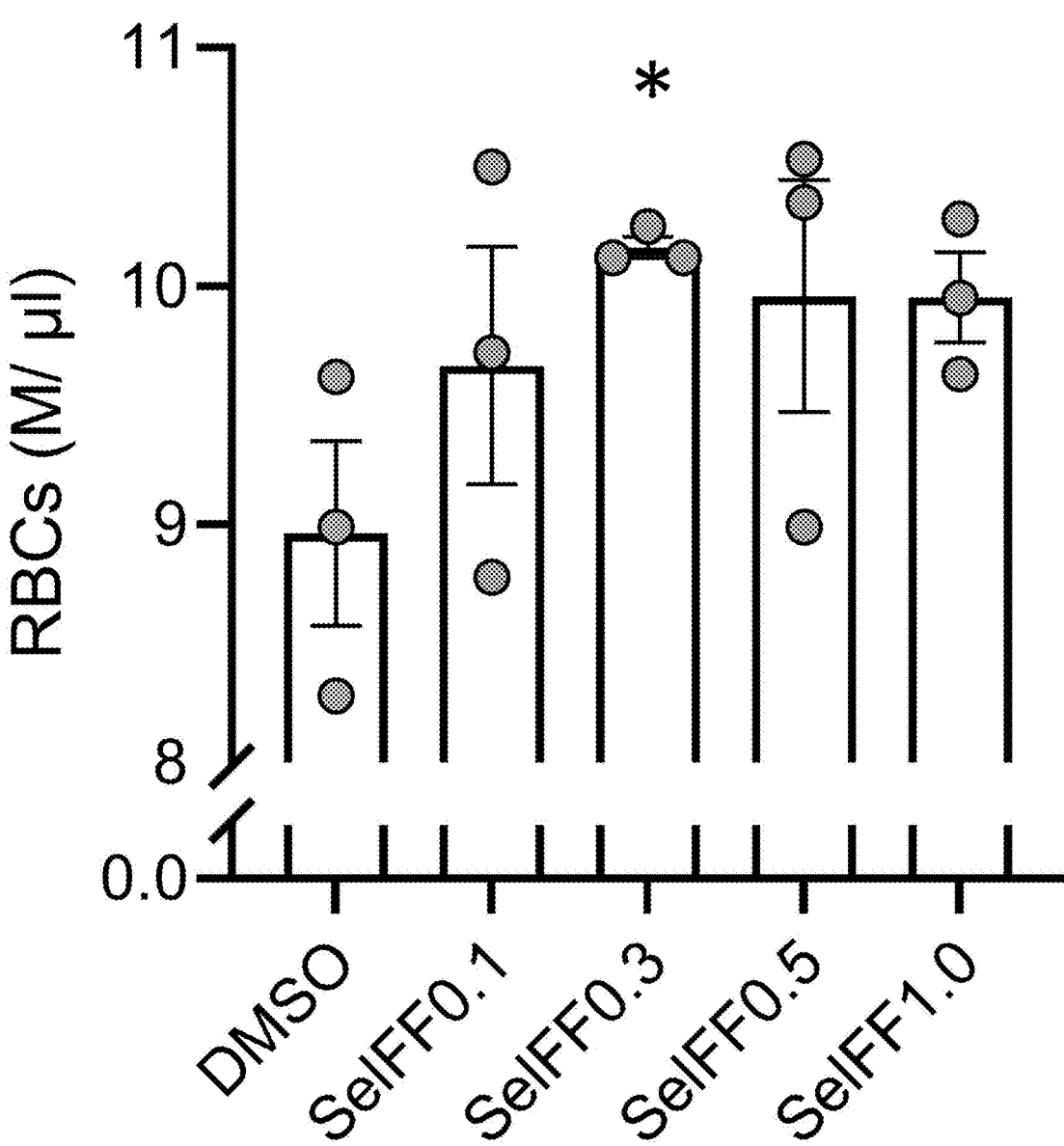
Figure 14D:
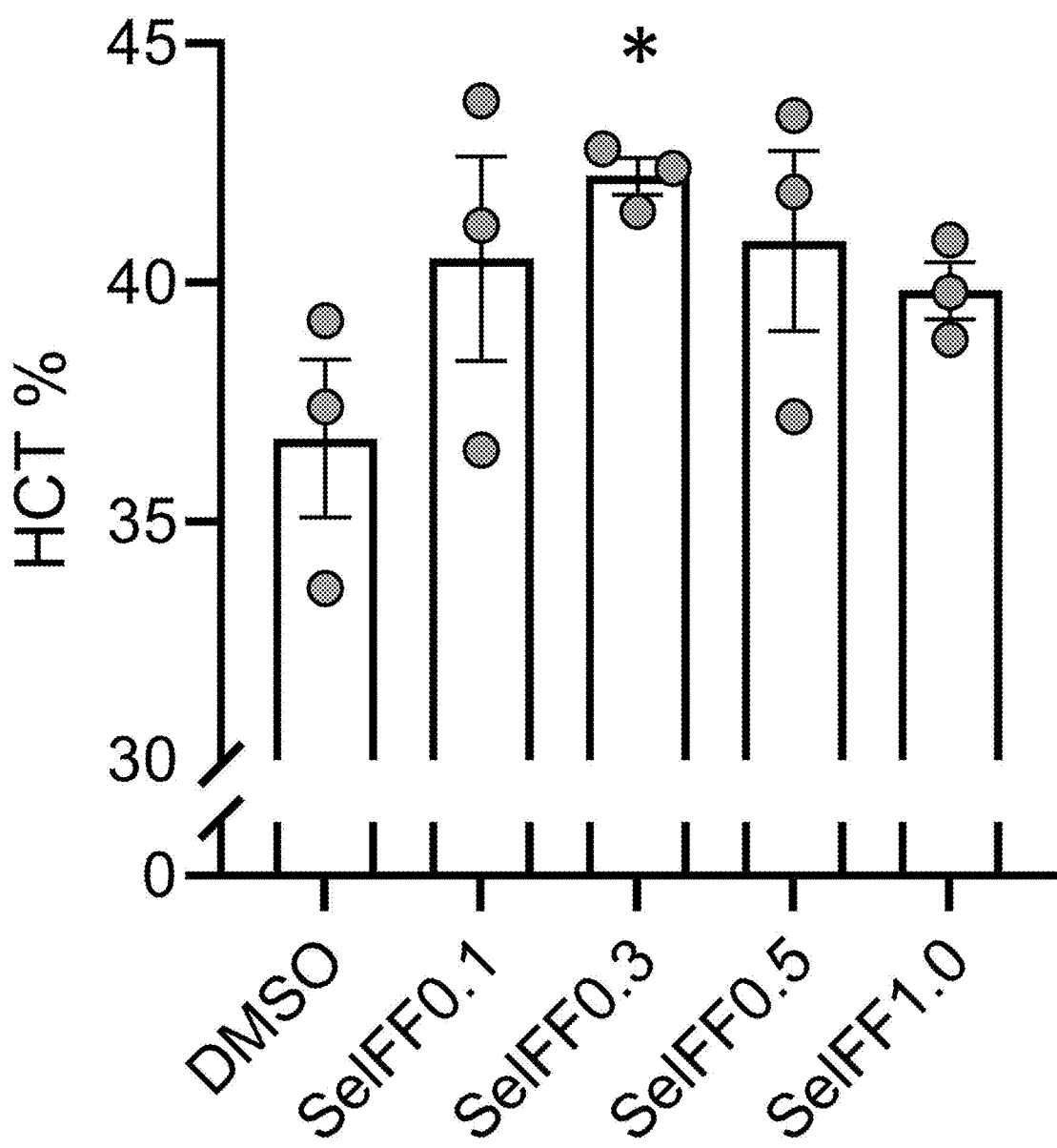
Figure 14E:
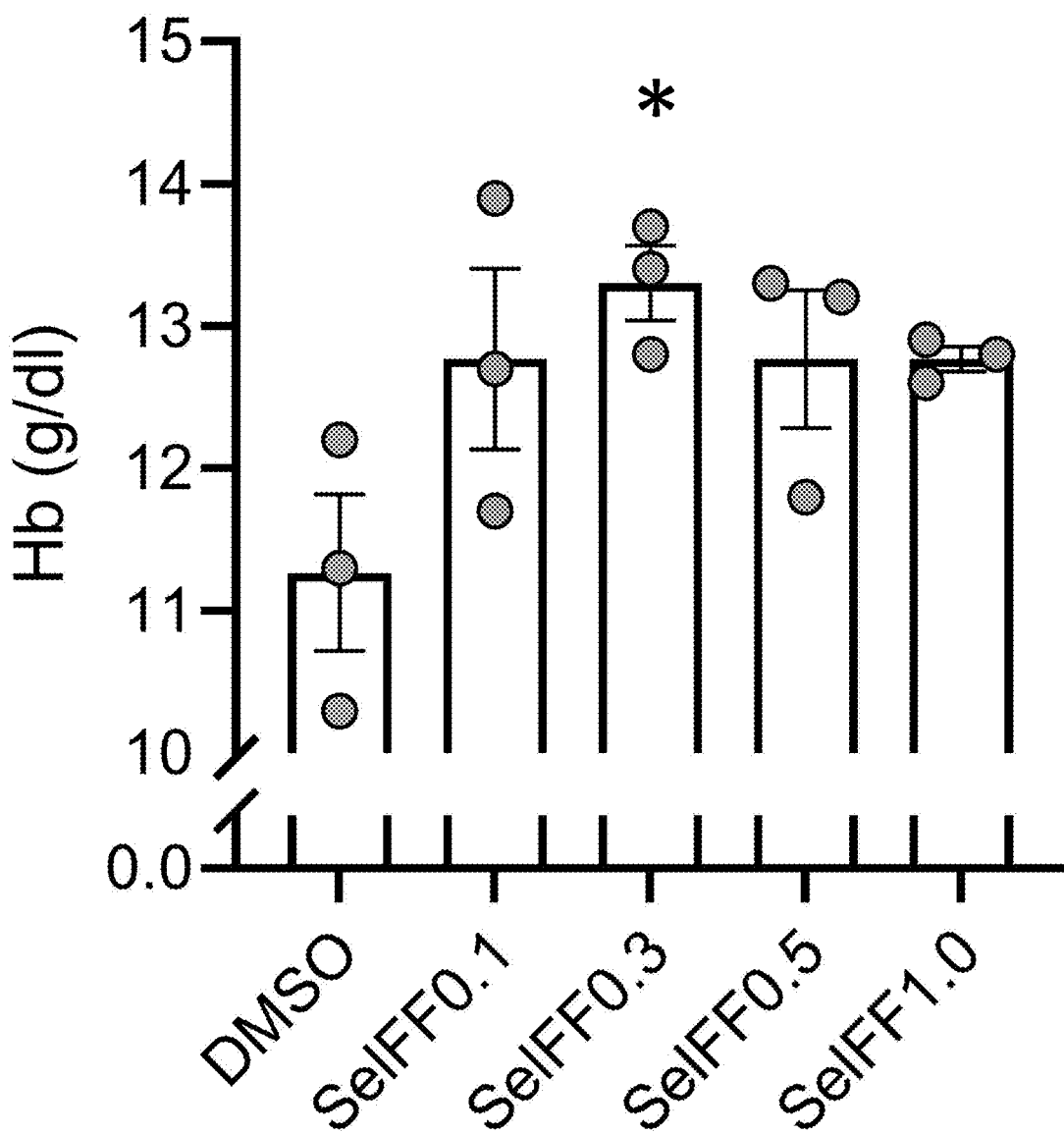
Figure 14F:
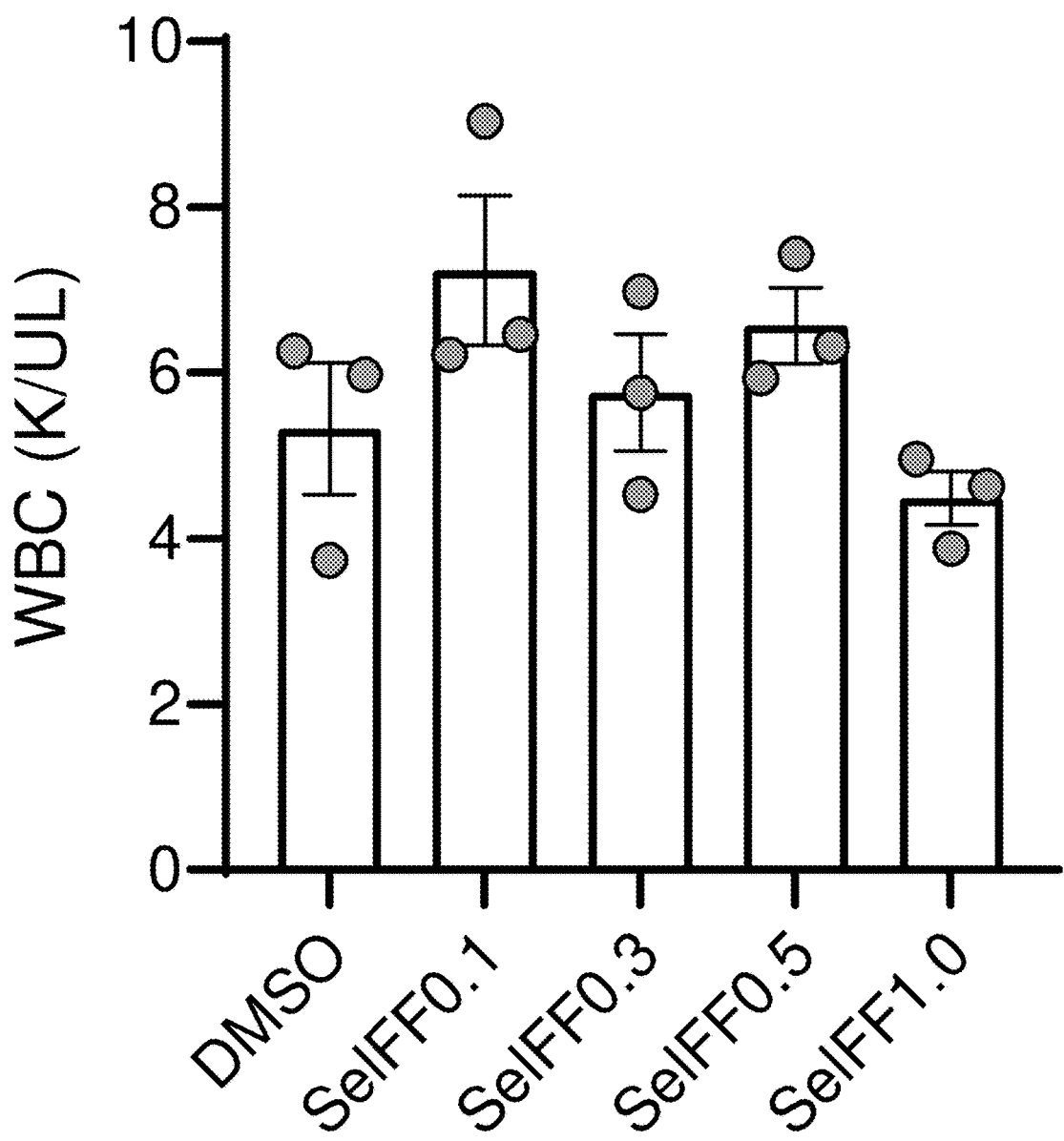
Figure 14G:
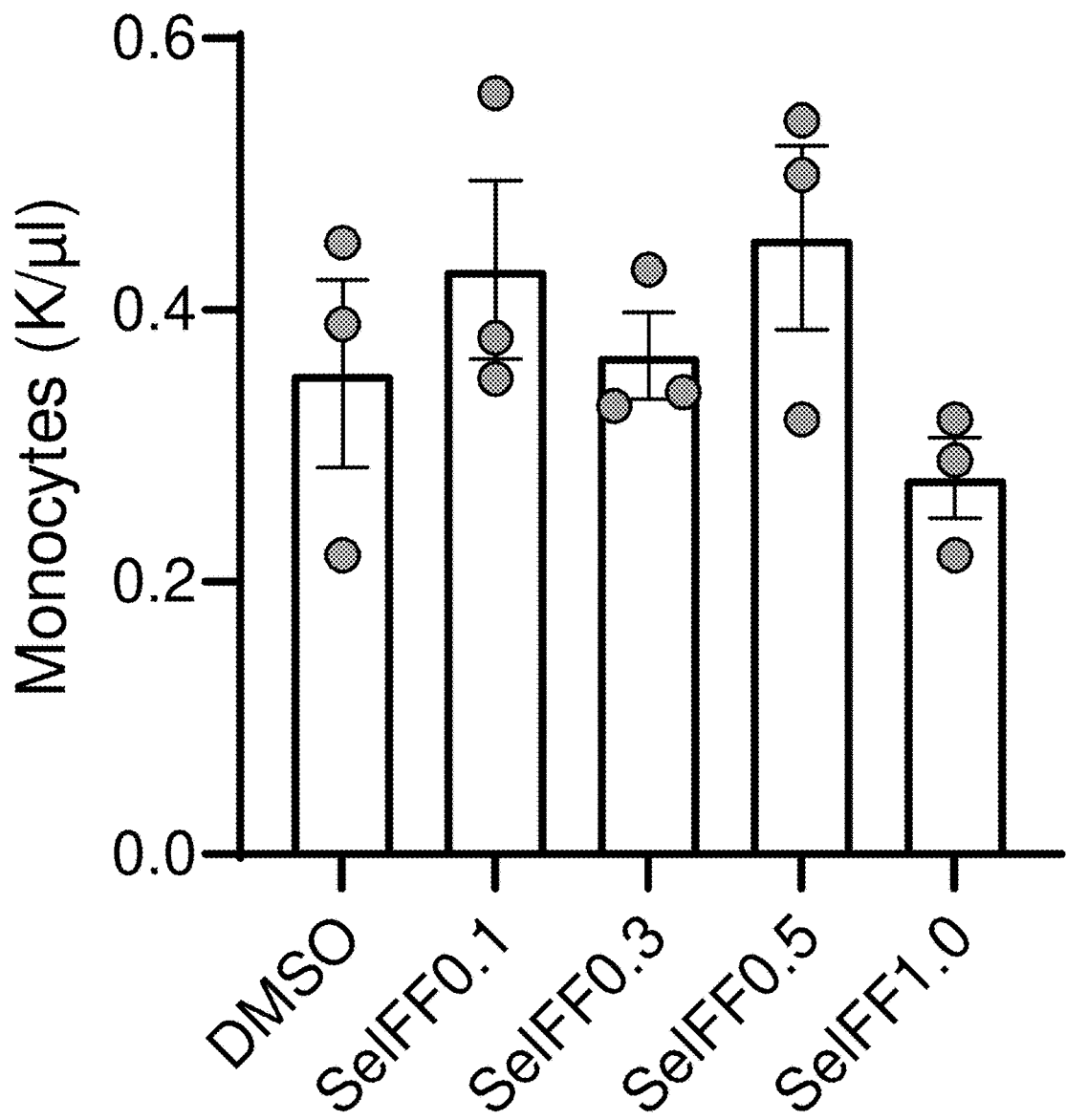
Figure 15:
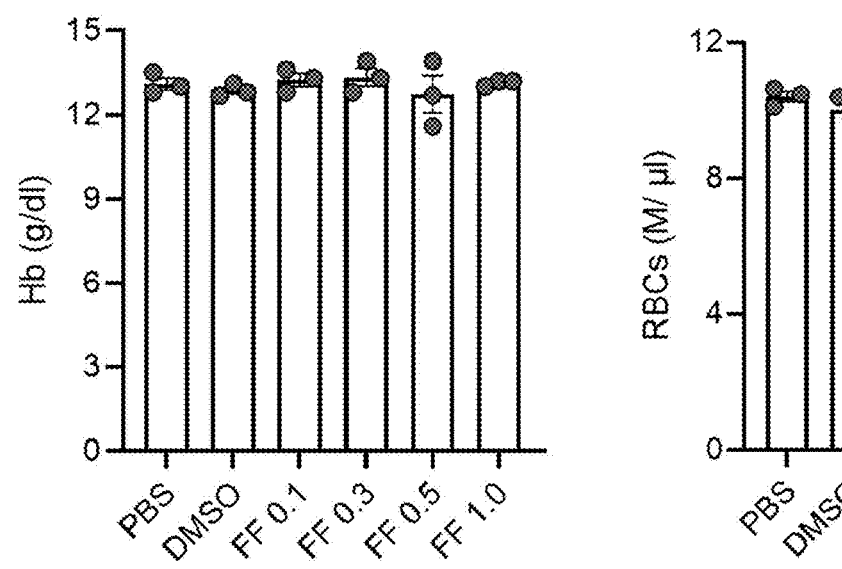
FIG. 15 shows the complete blood count (CBC) results on Day 8 of formoterol fumarate (FF) treatment via intraperitoneal injection in wild-type C57BL/6J mice. "Ns" (non-significant) applies where statistical significance is not shown.
Figure 15:
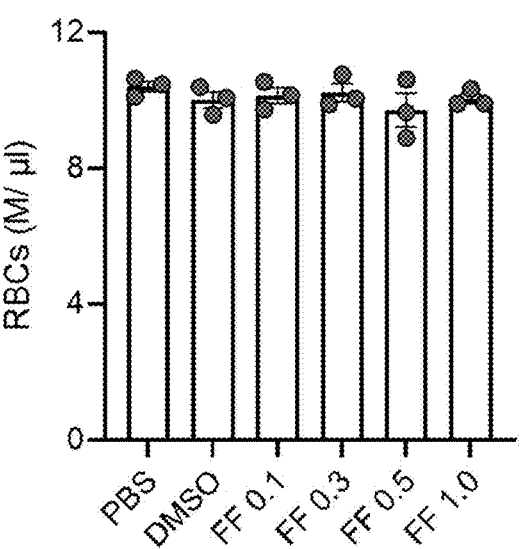
Figure 15:
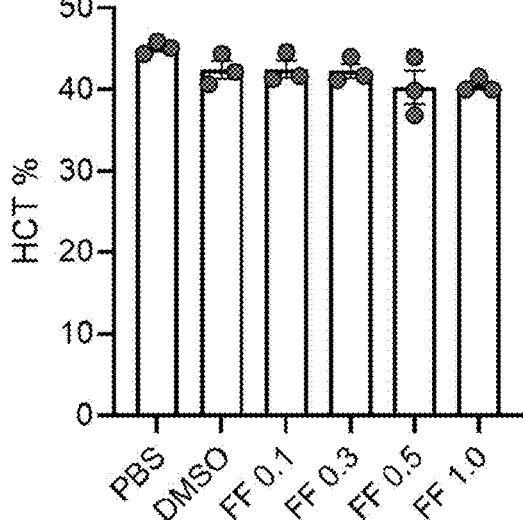
Figure 16:
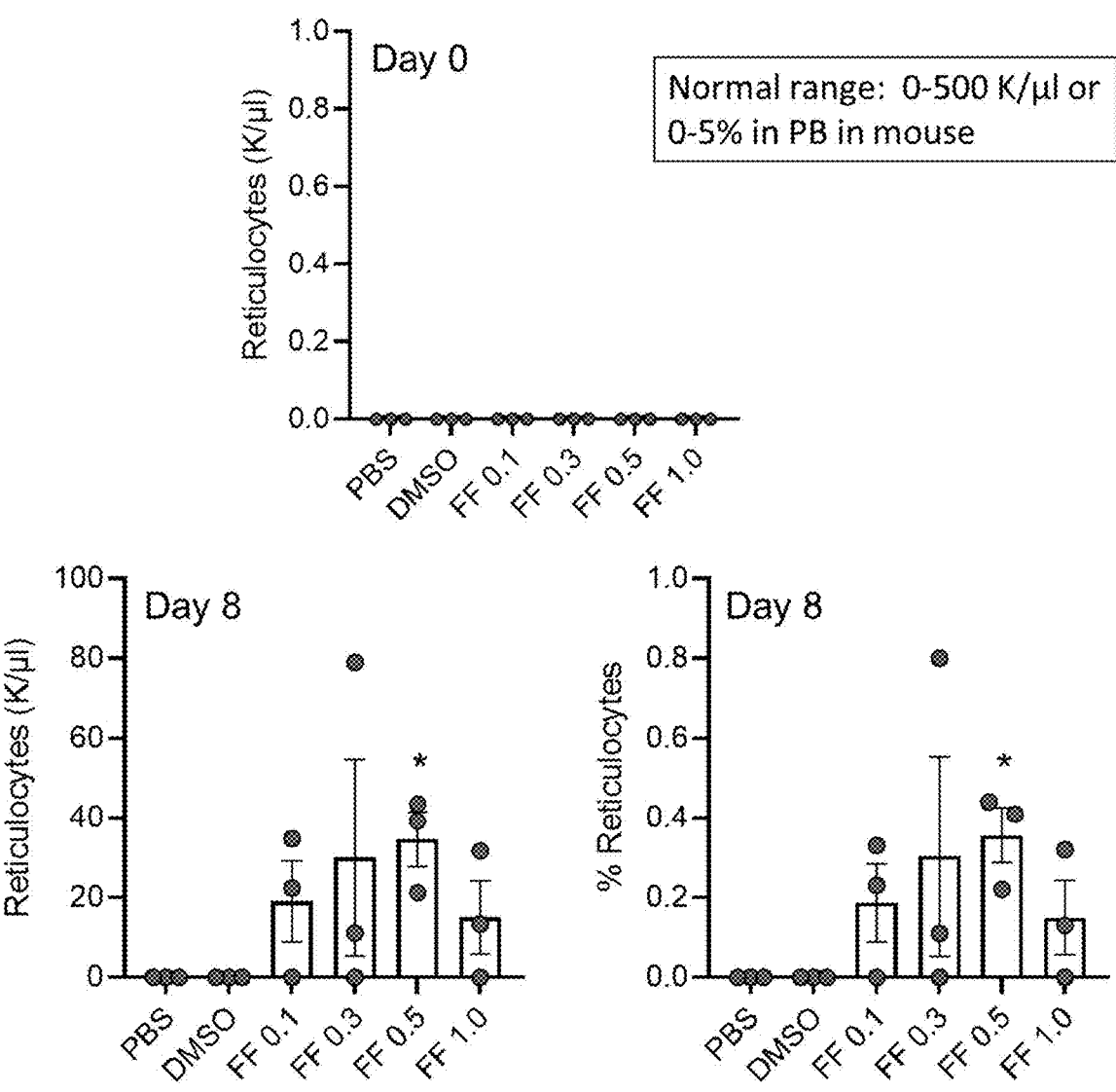
FIG. 16 shows the reticulocyte counts on Day 8 post daily injections of the formoterol fumarate (FF) treatment via intraperitoneal injection in wild-type C57BL/6J mice. * p<0.05, ANOVA. "Ns"(non-significant) applies where statistical significance is not shown.

The murine β2-adrenoreceptor has 87.08% similarity to the protein composition of the human analog. This encouraged further testing to determine whether formoterol fumarate (FF) treatment in wild-type mice under steady state or hemolytic anemia produces any alleviating effect in vivo. To address this, varying doses of FF 0.1-0.3-0.5-1.0 mg/kg or vehicle (0.3% DMSO in saline) were administered via intraperitoneal (i.p.) injection in 10-12 week old wild-type C57BL/6J mice daily for 3 weeks along with weekly submandibular cheek bleeding to analyze complete blood counts (CBC). The daily i.p. injections of FF were well-tolerated by the mice as seen by their body weights (FIG. 14A), mobility, activeness, and regular breathing patterns (as advised by Animal Research Facility veterinarians). The 0.3-0.5 and 1.0 mg/kg FF doses mildly increased body weights of mice, but the values did not reach significance (FIG. 14A). However, FF treatment at all doses significantly enhanced mitochondrial biogenesis in the peripheral blood mononuclear cells (PBMCs) of mice, as evidenced by the increase in MitoTracker® staining (FIG. 14B). Of note, the red blood cell (RBC) parameters, such as RBC counts, hematocrit (HCT) % and hemoglobin (Hb) were slightly elevated in FF-treated groups (FIGS. 14C-14E), whereas the white blood cell (WBC) and monocyte counts remained marginally affected (FIG. 14F and FIG. 14G).

Figure 18A:
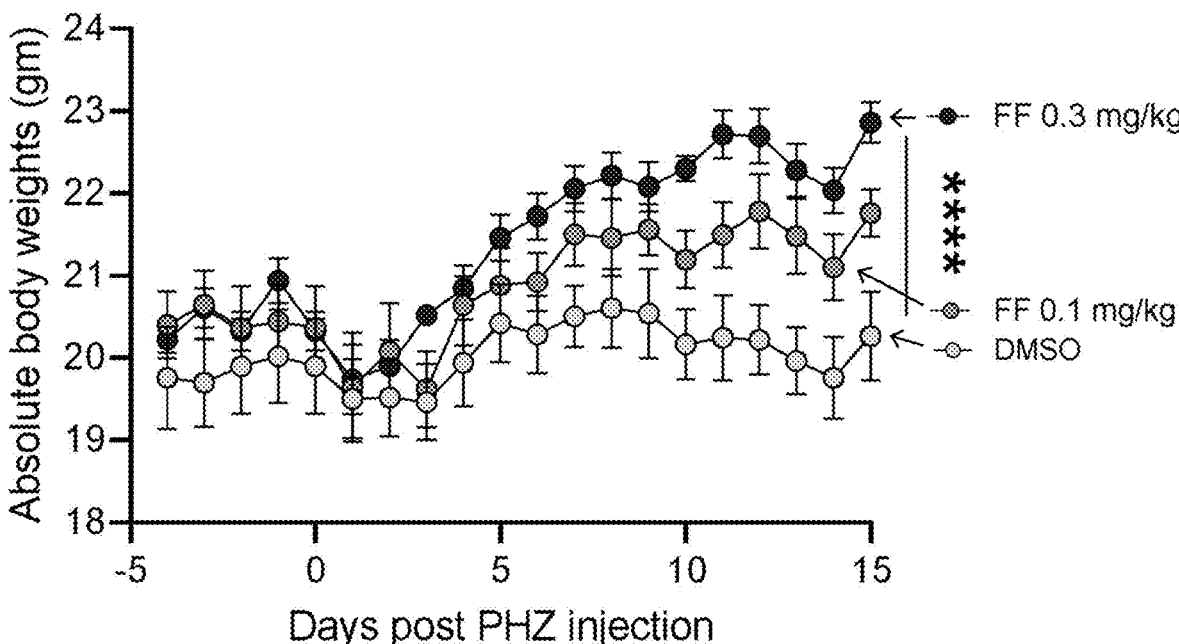
FIG. 18A-FIG. 18C show that formoterol fumarate (FF) treatment significantly increases RBC parameters in phenylhydrazine (PHZ)-mediated stress-induced anemic mice (10-12 week old mice).
Figure 18A:
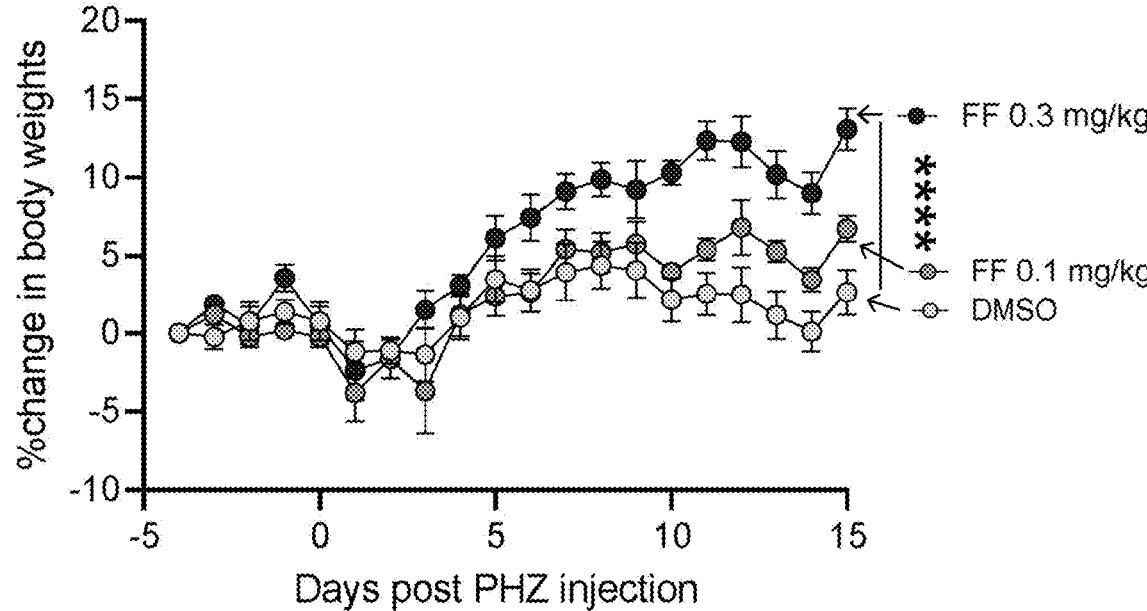
Figure 18B:
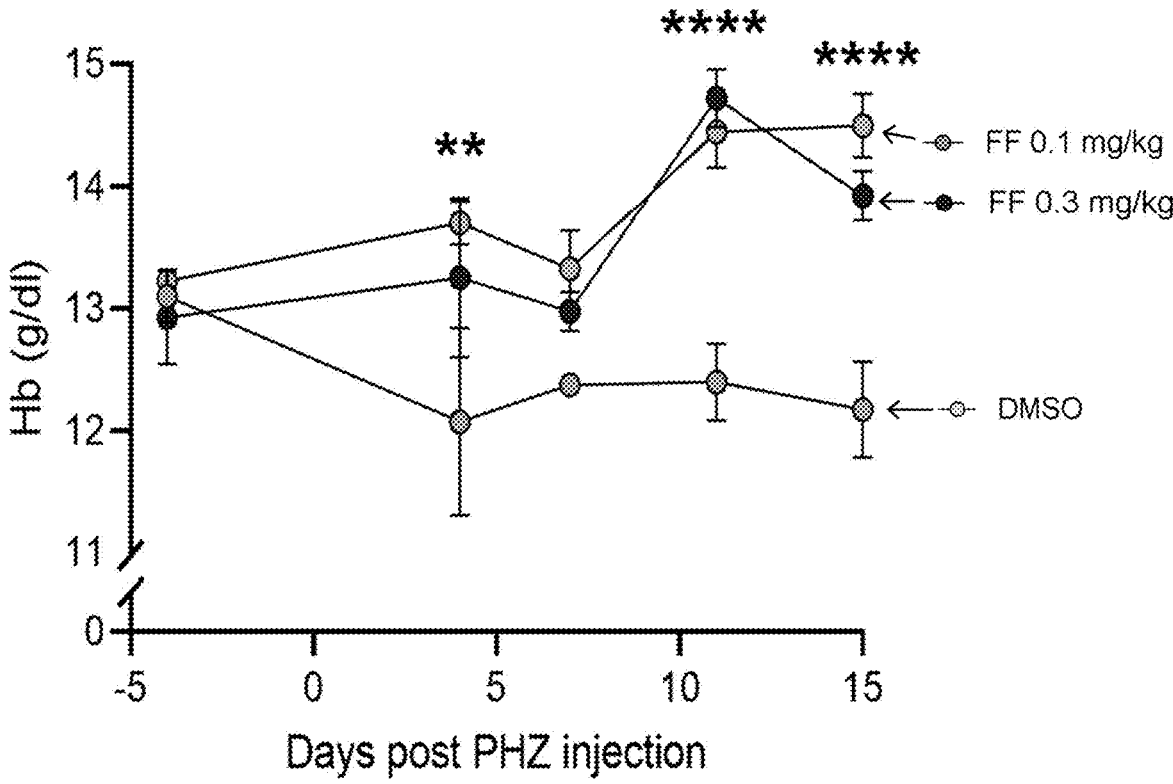
Figure 18B:
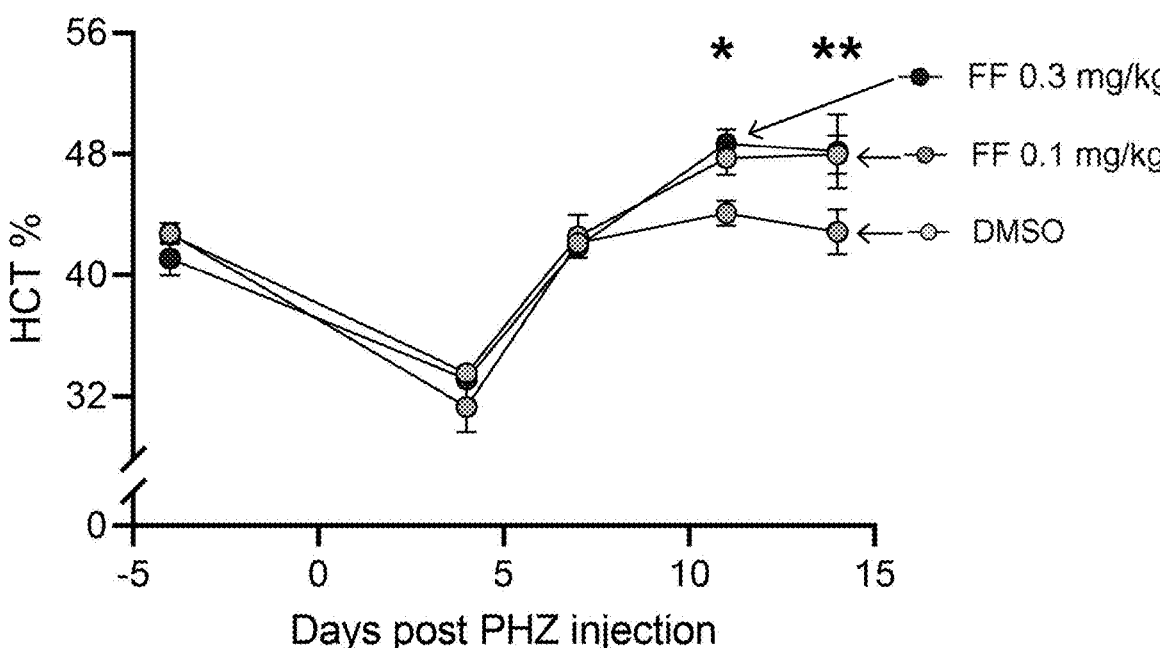
Figure 18B:
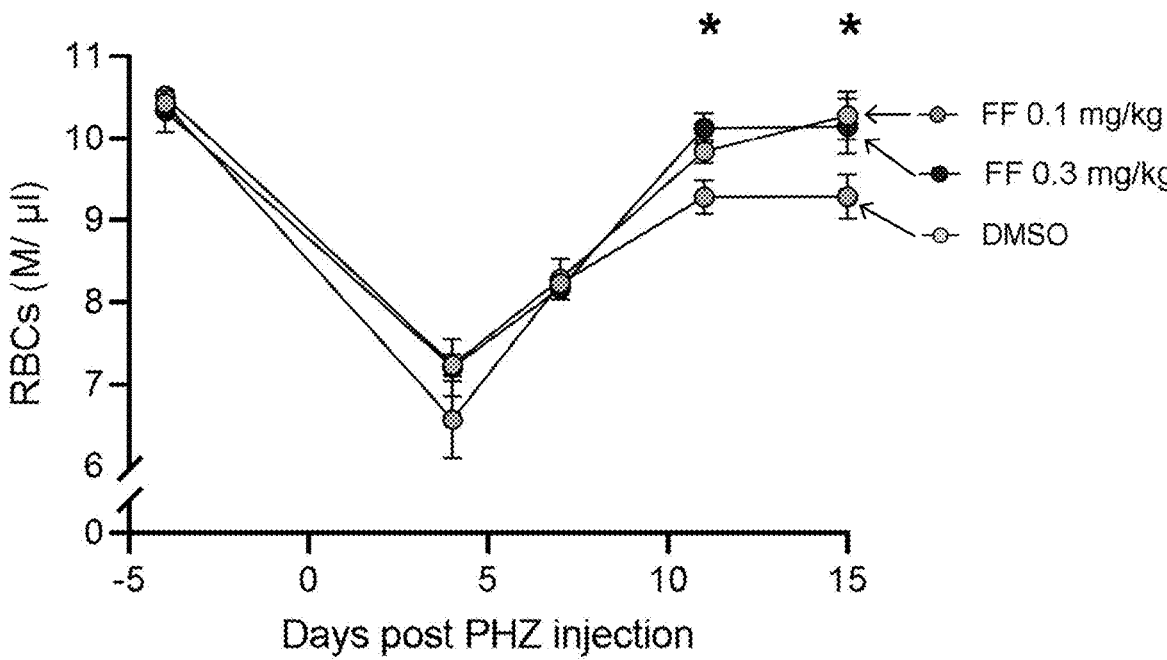
Figure 18C:
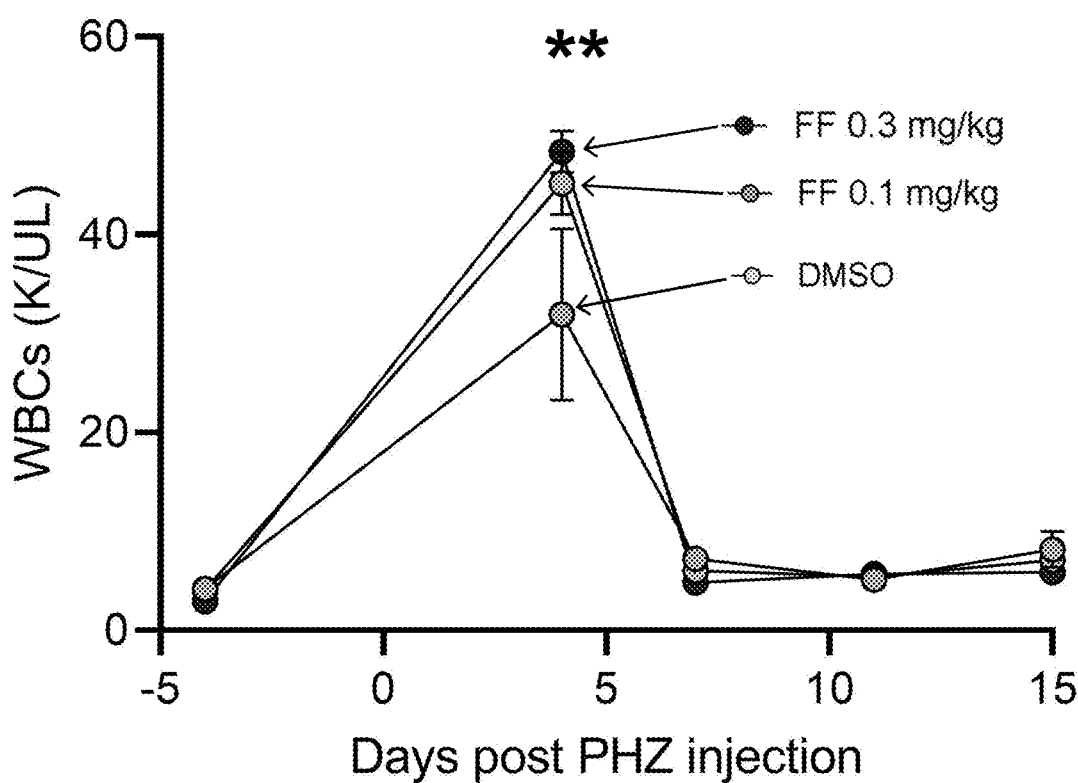
Figure 18C:
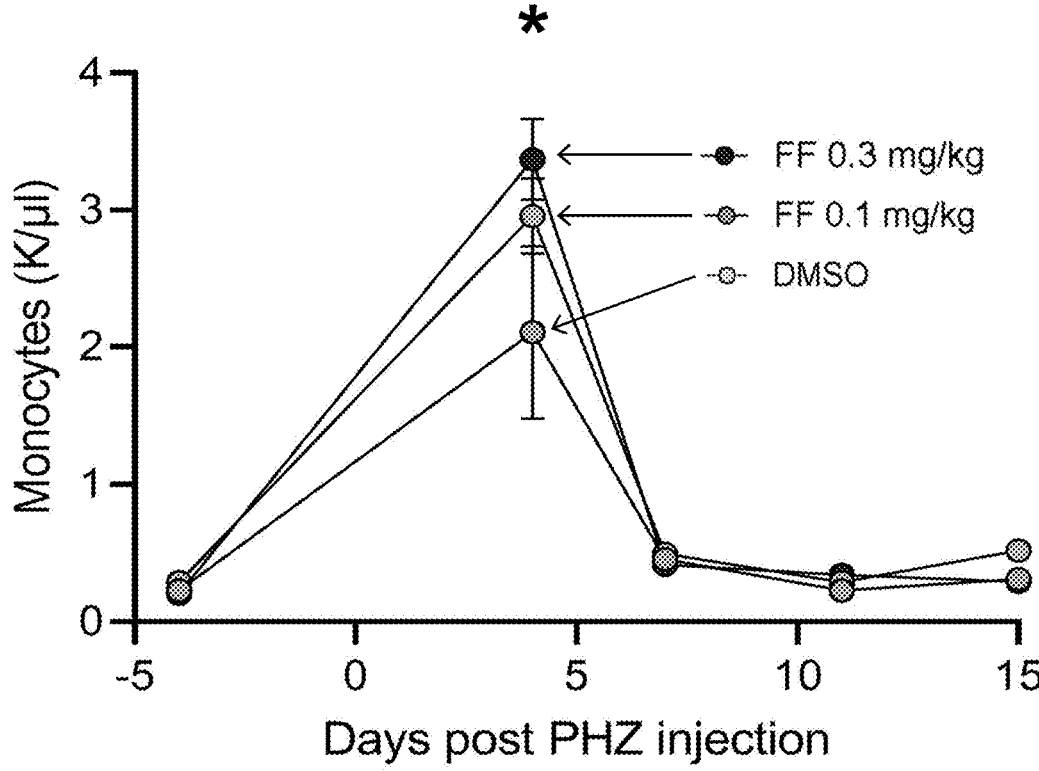
Figure 18C:
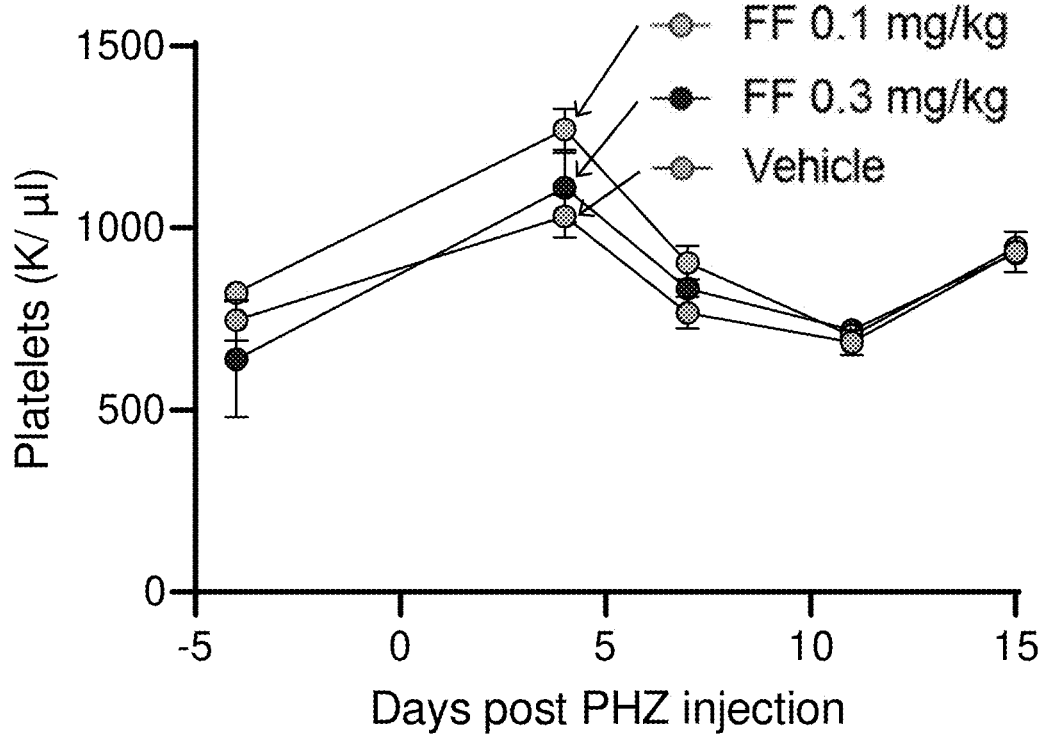
Figure 19A:
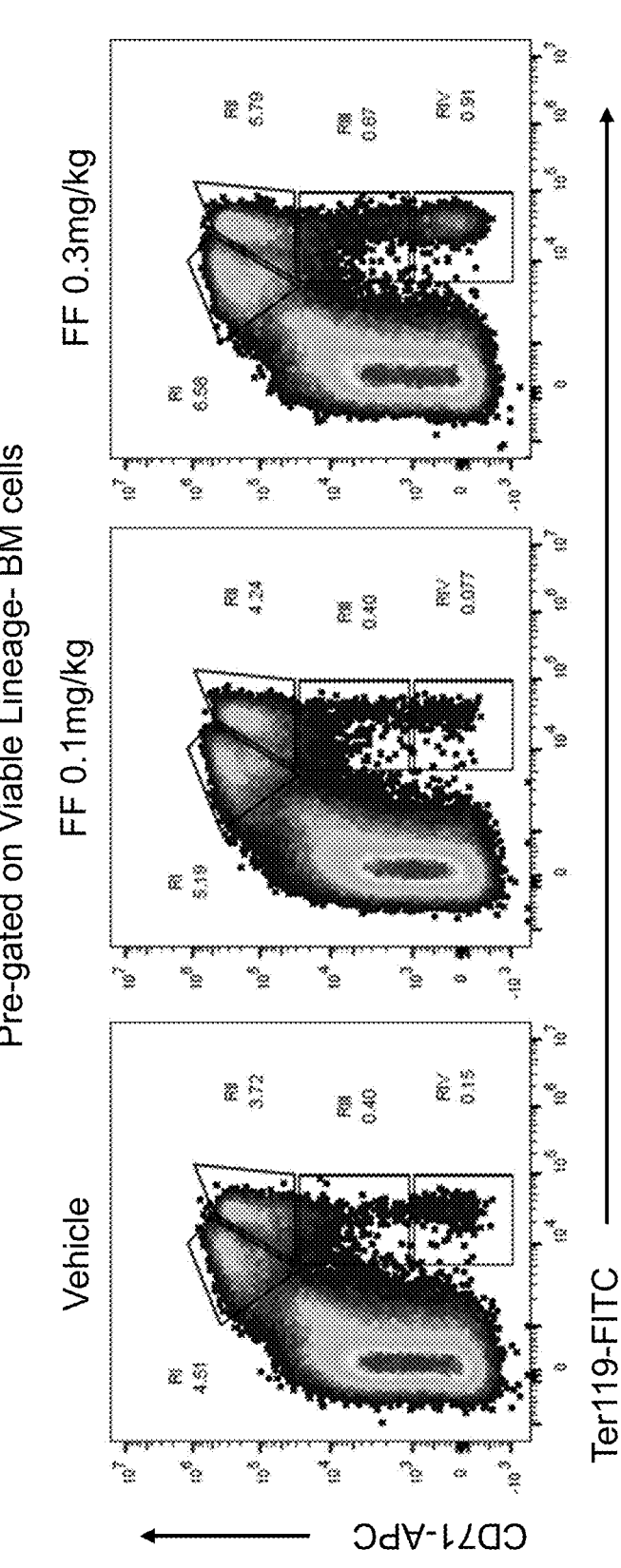
FIG. 19A-FIG. 19B show that formoterol fumarate (FF) treatment significantly elevates erythroid differentiation in the bone marrow (BM) of phenylhydrazine (PHZ)-mediated stress-induced anemic mice (10-12 week old mice).
Figure 19B:
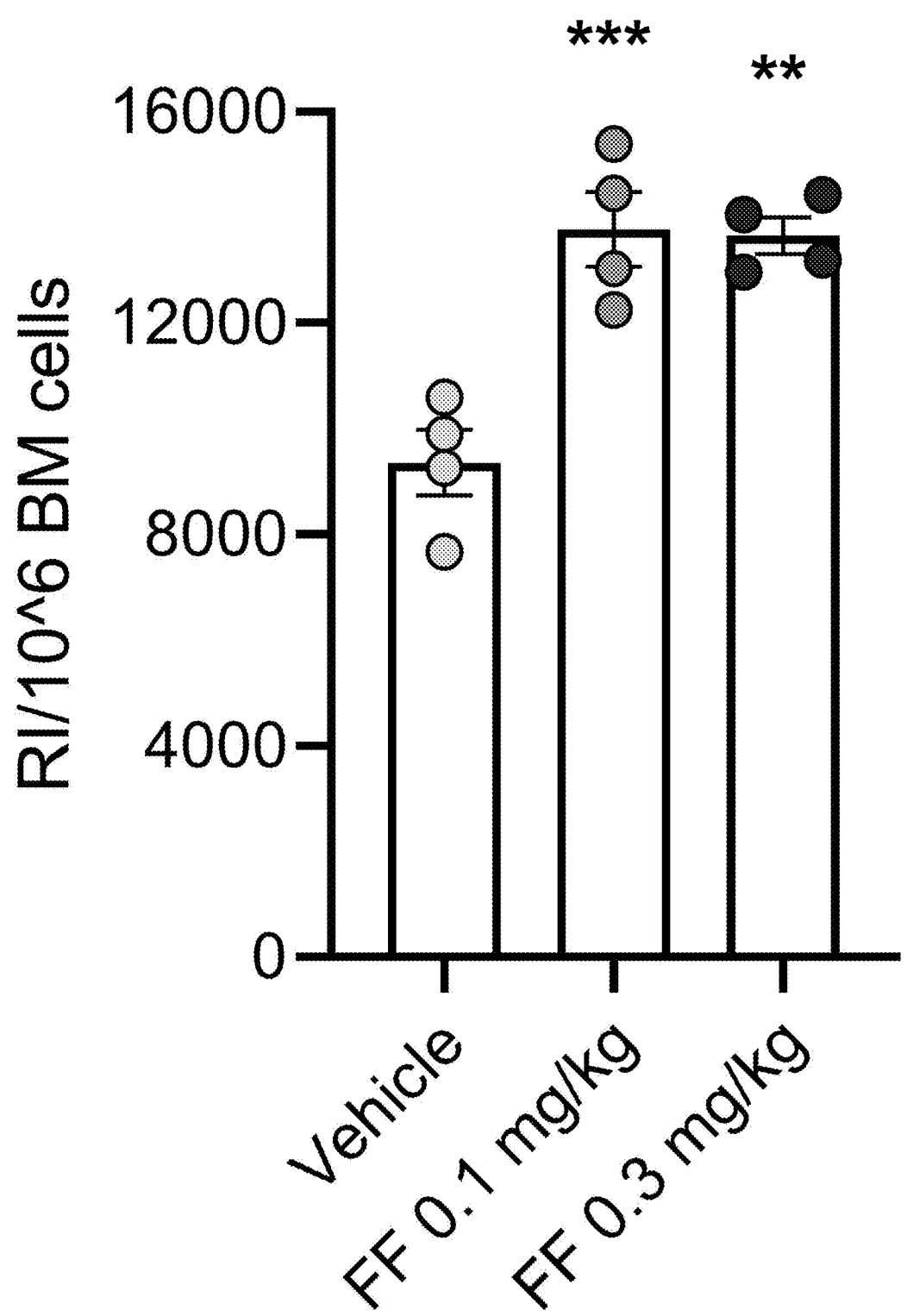
Figure 19B:
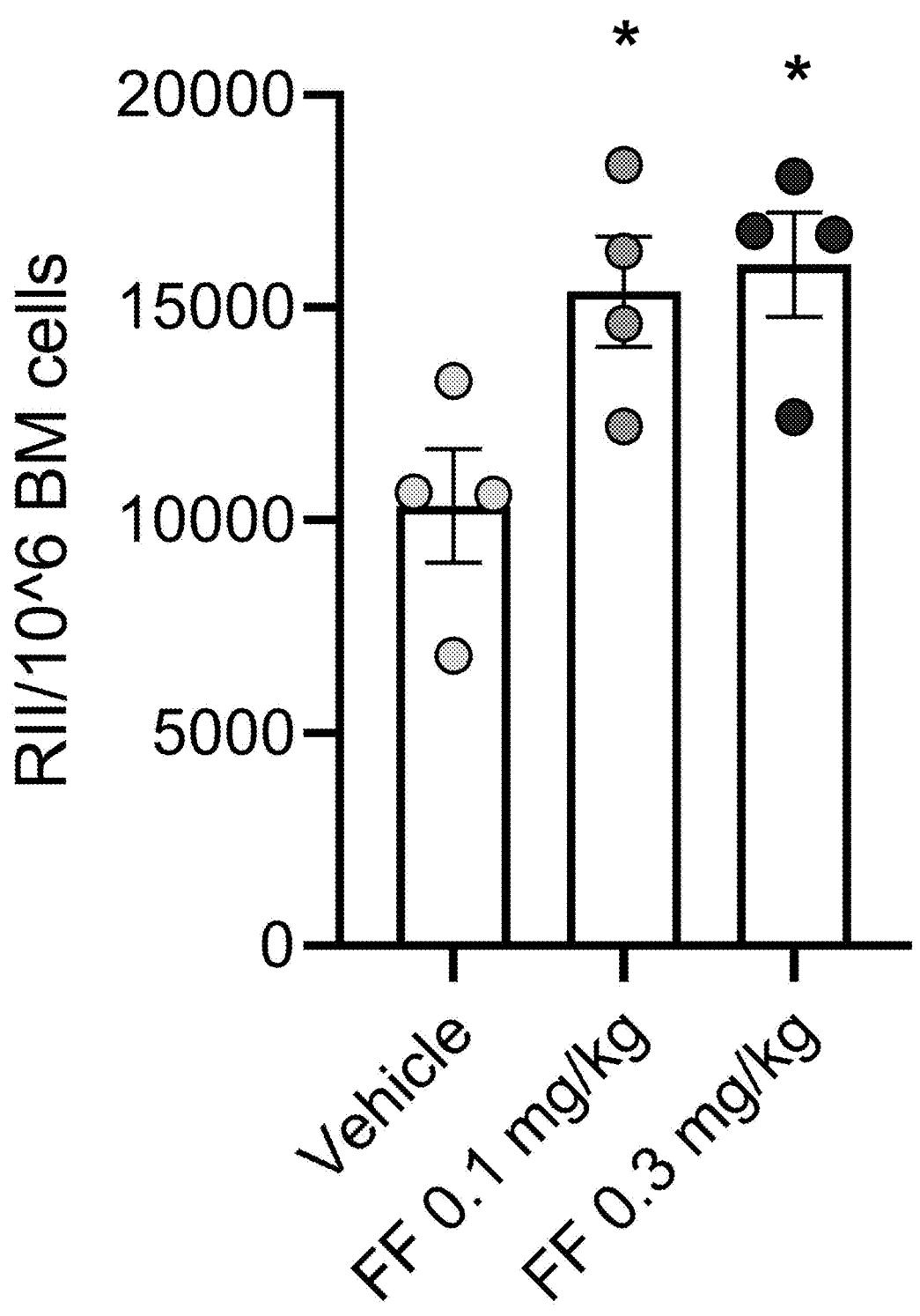
Figure 19B:
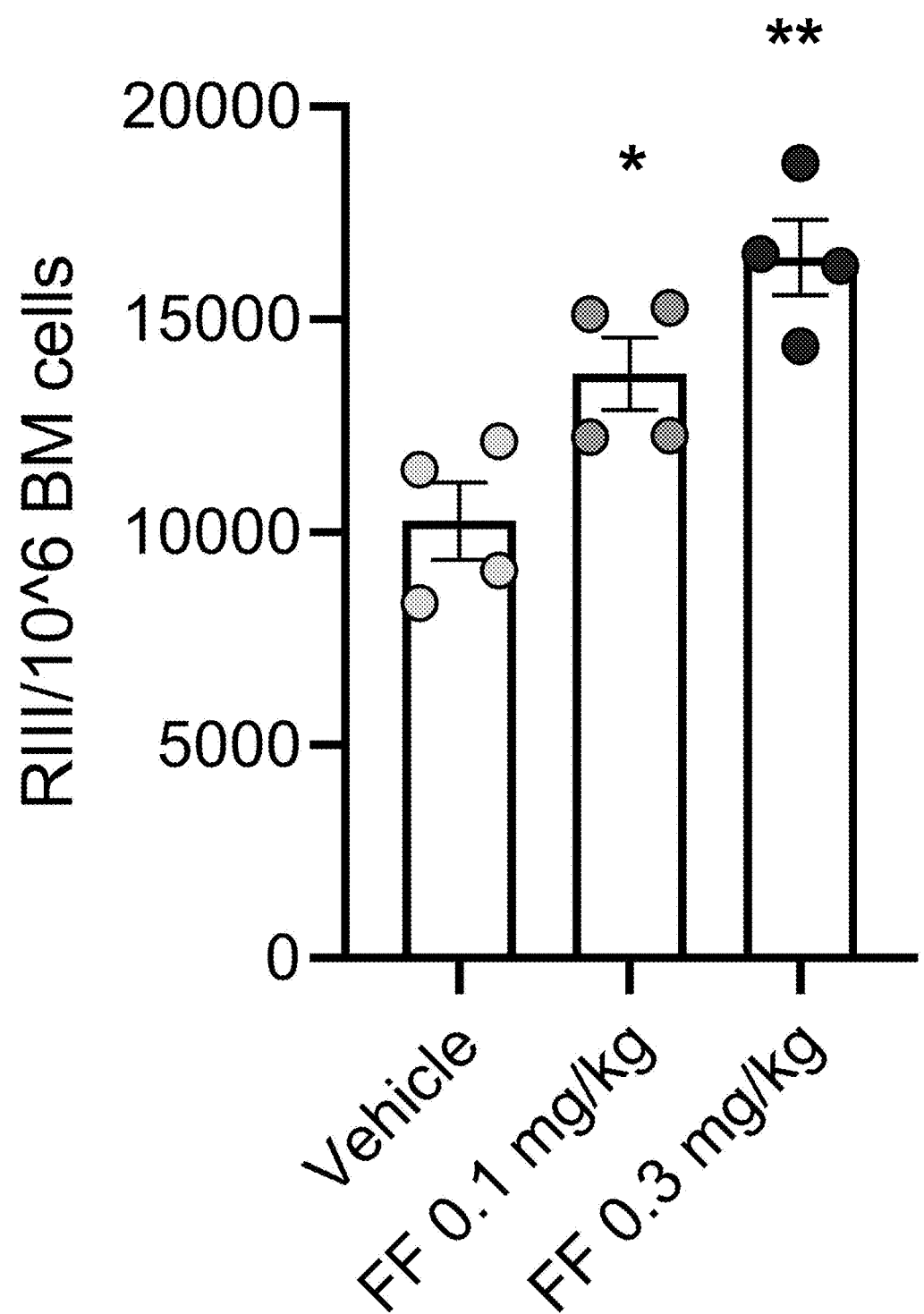
Figure 19B:
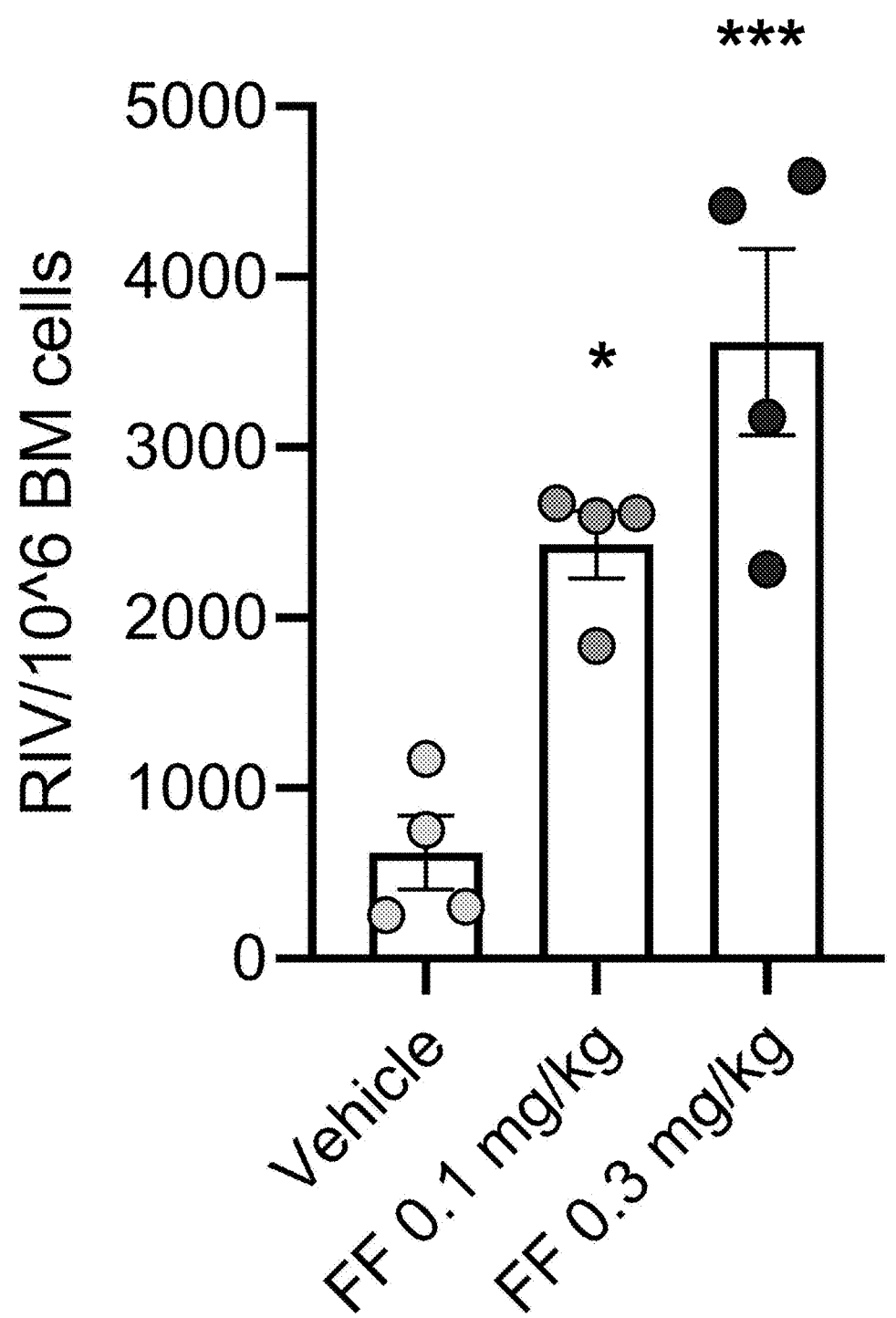
Figure 20:
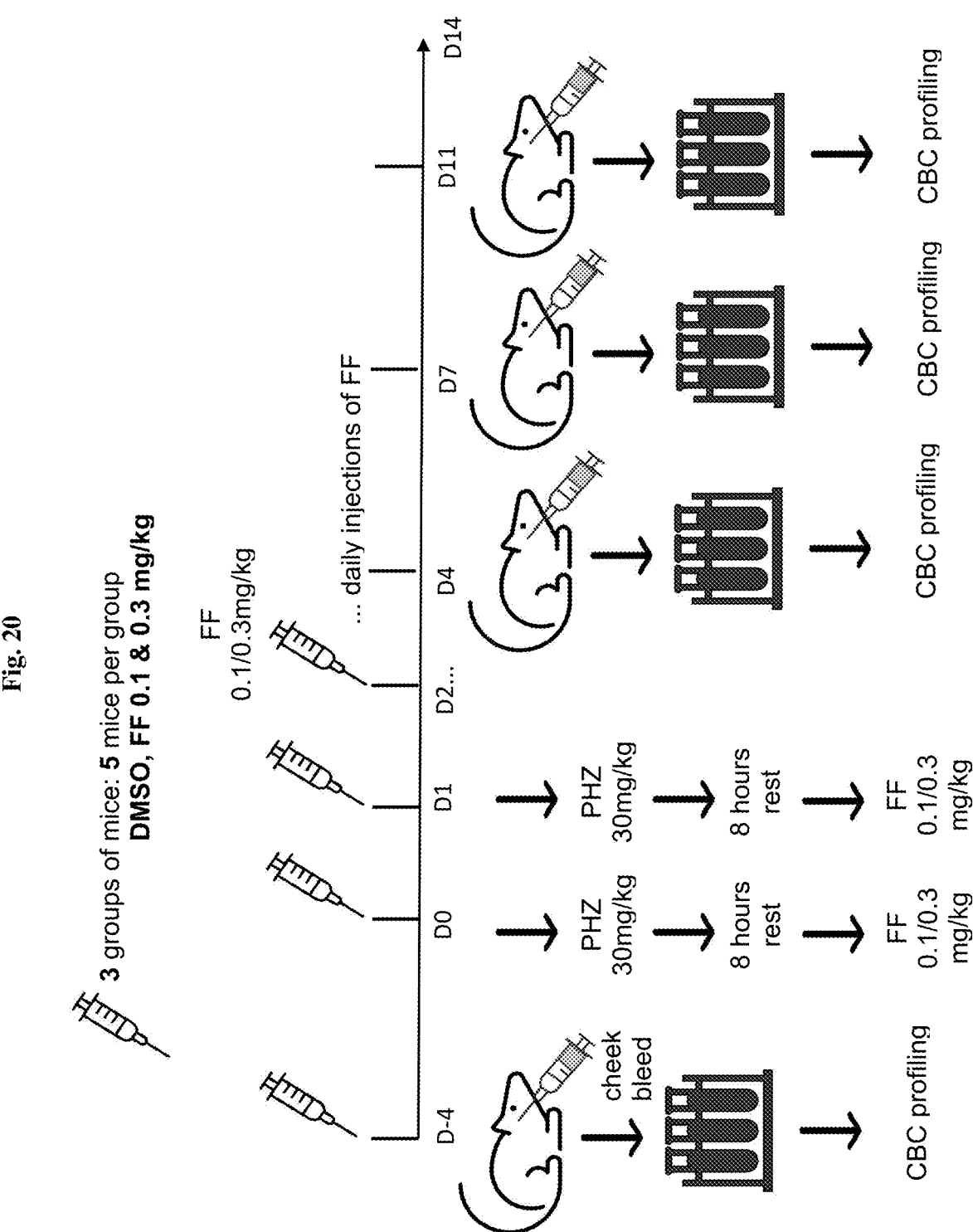
FIG. 20 shows an exemplary work-flow for formoterol fumarate (FF) treatment in vivo with phenylhydrazine (PHZ) study and sub-lethal dose (60 mg/kg).
Figure 21:
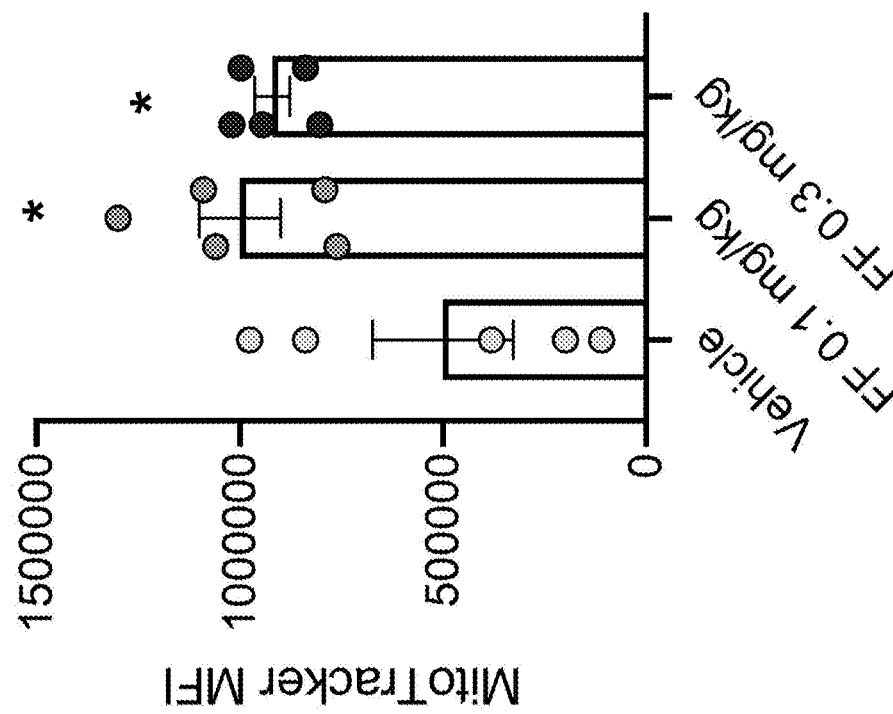
FIG. 21 shows that formoterol fumarate (FF) treatment increases MitoTracker® Staining showing mitochondrial mass in peripheral blood mononuclear cells (PBMCs) Day 4 after PHZ treatment.
Figure 21:
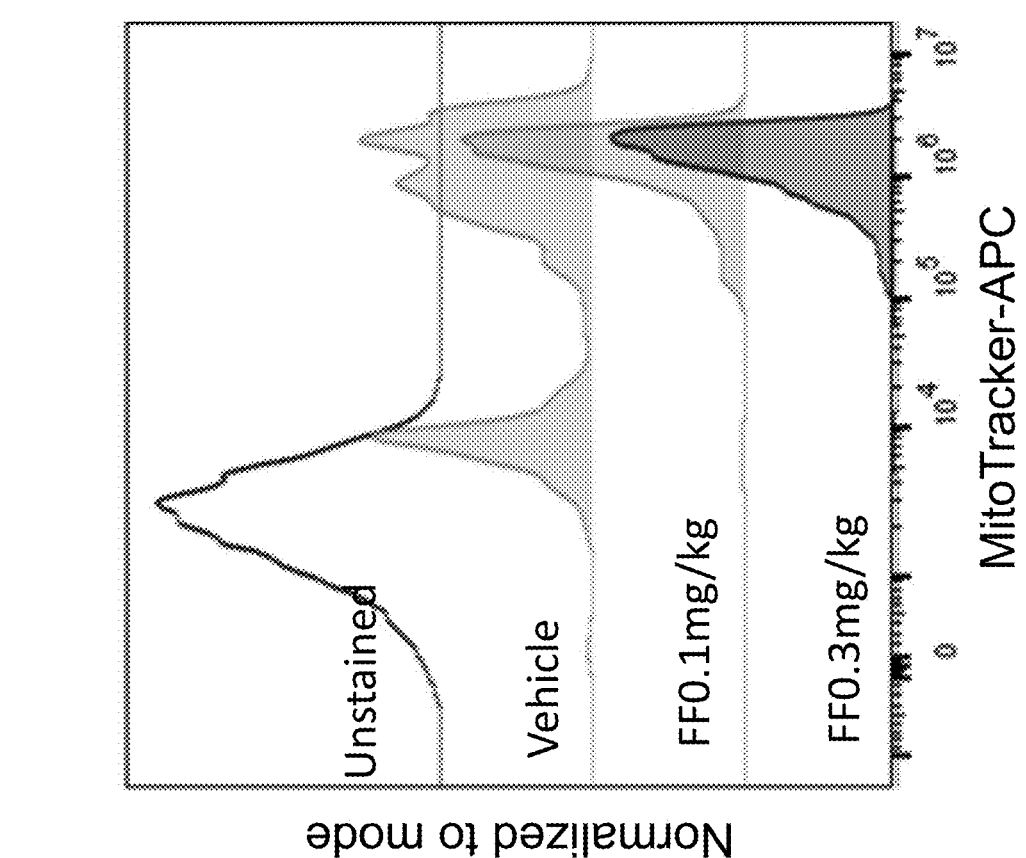
Figure 22A:
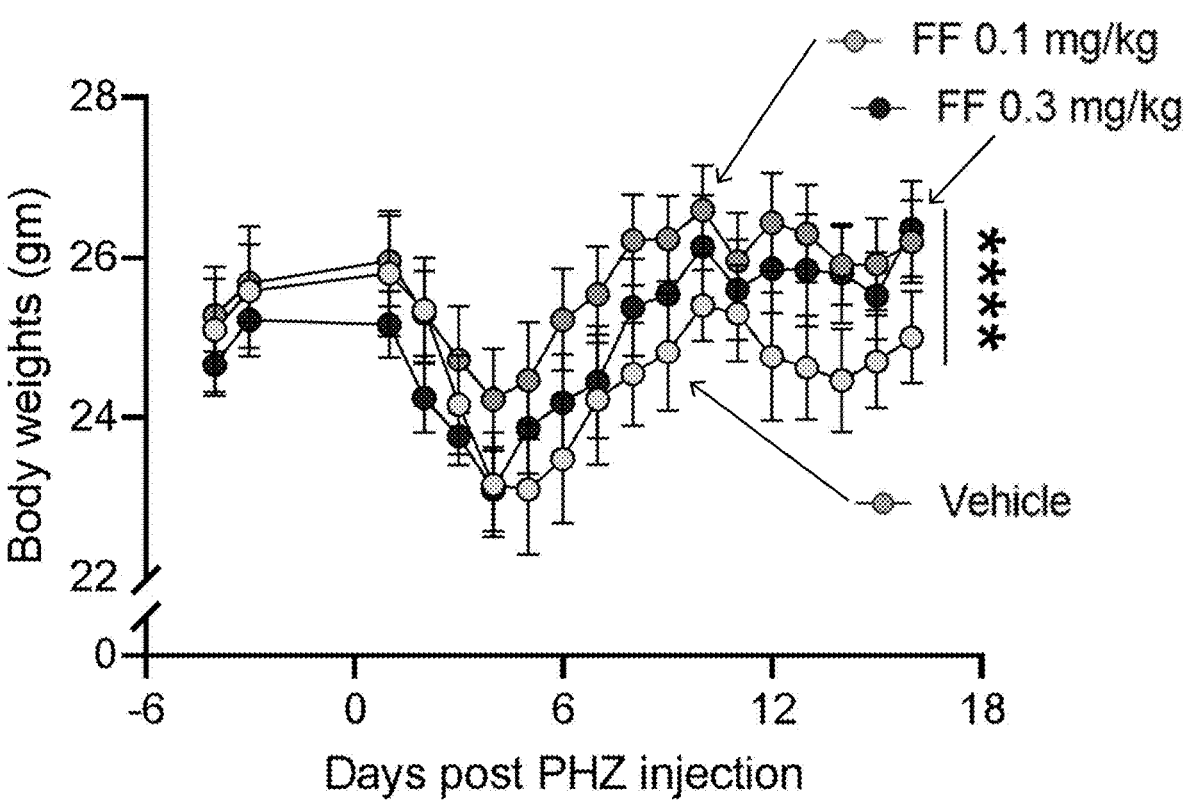
FIG. 22A-FIG. 22C show that formoterol fumarate (FF) treatment significantly increases RBC parameters in phenylhydrazine (PHZ)-mediated stress-induced anemic mice (10-12 week old mice).
Figure 22A:
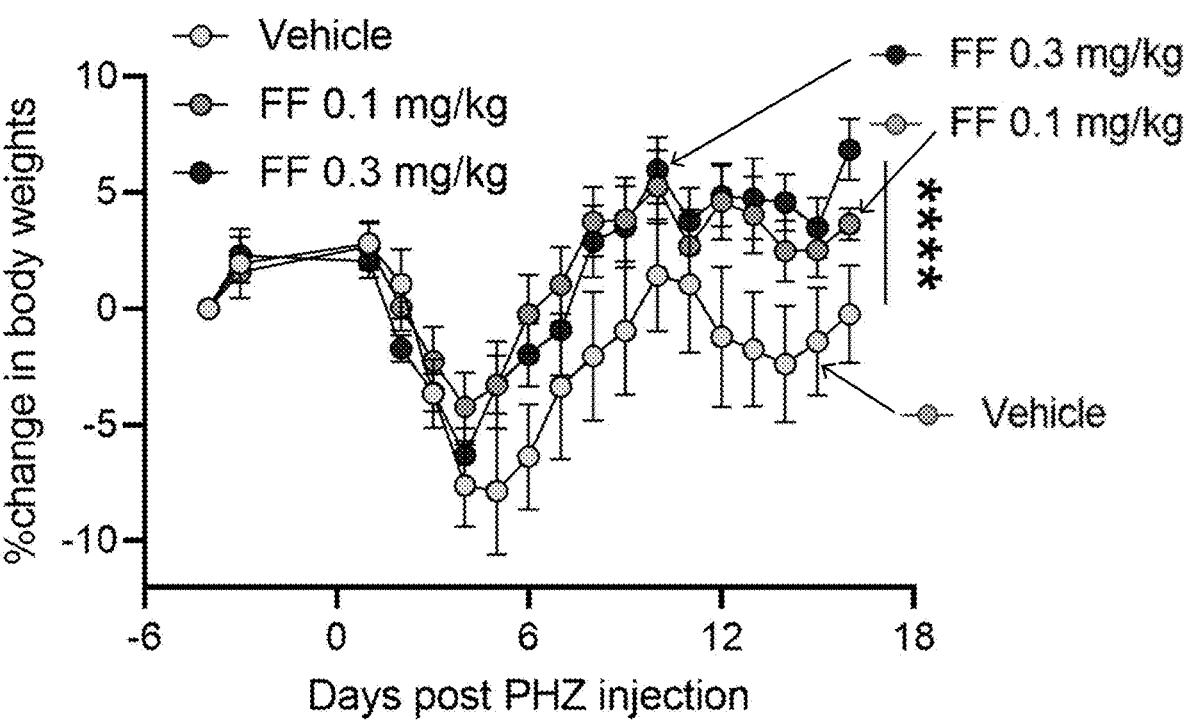
Figure 22B:
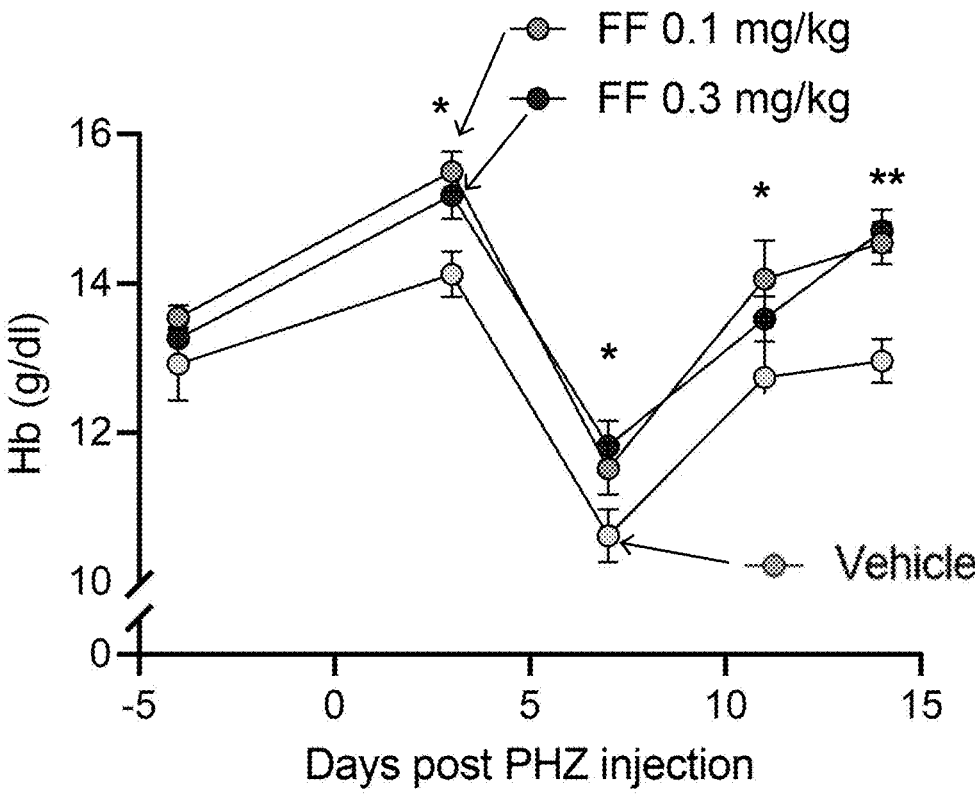
Figure 22B:
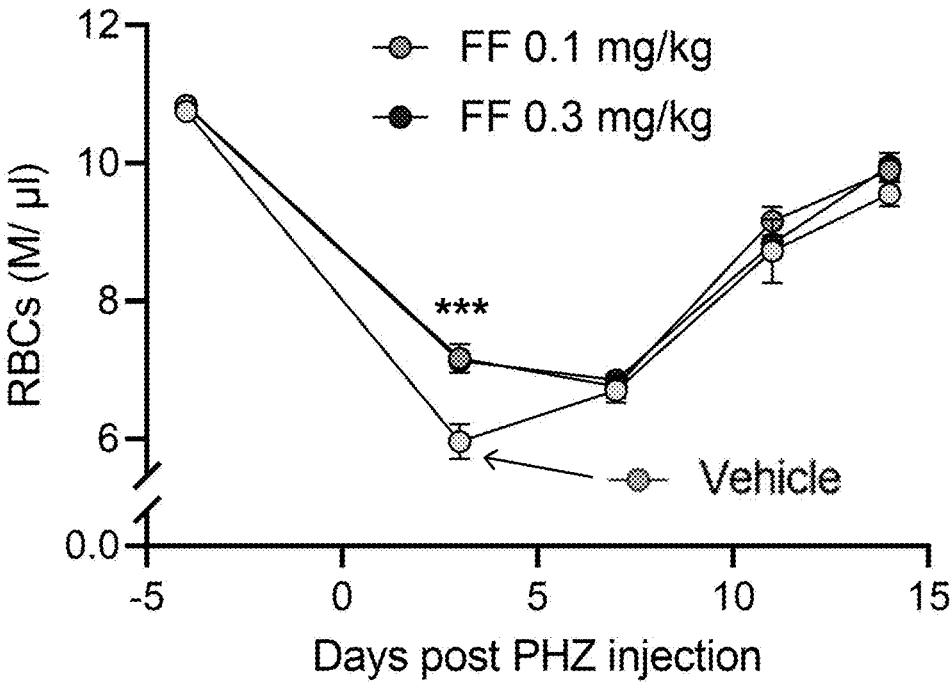
Figure 22B:
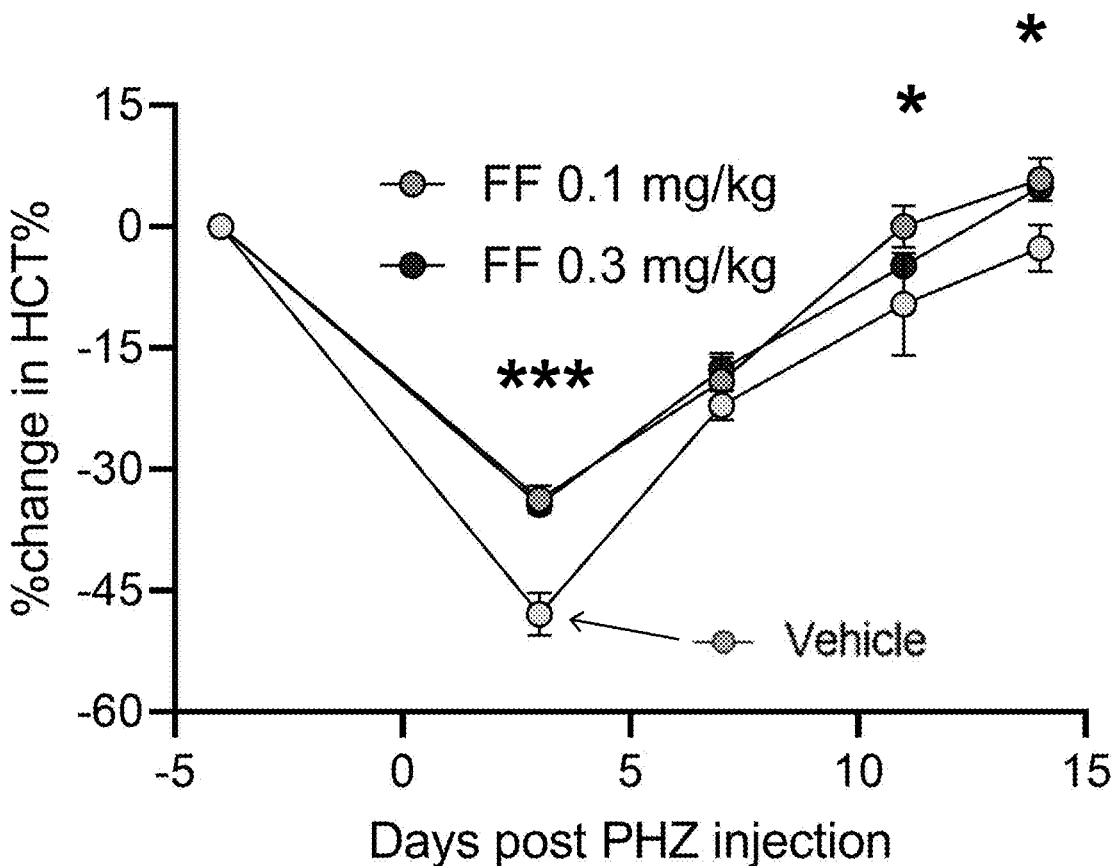
Figure 22C:
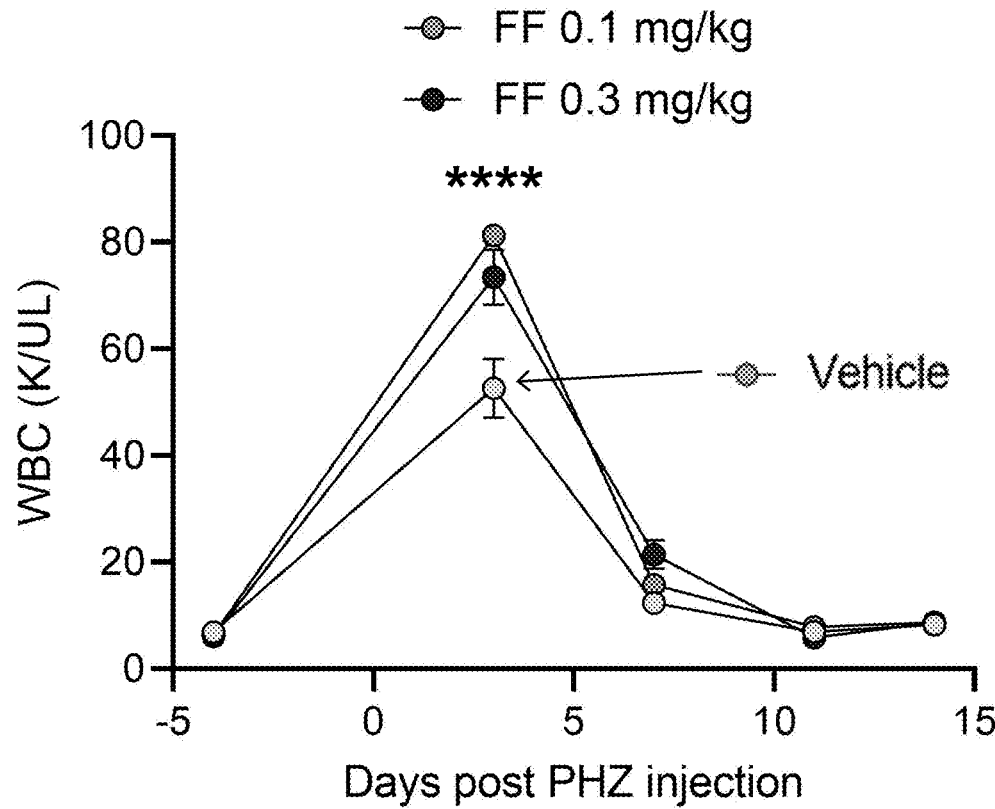
Figure 22C:
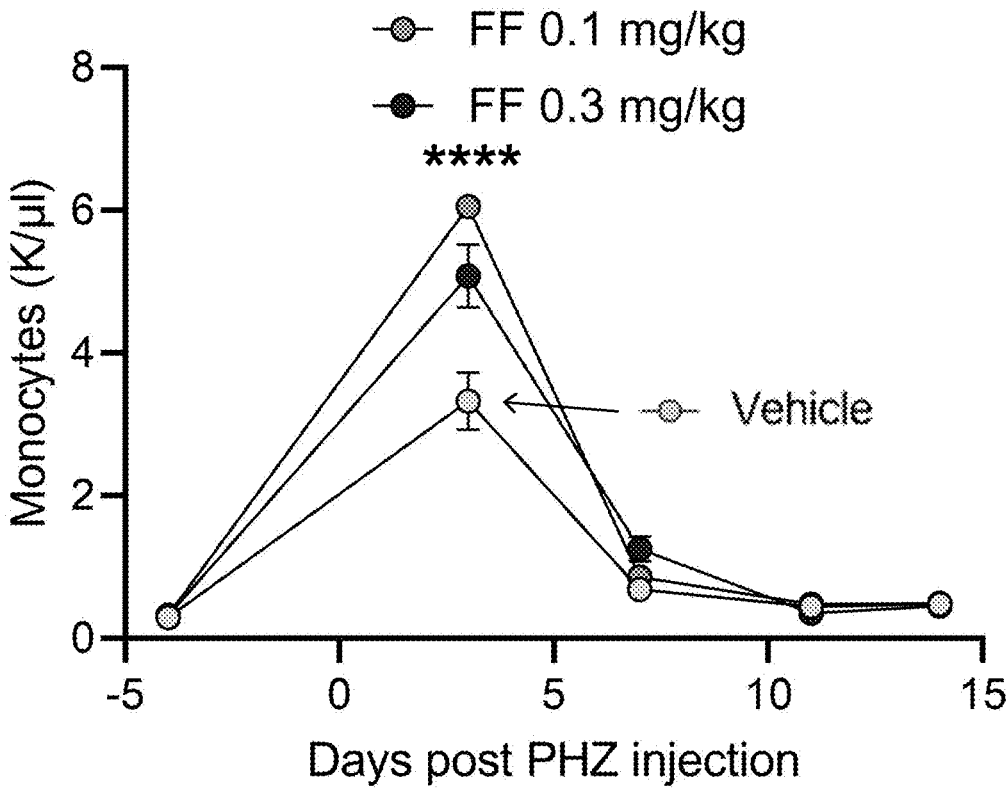
Figure 22C:
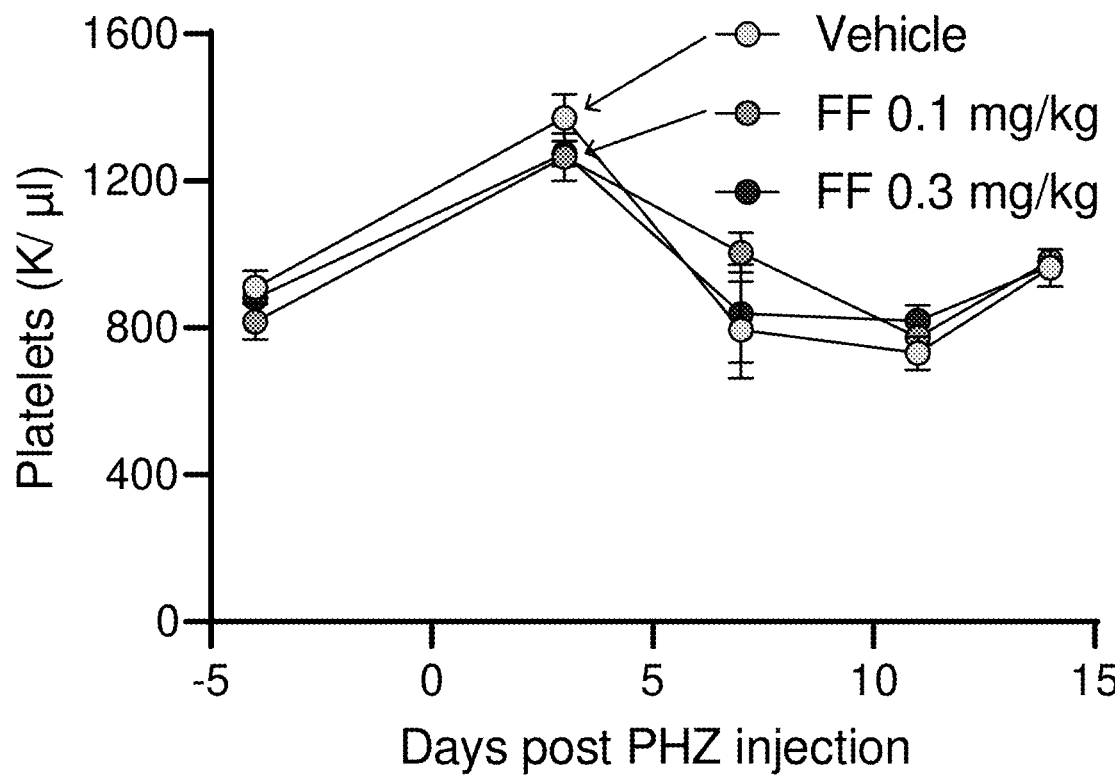
Figure 23A:
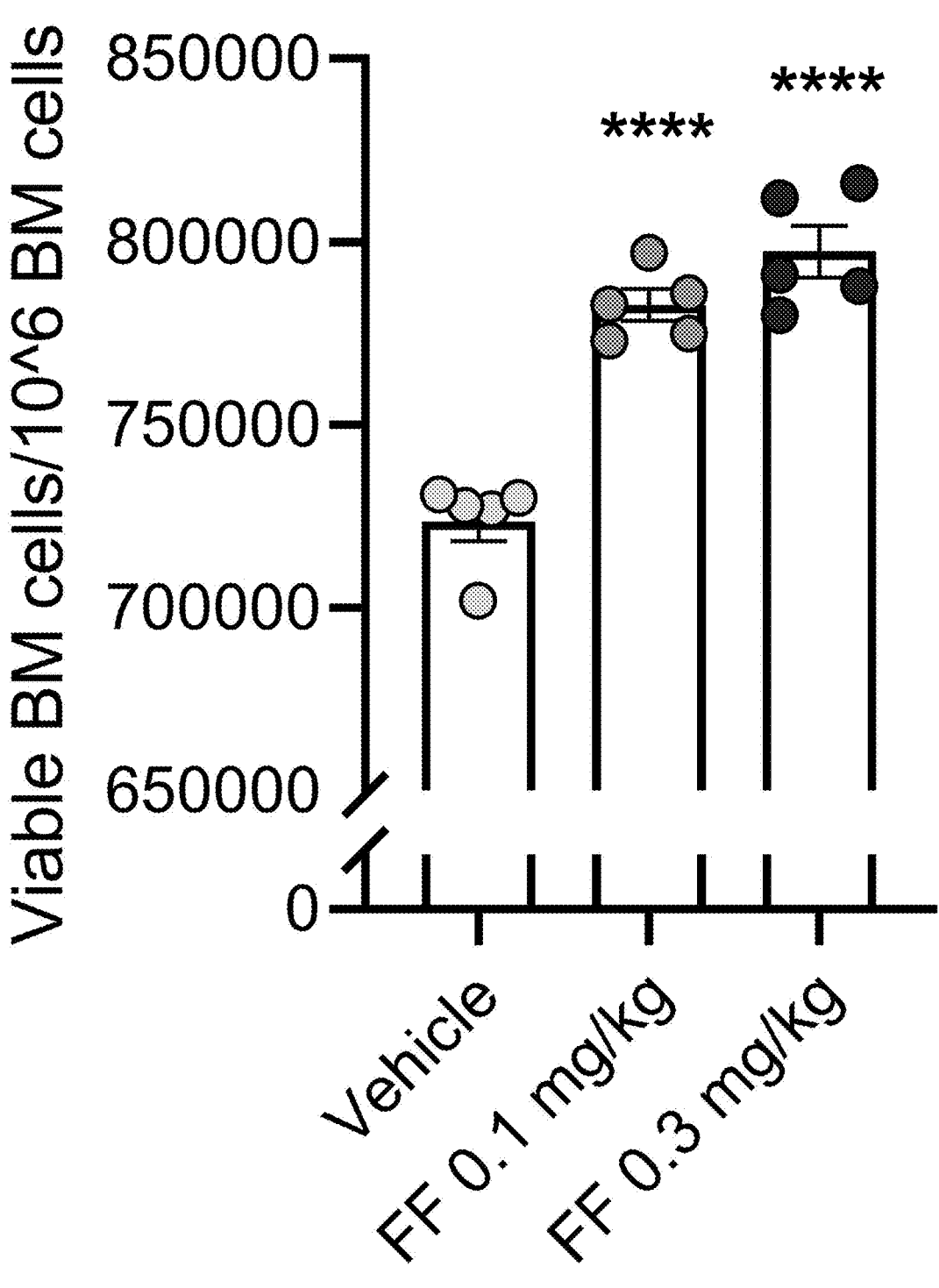
FIG. 23A-FIG. 23C show that formoterol fumarate (FF) treatment significantly enhances viability and mitochondrial biogenesis in the BM progenitors of phenylhydrazine (PHZ)-mediated stress-induced anemic mice (10-12 week old mice).
Figure 23B:
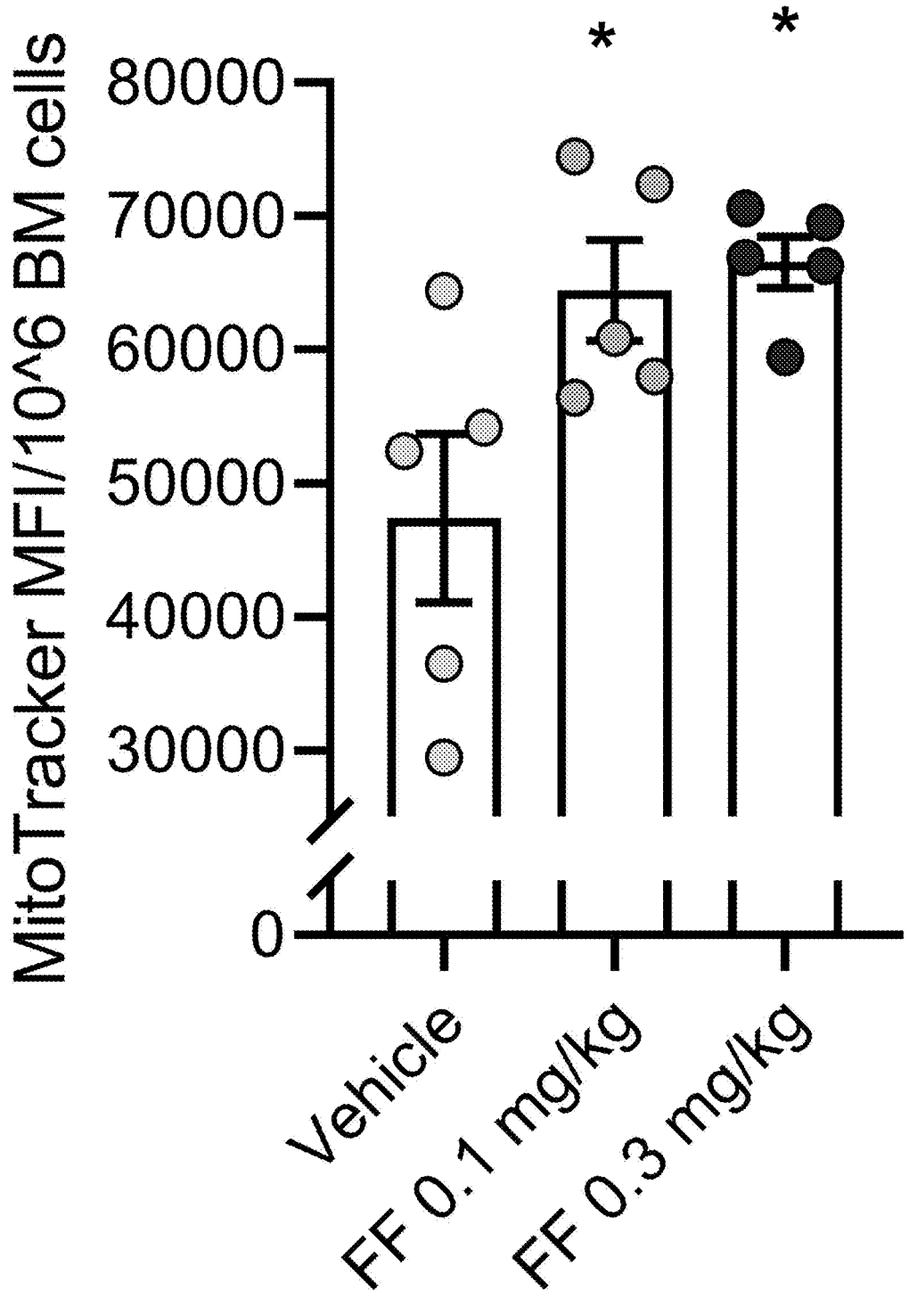
Figure 23C:
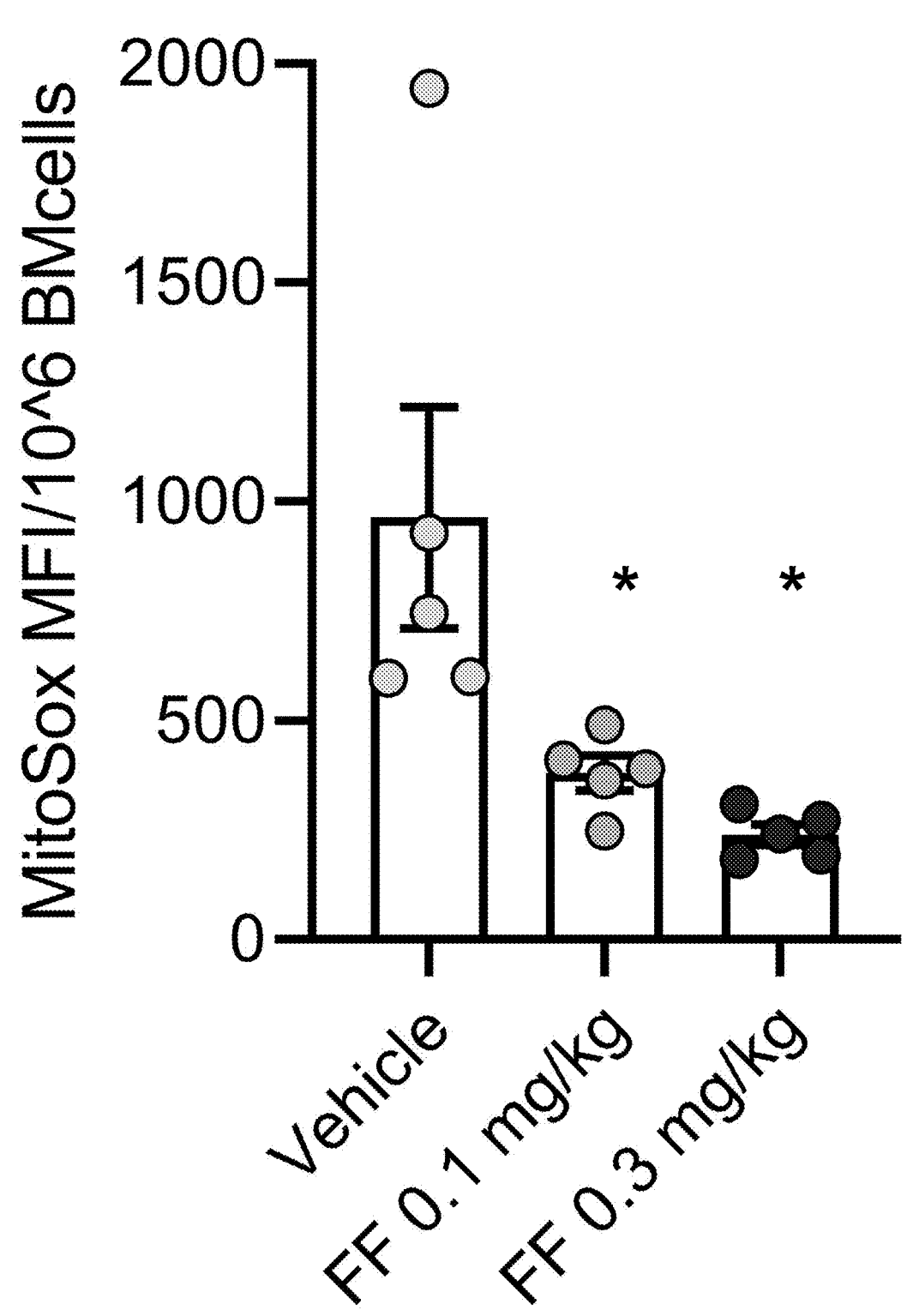
Figure 24:
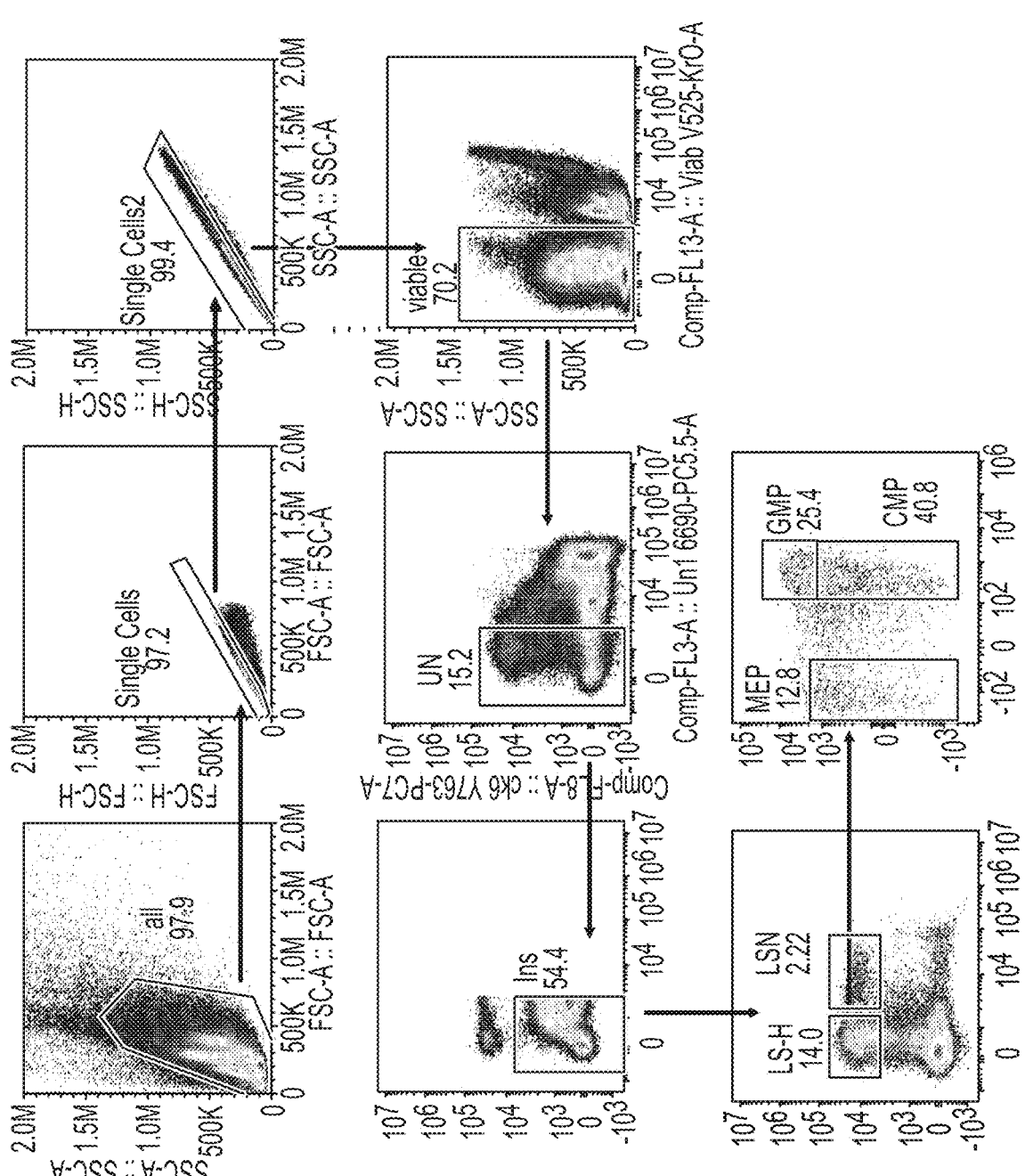
FIG. 24 shows the flow cytometry plots to study bone marrow progenitors (BMPs).
Figure 25A:
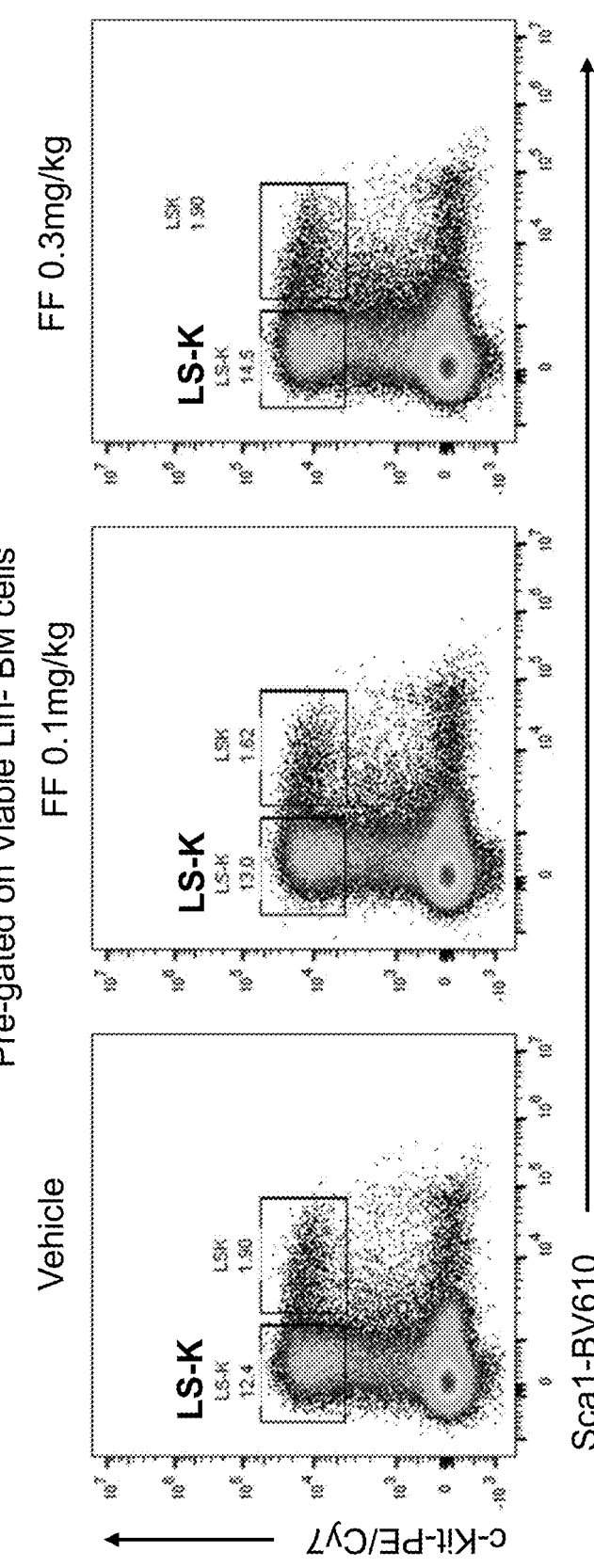
Figure 26A:
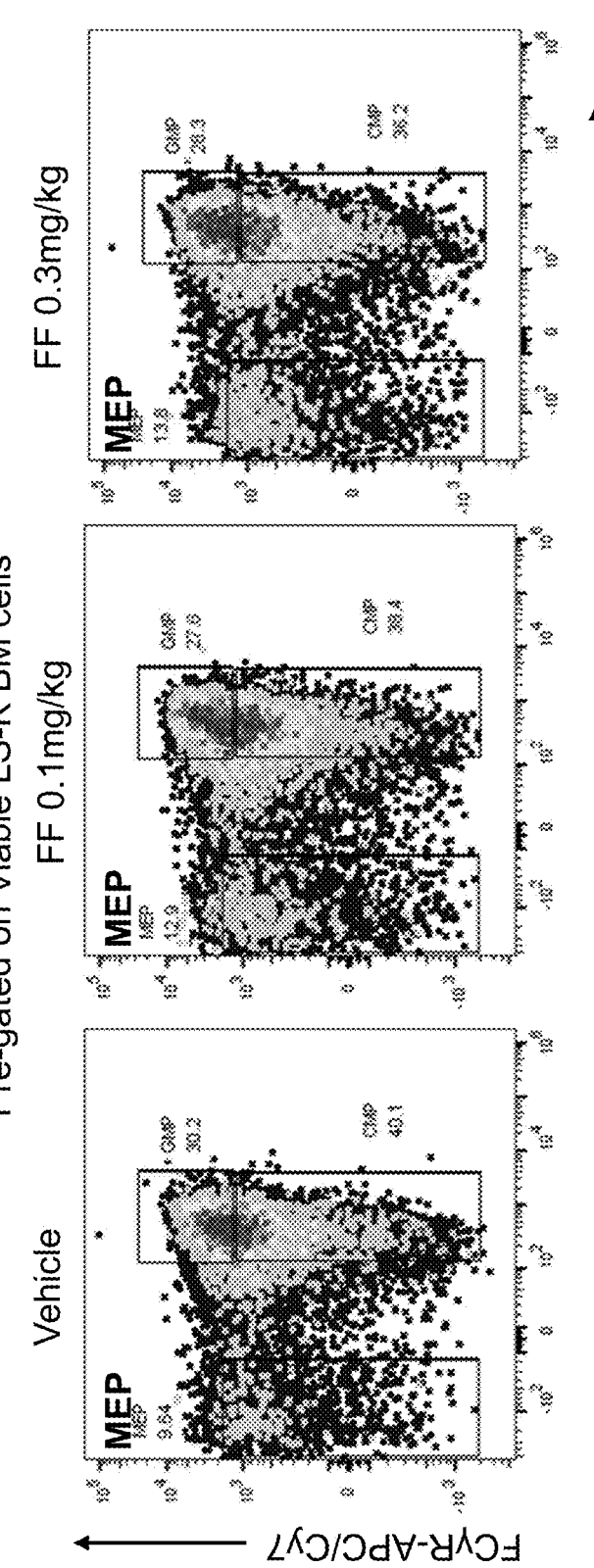
FIG. 26A-FIG. 26D show that formoterol fumarate (FF) treatment significantly elevates megakaryocyte erythroid progenitors (MEP), but not common myeloid progenitors (CMP) or granulocyte monocyte progenitors (GMP) in the BM of phenylhydrazine (PHZ)-mediated stress-induced anemic mice (10-12 week old mice).
Figure 26B:
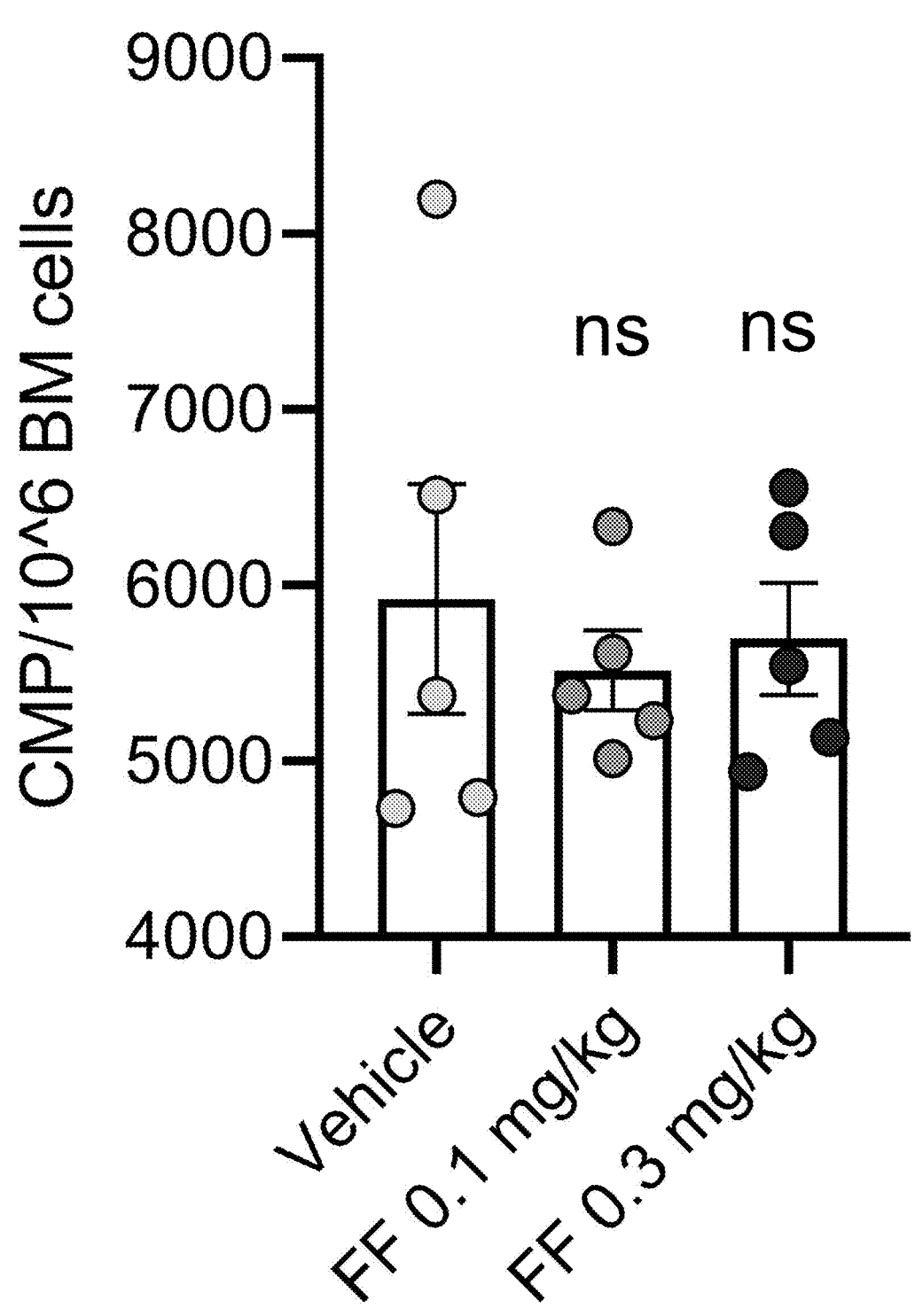
Figure 26C:
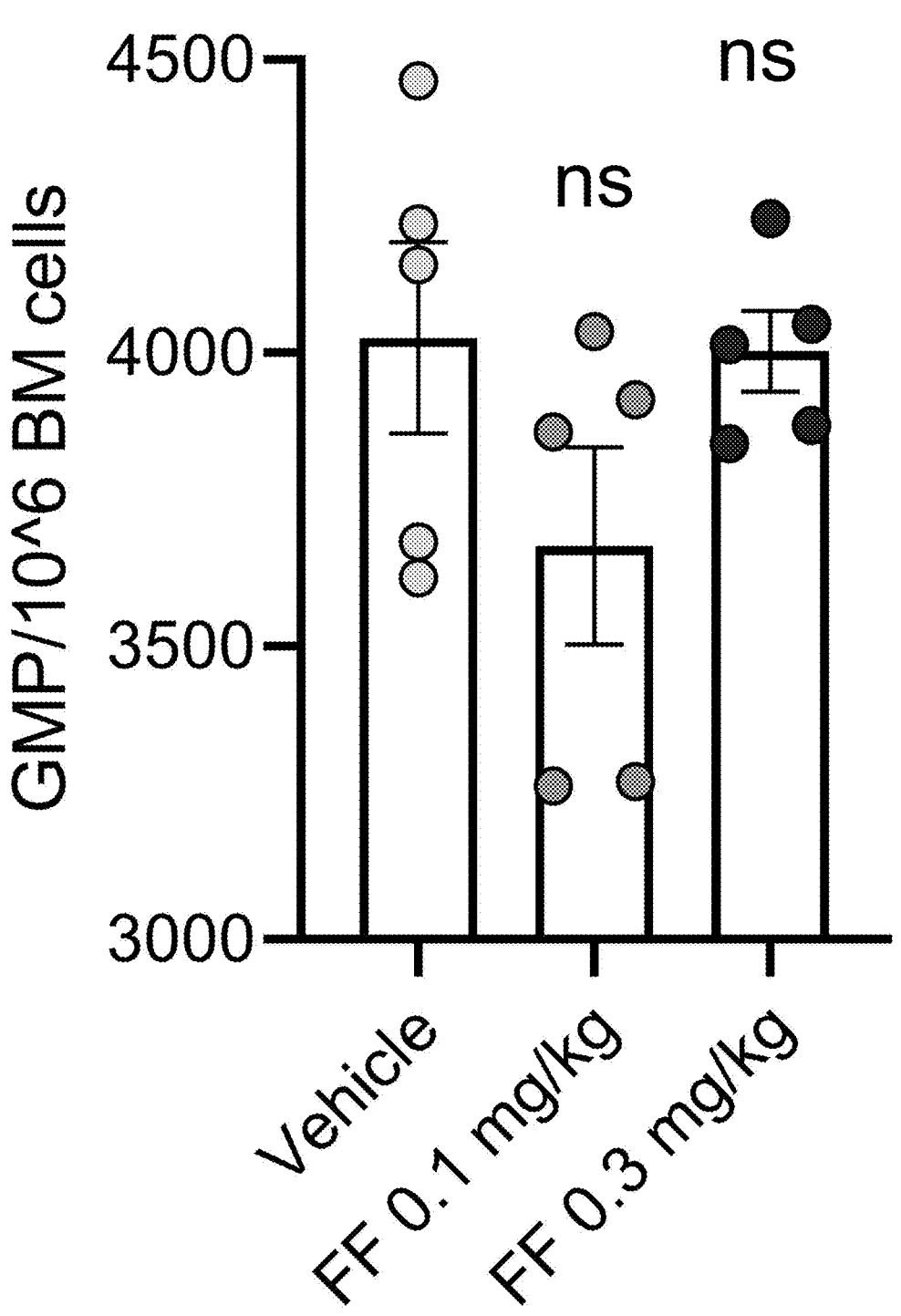
Figure 26D:
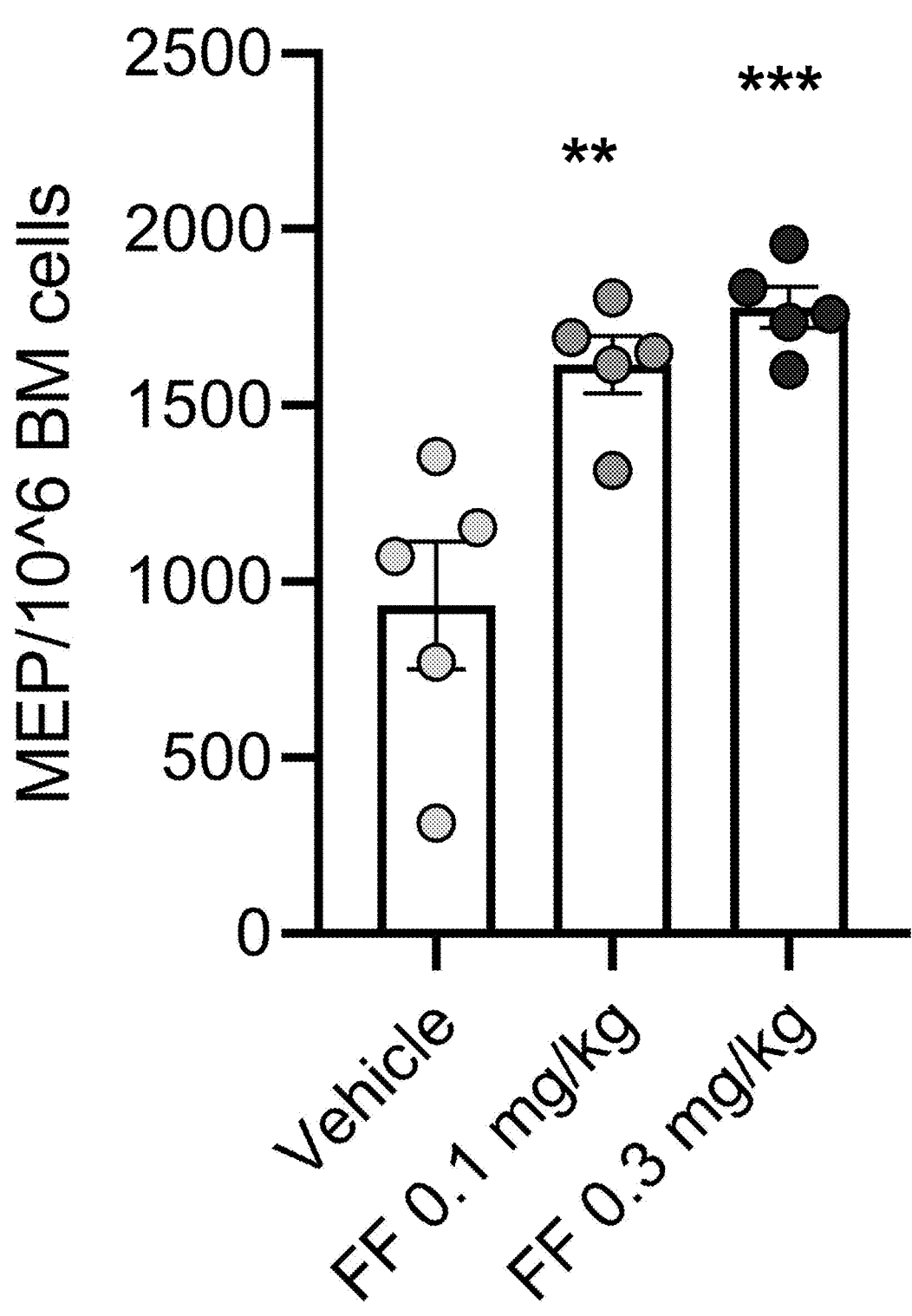
Figure 27:
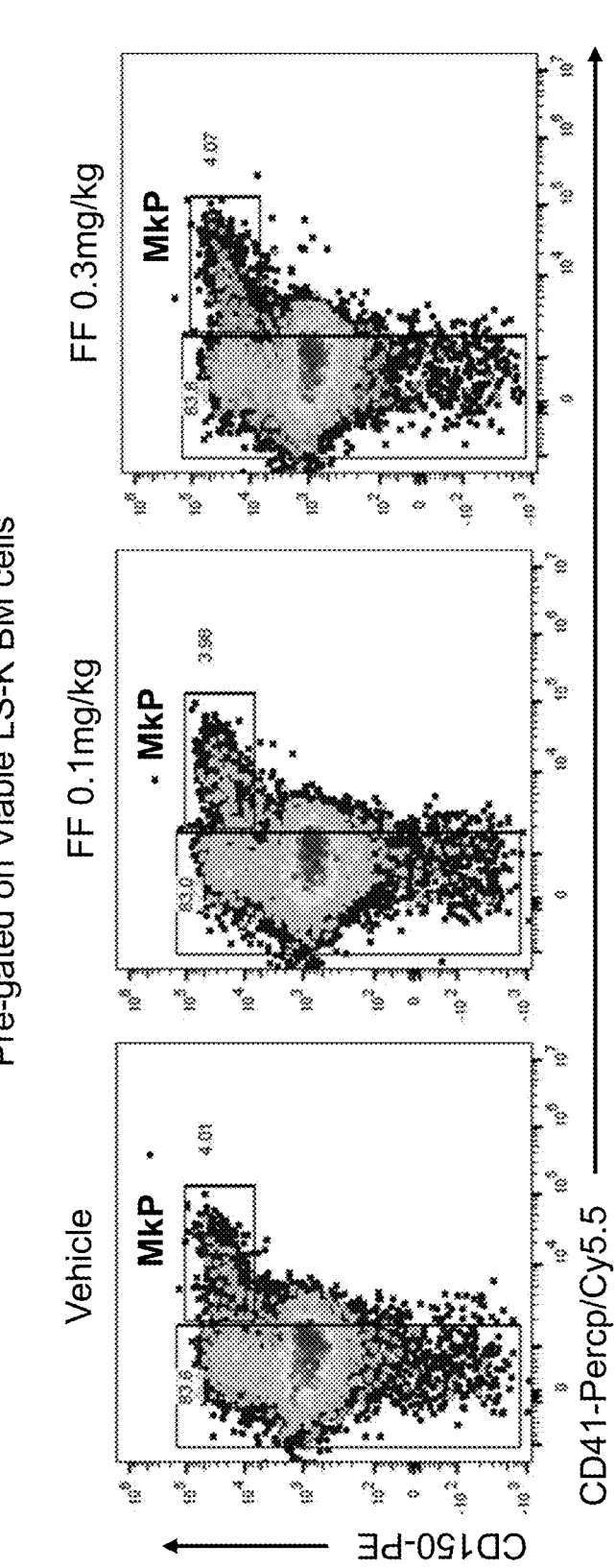
FIG. 27 shows that formoterol fumarate (FF) treatment does not affect megakaryocytic progenitors in the BM of phenylhydrazine (PHZ)-mediated stress-induced anemic mice. (10-12 week old mice). Flow plots depict that FF treatment at 0.1/0.3 mg/kg doses does not affect megakaryocytic progenitors (MkP) in the BM of mice after PHZ-induced sublethal hemolytic anemia. LS-K: Lineage—Scal—cKit+ BM cells. PHZ dose: 60 mg/kg. n=5 male mice per group.
Figure 28A:
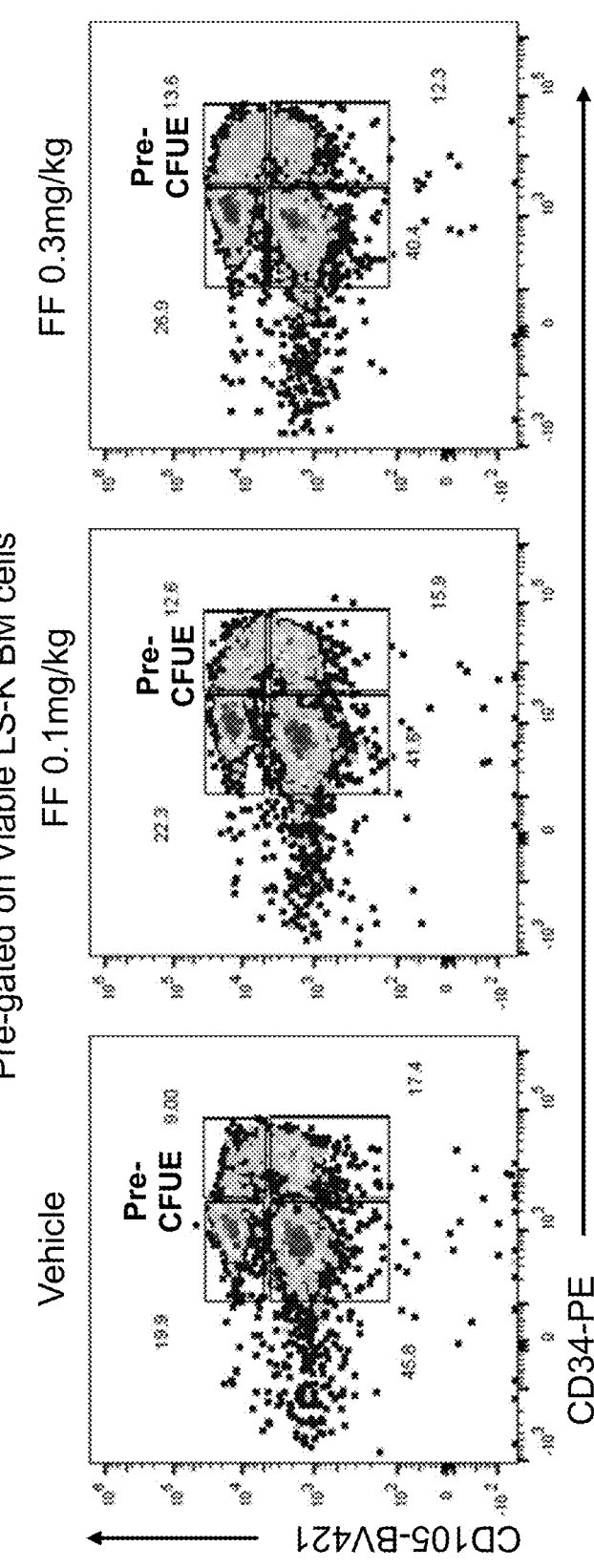
FIG. 28A-FIG. 28B show that formoterol fumarate (FF) selectively enhances Pre-CFU-E cells in the BM. * $p < 0.05$, *** $p < 0.001$, ANOVA.
Figure 28B:
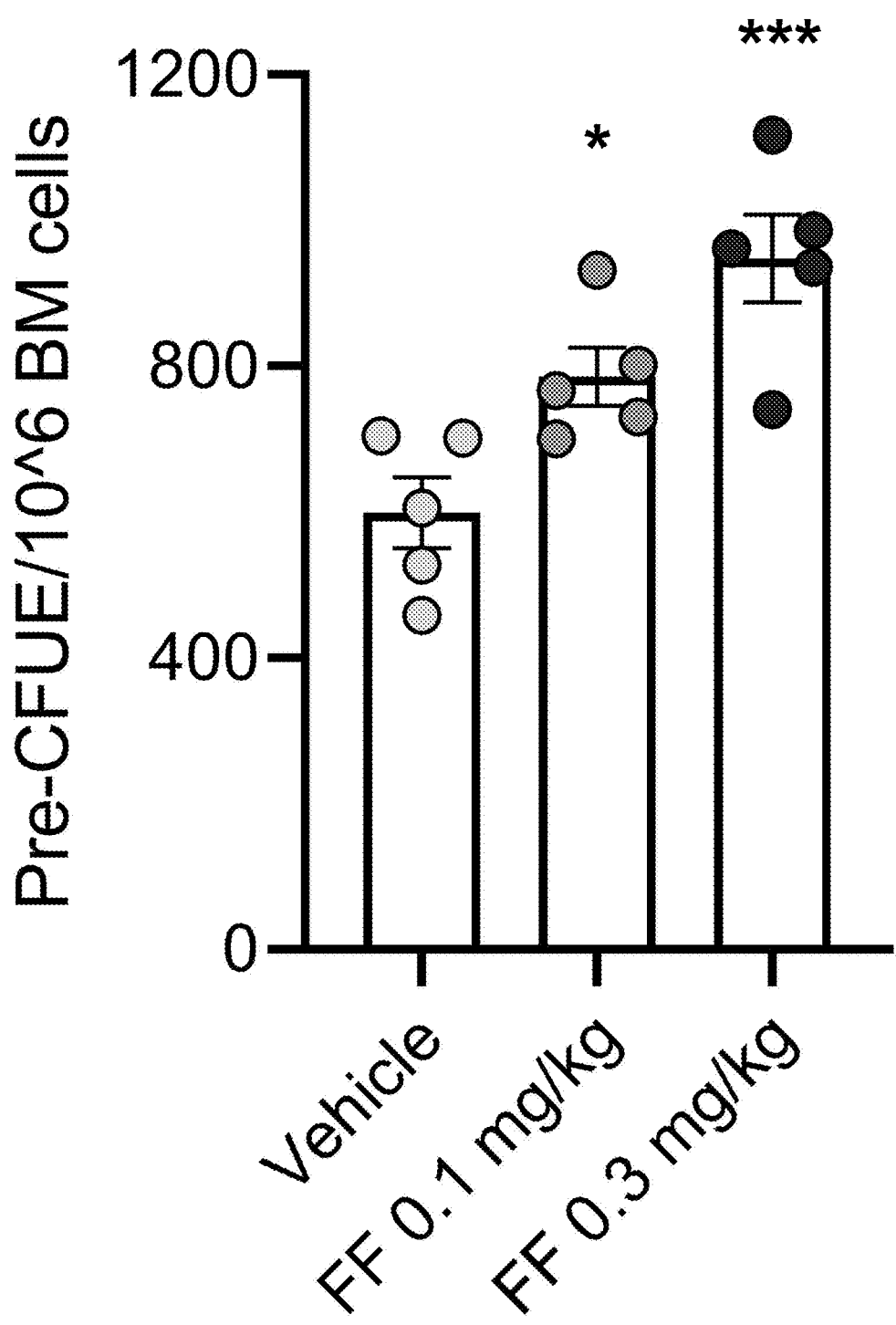
Figure 29A:
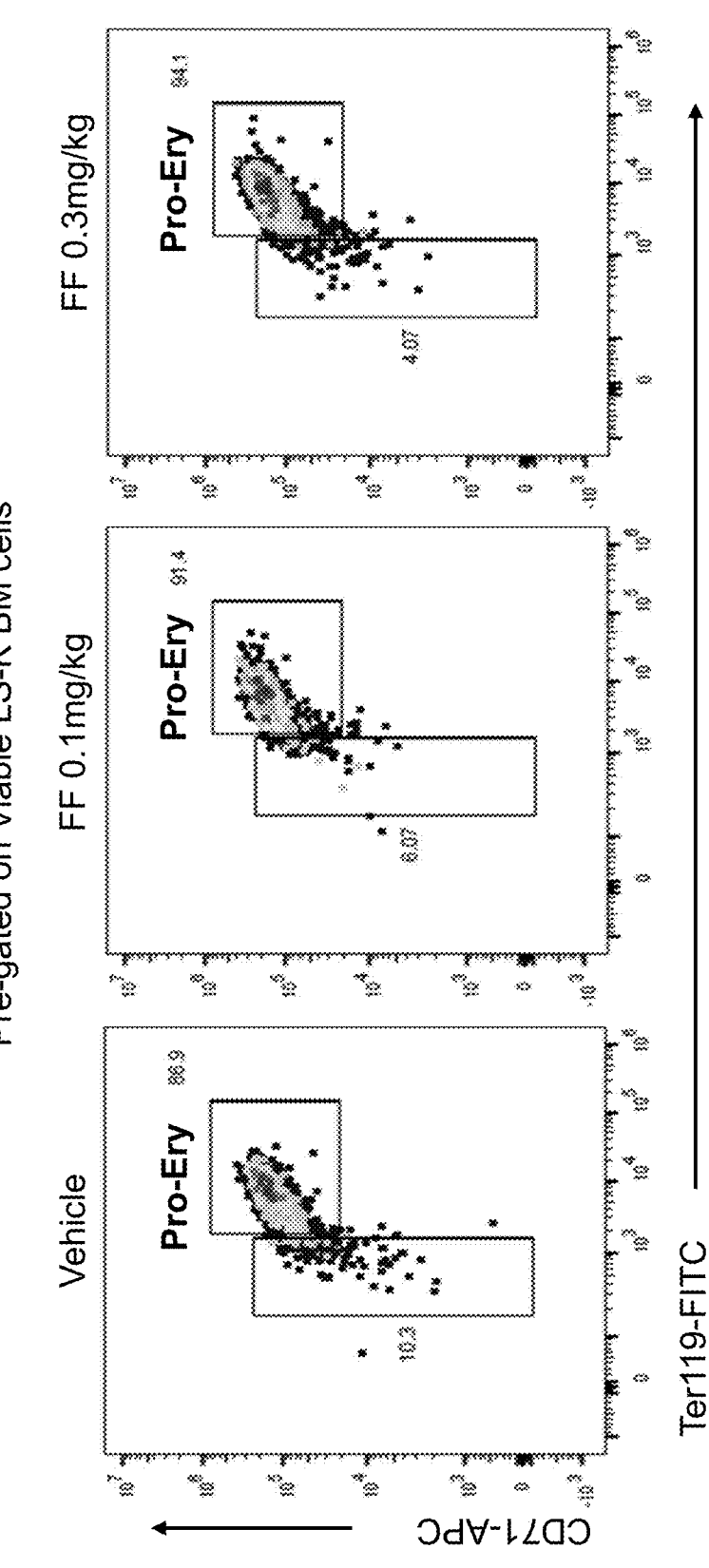
FIG. 29A-FIG. 29B show that formoterol fumarate (FF) selectively enhances pro-erythroblasts in the BM.
Figure 29B:
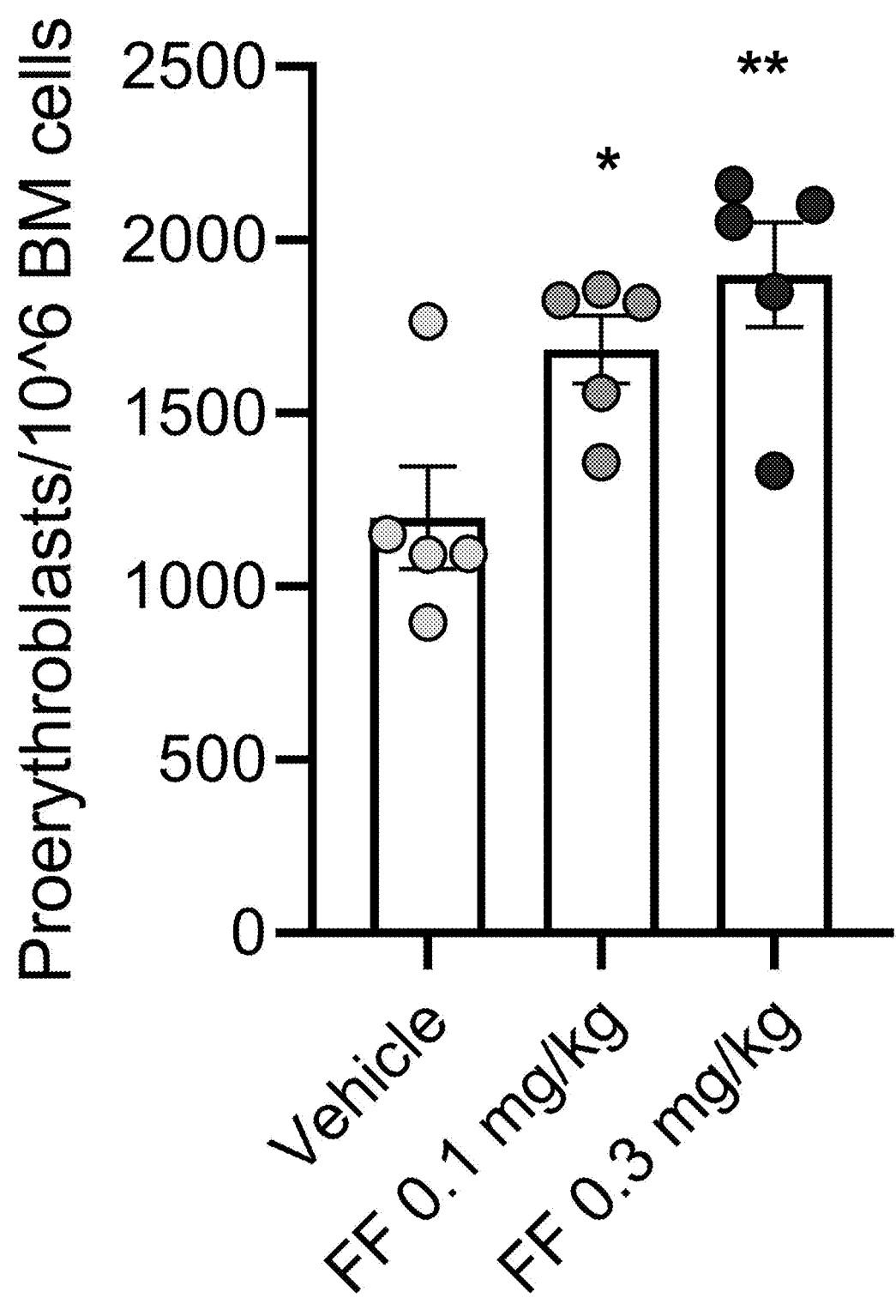
Figure 30A:
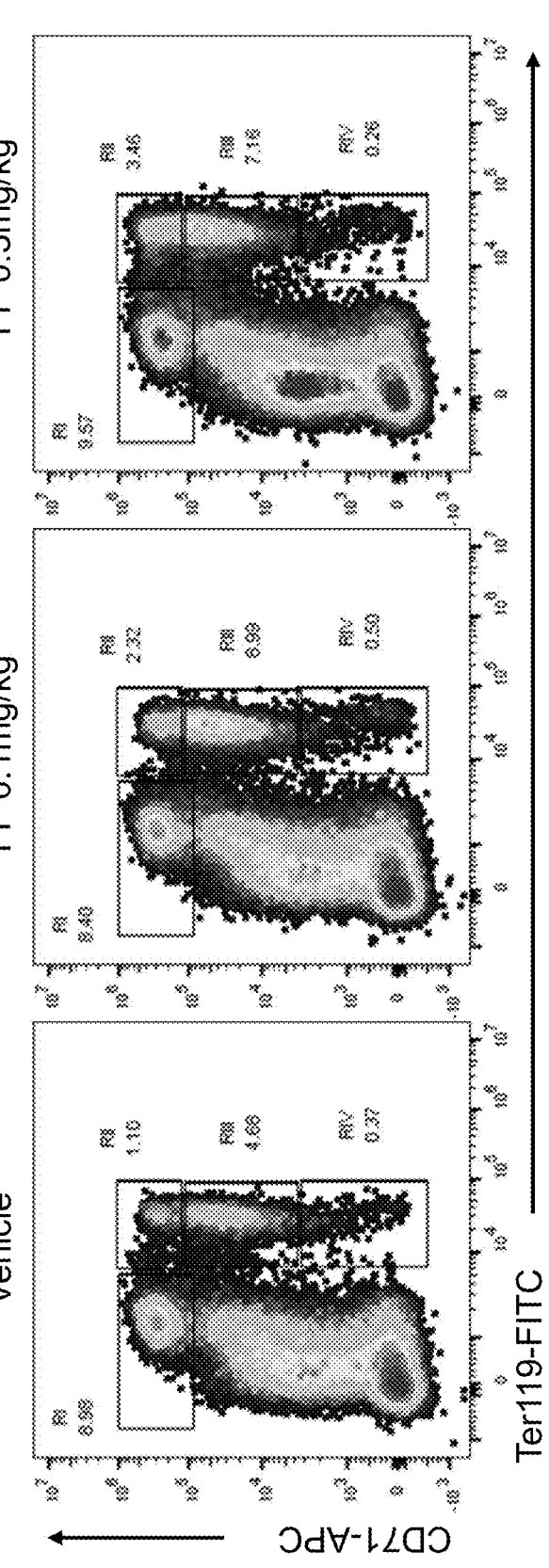
FIG. 30A-FIG. 30B show that formoterol fumarate (FF) treatment significantly elevates erythroid differentiation in the BM of phenylhydrazine (PHZ)-mediated stress-induced anemic mice (10-12 week old mice).
Figure 30B:
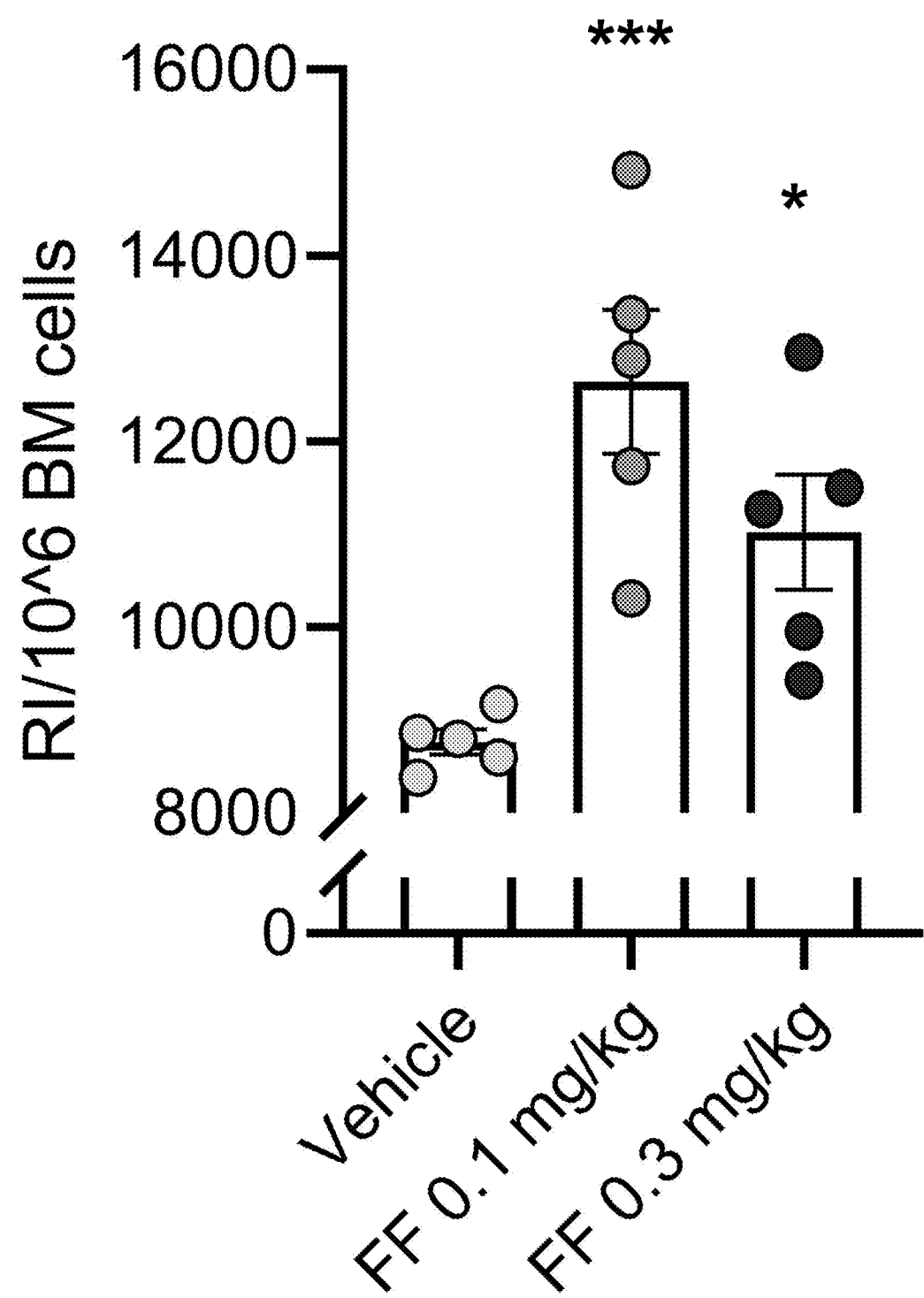
Figure 30B:
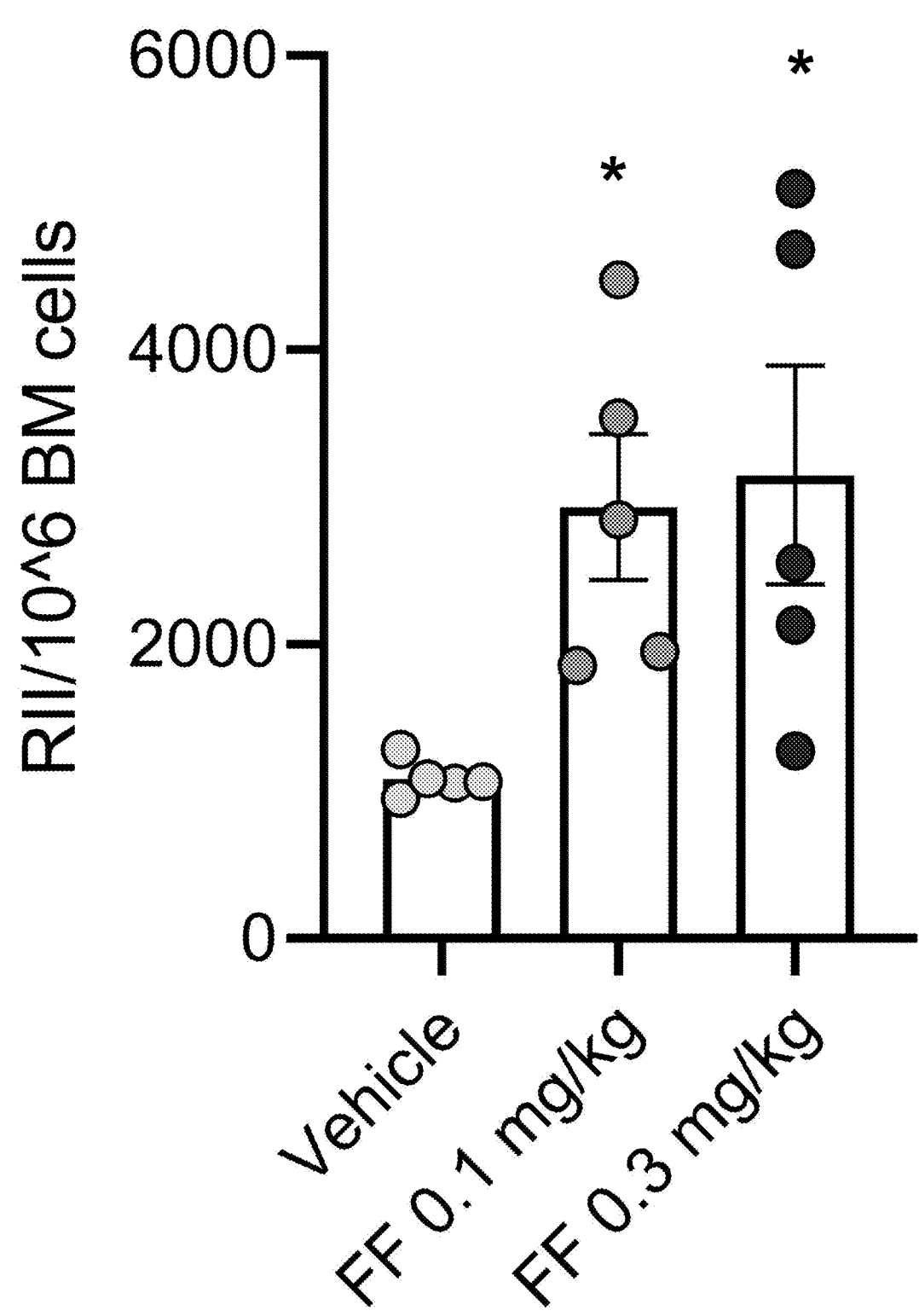
Figure 30B:
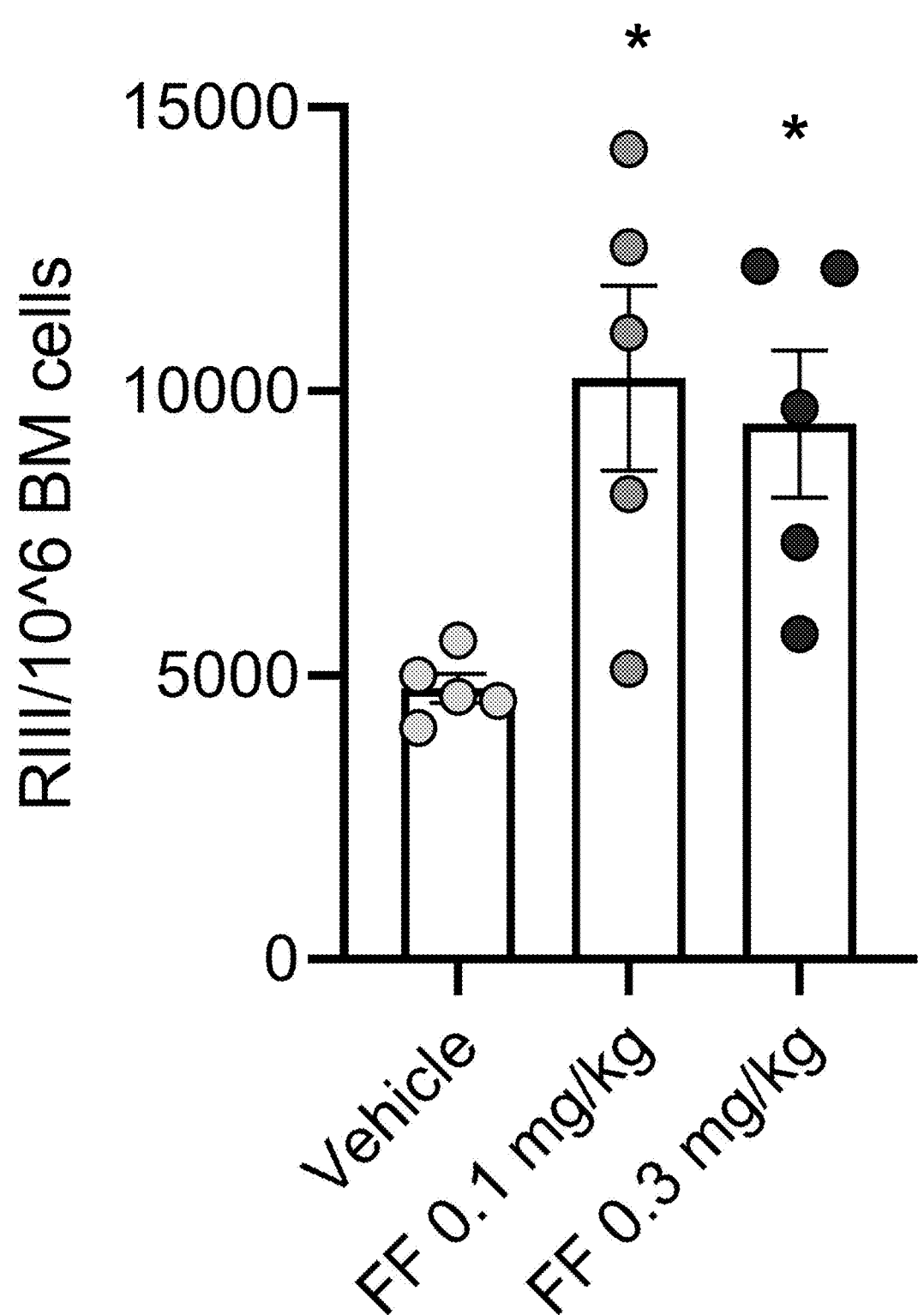
Figure 30B:
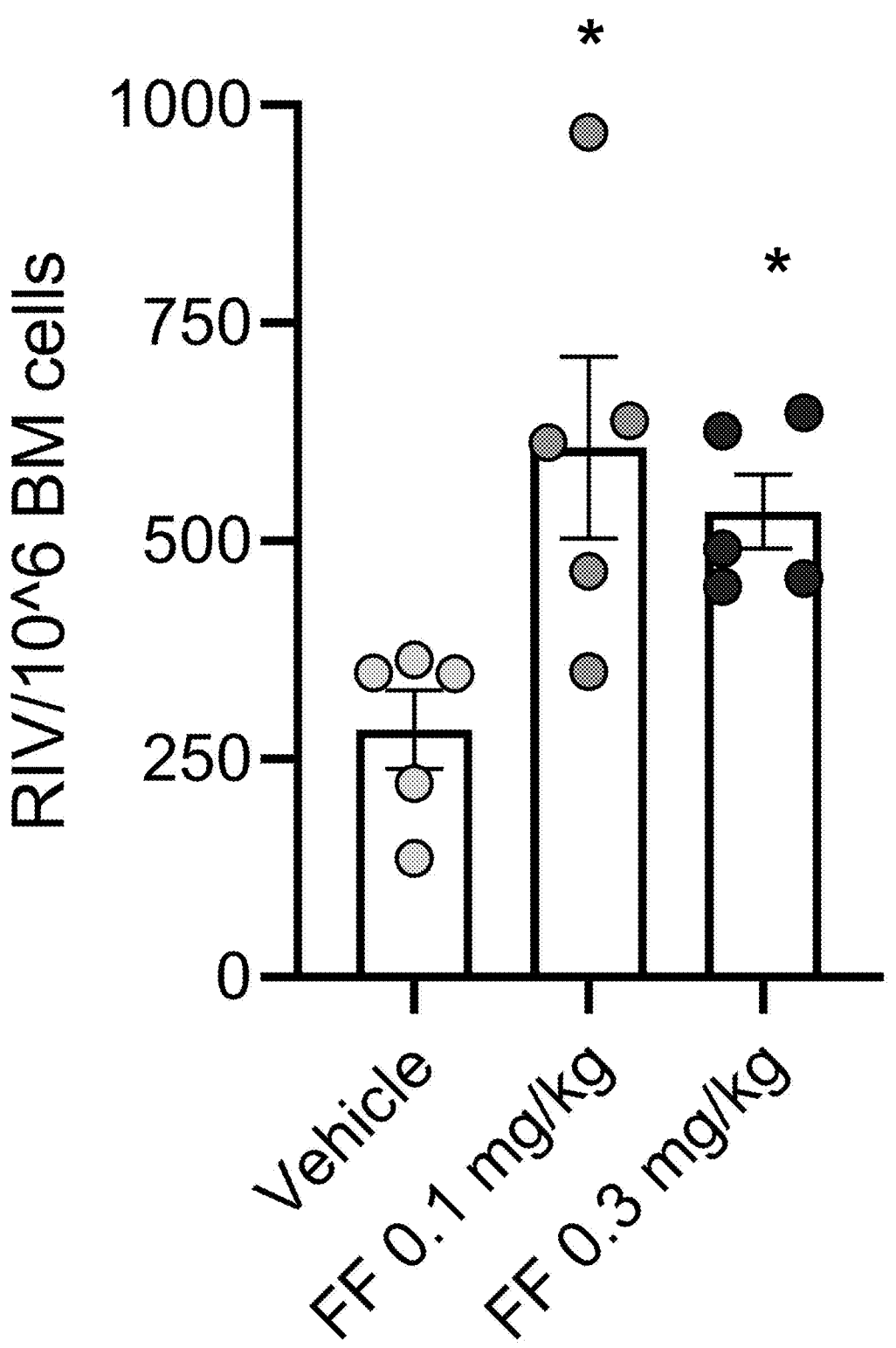
Figure 31:
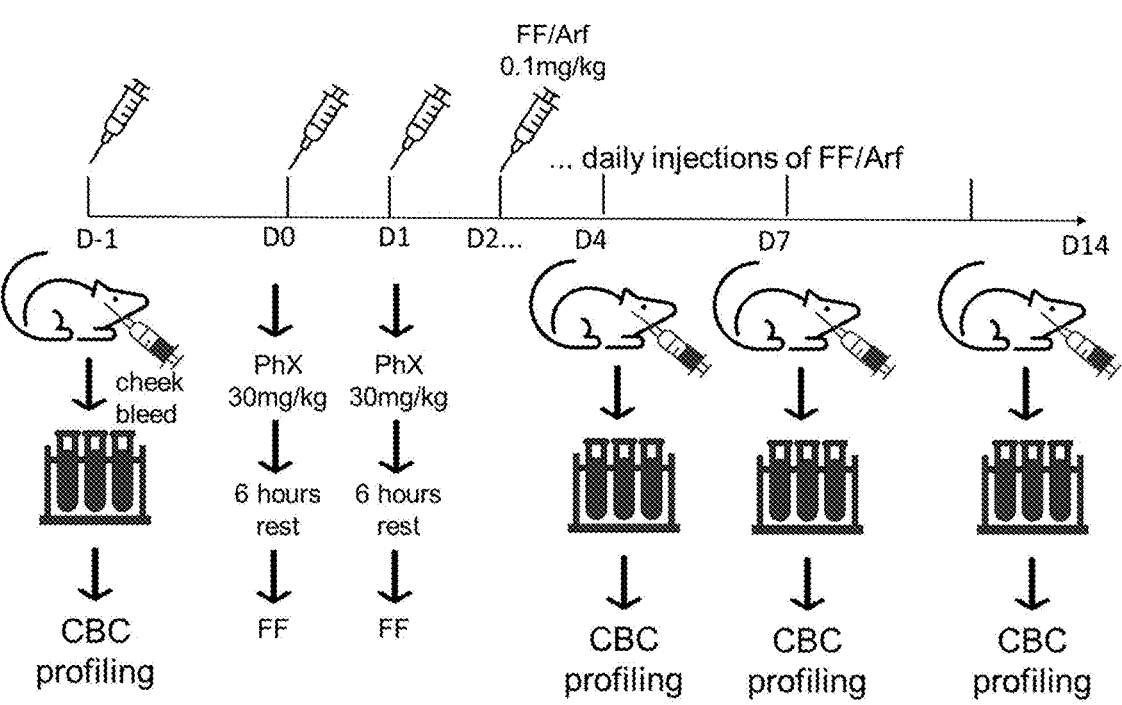
FIG. 31 shows the schematic of FF/Arf treatment via i.p. in phenylhydrazine (PHZ)-treated mice at sub-lethal dose of 60 mg/kg.
Figure 32:
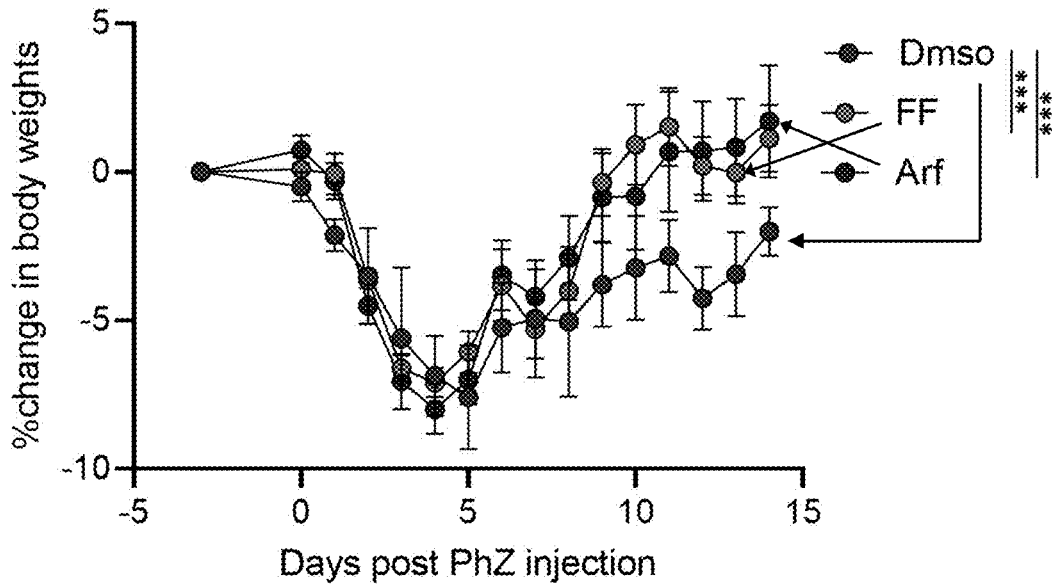
FIG. 32 shows that FF/Arf treatment via i.p. enhances body weights in phenylhydrazine (PHZ)-treated mice at sub-lethal dose (60 mg/kg). ns=non-significant.
Figure 33A:
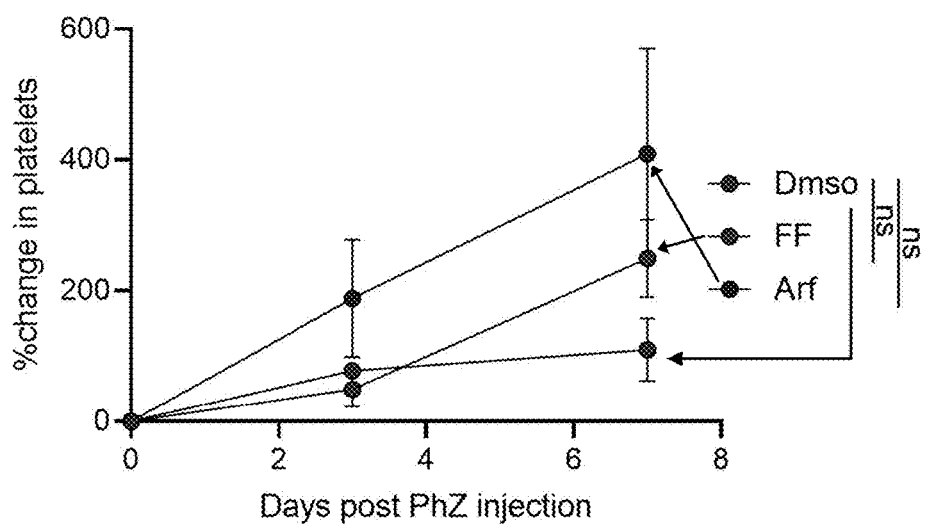
FIG. 33A-FIG. 33B show that FF/Arf treatment via i.p. does not affect WBC parameters in phenylhydrazine (PHZ)-treated mice at sub-lethal dose (60 mg/kg). FF/Arf treatments do not affect platelets and WBCs in the peripheral blood after i.p. administrations. *** $p < 0.001$, ANOVA. N=5 male mice per group. All comparisons were done w.r.t. vehicle (DMSO) treated controls. Ns=non-significant.
Figure 33B:
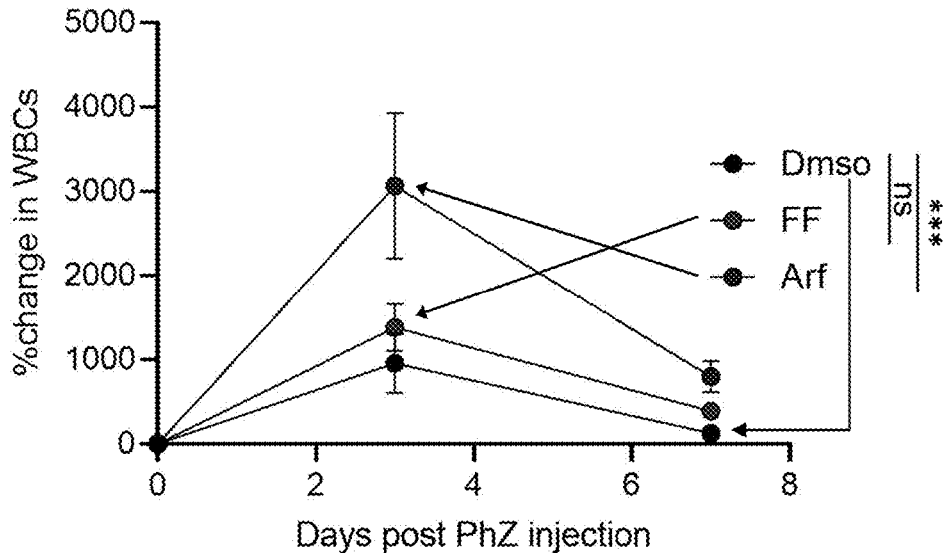

These results prompted further investigation to determine the possible effects of FF in mice undergoing sublethal hemolytic anemia. To address this, sublethal dose of phenylhydrazine (PHZ: 50 mg/kg) was first administered in 10-12 week old female mice followed by daily i.p. injections of 0.1/0.3 mg/kg FF or vehicle (0.3%DMSO in saline). PHZ is a strong oxidant that readily oxidizes hemoglobin in RBCs triggering their immediate lysis, thus causing hemolytic anemia. FF treatment at low doses of 0.1/0.3 mg/kg were sufficient to revive body weights of mice undergoing PHZ-induced hemolytic anemia (FIG. 18A). FF treatment significantly enhanced Hb production as compared to the vehicle-treated group (FIG. 18B). Also, FF administration produced long-term benefits in elevating HCT % and RBC counts in the mice as compared to the control group (FIG. 18B). Although FF treatment provided an immediate boost to WBC and monocyte counts after PHZ administration, no long term benefits were observed in FF-treated groups in contrary to the RBC parameters (FIG. 18C). The platelet counts were not statistically significant in FF treated groups (FIG. 18C). These findings are consistent with our in vitro and ex vivo experiments where FF treatment specifically enhanced erythroid differentiation and produced insignificant changes in the myeloid and megakaryocytic compartments (FIGS. 1A-1D and FIGS. 11A-11D). To eliminate the possibility that FF-mediated increase in RBC parameters may be a pseudo-effect, the mice were sacrificed after study end-point (14 days) and their bone marrow (BM) progenitors were analyzed. Intriguingly, FF-treatment at low doses of 0.1-0.3 mg/kg significantly enhanced erythroid differentiation, as evidenced by the marked increases in RI, RII, RIII and RIV erythroid progenitors in the BM of mice (FIGS. 19A and 19B). This clearly indicates that FF directly acts on the BM progenitor cells to induce erythroid differentiation. To substantiate these findings, this experiment was repeated in 10-12 week old male C57BL/6J mice and marked revival was similarly observed in body weights in the FF (0.1/0.3 mg/kg)-treated mice as compared to the vehicle-treated group in response to sublethal PHZ-induced hemolytic anemia (PHZ dose: 60 mg/kg) (FIG. 22A). FF treatment consistently improved RBC parameters in the PB, such as Hb, RBC counts and HCT% in the anemic mice as compared to vehicle-treated controls (FIG. 22B). Again, no long term impact was observed in the WBC parameters or platelets in the FF-treated groups, apart from an immediate boost after PHZ treatment (FIG. 22C). Strikingly, the BM cells from FF-treated groups exhibited marked increase in viability (FIG. 23A), in part due to elevated mitochondrial biogenesis as evidenced from increased mito Tracker® staining (FIG. 23B) and reduced mitochondrial superoxide production (mitoSOX staining) (FIG. 23C). A thorough analysis of the viable lineage-negative BM progenitors indicated that FF-treatment specifically boosted megakaryocyte erythroid progenitors (MEP), but not common myeloid progenitors (CMP) or granulocyte monocyte progenitors (GMP) (FIGS. 26A-26D). Since MEP gives rise to either megakaryocytes or erythroid progenitors, both BM cellular compartments were checked. However, no stark differences were observed in megakaryocytic progenitors (FIG. 27), consistent with the insignificant impact of FF treatment on PB platelets (FIG. 22C). FF treatment significantly enhanced RI, RII, RIII and RIV erythroid progenitors in the BM of male mice (FIGS. 30A-30B), in line with the FF-mediated improvement of erythroid differentiation in the BM of female mice (FIGS. 19A-19C). These findings demonstrate that formoterol fumarate (FF) directly functions on the early BM progenitors to stimulate erythroid differentiation that culminates into enhanced RBC parameters in the peripheral blood (PB) in vivo.

The stark alleviation of RBC parameters and revival in body weights of FF-treated anemic mice encouraged further testing of the survival benefits of FF in response to phenyl-hydrazine (PHZ)-mediated lethal hemolytic anemia. To this end, 10-12 week old male C57BL/6J mice were first treated with a single lethal dose of 150 mg/kg PHZ followed by daily i.p. injections of either vehicle or 0.1/0.3 mg/kg FF. FF treatment at low doses of 0.1/0.3 mg/kg produced striking survival benefits as compared to the vehicle-treated group (FIG. 42A). All control mice (n=5) were moribund and died by 3 days of lethal PHZ dose, whereas 3-4 mice in 0.1/0.3 mg/kg FF treatment groups are still surviving post 2 weeks of lethal dose (FIG. 42A). FF treatment produced remarkable revival in body weights of mice within the first 7 days of lethal PHZ dose (FIG. 42B). FF injections were stopped after 7 days of lethal PHZ treatment and it was observed that the body weights of mice were held steady (FIG. 42B). The body weights and survival of these mice are being monitored daily. This unexpected finding prompted us to repeat this lethal hemolytic anemia model in the female mice. Consistently, FF treatment at 0.1/0.3 mg/kg doses provided prominent survival benefits to female mice, where all (n=5) vehicle-treated mice were either moribund or dead by day 3 of lethal PHZ dose (FIG. 42C). FF treatment similarly revived body weights of the mice after lethal anemic stress (FIG. 42D). The FF treatment lasted for 7 days after lethal PHZ dose and the body weights and survival of these mice are being monitored daily. These data establish that FF generates significant survival benefits in vivo in response to hemolytic anemia, thus signifying the therapeutic potential of FF in treating anemia.

Example 2: Materials and Methods for Example 1

Mouse Experiments

C57BL/6J mice were obtained from Jackson laboratories and were housed for at least 2 weeks at the Dana-Farber Cancer Institute (DFCI) animal resources facility before beginning experiments. All drug treatments have been mentioned in detail in the text.

Primary and Secondary Cell Culture

CD34+ primary human hematopoietic stem and progenitor cells (HSPCs) were obtained from Fred-Hutchinson Cancer Research center, Seattle, USA and cultured, as previously described. Formoterol fumarate was purchased from Selleckchem (#S2020) and Sigma (#F9552), dissolved (in DMSO) and stored as per manufacturer's instructions, and used at the final working concentrations as indicated. Frozen BM aspirates from de-identified MDS patients were obtained using our IRB approved protocol (#21-632) from the Pasquarello tissue bank at DFCI.

Mitochondrial Fitness Tests

TMRE (T669, Invitrogen) and Mitotracker® (M22426, Life Technologies) and MitoSox® (M36008, Life Technologies) staining were performed as per the manufacturer's instructions.

CRISPR/Cas9 Gene Editing

Primary human HSPCs were genome-edited, as previously described (Ghosh, S., Raundhal, M., Myers, S. A., Carr, S. A., Chen, X., Petsko, G. A., and Glimcher, L. H. (2022). Identification of RIOK2 as a master regulator of human blood cell development. Nat Immunol 23, 109-121).

Quantitative RT-PCR

As previously described herein.

Flow Cytometry and Sorting

FACS staining and sorting were performed as previously described (Ghosh et al. (2022) Nat Immunol 23:109-121).

Methylcellulose Assay

After genome editing, primary human HSPCs were washed twice with 1× PBS and mixed with semi-solid methylcellulose medium (H4034 StemCell Technologies) by brief vortexing. Cells were plated at a density of 2000 per well in a 6-well plate followed by incubation in a humidified chamber at 37° C. for 14 days. Imaging of the colonies was performed using EVOS M5000 Imaging system® (ThermoFisher Scientific). The colony-forming cells were then collected by triturating the wells using staining buffer and multi-color flow cytometry was performed as previously described (Li et al. (2014) Blood 124: 3636-3645).

Statistical Tests

Data are presented as mean±SEM. Unpaired two-tailed t-test was used for comparing two groups. Analysis of variance (ANOVA) with Tukey's correction or Kruskal-Wallis test with Dunn's correction was used for comparisons amongst multiple groups, wherever applicable as per requirements of data and quantification. GraphPad Prism v8.0/9.0 (GraphPad Software Inc., San Diego, CA) was used to perform statistical analyses. Sample size was not predetermined.

Example 3: Non-Linear Dose-Specific Effects of Formoterol Fumarate (FF) Treatment in Wild-Type Mice As described in Example 1 above, formoterol fumarate (FF) treatment of wild-type mice was well-tolerated (FIGS. 14A-14E). The effects of varying doses of FF from 0.1 up to 1.0 mg/kg were evaluated in naive mice without any external stress of phenylhydrazine (PHZ). Specifically, varying doses of FF 0.1-0.3-0.5-1.0 mg/kg or vehicle (0.3% DMSO in saline) were administered via intraperitoneal (i.p.) injection in 10-12 week old wild-type C57BL/6J mice daily for a period of 30 days.

0.1-1.0 mg/kg FF treatment showed a dose-dependent increase in body-weight with doses of 0.1-0.5 mg/kg modestly increasing body weights of naive mice. Notably, a pronounced increase in body weights was observed at the highest dose of 1.0 mg/kg FF (FIG. 83).

Interestingly, a dose-dependent effect was observed on the red blood cell (RBC) parameters, with an effect being observed at low to moderate doses, but not at the highest dose. As shown in FIG. 84A hemoglobin (Hb) levels increased with dose from 0.1 mg/kg FF to 0.5 mg/kg FF, but no effect was observed at the highest dose of 1.0 mg/kg FF. Similarly, hematocrit (HCT) % and RBC counts, were elevated in those mice treated with FF at 0.3 mg/kg and 0.5 mg/kg doses, but not at the lowest (0.1 mg/kg FF) or highest doses (1.0 mg/kg FF) (FIGS. 84B-84C).

The white blood cell (WBC) count was only marginally affected at the highest dose of 1.0 mg/kg FF (FIG. 85A), while monocyte counts were marginally affected only at the 0.3 mg/kg and 0.5 mg/kg doses of FF, but not at the highest or lowest doses (1.0 mg/kg and 0.1 mg/kg FF, respectively) (FIG. 85B). No effect was observed on platelets with administration of FF at any dose (FIG. 85C).

These results support that in contrast to the effect on bodyweight, FF has non-linear dose-specific effects on blood cell parameters.

Example 4: Bone Mass in Formoterol Fumarate (FF) Treated Mice

As described in Example 1 above, formoterol fumarate (FF) treatment is associated with an increase in bodyweight and FF-treatment also revived body weight of phenylhydrazine (PHZ)-mediated anemic mice. FF has been shown to have anabolic effects on bone in ovariectomized rat models, which may be at least in part due to agonistic effects of FF on β-adrenergic receptors expressed on bone cells. See Kellenberger et al., (1998) *Bone* 22(5): 471-478, which is incorporated by reference. FF has also been demonstrated to increase muscle mass in mice and to improve muscle structure and function after injury. See Gehrig et al., (2010) *The American Journal of Pathology* 176(1): 29-33 and Ryall et al. (2008) *J. Appl. Physiol.* 105:165-172. To investigate whether the increase in body weight was associated with an increase in bone mass and/or muscle mass, dexascanning is performed. Specifically, C57BL/6J mice (2-3 months old wild-type, steady state mice (that have not been phenylhydrazine treated) are treated with FF at a dose of 0.3 mg/kg or vehicle (0.3% DMSO in saline) by via intraperitoneal (i.p.) injection 5 times weekly for a month followed by Dexascanning to measure bone densities, muscle and fat mass, and also free and total water content of the mice. Mice treated with other β2 adrenergic receptor agonists that are not associated with weight gain are also assessed.

Example 5: RNA Sequencing of Formoterol Fumarate (FF) Treated Mice

This example describes the effects of formoterol fumarate treatment on expression of genes that have been linked to erythropoiesis including Klf9 (Ren et al., (2018) *Yi Chuan.* 40(11):998-1006 and Zhang et al., (2017) *Blood* 130(20): 2161-2170), Klf13, Klf11 (Emery (2007) *J. Cell. Biochem* 100(4):1045-55), Hif1a (Wellmann, et al., (2004) *J. Cell Sci.* 117:175-94; Feng et al., (2022) *Nature* 610(7933):783-790; and Chen et al., (2019) *N Engl J Med* 381:1011-1022), Epas1 (Scortegagna et al. (2003) Blood 102:1634-40), Ddit4 (Yoshikawa (2023) *Cancer Biomark.* 37(4): 217-225), Cirbp, and Rora (Kim et al. (2008) *Arterioscler Throm Vasc Biol* 28(10):1796-802 and Chauvet et al., (2004) *Biochem. J.* 384:79-85). Differential gene expression in naïve wild-type mice was analyzed by bulk RNA sequencing according to an example workflow as depicted in FIG. 86. Example differential gene expression in erythroid progenitors isolated from bone marrow of FF-treated vs. vehicle-treated mice are shown in FIG. 87A-B. Expression of numerous genes implicated in erythropoiesis were increased in FF-treated mice including Klf9, Klf13, Klf11, Hif1a, Epas1, Ddit4, Cirbp, and Rora. Notably, FIG. 88A-B show that expression of HIF-1α and VEGFA were both significantly increased during FF-treatment of wild-type mice, as validated by qPCR analyses. These data support that formoterol has multi-target effects for increasing erythropoiesis and treating anemia.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.
Other Abbreviations
    CFU-GM: Colony forming unit-granulocyte macrophage
    CFU-Mk: Colony forming unit-megakaryocytes
    COPD: Chronic obstructive pulmonary disease
    RIOK2: Right open reading frame kinase 2
    TMRE: Tetramethylrhodamine ethyl ester

What is claimed is:

1. A method of treating anemia in a human subject, the method comprising administering to the human subject an effective amount of formoterol or a pharmaceutically acceptable salt thereof.

2. The method of claim 1, wherein the anemia is selected from the group consisting of macrocytic anemia, hemolytic anemia, anemia caused by a ribosomopathy, anemia caused by insufficiency of serine/threonine-protein kinase RIOK2, anemia associated with chronic kidney disease (CKD), anemia caused by one or more mutations or deletions in human chromosome 5 or in an ortholog thereof, anemia caused by one or more mutations and deletions in human chromosome 5 or in an ortholog thereof, stress-induced anemia, Diamond Blackfan anemia, aplastic anemia, Schwachman-Diamond syndrome, an anemia associated with an inflammatory disease, anemia associated with rheumatoid arthritis, anemia associated with multiple sclerosis, anemia secondary to chemotherapy in cancer patients, and anemia associated with a bone marrow failure syndrome.

3. The method of claim 1, wherein the anemia is associated with a cancer, and wherein the cancer is an intestinal cancer or a hematologic malignancy selected from myelodysplastic syndrome (MDS), acute myeloid leukemia (AML), chronic lymphocytic leukemia (CLL) and multiple myeloma (MM).

4. The method of claim 3, wherein the intestinal cancer is colorectal cancer.

5. A method of promoting differentiation of an erythroid progenitor cell toward a mature red blood cell in a human subject, comprising administering to the human subject in need thereof an effective amount of formoterol or a pharmaceutically acceptable salt thereof.

6. The method of claim 5, wherein the human subject is suffering from anemia.

7. The method of claim 6, wherein the anemia is selected from the group consisting of macrocytic anemia, hemolytic anemia, anemia caused by a ribosomopathy, anemia caused by insufficiency of serine/threonine-protein kinase RIOK2, anemia associated with chronic kidney disease (CKD), anemia caused by one or more mutations or deletions in human chromosome 5 or in an ortholog thereof, anemia caused by one or more mutations and deletions in human chromosome 5 or in an ortholog thereof, stress-induced anemia, Diamond Blackfan anemia, aplastic anemia, Schwachman-Diamond syndrome, an anemia associated with an inflammatory disease, anemia associated with rheumatoid arthritis, anemia associated with multiple sclerosis, anemia secondary to chemotherapy in cancer patients, and anemia associated with a bone marrow failure syndrome.

8. The method of claim 6, wherein the anemia is associated with a cancer, and wherein the cancer is an intestinal cancer or a hematologic malignancy selected from a myelodysplastic syndrome (MDS), acute myeloid leukemia (AML), chronic lymphocytic leukemia (CLL) and multiple myeloma (MM).

9. The method of claim 8, wherein the intestinal cancer is colorectal cancer.

10. The method of claim 1, further comprising administering to the human subject in need thereof an effective amount of an erythropoiesis-stimulating agent selected from erythropoietin, epoetin alfa, epoetin beta, epoetin omega, epoetin zeta, and darbepoetin alfa.

11. A method of treating anemia in a human subject, the method comprising administering to the human subject an effective amount of formoterol or a pharmaceutically acceptable salt thereof conjointly with an erythropoiesis-stimulating agent, wherein the anemia is refractory to the erythropoiesis-stimulating agent.

12. The method of claim 11, wherein the anemia is selected from the group consisting of macrocytic anemia, hemolytic anemia, anemia caused by a ribosomopathy, anemia caused by insufficiency of serine/threonine-protein kinase RIOK2, anemia associated with chronic kidney disease (CKD), anemia caused by one or more mutations or deletions in human chromosome 5 or in an ortholog thereof, anemia caused by one or more mutations and deletions in human chromosome 5 or in an ortholog thereof, stress-induced anemia, Diamond Blackfan anemia, aplastic anemia, Schwachman-Diamond syndrome, an anemia associated with an inflammatory disease, anemia associated with rheumatoid arthritis, anemia associated with multiple sclerosis, anemia secondary to chemotherapy in cancer patients, and anemia associated with a bone marrow failure syndrome.

13. The method of claim 11, wherein the anemia is associated with a cancer, and wherein the cancer is an intestinal cancer or a hematologic malignancy selected from a myelodysplastic syndrome (MDS), acute myeloid leukemia (AML), chronic lymphocytic leukemia (CLL) and multiple myeloma (MM).

14. The method of claim 13, wherein the intestinal cancer is colorectal cancer.

15. The method of claim 11, wherein the erythropoiesis-stimulating agent is erythropoietin, epoetin alfa, epoetin beta, epoetin omega, epoetin zeta, or darbepoetin alfa.

16. The method of claim 1, wherein formoterol or the pharmaceutically acceptable salt thereof is orally administered to the human subject.

17. The method of claim 1, wherein formoterol or the pharmaceutically acceptable salt thereof is formoterol fumarate.

18. The method of claim 1, wherein formoterol or the pharmaceutically acceptable salt thereof is arformoterol.

19. The method of claim 18, wherein the arformoterol is arformoterol tartrate.

20. The method of claim 1, wherein formoterol or the pharmaceutically acceptable salt thereof is administered conjointly with luspatercept, lenalidomide, an erythropoiesis-stimulating agent (ESA), wherein the erythropoiesis-stimulating agent is optionally epoetin alfa or darbepoetin alfa, a hypomethylating agent, wherein the hypomethylating agent is optionally azacitidine, decitabine, or azacitidine and decitabine, or any combination thereof.

* * * * *